(12) United States Patent
Wu et al.

(10) Patent No.: US 10,618,898 B2
(45) Date of Patent: Apr. 14, 2020

(54) HYDROXYL PURINE COMPOUNDS AND USE THEREOF

(71) Applicant: GUANGDONG RAYNOVENT BIOTECH CO., LTD., Guangdong (CN)

(72) Inventors: Linyun Wu, Pudong New Area (CN); Xiaoxin Chen, Dongguan (CN); Peng Zhang, Pudong New Area (CN); Xing Liu, Dongguan (CN); Li Zhang, Pudong New Area (CN); Zhuowei Liu, Dongguan (CN); Shuhui Chen, Pudong New Area (CN); Chaofeng Long, Dongguan (CN)

(73) Assignee: GUANGDONG RAYNOVENT BIOTECH CO., LTD., Guangdong (CN)

( * ) Notice: Subject to any disclaimer, the term of this patent is extended or adjusted under 35 U.S.C. 154(b) by 0 days.

(21) Appl. No.: 15/575,315

(22) PCT Filed: May 5, 2016

(86) PCT No.: PCT/CN2016/081103
§ 371 (c)(1),
(2) Date: Nov. 17, 2017

(87) PCT Pub. No.: WO2016/184313
PCT Pub. Date: Nov. 24, 2016

(65) Prior Publication Data
US 2018/0148451 A1  May 31, 2018

(30) Foreign Application Priority Data

May 20, 2015 (CN) .................. 2015 1 0260884

(51) Int. Cl.
| | | |
|---|---|---|
| C07D 473/10 | (2006.01) |
| C07D 473/06 | (2006.01) |
| C07D 487/04 | (2006.01) |
| C07D 471/04 | (2006.01) |
| C07D 475/02 | (2006.01) |

(52) U.S. Cl.
CPC ......... *C07D 473/10* (2013.01); *C07D 471/04* (2013.01); *C07D 473/06* (2013.01); *C07D 475/02* (2013.01); *C07D 487/04* (2013.01)

(58) Field of Classification Search
CPC .. C07D 473/06; C07D 473/10; C07D 487/04; C07D 471/04; C07D 475/02
See application file for complete search history.

(56) References Cited

U.S. PATENT DOCUMENTS

| | | | |
|---|---|---|---|
| 9,085,584 B2 * | 7/2015 | Giovannini | C07D 487/14 |
| 10,278,973 B2 * | 5/2019 | Wu | A61K 31/519 |
| 2017/0326149 A1 | 11/2017 | Wu et al. | |

FOREIGN PATENT DOCUMENTS

| | | |
|---|---|---|
| CN | 104428302 A | 3/2015 |
| CN | 105566324 A | 5/2016 |
| EP | 3205652 A1 | 8/2017 |
| TW | 201625619 A | 7/2016 |
| WO | 9852948 A1 | 11/1998 |
| WO | 02064080 A2 | 8/2002 |
| WO | 02068420 A1 | 9/2002 |
| WO | 2004006912 A2 | 1/2004 |
| WO | 2004013068 A1 | 2/2004 |
| WO | 2006136822 A1 | 12/2006 |
| WO | WO 2014/019979 A1 | 2/2014 |
| WO | 2015169999 A1 | 11/2015 |
| WO | 2016044792 A1 | 3/2016 |
| WO | 2016054971 A1 | 4/2016 |

OTHER PUBLICATIONS

M. Gorczyca et al., Farmaco, Edizione Scientifica (1966), 21(5), 338-45.*
International Search Report dated Jul. 4, 2016 for PCT Application No. PCT/CN2016/081103 and English Translation (4 pages).
Larsen et al., "Predictable Stereoselective and Chemoselective Hydroxylations and Epoxidations with P450 3A4", J. Am. Chem. Soc., No. 133, Apr. 29, 2011, pp. 7853-7858.
Avico et al. (Farmaco, Edizione Scientitica (1962), 17, 73-80). Abstract. (On Order).
Berge et al. "Pharmaceutical salts", Journal of pharmaceutical Science, 1977, 66:1-19. (On Order).
Extended European Search Report of counterpart European Application No. 16795799.2, dated May 17, 2018, 10 pages. (On Order).
H Maehr, "A proposed new convention for graphic presentation of molecular geometry and topography.", J. Chem. Ed., 1985, 62:114-120. (On Order).
PCT International Search Report and Written Opinion dated Aug. 19, 2016 from corresponding Application No. PCT/CN2016/081102, 16 pages. (On Order).
Remington: The Science and Practice of Pharmacy, 21st Ed., Lippincott, Williams & Wilkins (2005), (Part 1 of 3; pp. 702-798). (On Order).
Remington: The Science and Practice of Pharmacy, 21st Ed., Lippincott, Williams & Wilkins (2005), (Part 2 of 3; pp. 799-948). (On Order).

(Continued)

*Primary Examiner* — Alexander R Pagano
*Assistant Examiner* — Ebenezer O Sackey
(74) *Attorney, Agent, or Firm* — Lewis Roca Rothgerber Christie LLP

(57) ABSTRACT

Disclosed are a series of hydroxyl purine compounds and the use thereof as PDE2 or TNFα inhibitors, in particular, the compounds as shown in formula (I), or tautomers or pharmaceutically acceptable salts thereof.

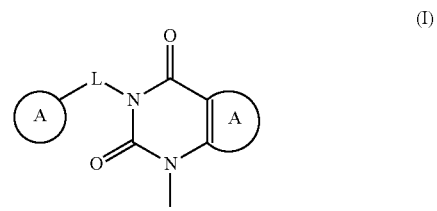

(I)

14 Claims, No Drawings

(56) References Cited

OTHER PUBLICATIONS

Remington: The Science and Practice of Pharmacy, 21st Ed., Lippincott, Williams & Wilkins (2005), (Part 3 of 3; pp. 949-1057). (On Order).
Sinha et al., Eur. J. Immunol, 1995, 147-153. (On Order).
STN Retrieval System CA Registry Database Retrieval Result (Mar. 16, 2011) Compound CA registration No. 1268606-01-4. (On Order).
Weil et al. (Bull. pharm. inst. Poland (1928), No. 2, 175-6). Abstract. (On Order).
Yago (Japan. Circulation J. (1962), 26, 407-18). Abstract. (On Order).
Yoshida et al. (JP 37004545). (1962). Abstract. (On Order).
TIPO Office Action dated Nov. 5, 2019 for corresponding Taiwanese Patent Application No. 105115049 (5 pages).
Partial English translation of TIPO Office Action dated Nov. 5, 2019 for corresponding Taiwanese Patent Application No. 105115049 (2 pages).
Larsen et al., "Predictable Stereoselective and Chemoselective Hydroxylations and Epoxidations with P450 3A4", Journal of the American Chemical Society, 2011, 133(20), pp. 7853-7858.

* cited by examiner

HYDROXYL PURINE COMPOUNDS AND USE THEREOF

CROSS-REFERENCE TO RELATED APPLICATION(S)

This application is a National Phase Patent Application of International Patent Application Number PCT/CN2016/081103, filed on May 5, 2016, which claims priority of Chinese Patent Application 201510260884.9, filed May 20, 2015. The entire contents of both of which are incorporated herein by reference.

TECHNICAL FIELD

The present invention relates to a series of hydroxyl purine compounds and the use thereof as PDE2 or TNFα inhibitors, in particular, the compounds as shown in Formula (I), or tautomers or pharmaceutically acceptable salts thereof.

BACKGROUND TECHNOLOGIES

Phosphodiesterase (PDE) catalyzes the hydrolysis of cyclic nucleotides cGMP and cAMP, and thereby regulates various physiological responses by controlling the intracellular concentrations of these two important secondary signaling factors. Abnormal regulation of the cyclic nucleotides cGMP and cAMP molecules is the cause of many diseases. There are a number of drugs ameliorating and treating diseases by inhibiting PDE activity, for example, PDE5 inhibitor used for pulmonary hypertension, and PDE4 inhibitor used for arthritis caused by psoriasis. Currently, the known phosphodiesterase genes can be classified into eleven major categories, each of which can be expressed into several subtypes, with a total of more than 100 PDE subtypes. Different subtypes have different structures and different tissue distributions, and have great differences in the activities against the cyclic nucleotides cGMP and cAMP, so that they can regulate various physiological functions.

PDE2 phosphodiesterase can catalyze the hydrolysis of cyclic nucleotides cGMP and cAMP, in the meantime, the activity of cAMP is regulated by cGMP, which plays a critical role in balancing the functions of cGMP and cAMP in cells. PDE2 is widely expressed in human tissues, mainly distributed in heart, central nervous system, liver, adrenal gland, endothelial cells, platelets, and etc. PDE2 is involved in regulating various physiological activities, such as central learning, memory, cognition and other processes, maintaining the basic rhythm of heart, smooth muscles and endothelial cells, the permeability of endothelial cells, and regulating inflammatory response. PDE2 gene-knockout mice directly lead to embryonic death. Inhibition of PDE2 activity might be applied to various central and cardiovascular diseases, and to controlling the inflammatory response.

It was found long time ago that a variety of natural and synthetic purine compounds, such as caffeine, theophylline, pentoxifylline and the like, have non-selective PDE inhibitory activity. Pentoxifylline (with PDE2 activity) has been clinically approved for use in the treatment of lower limb claudication caused by obstruction of the peripheral blood vessels, and its primary roles are to reduce blood viscosity, improve erythrocyte deformation, inhibit platelet aggregation and etc. It has also been reported that some novel high selective PDE2 inhibitors can be used for controlling endothelial cell division and revascularization, and improving central cognitive disorder. In generally, however, the development and application of the novel PDE2 inhibitors is still very limited, and the discovery and application of the novel PDE2 inhibitors has broad prospects.

Tumor necrosis factor α (TNF-α) is a kind of cytokines with multiple biological activities, has important influence on the occurrence, development and prognosis of various diseases. TNF-α is mainly produced by monocytes and macrophages, involved in the immune regulation and cytokine network coordination. Under normal circumstances, TNF-α plays an important role in immune defense and immune surveillance, but in some cases it has a negative effect. Studies have shown that TNF-α overexpression can induce the expression of proinflammatory cytokines such as interleukin-1 (IL-1), IL-6 and the like, improve the permeability of endothelial cells, up-regulate the expression of adhesion molecules, activate neutrophils and eosinophils, as well as induce bone synovial cells and chondrocytes to secrete acute phase substances, tissue degrading enzymes and the like so as to promote the occurrence of inflammation. These pathological responses play a very important role in the development of many immune-mediated inflammatory diseases (IMID), such as rheumatic arthritis (RA), psoriatic arthritis (PsA), ankylosing spondylitis (AS), inflammatory bowel disease (IBD), juvenile chronic arthritis (JCA), vasculitis and the like. Some studies have shown that TNF-α is an ideal target for multiple IMIDs mentioned above, and the use of TNF-α inhibitors to neutralize excess TNF-αt is an ideal way to prevent and treat chronic inflammatory diseases caused by TNF-α overexpression. PDE2 can regulate the expression of TNF-α in the theory of mechanism. Thus, the TNF-α level of can be controlled by regulating PDE2 activity, and therefore the inflammatory response can be controlled.

SUMMARY OF THE INVENTION

The present invention provides the compound as shown in Formula (I) and tautomers or pharmaceutically acceptable salts thereof,

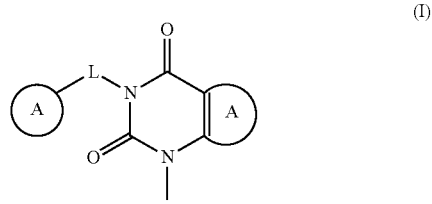

wherein,
Ring B is a 4- to 6-membered cyclic ether or alkoxycycloalkyl optionally substituted with 1 to 3 R groups;
L is $C_{1-3}$ alkyl optionally substituted with 1 to 2 R groups;
Ring A is selected from 5- to 6-membered aryl or heteroaryl optionally substituted with 1 or 2 $R_1$ groups;
$R_1$ is selected from halogen, OH, $NH_2$, and the following groups optionally substituted with 1 to 3 $R_2$ groups: $C_{1-6}$ alkyl or heteroalkyl, 3- to 6-membered cycloalkyl or heterocycloalkyl, $C_{1-6}$ alkyl or heteroalkyl substituted with 3- to 6-membered cycloalkyl or heterocycloalkyl;
$R_2$ is selected from halogen, OH, $NH_2$, Me, $CF_3$, OMe, $OCF_3$;
the "hetero" represents heteroatoms selected from O, S, N, and the numbers of heteroatoms on each heteroalkyl or heterocycloalkyl are each independently selected from 1, 2 or 3;

R is selected from halogen, N(R')(R'), $C_{1-3}$ alkyl or heteroalkyl optionally substituted with 1 to 3 R' groups;

R' is selected from H, halogen, $NH_2$, Me, $CF_3$, OMe, $OCF_3$.

In one embodiment of the present invention, the above-mentioned $R_1$ is selected from halogen, OH, $NH_2$, and the following groups optionally substituted with 1 to 3 $R_2$ groups: $C_{1-4}$ alkyl or heteroalkyl, $C_{1-3}$ alkyl or heteroalkyl substituted with a 3- to 5-membered cycloalkyl or heterocycloalkyl.

In one embodiment of the present invention, the above-mentioned $R_1$ is selected from: Me, $CF_3$, Et, $CH_2CF_3$,

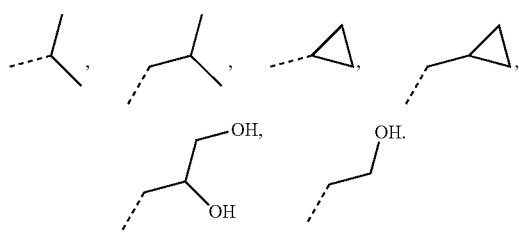

In one embodiment of the present invention, the above-mentioned R is selected from F, Cl, Br, I, Me,

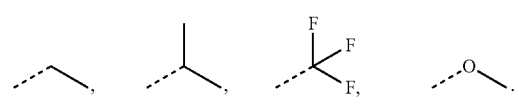

In one embodiment of the present invention, the above-mentioned Ring B is selected from the following groups optionally substituted with 1 to 3 R groups:

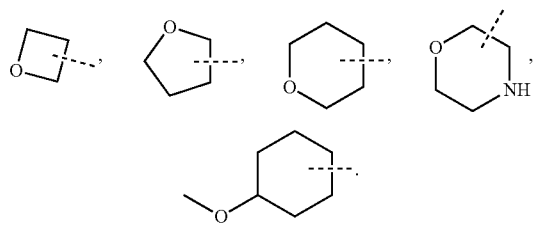

In one embodiment of the present invention, the above-mentioned B is selected from the following groups optionally substituted with 1 to 3 R groups:

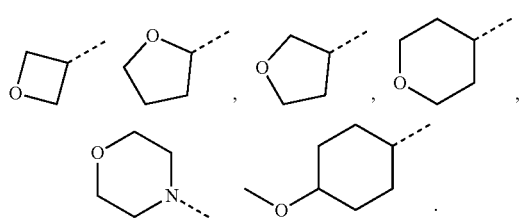

In one embodiment of the present invention, the above-mentioned B is selected from:

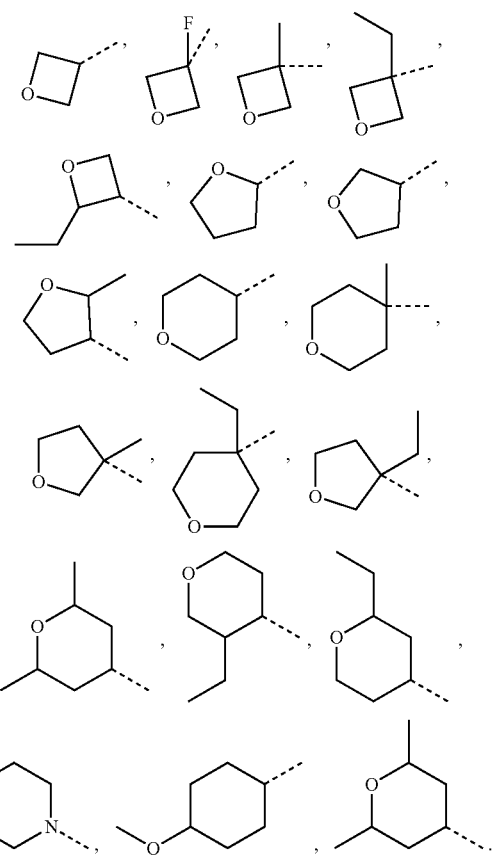

In one embodiment of the present invention, the above-mentioned L is selected from the following groups optionally substituted with 1 to 2 R groups: methylene,

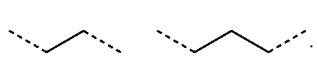

In one embodiment of the present invention, the above-mentioned L is selected from: methylene,

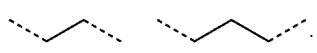

In one embodiment of the present invention, the above-mentioned Ring A is selected from the following groups optionally substituted with 1 or 2 $R_1$ groups: imidazolyl, pyrazolyl, pyridinyl, pyrazinyl, pyridazinyl, pyrimidinyl, and phenyl.

In one embodiment of the present invention, the above-mentioned Ring A is selected from the following groups optionally substituted with 1 or 2 $R_1$ groups:

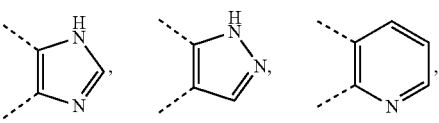

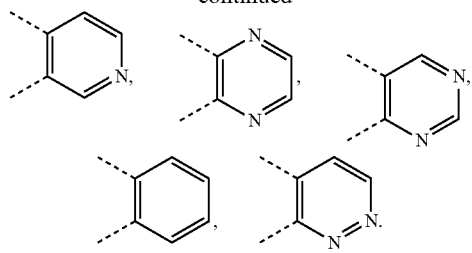
In one embodiment of the present invention, the above-mentioned Ring A is selected from:
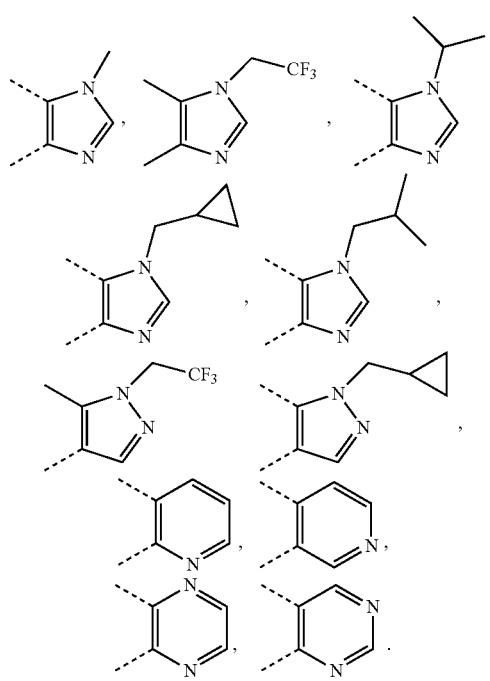
In one embodiment of the present invention, the above-mentioned structural unit
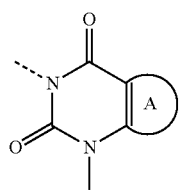
is selected from:
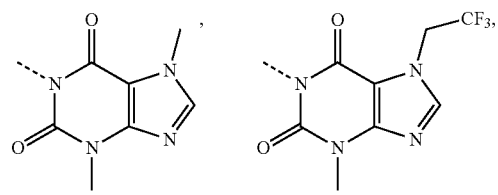
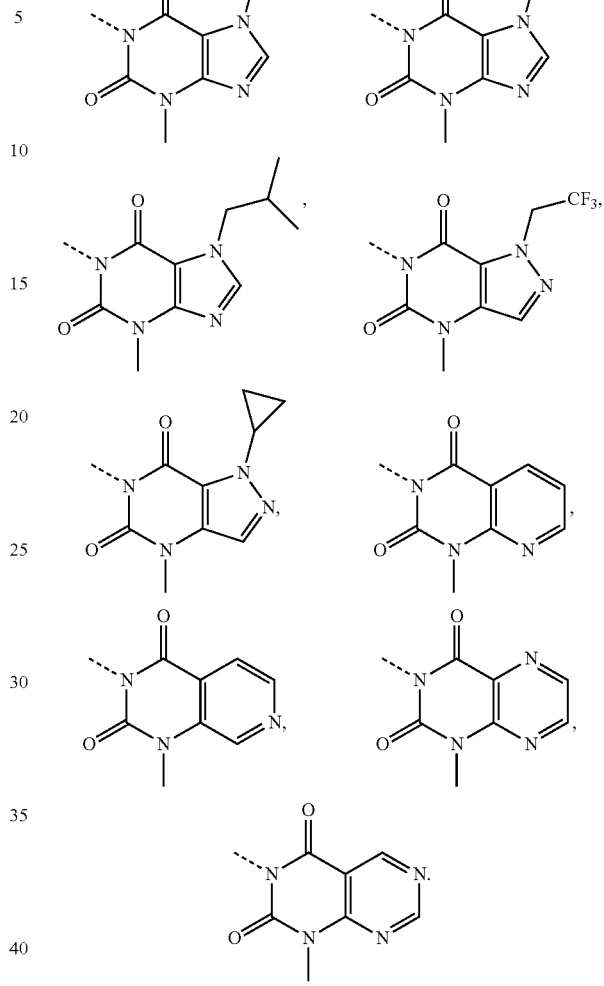
In one embodiment of the present invention, the above-mentioned compounds are selected from:
| Compound | Structure |
|---|---|
| 1 | 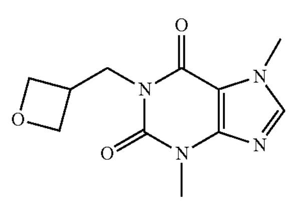 [SMILES: Cn1cnc2c1c(=O)n(CC1COC1)c(=O)n2C] |
| 2 | 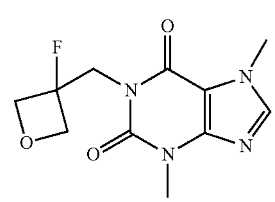 [SMILES: Cn1cnc2c1c(=O)n(CC1(F)COC1)c(=O)n2C] |
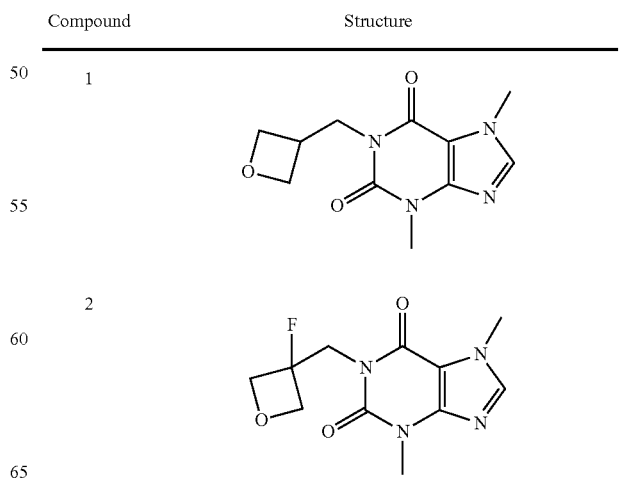

| Compound | Structure |
|---|---|
| 3 | 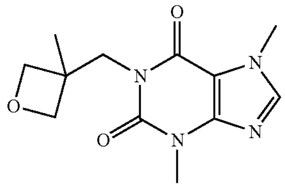 [SMILES: Cn1cnc2c1c(=O)n(CC1(C)COC1)c(=O)n2C] |
| 4 | 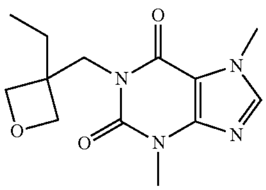 [SMILES: CCC1(Cn2c(=O)c3c(ncn3C)n(C)c2=O)COC1] |
| 5 | 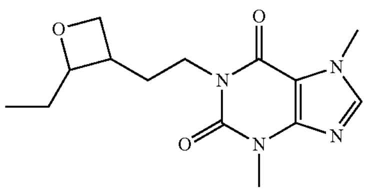 [SMILES: CCC1OCC1CCn1c(=O)c2c(ncn2C)n(C)c1=O] |
| 6 | 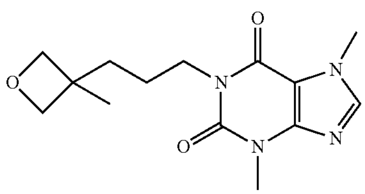 [SMILES: Cn1cnc2c1c(=O)n(CCCC1(C)COC1)c(=O)n2C] |
| 7 | 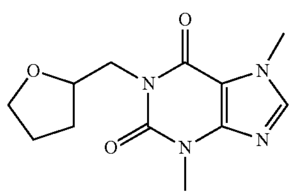 [SMILES: Cn1cnc2c1c(=O)n(CC1CCCO1)c(=O)n2C] |
| 8 | 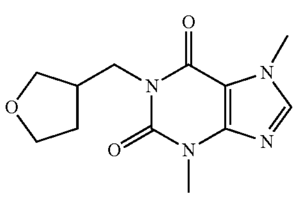 [SMILES: Cn1cnc2c1c(=O)n(CC1CCOC1)c(=O)n2C] |
| 9 | 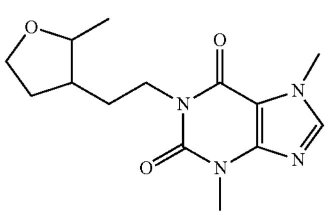 [SMILES: CC1OCCC1CCn1c(=O)c2c(ncn2C)n(C)c1=O] |
| 10 | 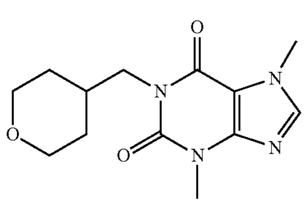 [SMILES: Cn1cnc2c1c(=O)n(CC1CCOCC1)c(=O)n2C] |

| Compound | Structure |
|---|---|
| 11 | 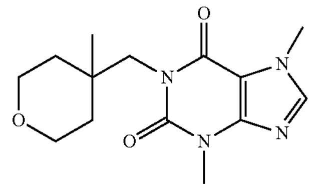 |
| 12 | 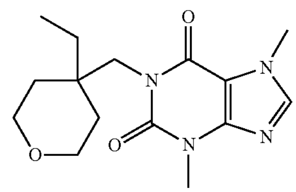 |
| 13 | 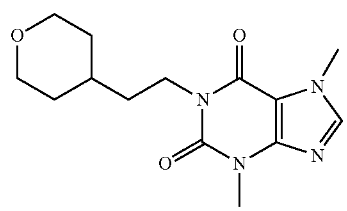 [SMILES: Cn1cnc2c1c(=O)n(CCC1CCOCC1)c(=O)n2C] |
| 14 | 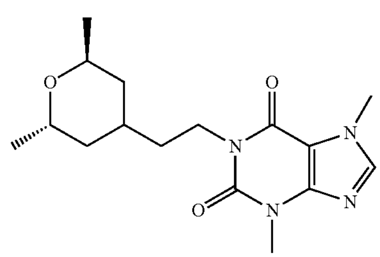 [SMILES: C[C@H]1CC(CCn2c(=O)c3c(ncn3C)n(C)c2=O)C[C@H](C)O1] |
| 15 | 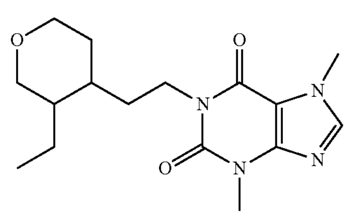 [SMILES: CCC1COCCC1CCn1c(=O)c2c(ncn2C)n(C)c1=O] |

-continued
| Compound | Structure |
|---|---|
| 16 | 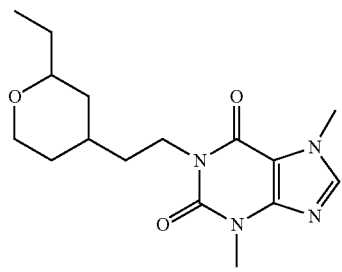 [SMILES: CCC1CC(CCn2c(=O)c3c(ncn3C)n(C)c2=O)CCO1] |
| 17 | 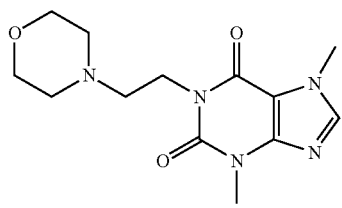 [SMILES: Cn1cnc2c1c(=O)n(CCN1CCOCC1)c(=O)n2C] |
| 18 | 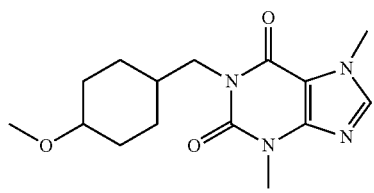 |
| 19 | 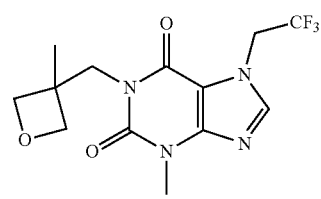 [SMILES: Cn1c(=O)n(CC2(C)COC2)c(=O)c2c1ncn2CC(F)(F)F] |
| 20 | 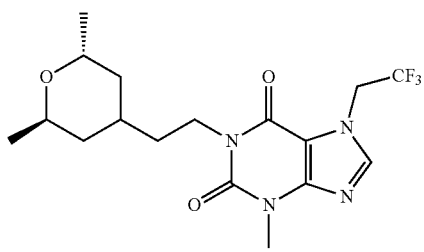 [SMILES: C[C@@H]1CC(CCn2c(=O)c3c(ncn3CC(F)(F)F)n(C)c2=O)C[C@@H](C)O1] |
| 21 | 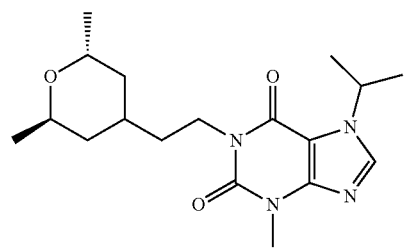 [SMILES: CC(C)n1cnc2c1c(=O)n(CCC1C[C@@H](C)O[C@H](C)C1)c(=O)n2C] |
| 22 | 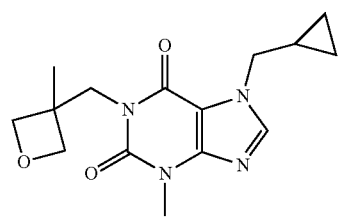 [SMILES: Cn1c(=O)n(CC2(C)COC2)c(=O)c2c1ncn2CC1CC1] |
-continued
| Compound | Structure |
|---|---|
| 23 | 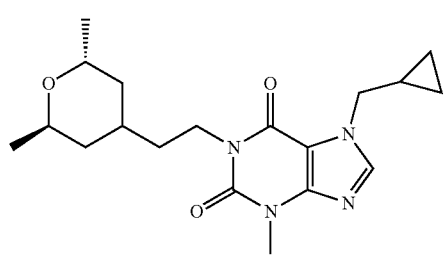 [SMILES: C[C@@H]1CC(CCn2c(=O)c3c(ncn3CC3CC3)n(C)c2=O)C[C@@H](C)O1] |
| 24 | 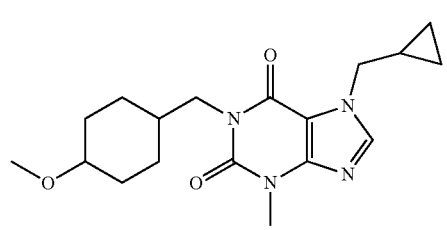 [SMILES: COC1CCC(Cn2c(=O)c3c(ncn3CC3CC3)n(C)c2=O)CC1] |
| 25 | 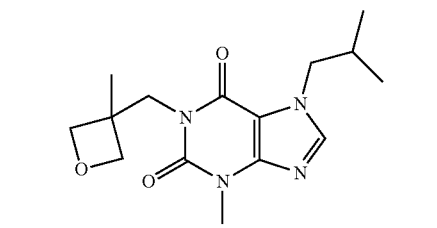 [SMILES: CC(C)Cn1cnc2c1c(=O)n(CC1(C)COC1)c(=O)n2C] |
| 26 | 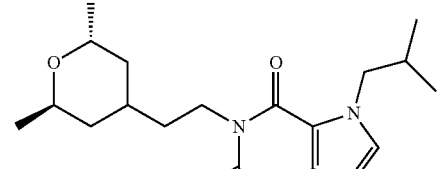 |
| 27 | 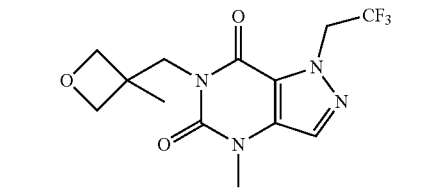 [SMILES: Cn1c(=O)n(CC2(C)COC2)c(=O)c2c1cnn2CC(F)(F)F] |
| 28 | 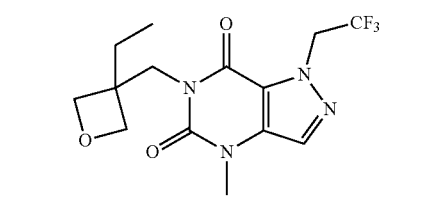 [SMILES: CCC1(Cn2c(=O)c3c(cnn3CC(F)(F)F)n(C)c2=O)COC1] |
| 29 | 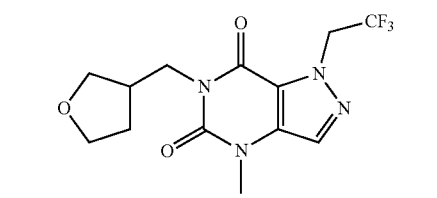 [SMILES: Cn1c(=O)n(CC2CCOC2)c(=O)c2c1cnn2CC(F)(F)F] |

-continued

| Compound | Structure |
|----------|-----------|
| 30 | 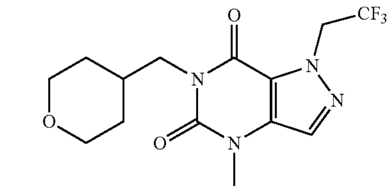 [SMILES: Cn1c(=O)n(CC2CCOCC2)c(=O)c2c1cnn2CC(F)(F)F] |
| 31 | 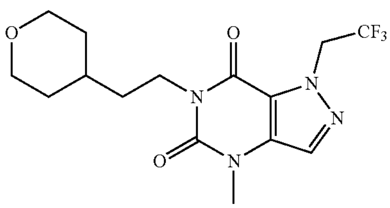 [SMILES: Cn1c(=O)n(CCC2CCOCC2)c(=O)c2c1cnn2CC(F)(F)F] |
| 32 | 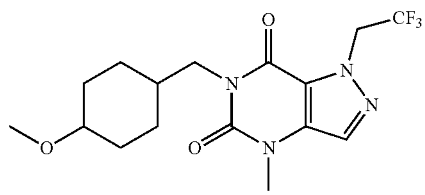 [SMILES: COC1CCC(Cn2c(=O)c3c(cnn3CC(F)(F)F)n(C)c2=O)CC1] |
| 33 | 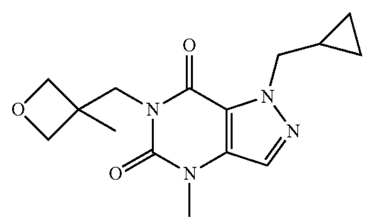 [SMILES: Cn1c(=O)n(CC2(C)COC2)c(=O)c2c1cnn2CC1CC1] |
| 34 | 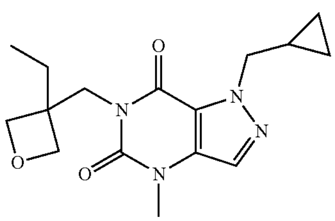 [SMILES: CCC1(Cn2c(=O)c3c(cnn3CC3CC3)n(C)c2=O)COC1] |
| 35 | 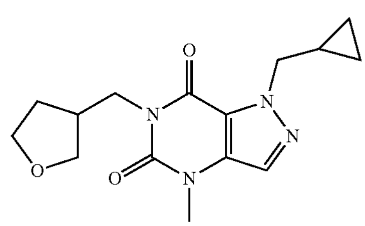 [SMILES: Cn1c(=O)n(CC2CCOC2)c(=O)c2c1cnn2CC1CC1] |
| 36 | 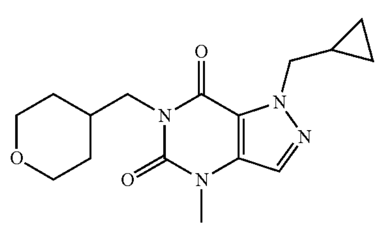 [SMILES: Cn1c(=O)n(CC2CCOCC2)c(=O)c2c1cnn2CC1CC1] |

-continued

| Compound | Structure |
|----------|-----------|
| 37 | 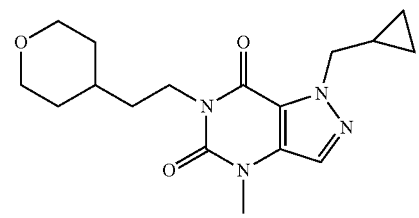 [SMILES: Cn1c(=O)n(CCC2CCOCC2)c(=O)c2c1cnn2CC1CC1] |
| 38 | 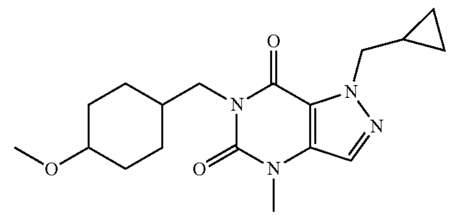 [SMILES: COC1CCC(Cn2c(=O)c3c(cnn3CC3CC3)n(C)c2=O)CC1] |
| 39 | 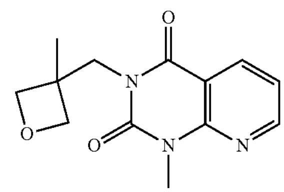 [SMILES: Cn1c(=O)n(CC2(C)COC2)c(=O)c2cccnc21] |
| 40 | 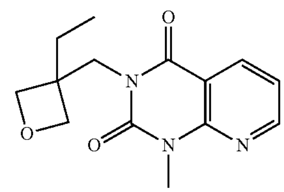 [SMILES: CCC1(Cn2c(=O)c3cccnc3n(C)c2=O)COC1] |
| 41 | 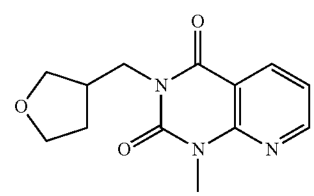 [SMILES: Cn1c(=O)n(CC2CCOC2)c(=O)c2cccnc21] |
| 42 | 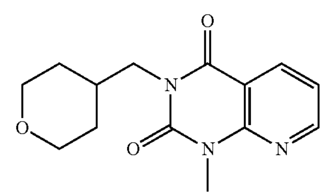 [SMILES: Cn1c(=O)n(CC2CCOCC2)c(=O)c2cccnc21] |
| 43 | 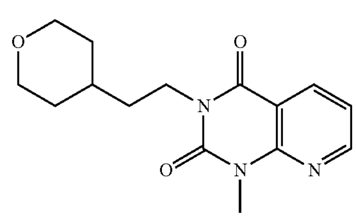 [SMILES: Cn1c(=O)n(CCC2CCOCC2)c(=O)c2cccnc21] |

-continued
| Compound | Structure |
|---|---|
| 44 | 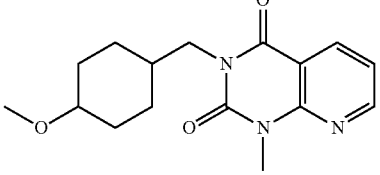 |
| 45 | 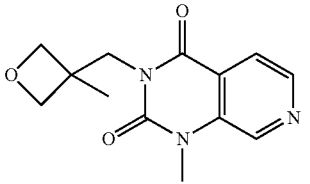 [SMILES: Cn1c(=O)n(CC2(C)COC2)c(=O)c2ccncc21] |
| 46 | 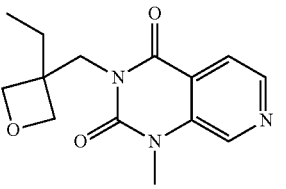 |
| 47 | 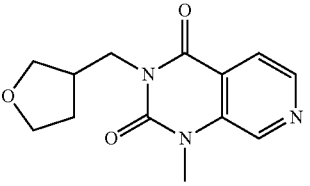 [SMILES: Cn1c(=O)n(CC2CCOC2)c(=O)c2ccncc21] |
| 48 | 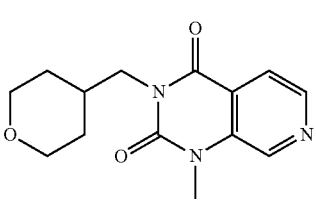 [SMILES: Cn1c(=O)n(CC2CCOCC2)c(=O)c2ccncc21] |
| 49 | 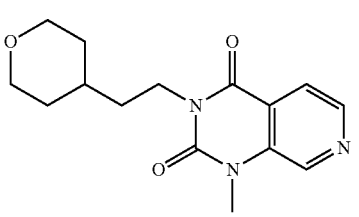 [SMILES: Cn1c(=O)n(CCC2CCOCC2)c(=O)c2ccncc21] |
| 50 | 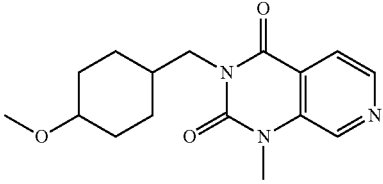 [SMILES: COC1CCC(Cn2c(=O)c3ccncc3n(C)c2=O)CC1] |
| 51 | 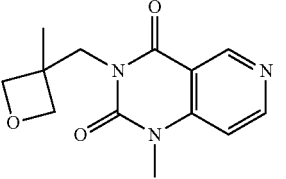 [SMILES: Cn1c(=O)n(CC2(C)COC2)c(=O)c2cnccc21] |
-continued
| Compound | Structure |
|---|---|
| 52 | 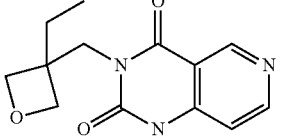 |
| 53 | 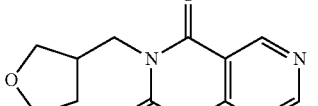 |
| 54 | 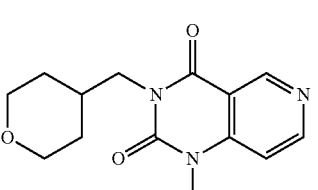 |
| 55 | 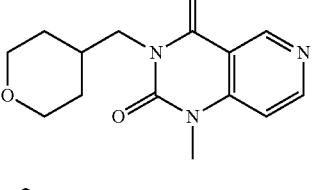 |
| 56 | 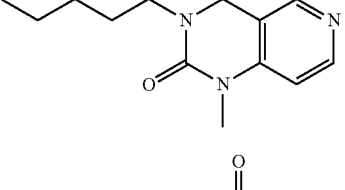 |
| 57 | 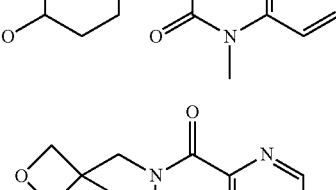 |
| 58 | 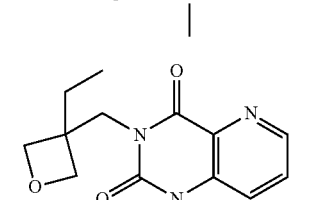 |
| 59 | 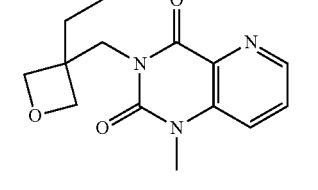 |

-continued

| Compound | Structure |
| --- | --- |
| 60 | 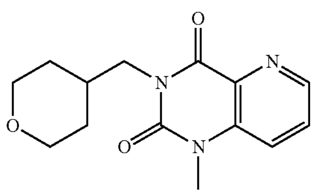 [SMILES: Cn1c(=O)n(CC2CCOCC2)c(=O)c2ncccc21] |
| 61 | 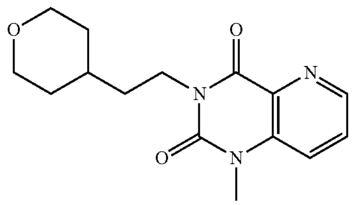 [SMILES: Cn1c(=O)n(CCC2CCOCC2)c(=O)c2ncccc21] |
| 62 | 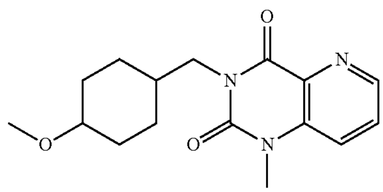 [SMILES: COC1CCC(Cn2c(=O)c3ncccc3n(C)c2=O)CC1] |
| 63 | 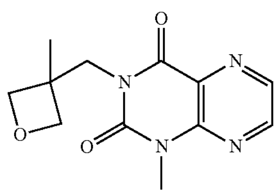 [SMILES: Cn1c(=O)n(CC2(C)COC2)c(=O)c2nccnc21] |
| 64 | 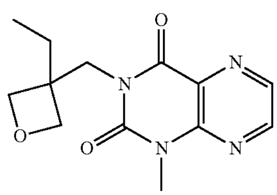 [SMILES: CCC1(Cn2c(=O)c3nccnc3n(C)c2=O)COC1] |

The present invention also provides the use of the above-mentioned compounds and tautomers or chemically acceptable salts thereof in preparation of PDE2 inhibitors and TNF-α inhibitors.

Relevant Definitions

Unless otherwise indicated, the following terms and phrases used herein are intended to have the following meanings. A specific term or phrase should not be considered to be uncertain or unclear unless specifically defined, but should be understood in the ordinary sense. When a trade name appears herein, it is intended to refer to its corresponding commodity or its active ingredient.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

The term "pharmaceutically acceptable" as used herein is for those compounds, materials, compositions and/or dosage forms, which are suitable for use in contact with human and animal tissues without excessive toxicity, irritation, allergic reactions or other problems or complications and are commensurate with a reasonable benefit/risk ratio, within a range of reliable medical judgment.

The term "pharmaceutically acceptable salts" refers to the salts of the compound of the present invention, prepared from the compounds having specific substituents found by the present invention with relatively non-toxic acids or bases. When the compound of the present invention comprises a relatively acidic functional group, the alkali addition salt can be obtained by contacting a neutral form of the compound with a sufficient amount of alkali in a pure solution or a suitable inert solvent. The pharmaceutically acceptable alkali addition salts include the salts of sodium, potassium, calcium, ammonium, organic amine or magnesium or other similar salts. When the compound of the present invention comprises a relatively alkaline functional group, the acid addition salt can be obtained by contacting a neutral form of the compound with a sufficient amount of alkali in a pure solution or a suitable inert solvent. Examples of the pharmaceutically acceptable acid addition salts include inorganic acid salts, wherein the inorganic acids include such as hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid, phosphorous acid and the like; as well as organic acid salts, wherein the organic acids include such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and other similar acids; also include the salts of amino acids (such as arginine), and the salts of glucuronic acid and other organic acids (see Berge et al., "Pharmaceutical Salts", Journal of Pharmaceutical Science 66:1-19 (1977)). Some specific compounds of the present invention comprise alkaline and acidic functional groups, and thereby they can be converted to any alkali or acid addition salt.

Preferably, the salt is contacted with the alkali or acid in a conventional manner and then the parent compound is separated, thereby the neutral form of the compound is regenerated. The parent form of the compound differs from its various salt forms on some physical properties, such as different solubility in polar solvents.

The "pharmaceutically acceptable salts" as used herein belongs to the derivatives of the compounds of the present invention, wherein the parent compounds are modified by salt-forming with acid or alkali. Examples of pharmaceutically acceptable salts include, but not limited to, the inorganic or organic acid salts of a basic group such as amine, the alkali metal or organic salts of an acid radical such as carboxylic acid, and the like. The pharmaceutically acceptable salts include conventional non-toxic salts or the quaternary ammonium salts of the parent compound, such as the salts formed by non-toxic inorganic or organic acids. Conventional non-toxic salts include, but not limited to, those salts derived from inorganic and organic acids selected from 2-acetoxybenzoic acid, 2-hydroxyethanesulfonic acid, acetic acid, ascorbic acid, benzenesulfonic acid, benzoic acid, bicarbonate radical, carbonic acid, citric acid, edetic acid, ethanedisulfonic acid, ethanesulfonic acid, fumaric acid, glucoheptone, gluconic acid, glutamic acid, glycolic acid, hydrobromic acid, hydrochloric acid, hydroiodic acid, hydroxy, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, calcium folinate, succinic acid, sulfamic acid, sulfanilic acid, sulfuric acid, tannin, tartaric acid and p-toluenesulfonic acid.

The pharmaceutically acceptable salts of the present invention can be synthesized from the parent compound containing an acid radical or basic group by routine chemical methods. In general, the method of preparing such salts comprises reacting the free acid or alkali form of such compounds with a stoichiometric amount of an alkali or acid in water or an organic solvent or a mixture of the two. Generally, nonaqueous media such as ether, ethyl acetate, ethanol, isopropanol or acetonitrile are preferred.

In addition to the salt forms, the compounds provided by the present invention are also in the forms of prodrugs. The prodrugs of the compounds described herein are readily chemically altered under physiological conditions and thereby converted into the compounds of the present invention. In addition, the prodrugs may be converted to the compounds of the present invention by chemical or biochemical methods in an in vivo environment.

Some compounds of the present invention may exist in non-solvate forms or solvate forms, including hydrate forms. In general, the solvate forms are comparable to the solvate forms, which are all encompassed within the scope of the present invention.

Some compounds of the present invention may have asymmetric carbon atoms (optical center) or a double bond. Racemates, diastereomers, geometrical isomers and individual isomers are all included within the scope of the present invention.

The illustrations of the racemate, ambiscalemic and scalemic or enantiomorph of the pure compounds herein are from Maehr, J. Chem. Ed. 1985, 62:114-122, 1985, 62:114-120. Unless otherwise indicated, the absolute configuration of a stereocenter center is indicated by a wedge bond and a dashed bond. When the compounds described herein comprise olefinic double bond or other geometrically asymmetric center, unless otherwise specified, they include E, Z geometrical isomers. Likewise, all tautomeric forms are all included within the scope of the present invention.

The compounds of the present invention may exist in the specific geometrical or stereo isomeric forms. It is envisaged in the present invention that all such compounds are within the scope of the present invention, including cis- and trans-isomers, (−)- and (+)-enantiomers, (R)- and (S)-enantiomers, diastereomers, (D)-isomers, (L)-isomers, their racemic mixtures and other mixtures, such as the enantiomer or diastereomer-enriched mixtures. Alkyl and other substituents may comprise additional asymmetric carbon atoms. All of these isomers and their mixtures are all included within the scope of the present invention.

The optically active (R)- and (S)-isomers and D and L isomers can be prepared by chiral synthesis or chiral reagents or other conventional techniques. If an enantiomer of the compound of the present invention is desired, it can be prepared by asymmetric synthesis or by derivatization with chiral auxiliaries in which the resulting diastereomer mixture is separated and the auxiliary group is cleaved to provide a pure desired enantiomer. Alternatively, when the molecule comprises a alkaline functional group (e.g., amino) or an acidic functional group (e.g., carboxyl), it can form a salt of diastereomers with an appropriately optically active acid or alkali, and then the diastereomers are subjected to enantiomeric separation by a separation method known in the art, and then recovered to get pure enantiomers. In addition, the separation of enantiomers and diastereomers is usually accomplished by using chromatography which uses a chiral stationary phase and is optionally combined with a chemical derivatization method (e.g., carbamate is formed from an amine).

The compounds of the present invention may comprise non-natural proportions of atomic isotopes on one or more atoms constituting the compound. For example, the compounds can be labeled with radioisotopes, such as tritium ($^3$H), iodine-125 ($^{125}$I) or C-14 ($^{14}$C). All of the isotopic compositions of the compounds of the present invention, no matter radioactive or not, are all included within the scope of the present invention.

The term "pharmaceutically acceptable carries" refers to any formulations or carrier media capable of delivering an effective amount of the active substance of the present invention without interfering with the biological activity of the active substance and having no toxic side effects to the host or patient, wherein the typical carries include water, oils, vegetables and minerals, cream bases, lotion bases, ointment bases and the like. These bases include suspending agents, tackifiers, transdermal enhancers and the like. The formulations are well known to those skilled in the art of cosmetics or topical drugs. Additional information about carries can be found in Remington: The Science and Practice of Pharmacy, 21st Ed., Lippincott, Williams & Wilkins (2005), the contents of which are hereby incorporated by reference.

The term "excipients" typically refers to carries, diluents and/or media required for the preparation of an effective pharmaceutical composition.

For drugs or pharmacologically active agents, the term "effective amount" or "therapeutically effective amount" refers to a sufficient amount of a drug or agentia that is non-toxic but achieves the desired effect. For the oral dosage form of the present invention, the "effective amount" of an active substance in the composition refers to the amount required to achieve the desired effect when used in combination with another active substance in the composition. The amount of the effective amount varies from person to person, depending on the age and general condition of the recipient and also on the particular active substance, and the appropriate effective amount in the case can be determined by a person skilled in the art in accordance with routine testing.

The term "active ingredient", "therapeutic agent", "active substance" or "active agent" refers to a chemical entity which is effective in treating a target disorder, disease or condition.

The term "substituted" means that any one or more of hydrogen atoms on a particular atom is substituted with a substituent, including heavy hydrogens and variants of hydrogen, as long as the valence of the particular atom is normal and the substituted compound is stable. When the substituent is a ketone group (i.e., =O), it means that two hydrogen atoms are substituted. Ketone substitutions do not occur on aromatic groups. The term "optionally substituted" means that one may or may not be substituted, unless otherwise specified, and the kind and number of the substituents may be arbitrarily as long as they are chemically achievable.

When any variable (e.g., R) occurs more than once in the composition or structure of the compound, its definition in each case is independent. Thus, for example, if a group is substituted with 0-2 R, the group may be optionally substituted with up to two R, and in each case R has an independent option. In addition, combinations of substituents and/or their variants are permissible only if such a combination produces a stable compound.

When one of the variables is selected from a single bond, it indicates that the two groups attaching to the single bond are directly connected, for example, when L represents a single bond in A-L-Z, the structure is actually A-Z.

When a substituent can be cross-linked to two atoms on a ring, this substituent can be bonded to any atom on the ring. When it is not indicated specifically which atom in the listed substituent is used to link to a not specifically mentioned compound concluded in the chemical general formula, the substituent can be bonded by any of its atoms. The combinations of substituents and/or their variants are permissible only if such a combination produces a stable compound. For example, the structural unit,

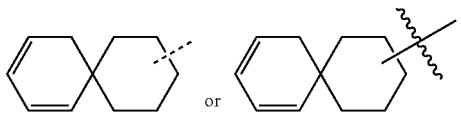

indicates that it can be substituted at any position on the cyclohexyl or cyclohexadiene.

The substituents of alkyl and heteroalkyl radicals are generally referred to as "alkyl substituents", which may be selected from, but not limited to, one or more of the following groups: —R', —OR', =O, =NR', =N—OR', —NR'R", —SR', halogen, —SiR'R"R'", OC(O)R', —C(O)R', —CO$_2$R', —CONR'R", —OC(O)NR'R", —NR"C(O)R', NR'C(O)NR"R"', —NR"C(O)$_2$R', —NR""-C(NR'R"R'")=NR"", NR""C(NR'R")=NR"', —S(O)R', —S(O)$_2$R', —S(O)$_2$NR'R", NR"SO$_2$R', —CN, —NO$_2$, —N$_3$, —CH(Ph)$_2$ and fluoro (C$_1$-C$_4$) alkyl, and the number of the substituents is 0 to (2m'+1), wherein m' is the total number of carbon atoms in such radicals. R', R", R'", R"" and R""' are each independently selected preferably from hydrogen, substituted or unsubstituted heteroalkyl, substituted or unsubstituted aryl (e.g., aryl substituted with 1 to 3 halogen), substituted or unsubstituted alkyl, alkoxy, thioalkoxy or aralkyl. When the compound of the present invention comprises more than one R group, for example, each R group is independently selected, as each of these groups if one or more R', R", R'", R"" and R""' groups are present. When R' and R" are attached to the same nitrogen atom, they may bind to the nitrogen atom to form a 5-, 6- or 7-membered ring. For example, —NR'R" is intended to include but not limited to I-pyrrolidine and 4-morpholinyl.

According to the above discussion of the substituents, it will be understood by those skilled in the art that the term "alkyl" is intended to include groups composed of carbon atoms bonded to non-hydrogen groups, such as haloalkyl (e.g., —CF$_3$, —CH$_2$CF$_3$) and acyl (e.g. —C(O)CH$_3$, —C(O)CF$_3$, —C(O)CH$_2$OCH$_3$, etc.).

Similar to the substituents described for the alkyl radicals, the substituents of aryl and heteroaryl are generally referred to as "aryl substituents", selected from for example —R', —OR', —NR'R", —SR', -halogen, —SiR'R"R'", OC(O)R', —C(O)R', —CO$_2$R', —CONR'R", —OC(O)NR'R", —NR"C(O)R', NR'C(O)NR"R"', —NR"C(O)$_2$R', —NR""-C(NR'R"R'")=NR"", NR""C(NR'R")=NR"', —S(O)R', —S(O)$_2$R', —S(O)$_2$NR'R", NR"SO$_2$R', —CN, —NO$_2$, —N$_3$, —CH(Ph)$_2$, fluoro (C$_1$-C$_4$) alkoxy and fluoro (C$_1$-C$_4$) alkyl, and the number of the substituents is between 0 and the total number of open valences on the aromatic ring; wherein R', R", R'", R"" and R""' are independently selected preferably from hydrogen, substituted or unsubstituted alkyl, substituted or unsubstituted heteroalkyl, substituted or unsubstituted aryl and substituted or unsubstituted heteroaryl. When the compound of the present invention comprises more than one R group, for example, each R group is independently selected, as each of these groups if one or more R', R", R'", R"" and R""' groups are present.

The two substituents on adjacent atoms of an aryl or heteroaryl ring may be optionally substituted with a substituent having the general formula of -T-C(O)—(CRR')q-U—, wherein T and U are independently selected from —NR—, O—, CRR'— or a single bond, and q is an integer of 0 to 3. As an alternative, the two substituents on adjacent atoms of an aryl or heteroaryl ring may be optionally substituted with a substituent having the general formula of -A(CH$_2$)r B—, wherein A and B are independently selected from —CRR'—, —O—, —NR—, —S—, —S(O)—, S(O)$_2$—, —S(O)$_2$NR'— or a single bond, r is an integer of 1 to 4. Optionally, the single bond on such formed new ring can be replaced by a double bond. As an alternative, the two substituents on adjacent atoms of an aryl or heteroaryl ring may be optionally substituted with a substituent having the general formula of -A(CH$_2$)r B—, wherein r is an integer of 0 to 3, and A and B are independently selected from —O—, —NR', —S—, —S(O)—, —S(O)$_2$— or —S(O)$_2$NR'—. The substituents R, R', R" and R'" are each independently selected preferably from hydrogen and substituted or unsubstituted (C$_1$-C$_6$) alkyl.

Unless otherwise specified, the term "halo" or "halogen" itself or as part of another substituent refers to fluorine, chlorine, bromine or iodine atoms. In addition, the term "haloalkyl" is intended to include monohaloalkyl and polyhaloalkyl. For example, the term "halo (C$_1$-C$_4$) alkyl" is intended to include but not limited to trifluoromethyl, 2,2, 2-trifluoroethyl, 4-chlorobutyl and 3-bromopropyl, etc.

Examples of haloalkyl included, but not limited to, trifluoromethyl, trichloromethyl, pentafluoroethyl, and pentachloroethyl. The "alkoxy" represents the above alkyl groups having a specific number of carbon atoms linked by an oxo bridge. C$_{1-6}$ alkoxy includes C$_1$, C$_2$, C$_3$, C$_4$, C$_5$ and C$_6$ alkoxy. Examples of alkoxy include but are not limited to methoxy, ethoxy, n-propoxy, isopropoxy, n-butoxy, sec-butoxy, tert-butoxy, n-pentyloxy and S-pentyloxy. The "cycloalkyl" includes saturated cyclyl such as cyclopropyl, cyclobutyl or cyclopentyl. The 3-7 cycloalkyl includes C$_3$, C$_4$, C$_5$, C$_6$ and C$_7$ cycloalkyl. The "alkenyl" includes hydrocarbon chains in a configuration of straight or branched chains, wherein one or more carbon-carbon double bonds, such as vinyl and propenyl, are present at any stable site on the chain.

The term "halo-" or "halogen" refers to fluorine, chlorine, bromine and iodine.

Unless otherwise specified, the term "hetero" refers to heteroatoms or heteroradicals (i.e. radicals containing heteroatoms), including atoms other than carbon (C) and hydrogen (H) and the radicals containing these heteroatoms, including, for example, oxygen (O), nitrogen (N), sulphur (S), silicon (Si), germanium (Ge), aluminum (Al), boron (B), —O—, —S—, =O, =S, —C(=O)O—, —C(=O)—, —C(=S)—, —S(=O), —S(=O)$_2$— and optionally substituted —C(=O)N(H)—, —N(H)—, —C(=NH)—, —S(=O)$_2$N(H)— or —S(=O)N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The so-called ring includes single ring, linked ring, spiro ring, and fused ring or bridged ring. The number of atoms on the ring is usually defined as the number of the ring, for example, "5- to 7-membered ring" means that 5 to 7 atoms are arranged in a circular fashion. Unless otherwise specified, the ring optionally contains 1-3 heteroatoms. Thus, the term "5- to 7-membered ring" includes, for example, phenyl, pyridinyl and piperidinyl; on the other hand, the term "5- to 7-membered heterocycloalkyl ring" includes pyridinyl and piperidinyl but does not include phenyl. The term "ring" also includes a ring system containing at least one ring in which each "ring" independently conforms to the above definition.

Unless otherwise specified, the term "heterocyclo" or "heterocyclyl" means stable monocyclic, bicyclic or tricyclic ring containing heteroatoms or heteroradicals, which may be saturated, partially unsaturated or unsaturated (aromatic), and comprise carbon atoms and 1, 2, 3 or 4 cycloheteroatoms independently selected from N, O and S, wherein any of the above heterocyclic rings may be fused to a benzene ring to form a bicyclic ring. The nitrogen and sulfur heteroatom may be optionally oxidized (i.e., NO and S(O)p). The nitrogen atom may be substituted or unsubstituted (i.e., N or NR, wherein R is H or other substituents which have been defined herein). The heterocyclic ring can be attached to the side group of any heteroatoms or carbon atoms to form a stable structure. If the resulting compound is stable, the heterocyclic ring described herein may be substituted at the carbon or nitrogen position. The nitrogen atom in the heterocyclic ring is optionally quaternized. One preferred embodiment is that these heteroatoms are not adjacent to each other when the total number of S and O atoms in a heterocyclic ring exceeds 1. Another preferred embodiment is that the total number of S and O atoms in a heterocyclic ring does not exceed 1. As used herein, the term "aromatic heterocyclic group" or "heteroaryl" means a stable aromatic ring of 5-, 6-, 7-membered monocyclic or bicyclic ring or 7-, 8-, 9- or 10-membered bicyclic heterocyclyl, wherein the aromatic ring comprises carbon atoms and 1, 2, 3 or 4 cycloheteroatoms independently selected from N, O and S. The nitrogen atom may be substituted or unsubstituted (i.e., N or NR, wherein R is H or other substituents which have been defined herein). Nitrogen and sulfur heteroatoms may be optionally oxidized (i.e., NO and S(O)p). It is worth noting that the total number of S and O atoms in the aromatic heterocyclic ring does not exceed 1. The bridge ring is also included in the definition of the heterocyclic ring. A bridge ring is formed when two non-adjacent carbon atoms or nitrogen atoms are linked by one or more atoms (i.e., C, O, N, or S). The preferred bridge ring includes, but not limited to, one carbon atom, two carbon atoms, one nitrogen atom, two nitrogen atoms and one carbon-nitrogen group. It is worth noting that a bridge always converts a monocyclic ring into a tricyclic ring. In a bridge ring, the substituents on the ring can also appear on the bridge.

Examples of the heterocyclic compound include, but not limited to, acridinyl, azocinyl, benzimidazolyl, benzofuryl, benzothiolfuryl, benzothiolphenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, benzodihydropyranyl, chromene, cinnolinyldecahydroquinolyl, 2H,6H-1,5,2-dithiazinyl, dihydrofuro[2,3-b]tetrahydrofuryl, furyl, furazanyl, imidazolidinyl, imidazolinyl, imidazolyl, 1H-indazolyl, indolylalkenyl, indolinyl, indolizinyl, indolyl, 3H-indolyl, isatinyl, isobenzofuryl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, hydroxyindolyl, pyrimidinyl, phenanthridyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridoxazole, pyridoxazole, pyridoimidazole, pyridothiazole, pyridinyl, pyrimidinyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compounds are also included.

Unless otherwise specified, the term "hydrocarbonyl" or its subordinate concept (e.g., alkyl, alkenyl, alkynyl, phenyl, etc.) itself or as part of another substituents refers to linear, branched or cyclic hydrocarbon radicals or combinations thereof, which can be fully saturated, mono- or poly-unsaturated, can be mono-, di- or poly-substituted, can be monovalent (e.g., methyl), divalent (e.g., methylene) or polyvalent (e.g., methylidyne), can include divalent or polyvalent radicals, and have a specified amount of carbon atoms (e.g., $C_1$-$C_{10}$ referring to 1 to 10 carbons). The "hydrocarbonyl" include, but not limited to, aliphatic hydrocarbonyl and aromatic hydrocarbonyl, wherein the aliphatic hydrocarbonyl includes a chain or cyclic group, specifically includes, but not limited to, alkyl, alkenyl, alkynyl, and the aromatic hydrocarbonyl includes, but not limited to, 6- to 12-membered aromatic hydrocarbonyl, such as benzene, naphthalene and etc. In some embodiments, the term "hydrocarbonyl" refers to linear or branched radicals or combinations thereof, which can be fully saturated, mono- or poly-unsaturated, and can include divalent and polyvalent radicals. Examples of saturated hydrocarbon radicals include, but not limited to, methyl, ethyl, n-propyl, isopropyl, n-butyl, t-butyl, isobutyl, sec-butyl, isobutyl, cyclohexyl, (cyclohexyl) methyl, cyclopropylmethyl, and the homologues or isomers of n-pentyl, n-hexyl, n-heptyl, n-octyl and other radicals. The unsaturated alkyl has one or more double bonds or triple bonds, examples of which include, but not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologues and isomers.

Unless otherwise specified, the term "heterohydrocarbonyl" or its subordinate concept (e.g., heteroalkyl, heteroalkenyl, heteroalkynyl heteroaryl, etc.) itself or in combination with another term refers to stable linear, branched or cyclic hydrocarbon radicals or combinations thereof, and consists of a certain number of carbon atoms and at least one heteroatom. In some embodiments, the term "heteroalkyl" itself or in combination with another term refers to stable linear, branched hydrocarbon radicals or combinations thereof, and consists of a certain number of carbon atoms and at least one heteroatom. In a typical embodiment, the heteroatom is selected from B, O, N and S, wherein the nitrogen and sulfur heteroatom may be optionally oxidized, and the nitrogen atom is optionally quaternized. The heteroatoms or heteroradicals can be at any internal position of the heterohydrocarbonyl including the position by which the hydrocarbonyl is attached to the remainder of the molecule). The examples include, but not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—CH₃, —CH₂—CH₂—S(O)₂—CH₃, —CH=CH—O—CH₃, —CH₂—CH=N—OCH₃ and —CH=CH—N(CH₃)—CH₃. Two heteroatoms at most can be continuous, for example, —CH₂—NH—OCH₃.

The term "alkoxy", "alkylamino" and "alkylthiol" (or thioalkoxy) are conventional expressions and refer to those alkyl groups that are linked to the remainder of the molecule by an oxygen atom, amino group or sulfur atom, respectively.

Unless otherwise specified, the term "cyclohydrocarbonyl", "heterocyclohydrocarbonyl" or its subordinate concept (e.g., aryl, heteroaryl, cycloalkyl, heterocycloalkyl, cycloalkenyl, heterocycloalkenyl, cycloalkynyl, heterocycloalkynyl, etc.) itself or in combination with other terms refers to cyclized "hydrocarbonyl", "heterohydrocarbonyl", respectively. In addition, in the case of heterohydrocarbonyl or heterocyclohydrocarbonyl (e.g., heteroalkyl, heterocycloalkyl), the heteroatoms can occupy the position by which the heterocyclic ring is attached to the remainder of the molecule. Examples of the cycloalkyl include, but not limited to, cyclopentyl, cyclohexyl, 1-cyclohexenyl, 3-cyclohexenyl, cycloheptyl and the like. Non-limiting examples of the heterocyclyl include 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuranindol-3-yl, thiolan-2-yl, thiolan-3-yl, 1-piperazinyl and 2-piperazinyl.

Unless otherwise specified, the term "aryl" refers to poly-unsaturated aromatic hydrocarbon substituents, and can be mono-, di- or poly-substituted; can be monovalent, divalent or polyvalent; can be monocyclic or polycyclic ring (e.g., 1 to 3 rings, wherein at least one ring is aromatic), which are fused together or covalently linked. The term "heteroaryl" refers to an aryl (or ring) comprising one to four heteroatoms. In one exemplary example, the heteroatom is selected from B, N, O and S, wherein the nitrogen and sulfur heteroatom may be optionally oxidized, and the nitrogen atom is optionally quaternized. The heteroaryl can be linked to the remainder of the molecule by heteroatoms. Non-limiting examples of the aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidinyl, 4-pyrimidinyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituents of any one of the above-mentioned aryl and heteroaryl ring system are selected from the acceptable substituents as described hereinafter.

For the sake of convenience, the aryl when used in combination with other terms (e.g., aryloxy, arylthiol, aralkyl) includes the aryl and heteroaryl rings as defined above. Thus, the term "aralkyl" is intended to include those radicals comprising an aryl attached to an alkyl (e.g., benzyl, phenethyl, pyridinylmethyl, etc.), including those alkyl groups in which carbon atoms (eg, methylene) have been replaced by, for example, phenoxymethyl, 2-pyridyloxymethyl, 3-(1-naphthyloxy)propyl and the like.

The "leaving group" refers to a functional group or atom that may be substituted by another functional group or atom by a substitution reaction (e.g., an affinity substitution reaction). For example, the representative leaving group includes trifluoromethanesulfonate; chlorine, bromine, iodine; sulfonate groups, such as methanesulfonate, tosylate, p-bromobenzenesulfonate, p-toluenesulfonate and the like; acyloxy, such as acetoxy, trifluoroacetoxy and the like.

The term "protecting group" includes, but not limited to, "amino protecting group", "hydroxy protecting group" or "thiol protecting group". The term "amino protecting group" refers to a protecting group suitable for preventing side reactions at the nitrogen position of the amino group. The representative amino protecting group include, but not limited to, formyl; acyl such as alkanoyl (e.g., acetyl, trichloroacetyl or trifluoroacetyl); alkoxycarbonyl such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-di-(4'-methoxyphenyl)methyl; silicyl such as trimethylsilicyl (TMS) and t-butyldimethylsilicyl (TBS) etc. The term "hydroxy protecting group" refers to a protecting group suitable for preventing side reactions on hydroxyl. The representative hydroxy protecting group includes, but not limited to, alkyl such as methyl, ethyl and t-butyl; acyl, such as alkanoyl (e.g., acetyl); arylmethyl such as benzyl (Bn), methoxybenzyl (PMB), 9-fluorenylmethyl (Fm) and benzhydryl (diphenylmethyl, DPM); silicyl such as trimethylsilicyl (TMS) and t-butyldimethylsilicyl (TBS) etc.

The compounds of the present invention may be prepared by a variety of synthetic methods well-known to those skilled in the art, including the specific embodiments listed below, embodiments thereof in combination with other chemical synthesis methods, and the equivalents well-known to those skilled in the art, and the preferred embodiments include, but not limited to, the examples of the present invention.

All of the solvents used in the present invention are commercially available and can be used without further purification. The present invention adopts the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equal quantity; CDI represents carbonyldiimidazole; DCM represents methylene chloride; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, which is an amine protecting group; BOC represents t-butoxycarbonyl, which is an amine protecting group; HOAc represents acetic acid; NaCNBH₃ represents sodium cyanoborohydride; r.t. represents room temperature; O/N represents overnight; THF represents tetrahydrofuran; Boc₂O represents di-t-butyl dicarbonate; TFA represents trifluoroacetic acid; DIPEA represents diisopropylethylamine; SOCl₂ represents thionyl chloride; CS₂ represents carbon disulfide; TsOH represents p-toluenesulfonic acid; NFSI represents N-fluoro-N-(phenylsulfonyl) benzenesulfonamide; NCS represents 1-chloropyrrolidine-2,5-dione; n-Bu₄NF represents tetrabutylammonium fluoride; iPrOH represents 2-propanol; mp represents melting point; LDA represents lithium diisopropylamine; TMSCF₃ represents trifluoromethyl trimethylsilane; Ti(Oi-Pr)₄ represents tetraisopropyl titanate; MSCI represents methanesulfonyl chloride; DMAP represents N,N-dimethyl-4-aminopyridine; TEA represents trimethylamine; BnBr stands for benzyl bromide; DIEA represents diisopropylethylamine; BH₃DMS represents borane-methyl sulfide; DMP represents Dess-Martin periodinane; TBAF stands for tetrabutyl ammonium fluoride; HOBT represents 1-hydroxybenzotriazole; AIBN represents azodiisobutyronitrile; NBS stands for N-bromosuccinimide.

The compounds are named manually or by ChemDraw® software, while for the commercially available compounds, the names listed in the supplier catalogs are adopted.

EXAMPLES

The present invention will be described in detail by way of examples, but is not intended to be a limitation to the present invention.

Example 1

3,7-Dimethyl-1-(oxetan-3-ylmethyl)purin-2,6-dione

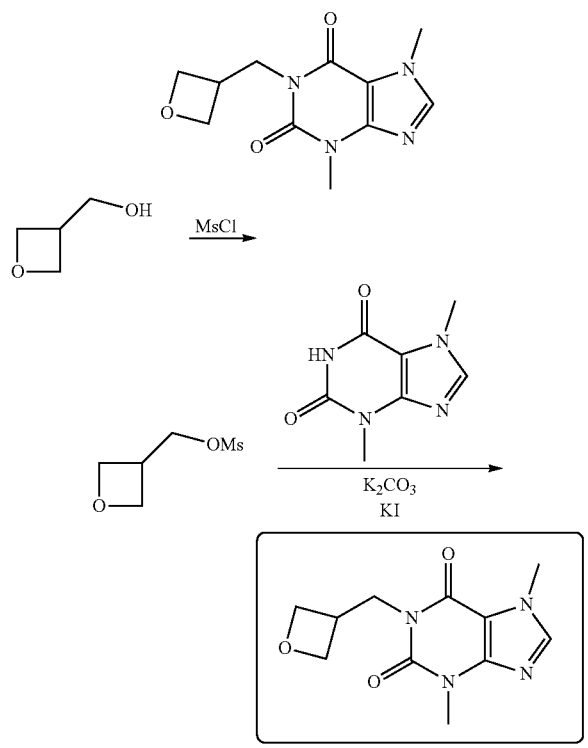

Step 1

Oxetan-3-yl-methyl methanesulfonate

Oxetan-3-yl-methanol (150 mg, 1.70 mmol) and triethylamine (344 mg, 3.40 mmol) were dissolved in methylene chloride (5 mL), and then methanesulfonyl chloride (390 mg, 3.40 mmol) was added at 0° C. The reaction solution was slowly warmed to room temperature and stirred for 2 hours. The reaction was quenched by adding saturated aqueous sodium bicarbonate solution (10 mL), followed by extraction with methylene chloride (10 mL×3). The organic phases were combined, washed with saturated brine (30 mL), dried over anhydrous sodium sulfate, and then filtered. The filtrate was concentrated under reduced pressure to give oxetan-3-yl-methyl methanesulfonate (200 mg, yellow oily) with a yield of 70%. MS-ESI calculated value: [M+H]+ 167; measured value: 167.

Step 2

3,7-Dimethyl-1-(oxetan-3-yl-methyl)purin-2,6-dione

Oxetan-3-yl-methyl methanesulfonate (200 mg, 1.20 mmol), 3,7-dimethyl-1H-purin-2,6(3H,7H)-dione (216 mg, 1.20 mmol), potassium iodide (20.0 mg, 0.120 mmol) and potassium carbonate (250 mg, 1.81 mmol) were dissolved in N,N-dimethylformamide (10 mL). The reaction solution was heated to 120° C. and stirred for 3 hours, and then cooled to room temperature, followed by filtration. The filtrate was concentrated under reduced pressure and purified by preparative high performance liquid chromatography to give 3,7-dimethyl-1-(oxetan-3-yl-methyl)purin-2,6-dione (100 mg), with a yield of 33%.

$^1$H NMR: (400 MHz, Methonal-d$_4$) δ7.87 (s, 1H), 4.74 (t, J=6.8 Hz, 2H), 4.61 (t, J=6.8 Hz, 2H), 4.30 (d, J=6.8 Hz, 2H), 3.96 (s, 3H), 3.51 (s, 3H), 3.42-3.35 (m, 1H). MS-ESI calculated value: [M+H]+ 251; measured value: 251.

Example 2

1-(3-Fluoro-oxetan-3-yl-methyl)-3,7-dimethyl-3,7-dihydro-purin-2,6-dione

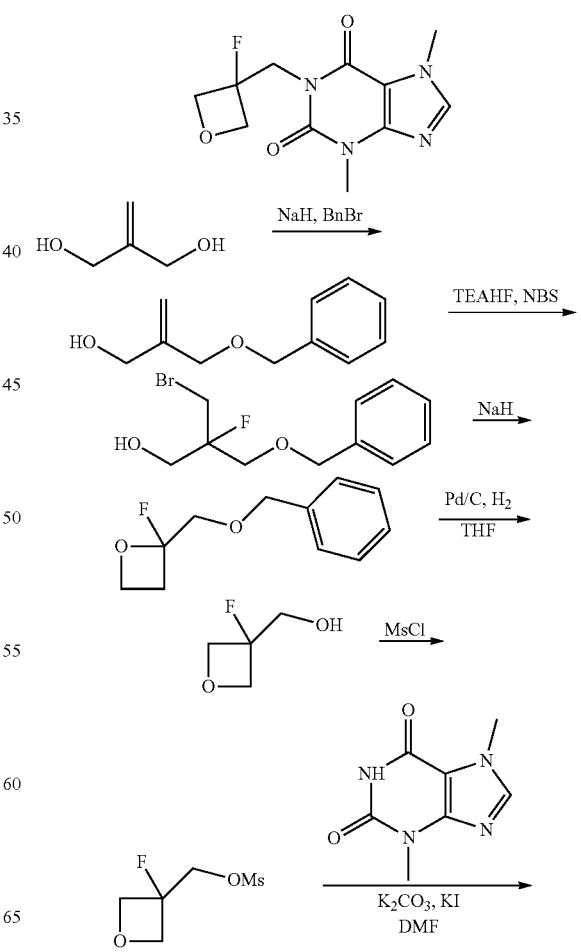

-continued

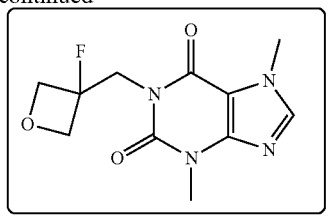

Step 1

2-((Benzyloxy)methyl)prop-2-enyl-1-ol

In the condition of 0° C., the tetrahydrofuran solution (20 mL) of 2-methylenepropan-1,3-diol (8.00 g, 90.8 mmol) was added into the tetrahydrofuran solution (180 mL) of sodium hydride (3.63 g, 90.8 mmol) dropwise. The reaction solution was stirred at 0° C. for 1 hour. And tetrabutylammonium iodide (33.5 g, 90.8 mmol) and benzyl bromide (15.5 g, 90.8 mmol) were then added. The reaction mixture was allowed for reaction at room temperature for 3 hours. The reaction solution was cooled to 0° C., quenched by adding water (200 mL), and then extracted with ethyl acetate (100 mL×3). The organic phases were combined, dried over anhydrous sodium sulfate, and then filtered. The filtrate was concentrated under reduced pressure, and then separated and purified by silica gel column chromatography (3:1 petroleum ether/ethyl acetate) to give 2-((benzyloxy)methyl)prop-2-enyl-1-ol (7.00, colorless liquid) with a yield of 43%.

$^1$H NMR: (400 MHz, CDCl$_3$) δ7.38-7.30 (m, 5H), 5.22 (s, 1H), 5.16 (s, 1H), 4.53 (s, 2H), 4.20 (s, 2H), 4.10 (s, 2H).

Step 2

3-(Benzyloxy)-2-(bromomethyl)-2-fluoropropan-1-ol

Under the condition of 0° C., triethylamine hydrofluoride (4.50 g, 27.9 mmol) and bromosuccinimide (3.00 g, 16.8 mmol) were added into the methylene chloride solution (30 mL) of 2-((benzyloxy)methyl)prop-2-enyl-1-ol (2.00 g, 11.2 mmol). The reaction solution was stirred at room temperature for 3 hours. The reaction was quenched by adding water (30 mL), followed by extraction with methylene chloride (30 mL×2). The organic phases were combined and then washed successively with saturated aqueous sodium bicarbonate solution and saturated brine. Then dried over anhydrous sodium sulfate and filtered. The filtrate was concentrated under reduced pressure, and then separated and purified by silica gel column chromatography (5:1 petroleum ether/ethyl acetate) to give 3-(benzyloxy)-2-(bromomethyl)-2-fluoropropan-1-ol (1.40 g, colorless oil) with a yield of 45%.

$^1$H NMR: (400 MHz, CDCl$_3$) δ7.38-7.31 (m, 5H), 4.60 (s, 2H), 3.89 (d, J=16.0 Hz, 2H), 3.77 (d, J=16.0 Hz, 2H), 3.70-3.65 (m, 2H).

Step 3

3-((Benzyloxy)methyl)-3-fluoropropylene oxide

In the condition of 0° C., sodium hydride (75.0 mg, 1.88 mmol) were added into the anhydrous tetrahydrofuran solution (2 mL) of 3-(benzyloxy)-2-(bromomethyl)-2-fluoropropan-1-ol (200 mg, 0.721 mmol). The reaction solution was stirred overnight under the condition of room temperature. The reaction was quenched by adding ice-cold water (20 mL), followed by extraction with ethyl acetate (10 mL×3). The organic phases were combined, dried over anhydrous sodium sulfate, and then filtered. The filtrate was concentrated under reduced pressure, and then separated and purified by silica gel column chromatography (3:1 petroleum ether/ethyl acetate) to give 3-((benzyloxy)methyl)-3-fluoropropylene oxide (42.0 mg, colorless liquid) with a yield of 30%.

$^1$H NMR: (400 MHz, CDCl$_3$) δ7.40-7.32 (m, 5H), 4.79 (dd, J=20.0, 8.0 Hz, 2H), 4.64 (s, 2H), 4.60 (dd, J=20.0, 8.0 Hz, 2H), 3.82 (d, J=20.0 Hz, 2H).

Step 4

(3-Fluoro-oxetan-3-yl)methanol

After 3-benzyloxymethyl-3-fluoro-oxetane (190 mg, 0.968 mmol) was dissolved in tetrahydrofuran (10 mL), acetic acid (0.25 mL) and dry palladium-carbon (palladium 10%, water 1%, 20 mg) was added. The reaction solution was allowed for reaction at room temperature for 5 hours under hydrogen atmosphere (30 psi). The reaction solution was filtered to give a (3-fluoro-oxetan-3-yl)methanoltetrahydrofuran solution, which was used directly in the next step.

Step 5

Methyl 3-fluoro-oxetan-3-yl-methanesulfonate

Under the protection of nitrogen, triethylamine (298 mg, 2.94 mmol) and methanesulfonyl chloride (225 mg, 1.96 mmol) were added into the tetrahydrofuran solution of (3-fluoro-oxetan-3-yl)methanol (104 mg, 0.980 mmol) obtained in the previous step. The reaction solution was allowed for reaction at room temperature for 3 hours, followed by adding methylene chloride (30 mL). The reaction solution washed successively with 0.5N hydrochloric acid solution (15 mL) and saturated sodium bicarbonate solution (15 mL). The organic phases were washed with saturated brine (10 mL), dried over anhydrous sodium sulfate, and concentrated under reduced pressure to give methyl 3-fluoro-oxetan-3-yl-methanesulfonate (102 mg, yellow oil) with a yield of 57%.

$^1$H NMR: (400 MHz, CDCl$_3$) δ4.84 (dd, J=18.4, 8.4 Hz, 2H), 4.67-4.51 (m, 4H), 3.09 (s, 3H). M MS-ESI calculated value: [M+H]$^+$ 185; measured value: 185.

Step 6

1-(3-Fluoro-oxetan-3-ylmethyl)-3,7-dimethyl-3,7-dihydro-purin-2,6-dione

Methyl 3-fluoro-oxetan-3-yl-methanesulfonate (100 mg, 0.543 mmol) was dissolved in N,N-dimethylformamide (2 mL), followed by adding 3,7-dimethyl-1H-purin-2,6(3H, 7H)-dione (97.8 mg, 0.543 mmol), potassium carbonate (150 mg, 1.09 mmol) and potassium iodide (9.0 mg, 0.054 mmol). The reaction solution was heated to 120° C. and stirred for 3 hours, followed by concentration under reduced pressure. The residue was purified by high performance liquid chromatography to give 1-(3-fluoro-oxetan-3-ylmethyl)-3,7-dimethyl-3,7-dihydro-purin-2,6-dione (28.0 mg) with a yield of 19%.

¹H NMR: (400 MHz, CDCl₃) δ7.54 (s, 1H), 4.92 (d, J=9.2 Hz, 1H), 4.86 (d, J=9.2 Hz, 1H), 4.80 (d, J=8.8 Hz, 1H), 4.74 (d, J=8.8 Hz, 1H), 4.54 (d, J=10.0 Hz, 2H), 3.99 (s, 3H), 3.59 (s, 3H). MS-ESI calculated value: [M+H]⁺ 269; measured value: 269.

Example 3

3,7-Dimethyl-1-((3-methyloxetan-3-yl)methyl)-1H-purin-2,6(3H, 7H)-dione

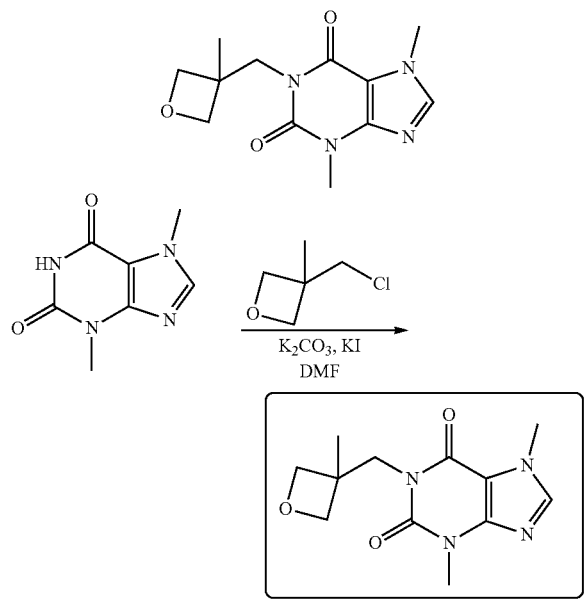

The mixture of 3,7-dimethyl-1H-purin-2,6(3H,7H)-dione (200 mg, 1.10 mmol), 3-(chloromethyl)-3-methyloxetane (198 mg, 1.65 mmol), potassium carbonate (304 mg, 2.20 mmol) and iodomethane (18.0 mg, 0.109 mmol) was dissolved in N,N-dimethylformamide (2 mL). The reaction solution was allowed for reaction in a microwave reactor at 130° C. for 15 minutes. The reaction solution was concentrated under reduced pressure, and then separated and purified by preparative high performance liquid chromatography to give 3,7-dimethyl-1-((3-methyloxetan-3-yl)methyl)-1H-purin-2,6(3H,7H)-dione.

¹H NMR: (400 MHz, Methonal-d₄) δ7.91 (s, 1H), 4.78 (d, J=6.4 Hz, 2H), 4.23 (d, J=6.4 Hz, 2H), 4.13 (s, 2H), 3.99 (s, 3H), 3.54 (s, 3H), 1.36 (s, 3H). MS-ESI calculated value: [M+H]⁺ 265; measured value: 265.

Example 4

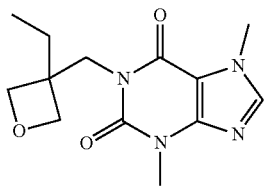

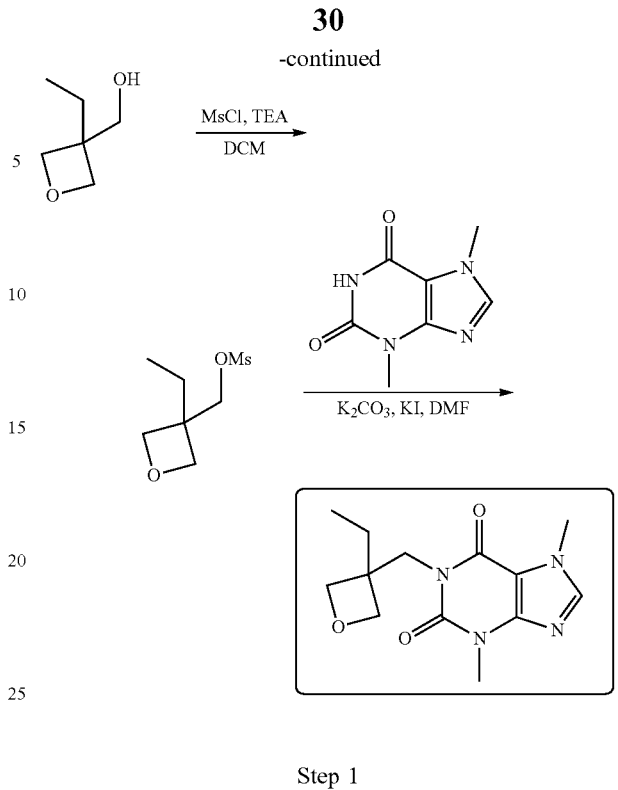

Step 1

(3-Ethyloxetan-3-yl)methyl methanesulfonate (3-Ethyloxetan-3-yl)methanol (64.0 mg, 0.552 mmol) and triethylamine (111 mg, 1.10 mmol) were dissolved in methylene chloride (20 mL), and methanesulfonyl chloride (94.9 mg, 0.829 mmol) was then added under the condition of 0° C. The reaction solution was stirred at room temperature for 2 hours, and then diluted by adding methylene chloride (20 mL), followed by washing with saturated sodium bicarbonate solution (20 mL×2). The organic phases were dried over anhydrous sodium sulfate, and then filtered. The filtrate was concentrated under reduced pressure, and then separated and purified by silica gel column chromatography (4:1 petroleum ether/ethyl acetate, Rf=0.5) to give (3-ethyloxetan-3-yl)methyl methanesulfonate (100 mg, colorless oil) with a yield of 93%.

MS-ESI calculated value: [M+H]⁺ 195; measured value: 195.

Step 2

1-((3-Ethyloxetan-3-yl)methyl)3,7-dimethyl-1H-purin-2,6(3H,7H)-dione (3-Ethyloxetan-3-yl)methyl methanesulfonate (100 mg, 0.520 mmol) was dissolved in N,N-dimethylformamide (20 mL). 3,7-dimethyl-1H-purin-2,6(3H,7H)-dione (92.7 mg, 0.520 mmol), potassium carbonate (107 mg, 0.780 mmol) and potassium iodide (86.3 mg, 0.520 mmol) were added into the reaction solution under the condition of room temperature. The reaction solution was heated to 100° C. and allowed for reaction for 2 hours, followed by dilution by adding ethyl acetate (20 mL). The organic phases were washed with saturated sodium bicarbonate solution (20 mL×2), dried over anhydrous sodium sulfate, and then filtered. The filtrate was concentrated under reduced pressure, followed by purification by preparative high performance liquid chromatography to give 1-((3-ethyloxetan-3-yl)methyl)3,7-dimethyl-1H-purin-2,6(3H,7H)-dione (80.0 mg) with a yield of 56%.

$^1$H NMR: (400 MHz, CDCl$_3$) δ7.53 (s, 1H), 4.62 (d, J=6.4 Hz, 2H), 4.28 (d, J=6.4 Hz, 2H), 4.06 (s, 2H), 3.98 (s, 3H), 3.58 (s, 3H), 1.82 (q, J=7.2 Hz, 2H), 1.06 (t, J=7.2 Hz, 3H). MS-ESI calculated value: [M+H]$^+$ 279; measured value: 279.

Example 5

1-(2-(2-Ethyloxetan-3-yl)ethyl)-3,7-dimethyl-1H-purin-2,6(3H,7H)-dione

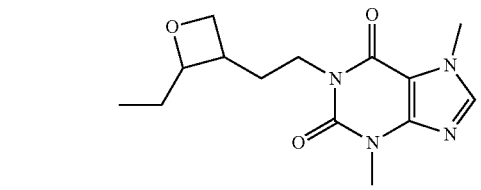

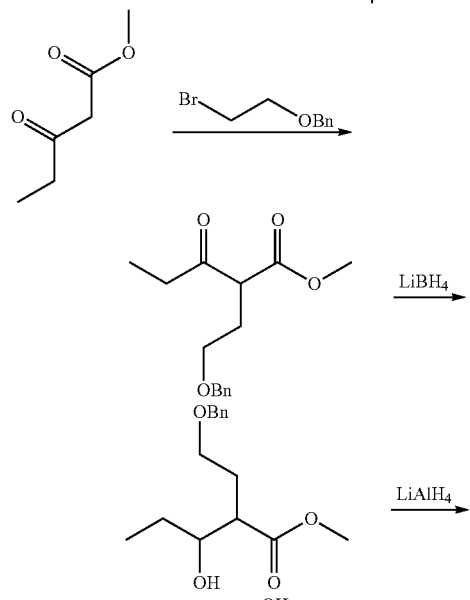

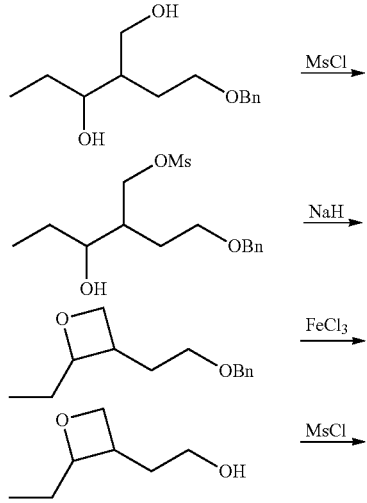

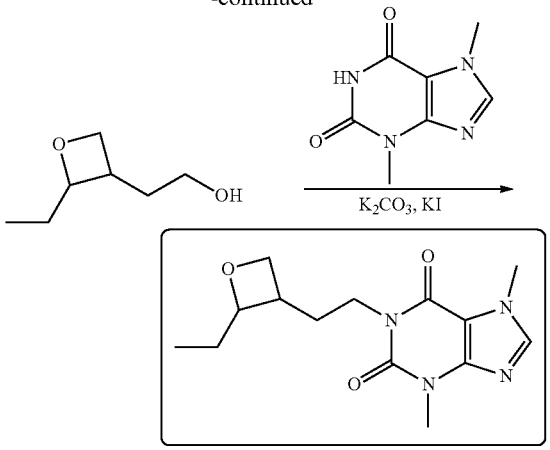

Step 1

Methyl 2-(2-(benzyloxy)ethyl)-3-oxopentanoate

Sodium hydride (842 mg, 35.1 mmol) was added into the tetrahydrofuran solution (100 mL) of methyl 3-oxopentanoate (3.04 g, 23.4 mmol) at 0° C. The reaction solution was stirred at 0° C. for 1 hour. The tetrahydrofuran solution (10 mL) of ((2-bromoethoxy)-methyl)-benzene (10.0 g, 46.7 mmol) was added dropwise into the reaction solution at 0° C. The reaction solution was stirred at 70° C. for 24 hours and then cooled to 0° C. Then, the reaction was quenched by adding saturated ammonium chloride solution (20 mL), followed by extraction with ethyl acetate (20 mL×3). The organic phases were washed with saturated brine (100 mL×3), dried over anhydrous sodium sulfate, and then concentrated under reduced pressure. The concentrate was separated and purified by silica gel column chromatography (20:1 petroleum ether/ethyl acetate, Rf=0.3) to give methyl 2-(2-(benzyloxy)ethyl)-3-oxopentanoate (3.01 g, colorless oily) with a yield of 49%.

Step 2

Methyl 2-(2-(benzyloxy)ethyl)-3-hydroxypentanoate

Methyl 2-(2-(benzyloxy)ethyl)-3-oxopentanoate (2.50 g, 9.47 mmol) was dissolved in methanol (30 mL), and then lithium borohydride (208 mg, 9.47 mmol) was added under the condition of 0° C. The reaction solution was stirred at 25° C. for 1 hour. The reaction was quenched by adding water (10 mL), and then extracted with ethyl acetate (30 mL×3). The organic phases were washed with saturated sodium chloride solution (20 mL×3), dried over anhydrous sodium sulfate, and then filtered. The filtrate was concentrated under reduced pressure, and then separated and purified by silica gel column chromatography (3:1 petroleum ether/ethyl acetate, Rf=0.5) to give Methyl 2-(2-(benzyloxy)ethyl)-3-hydroxypentanoate (2.01 g, colorless oil) with a yield of 80%.

$^1$H NMR: (400 MHz, Methonal-d$_4$) δ7.35-7.33 (m, 5H), 4.47 (s, 2H), 3.63-3.61 (m, 3H), 3.52-3.49 (m, 1H), 2.62-2.45 (m, 2H), 2.15-1.85 (m, 2H), 1.57-1.25 (m, 3H), 1.00-0.98 (m, 3H).

Step 3

2-(2-(Benzyloxy)ethyl)pentan-1,3-diol

Under the protection of nitrogen, lithium aluminium hydride (323 mg, 8.27 mmol) was slowly added into the tetrahydrofuran solution (100 mL) of methyl 2-(2-(benzyloxy)ethyl)-3-hydroxypentanoate (2.00 g, 7.52 mmol) at 0° C. The reaction solution was stirred at 0° C. for 1 hour. The reaction solution was cooled to 0° C., and then water (0.33 mL), 15% sodium hydroxide solution (0.33 mL) and water (0.99 mL) were slowly added, successively, followed by filtration. The filtrate was concentrated under reduced pressure to give a product 2-(2-(benzyloxy)ethyl)pentan-1,3-diol (1.50 g, yellow oily) with a yield of 76%.

$^1$H NMR: (400 MHz, Methonal-$d_4$) δ7.36-7.28 (m, 5H), 4.52 (s, 2H), 3.66-3.57 (m, 5H), 1.73-1.69 (m, 5H), 1.00-0.95 (m, 3H).

Step 4

2-(2-(benzyloxy)ethyl)-3-hydroxypentyl methanesulfonate 2-(2-(Benzyloxy)ethyl)pentan-1,3-diol (1.50 g, 6.30 mmol) and triethylamine (1.91 g, 18.9 mmol) were dissolved in methylene chloride (20 mL), and then methanesulfonyl chloride (846 mg, 7.56 mmol) was added slowly at 0° C. The reaction solution was slowly heated to 25° C. and stirred for 0.5 hour. The reaction was quenched by adding water (20 mL), followed by extraction with methylene chloride (30 mL×3). The organic phases were combined, washed with saturated sodium chloride solution (20 mL×3), dried over anhydrous sodium sulfate, and then filtered. The filtrate was concentrated under reduced pressure, and then purified by silica gel column chromatography (10:1 petroleum ether/ethyl acetate, Rf=0.4) to give a product 2-(2-(benzyloxy)ethyl)-3-hydroxypentyl methanesulfonate (1.50 g, yellow oil) with a yield of 74%.

$^1$H NMR: (400 MHz, Methonal-$d_4$) δ7.34-7.27 (m, 5H), 4.50 (s, 2H), 4.32-4.26 (m, 2H), 3.60-3.50 (m, 3H), 3.00 (s, 3H), 1.96-1.70 (m, 5H), 0.98-0.94 (m, 3H).

Step 5

3-(2-(Benzyloxy)ethyl)-2-ethyloxetane

Sodium hydride (228 mg, 9.49 mmol) was added into the tetrahydrofuran solution (10 mL) of 2-(2-(benzyloxy)ethyl)-3-hydroxypentyl methanesulfonate (1.50 g, 4.75 mmol) at 0° C. The reaction solution was slowly heated to 25° C. and stirred for 12 hours. The reaction was quenched by adding saturated ammonium chloride solution (5 mL), followed by extraction with ethyl acetate (20 mL×3). The organic phases were washed with saturated brine (20 mL×3), dried over anhydrous sodium sulfate and then concentrated under reduced pressure. The concentrate was separated and purified by silica gel column chromatography (15:1 petroleum ether/ethyl acetate, Rf=0.5) to give 3-(2-(benzyloxy)ethyl)-2-ethyloxetane (800 mg, colorless oily) with a yield of 77%.

$^1$H NMR: (400 MHz, Methonal-$d_4$) δ7.37-7.28 (m, 5H), 4.60-4.58 (m, 1H), 4.57-4.56 (m, 1H), 4.48 (s, 2H), 4.44-4.25 (m, 1H), 3.49-3.44 (m, 2H), 2.77-2.75 (m, 1H), 1.98-1.94 (m, 2H), 1.74-1.63 (m, 2H), 0.92-0.88 (m, 3H).

Step 6

2-(2-Ethyloxetan-3-yl)ethanol 3-(2-(Benzyloxy)ethyl)-2-ethyloxetane (800 mg, 3.64 mmol) was dissolved in the methylene chloride solution (10 mL), and then ferric trichloride (1.17 g, 7.27 mmol) was added. The reaction solution was stirred at 25° C. for 0.5 hour under the protection of nitrogen and then filtered. The filtrate was concentrated under reduced pressure, and then separated and purified by silica gel column chromatography (3:1 petroleum ether/ethyl acetate, Rf=0.5) to give 2-(2-ethyloxetan-3-yl)ethanol (60.0 mg, colorless oil) with a yield of 13%.

$^1$H NMR: (400 MHz, Methonal-$d_4$) δ3.85-3.82 (m, 3H), 3.77-3.75 (m, 2H), 2.08-2.03 (m, 2H), 1.61-1.52 (m, 3H), 1.05-0.96 (m, 3H).

Step 7

2-(2-ethyloxetan-3-yl)ethyl methanesulfonate 2-(2-Ethyloxetan-3-yl)ethanol (60.0 mg, 0.463 mmol) and triethylamine (93.0 mg, 0.923 mmol) were dissolved in methylene chloride (2 mL), and then methanesulfonyl chloride (62.2 mg, 0.556 mmol) was added slowly at 0° C. The reaction solution was slowly heated to 25° C. and stirred for 0.5 hour. The reaction was quenched by adding water (5 mL), followed by extraction with methylene chloride (10 mL×3). The organic phases were combined, washed with saturated sodium chloride solution (10 mL×3), dried over anhydrous sodium sulfate, and then filtered. The filtrate was concentrated under reduced pressure to give a product 2-(2-ethyloxetan-3-yl)ethyl methanesulfonate (40.0 mg, yellow oil) with a yield of 42%.

Step 8

1-(2-(2-Ethyloxetan-3-yl)ethyl)-3,7-dimethyl-1H-purin-2,6(3H,7H)-dione 2-(2-Ethyloxetan-3-yl)ethyl methanesulfonate (40.0 mg, 0.192 mmol), 3,7-dimethyl-1H-purin-2,6 (3H,7H)-dione (34.6 mg, 0.192 mmol), potassium iodide (3.5 mg, 0.019 mmol) and potassium carbonate (53.0 mg, 0.384 mmol) were dissolved in anhydrous N,N-dimethylformamide (2 mL). The reaction solution was heated to 120° C., and allowed for reaction for 3 hours. The reaction solution was cooled to 20° C. and then filtered. The filtrate was purified by preparative high performance liquid chromatography to give 1-(2-(2-ethyloxetan-3-yl)ethyl)-3,7-dimethyl-1H-purin-2,6(3H,7H)-dione (3.0 mg) with a yield of 5%.

$^1$H NMR: (400 MHz, Methonal-$d_4$) δ7.52 (s, 1H), 4.17-4.14 (m, 1H), 4.00 (s, 3H), 3.98-3.96 (m, 1H), 3.86-3.85 (m, 2H), 3.59 (s, 3H), 3.58-3.57 (m, 1H), 2.41-2.39 (m, 1H), 1.95-1.94 (m, 1H), 1.85-1.81 (m, 1H), 1.60-1.55 (m, 2H), 1.00-0.96 (m, 3H).

MS-ESI calculated value: [M+H]$^+$ 293; measured value: 293.

Example 6

3,7-Dimethyl-1-[3-(3-methyloxetan-3-yl)propyl]purin-2,6-dione

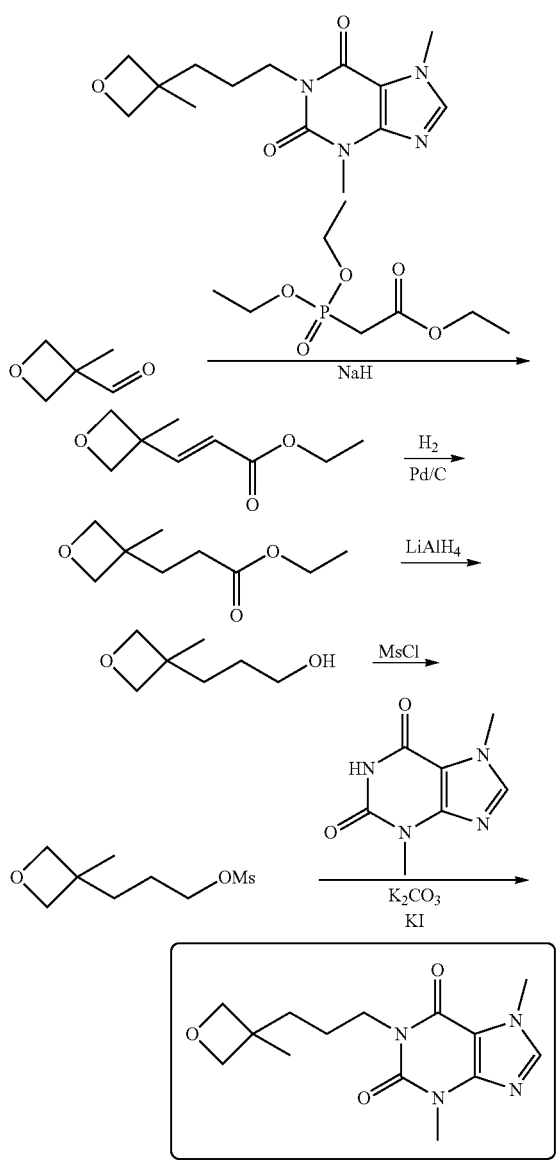

Step 1

Ethyl 3-(3-methyloxetan-3-yl)prop-2-enoate

Ethyl 2-ethoxyethyl phosphate (4.03 g, 17.9 mmol) was dissolved in tetrahydrofuran (20 mL), and then sodium-hydrogen (719 mg, 17.9 mmol) was added at 0° C. After reacting for 0.5 hour, 3-methyloxetan-3-formaldehyde (900 mg, 8.99 mmol) was added, followed by reaction at room temperature for 2 hours. The reaction was quenched by adding saturated ammonium chloride solution (10 mL), followed by extraction with ethyl acetate (20 mL×3), dried over anhydrous sodium sulfate, and then filtered. The filtrate was concentrated under reduced pressure, and then separated and purified by silica gel column chromatography (10:1 petroleum ether/ethyl acetate, Rf=0.2) to give ethyl 3-(3-methyloxetan-3-yl)prop-2-enoate (800 mg, yellow oily) with a yield of 52%.

$^1$H NMR: (400 MHz, Methonal-$d_4$) δ7.27 (d, J=16.0 Hz, 1H), 5.93 (d, J=16.0 Hz, 1H), 4.67 (d, J=6.0 Hz, 2H), 4.48 (d, J=6.0 Hz, 2H), 4.20 (q, J=7.2 Hz, 2H), 1.53 (s, 3H), 1.29 (t, J=7.2 Hz, 3H).

MS-ESI calculated value: [M+H]$^+$ 171; measured value: 171.

Step 2

Ethyl 3-(3-methyloxetan-3-yl)ethyl propionate

Ethyl 3-(3-methyloxetan-3-yl)prop-2-enoate (550 mg, 3.23 mmol), wet palladium-carbon (100 mg, 3.23 mmol) were mixed and dissolved in tetrahydrofuran (30 mL), and allowed for reaction under hydrogen (15 psi) atmosphere for 12 hours. The reaction solution was filtered and then the filtrate was concentrated under reduced pressure to give ethyl 3-(3-methyloxetan-3-yl)ethyl propionate (500 mg, yellow oily) with a yield of 90%.

$^1$H NMR: (400 MHz, Methonal-$d_4$) δ4.45 (d, J=6.0 Hz, 2H), 4.33 (d, J=6.0 Hz, 2H), 4.14 (q, J=7.2 Hz, 2H), 2.35 (t, J=4.8 Hz, 2H), 1.98 (t, J=4.8 Hz, 2H), 1.31 (s, 3H), 1.25 (t, J=7.2 Hz, 3H).

MS-ESI calculated value: [M+H]*173; measured value: 173.

Step 3

3-(3-Methyloxetan-3-yl)propan-1-ol

Ethyl 3-(3-methyloxetan-3-yl)ethyl propionate (550 mg, 3.19 mmol) was dissolved in tetrahydrofuran (10 mL), and then lithium aluminum hydride (242 mg, 6.38 mmol) was added at 0° C., followed by reaction for 1 hour. The reaction was quenched by adding water (10 mL), followed by extraction with ethyl acetate (10 mL×3). The resultant was dried over anhydrous sodium sulfate, and then filtered. The filtrate was concentrated under reduced pressure to give 3-(3-methyloxetan-3-yl)propan-1-ol (250 mg, colorless oily) with a yield of 60%.

MS-ESI calculated value: [M+H]$^+$ 131; measured value: 131.

Step 4

3-(3-Methyloxetan-3-yl)propyl methanesulfonate 3-(3-Methyloxetan-3-yl)propan-1-ol (250 mg, 1.92 mmol) and triethylamine (583 mg, 5.76 mmol) were dissolved in methylene chloride (5 mL), and then methanesulfonyl chloride (659 mg, 5.76 mmol) was added at 0° C. The reaction solution was slowly warmed to room temperature and stirred for 2 hours. The reaction was quenched by adding aqueous sodium bicarbonate solution (10 mL), followed by extraction with methylene chloride (10 mL×3). The organic phases were combined, washed with saturated brine, dried over anhydrous sodium sulfate, and then filtered. The filtrate was concentrated under reduced pressure to give 3-(3-methyloxetan-3-yl)propyl methansulfonate (200 mg, yellow oily) with a yield of 50%.

$^1$H NMR: (400 MHz, Methonal-$d_4$) δ4.47 (d, J=6.0 Hz, 2H), 4.37 (d, J=6.0 Hz, 2H), 4.28 (t, J=6.4 Hz, 2H), 3.09 (s, 3H), 1.71-1.50 (m, 4H), 1.31 (s, 3H). MS-ESI calculated value: [M+H]⁺ 209; measured value: 209.

Step 5

3,7-Dimethyl-1-[3-(3-methyloxetan-3-yl)propyl]purin-2,6-dione 3-(3-Methyloxetan-3-yl)propyl methansulfonate (200 mg, 0.960 mmol), 3,7-dimethyl-1H-purin-2,6(3H,7H)-dione (173 mg, 0.960 mmol), potassium iodide (15.9 mg, 0.0960 mmol) and potassium carbonate (265 mg, 1.92 mmol) were dissolved in N,N-dimethylformamide (10 mL). The reaction solution was heated to 120° C. and stirred for 3 hours, and then cooled to room temperature, followed by filtration. The filtrate was concentrated under reduced pressure and purified by preparative high performance liquid chromatography to give 3,7-dimethyl-1-[3-(3-methyloxetan-3-yl)propyl]purin-2,6-dione (50.0 mg) with a yield of 18%.

¹H NMR: (400 MHz, Methonal-d₄) δ7.89 (s, 1H), 4.46 (d, J=6.0 Hz, 2H), 4.36 (d, J=6.0 Hz, 2H), 4.03-3.95 (m, 5H), 3.55 (s, 3H), 1.74-1.61 (m, 4H), 1.31 (s, 3H). MS-ESI calculated value: [M+H]⁺ 293; measured value: 293.

Example 7

3,7-Dimethyl-1-((tetrahydrofuran-2-yl)methyl)-1H-purin-2,6(3H,7H)-dione

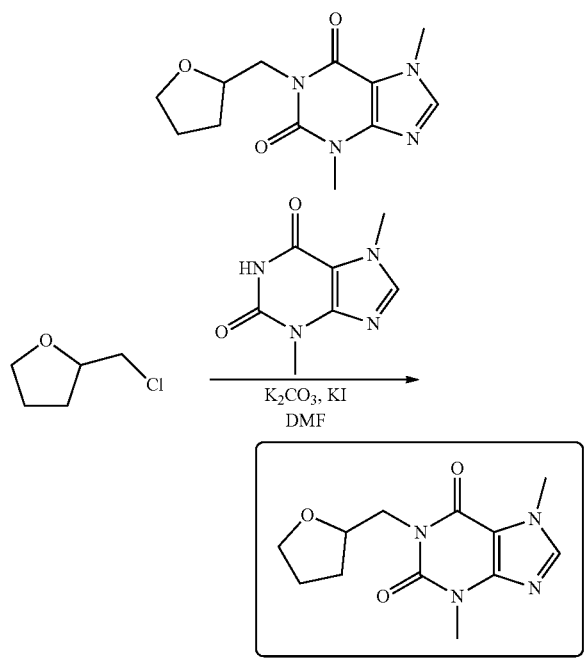

The mixture of 3,7-dimethyl-1H-purin-2,6(3H,7H)-dione (538 mg, 2.99 mmol), 2-(chloromethyl)tetrahydrofuran (300 mg, 2.49 mmol), potassium carbonate (688 mg, 4.98 mmol) and iodomethane (41.0 mg, 0.25 mmol) was dissolved in N,N-dimethylformamide (3 mL). The reaction solution was heated to 130° C. and allowed for reaction for 3 hours. The reaction solution was concentrated under reduced pressure, and then was separated and purified by preparative high performance liquid chromatography to give 3,7-dimethyl-1-((tetrahydrofuran-2-yl)methyl)-1H-purin-2,6(3H,7H)-dione (50.0 mg) with a yield of 8%.

¹H NMR: (400 MHz, Methonal-d₄) δ7.87 (s, 1H), 4.36-4.28 (m, 1H), 4.23-4.16 (m, 1H), 3.97 (s, 3H), 3.93-3.83 (m, 2H), 3.76-3.69 (m, 1H), 3.53 (s, 3H), 2.07-1.86 (m, 3H), 1.79-1.69 (m, 1H).

MS-ESI calculated value: [M+H]⁺ 265; measured value: 265.

Example 8

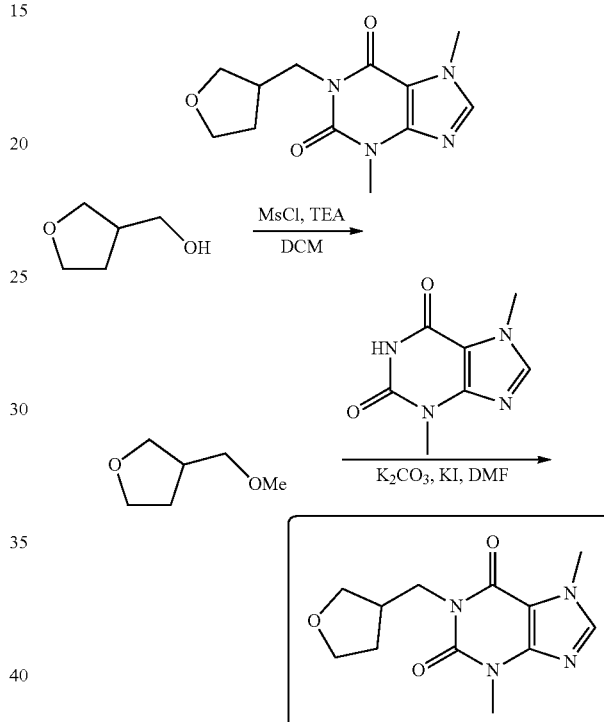

Step 1

(Tetrahydrofuran-3-yl)methyl methanesulfonate (Tetrahydrofuran-3-yl)methanol (56.0 mg, 0.552 mmol) and triethylamine (111 mg, 1.10 mmol) were dissolved in methylene chloride (20 mL), and then methanesulfonyl chloride (94.9 mg, 0.829 mmol) was added under the condition of 0° C. The reaction solution was stirred at room temperature for 2 hours, and then diluted by adding methylene chloride (20 mL), followed by washing with saturated sodium bicarbonate solution (20 mL×2), dried over anhydrous sodium sulfate, and then filtered. The filtrate was concentrated under reduced pressure, and then separated and purified by silica gel column chromatography (4:1 petroleum ether/ethyl acetate, Rf=0.5) to give (tetrahydrofuran-3-yl)methyl methanesulfonate (90.0 mg, colorless oil) with a yield of 90%.

MS-ESI calculated value: [M+H]⁺ 181; measured value: 181.

Step 2

3,7-Dimethyl-1-((tetrahydrofuran-3-yl)methyl)-1H-purin-2,6(3H,7H)-dione (Tetrahydrofuran-3-yl)methyl methanesulfonate (90.0 mg, 0.510 mmol) was dissolved in N,N-dimethylformamide (20 mL). 3,7-Dimethyl-1H-purin-2,6(3H,7H)-dione (92.7 mg, 0.520 mmol), potassium carbonate (107 mg, 0.780 mmol) and potassium iodide (86.3 mg, 0.520 mmol) were added into the reaction solution under the condition of room temperature. The reaction solution was heated to 100° C. and allowed for reaction for 2 hours, followed by dilution by adding ethyl acetate (20 mL). The organic phases were washed with saturated sodium bicarbonate (20 mL×2), dried over anhydrous sodium sulfate, and then filtered. The filtrate was concentrated under reduced pressure, followed by purification by preparative high performance liquid chromatography to give 3,7-dimethyl-1-((tetrahydrofuran-3-yl)methyl)-1H-purin-2,6(3H,7H)-dione (80.0 mg) with a yield of 60%.

$^1$H NMR: (400 MHz, CDCl$_3$) δ7.49 (s, 1H), 3.95-3.93 (m, 1H), 3.88 (s, 3H), 3.86 (m, 2H), 3.66-3.60 (m, 2H), 3.46-3.45 (m, 1H), 3.42 (s, 3H), 2.62-2.57 (m, 1H), 1.86-1.82 (m, 1H), 1.63-1.58 (m, 1H). MS-ESI calculated value: [M+H]$^+$ 265; measured value: 265.

Example 9

3,7-Dimethyl-1-[2-(2-methyltetrahydrofuran-3-yl)ethyl]purin-2,6-dione

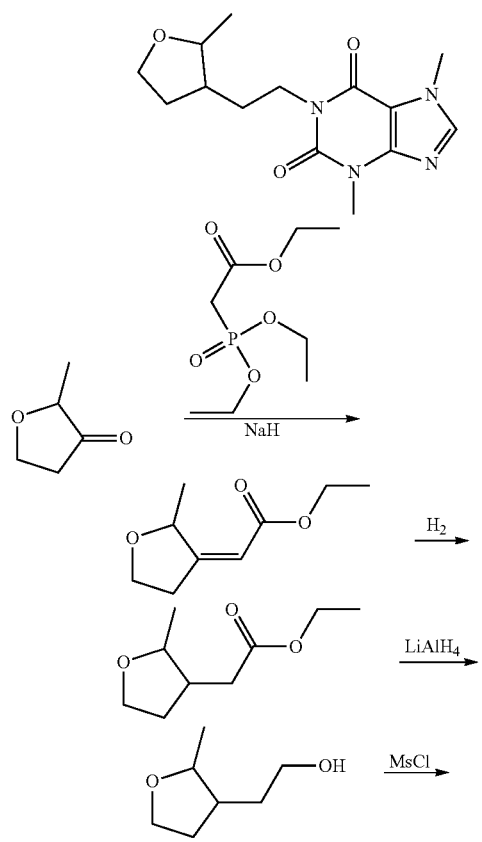

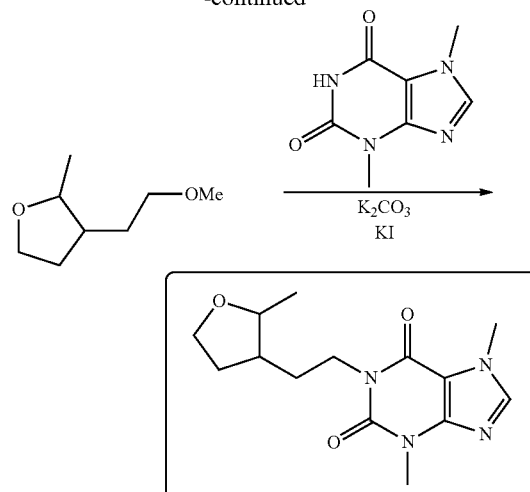

Step 1

2-(2-Methyl-3-ylidene)ethyl acetate

Ethyl-2-ethoxyethyl phosphate (2.24 g, 9.98 mmol) was dissolved in tetrahydrofuran (20 mL), and then sodium-hydrogen (399 mg, 9.98 mmol) was added at 0° C. After reacting for 0.5 hour, 2-methyltetrahydrofuran-3-one (500 mg, 4.99 mmol) was added, followed by reaction at room temperature for 2 hours. The reaction was quenched by adding saturated ammonium chloride solution (10 mL), followed by extraction with ethyl acetate (30 mL×3), dried over anhydrous sodium sulfate, and then filtered. The filtrate was concentrated under reduced pressure, and then separated and purified by silica gel column chromatography (10:1 petroleum ether/ethyl acetate, Rf=0.6) to give 2-(2-methyl-3-ylidene)ethyl acetate (400 mg, yellow oily) with a yield of 47%.

$^1$H NMR: (400 MHz, Methonal-d$_4$) δ5.76 (s, 1H), 4.45-4.42 (m, 1H), 4.19 (q, J=7.2 Hz, 2H), 4.12-4.09 (m, 1H), 3.80-3.76 (m, 1H), 3.17-3.11 (m, 1H), 2.98-2.92 (m, 1H), 1.34 (d, J=6.0 Hz, 3H), 1.28 (t, J=7.2 Hz, 3H). MS-ESI calculated value: [M+H]$^+$ 171; measured value: 171.

Step 2

2-(2-methyltetrahydrofuran-3-yl)ethyl acetate 2-(2-Methyl-3-ylidene)ethyl acetate (1.70 g, 9.99 mmol), wet palladium-carbon (100 mg, 3.23 mmol) were mixed and dissolved in tetrahydrofuran (30 mL), and allowed for reaction under hydrogen (15 psi) atmosphere for 12 hours. The reaction solution was filtered and then the filtrate was concentrated under reduced pressure to give ethyl 2-(2-methyltetrahydrofuran-3-yl)ethyl acetate (1.50 g, yellow oily) with a yield of 87%.

$^1$H NMR: (400 MHz, Methonal-d$_4$) δ4.17 (q, J=7.2 Hz, 2H), 3.92-3.55 (m, 3H), 2.62-2.10 (m, 4H), 1.72-1.64 (m, 1H), 1.32-1.22 (m, 6H). MS-ESI calculated value: [M+H]$^+$ 173; measured value: 173.

Step 3

2-(2-Methyltetrahydrofuran-3-yl)ethanol 2-(2-Methyltetrahydrofuran-3-yl)ethyl acetate (250 mg, 1.45 mmol) was dissolved in tetrahydrofuran (10 mL), and then lithium aluminum hydride (61.0 mg, 1.61 mmol) was added at 0° C., followed by reaction for 1 hour. The reaction was quenched by adding water (10 mL), followed by extraction with ethyl acetate (10 mL×3). The resultant was dried over anhydrous sodium sulfate, and then filtered. The filtrate was concentrated under reduced pressure to give 2-(2-methyltetrahydrofuran-3-yl)ethanol (180 mg, colorless oily) with a yield of 95%.

$^1$H NMR: (400 MHz, Methonal-$d_4$) δ3.96-3.51 (m, 5H), 2.26-2.08 (m, 2H), 1.77-1.62 (m, 2H), 1.48-1.35 (m, 1H), 1.31-1.13 (m, 3H). MS-ESI calculated value: [M+H]$^+$ 131; measured value: 131.

Step 4

2-(2-Methyltetrahydrofuran-3-yl)ethyl methanesulfonate 2-(2-Methyltetrahydrofuran-3-yl)ethanol (180 mg, 1.38 mmol) and triethylamine (280 mg, 2.77 mmol)) were dissolved in methylene chloride (5 mL), and then methanesulfonyl chloride (310 mg, 2.71 mmol) was added at 0° C. The reaction solution was slowly warmed to room temperature and stirred for 2 hours. The reaction was quenched by adding aqueous sodium bicarbonate solution (10 mL), followed by extraction with methylene chloride (10 mL×3). The organic phases were combined, washed with saturated brine (20 mL), dried over anhydrous sodium sulfate, and then filtered. The filtrate was concentrated under reduced pressure to give 2-(2-methyltetrahydrofuran-3-yl)ethyl methanesulfonate (200 mg, yellow oily) with a yield of 69%.

MS-ESI calculated value: [M+H]$^+$ 209; measured value: 209.

Step 5

3,7-Dimethyl-1-[2-(2-methyltetrahydrofuran-3-yl) ethyl]purin-2,6-dione 2-(2-Methyltetrahydrofuran-3-yl)ethyl methanesulfonate (200 mg, 0.960 mmol), 3,7-dimethyl-1H-purin-2,6(3H,7H)-dione (173 mg, 0.960 mmol), potassium iodide (16.0 mg, 0.0960 mmol) and potassium carbonate (200 mg, 1.45 mmol) were dissolved in N,N-dimethylformamide (10 mL). The reaction solution was heated to 120° C. and stirred for 3 hours, and then cooled to room temperature, followed by filtration. The filtrate was concentrated under reduced pressure, and then purified by preparative high performance liquid chromatography to give 3,7-dimethyl-1-[2-(2-methyltetrahydrofuran-3-yl)ethyl]purin-2,6-dione (20.0 mg) with a yield of 7%.

$^1$H NMR: (400 MHz, Methonal-$d_4$) δ7.86 (s, 1H), 4.13-4.03 (m, 3H), 3.99 (s, 3H), 3.95-3.44 (m, 2H), 3.52 (s, 3H), 2.22-1.65 (m, 4H), 1.60-1.53 (m, 1H), 1.25-1.02 (m, 3H). MS-ESI calculated value: [M+H]$^+$ 293; measured value: 293.

Example 10

3,7-Dimethyl-1-((tetrahydro-2H-pyran-4-yl)methyl)-1H-purin-2,6-(3H,7H)-dione

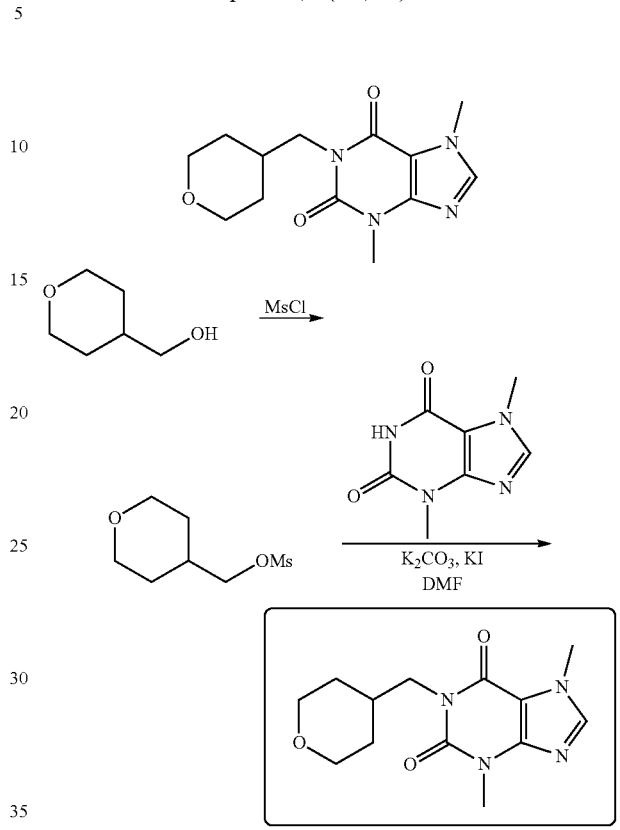

Step 1

(Tetrahydro-2H-pyran-4-yl)methyl methanesulfonate

Tetrahydropyran-4-ylmethanol (500 mg, 4.30 mmol) and triethylamine (870 mg, 8.60 mmol) were dissolved in methylene chloride (10 mL), and then methanesulfonyl chloride (985 mg, 8.60 mmol) was added at 0° C., followed by reaction at 25° C. for 1 hour. The reaction was quenched by adding water (10 mL), followed by extraction with methylene chloride (10 mL×3), dried over anhydrous sodium sulfate, and then filtered. The filtrate was concentrated under reduced pressure to give (tetrahydro-2H-pyran-4-yl)methyl methanesulfonate (700 mg, yellow oily) with a yield of 84%.

$^1$H NMR: (400 MHz, Methonal-$d_4$) δ4.10 (d, J=6.4 Hz, 2H), 3.99-3.96 (m, 2H), 3.48-3.42 (m, 2H), 3.09 (s, 3H), 2.05-2.03 (m, 1H), 1.72-1.67 (m, 2H), 1.43-1.39 (m, 2H). MS-ESI calculated value: [M+H]$^+$ 195; measured value: 195.

Step 2

3,7-Dimethyl-1-((tetrahydro-2H-pyran-4-yl)methyl)-1H-purin-2,6-(3H,7H)-dione (Tetrahydro-2H-pyran-4-yl)methyl methanesulfonate (700 mg, 3.60 mmol), 3,7-dimethyl-1H-purin-2,6-(3H,7H)-dione (649 mg, 3.60 mmol), potassium iodide (119 mg, 0.720 mmol) and potassium carbonate (995 mg, 7.20 mmol)

were dissolved in N,N-dimethylformamide (20 mL). The reaction solution was heated to 120° C. and stirred for 3 hours, and then cooled to room temperature, followed by filtration. The filtrate was concentrated under reduced pressure. The residue was washed with methanol (10 mL) to give 3,7-dimethyl-1-((tetrahydro-2H-pyran-4-yl)methyl)-1H-purin-2,6-(3H,7H)-dione (200 mg) with a yield of 20%.

$^1$H NMR: (400 MHz, Methonal-$d_4$) δ7.88 (s, 1H), 3.99 (s, 3H), 3.96-3.91 (m, 4H), 3.54 (s, 3H), 3.40-3.36 (m, 2H), 2.10-2.07 (m, 1H), 1.60-1.56 (m, 2H), 1.46-1.40 (m, 2H). MS-ESI calculated value: [M+H]$^+$ 279; measured value: 279.

Example 11

3,7-Dimethyl-1-((4-methyltetrahydro-2H-pyran-4-yl)methyl)-1H-purin-2,6-(3H,7H)-dione 3,7-Dimethyl-1-(2-(3-methyltetrahydrofuran-3-yl)ethyl)-1H-purin-2,6-(3H,7H)-dione

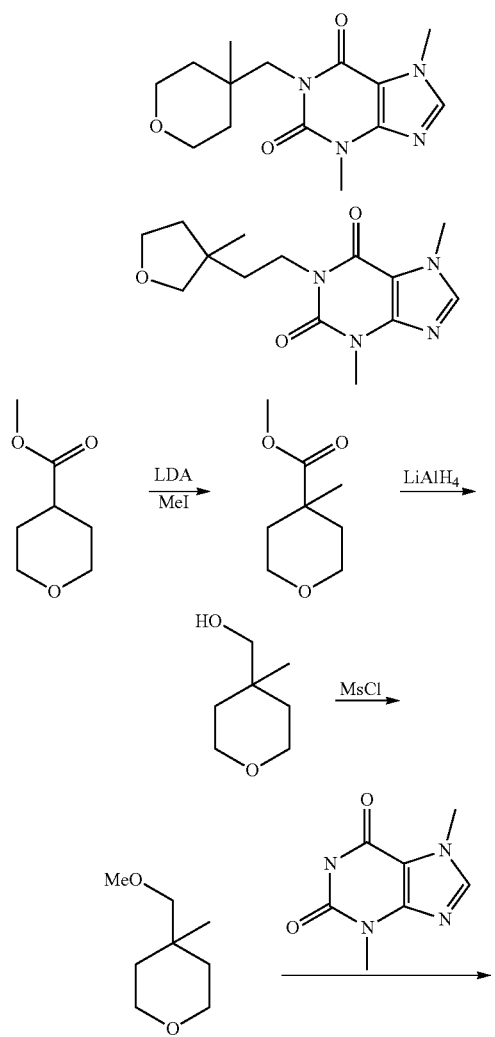

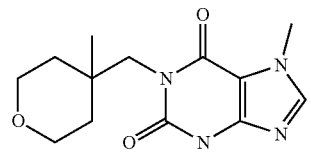

-continued

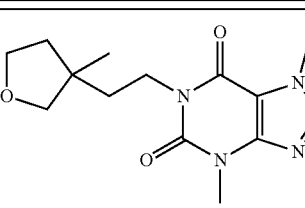

Step 1

Methyl 4-methyltetrahydro-2H-pyran-4-carboxylate

Methyl tetrahydro-2H-pyran-4-carboxylate (2.50 g, 17.3 mmol) was dissolved in anhydrous tetrahydrofuran (50 mL), and then lithium diisopropylamide solution (2M n-hexane solution, 10.4 mL, 20.8 mmol) was slowly added dropwise at -78° C. under the protection of nitrogen. The reaction solution was stirred at -78° C. for 1 hour. Iodomethane (4.92 g, 34.7 mmol) was added slowly, and stirred for 1 hour. The reaction was quenched by adding water (20 mL). The reaction solution was extracted with ethyl acetate (50 mL×3). The organic phases were combined, dried over anhydrous sodium sulfate, and then filtered. The filtrate was concentrated under reduced pressure, and then purified by silica gel column chromatography (10:1 petroleum ether/ethyl acetate, Rf=0.4) to give methyl 4-methyltetrahydro-2H-pyran-4-carboxylate (1.20 g, yellow oil) with a yield of 44%.

$^1$H NMR: (400 MHz, Methonal-$d_4$) δ3.79-3.75 (m, 2H), 3.71 (s, 3H), 3.48-3.42 (m, 2H), 2.06-2.02 (m, 2H), 1.51-1.44 (m, 2H), 1.20 (s, 3H).

Step 2

(4-Methyltetrahydro-2H-pyran-4-yl)methanol

Methyl 4-methyltetrahydro-2H-pyran-4-carboxylate (1.20 g, 7.59 mmol) was dissolved in anhydrous tetrahydrofuran (10 mL), and then lithium aluminum hydride (576 mg, 15.2 mmol) was added at 0° C. The reaction solution was heated to 25° C. and stirred for 1 hour. The reaction was quenched by adding water (20 mL), followed by extraction with ethyl acetate (50 mL×3). The resultant was dried over anhydrous sodium sulfate, and then filtered. The filtrate was concentrated under reduced pressure, and then purified by silica gel column chromatography (1:1 petroleum ether/ethyl acetate, Rf=0.2) to give (4-methyltetrahydro-2H-pyran-4-yl)methanol (700 mg, yellow oil) with a yield of 71%.

$^1$H NMR: (400 MHz, Methonal-$d_4$) δ3.75-3.71 (m, 2H), 3.68-3.66 (m, 2H), 3.33 (s, 2H), 1.62-1.55 (m, 2H), 1.31-1.26 (m, 2H), 1.03 (s, 3H).

45

Step 3

(4-Methyltetrahydro-2H-pyran-4-yl)methyl methanesulfonate (4-Methyltetrahydro-2H-pyran-4-yl)methanol (700 mg, 5.38 mmol) was dissolved in methylene chloride (10 mL), and then triethylamine (1.09 g, 10.8 mmol) and methanesulfonyl chloride (739 mg, 6.46 mmol) were added at 0° C. The reaction solution was allowed for reaction at 0° C. for 2 hours. The reaction was quenched by adding saturated aqueous sodium bicarbonate solution (10 mL), followed by extraction with methylene chloride (50 mL×3). The organic phases were combined, washed with saturated sodium chloride solution (50 mL×3), dried over anhydrous sodium sulfate, and then filtered. The filtrate was concentrated under reduced pressure to give (4-methyltetrahydro-2H-pyran-4-yl)methyl methanesulfonate (700 mg, yellow oil) with a yield of 63%.

$^1$H NMR: (400 MHz, Methonal-d$_4$) δ4.08 (s, 2H), 3.73-3.71 (m, 2H), 3.68-3.65 (m, 2H), 3.08 (s, 3H), 1.66-1.59 (m, 2H), 1.39-1.35 (m, 2H), 1.12 (s, 3H).

Step 4

3,7-Dimethyl-1-((4-methyltetrahydro-2H-pyran-4-yl)methyl)-1H-purin-2,6-(3H,7H)-dione

3,7-Dimethyl-1-(2-(3-methyltetrahydrofuran-3-yl)ethyl)-1H-purin-2,6-(3H,7H)-dione (4-Methyltetrahydro-2H-pyran-4-yl)methyl methanesulfonate (300 mg, 1.44 mmol), 3,7-dimethyl-1H-purin-2,6-(3H,7H)-dione (259 mg, 1.44 mmol), potassium iodide (23.9 mg, 0.144 mmol) and potassium carbonate (239 mg, 1.73 mmol) were dissolved in anhydrous N,N-dimethylformamide (10 mL). The reaction solution was heated to 130° C. and allowed for microwave reaction for 2 hours. The reaction solution was cooled to 20° C. and then filtered. The filtrate was purified by preparative high performance liquid chromatography to give 3,7-dimethyl-1-((4-methyltetrahydro-2H-pyran-4-yl)methyl)-1H-purin-2,6-(3H,7H)-dione (Isomer 1) (80.0 mg) with a yield of 19%, and 3,7-dimethyl-1-(2-(3-methyltetrahydrofuran-3-yl)ethyl)-1H-purin-2,6-(3H,7H)-dione (Isomer 2) (90.0 mg) with a yield of 24%.

3,7-Dimethyl-1-((4-methyltetrahydro-2H-pyran-4-yl)methyl)-1H-purin-2,6-(3H,7H)-dione. $^1$H NMR: (400 MHz, Methonal-d$_4$) δ7.87 (s, 1H), 3.97 (s, 3H), 3.96 (s, 2H), 3.78-3.74 (m, 2H), 3.66-3.64 (m, 2H), 3.33 (s, 3H), 1.68-1.62 (m, 2H), 1.35-1.31 (m, 2H), 1.02 (s, 3H). MS-ESI calculated value: [M+H]$^+$ 293; measured value: 293.

3,7-Dimethyl-1-(2-(3-methyltetrahydrofuran-3-yl)ethyl)-1H-purin-2,6-(3H,7H)-dione. $^1$H NMR: (400 MHz, Methonal-d$_4$) δ7.87 (s, 1H), 4.04-3.99 (m, 2H), 3.92 (s, 3H), 3.90-3.89 (m, 2H), 3.61-3.33 (m, 5H), 1.97-1.93 (m, 1H), 1.77-1.70 (m, 3H), 1.02 (s, 3H). MS-ESI calculated value: [M+H]$^+$ 293; measured value: 293.

46

Example 12

1-((4-Ethyltetrahydro-2H-pyran-4-yl)methyl)-3,7-dimethyl-1H-purin-2,6-(3H,7H)-dione

1-(2-(3-Ethyltetrahydro-furan-3-yl)ethyl)-3,7-dimethyl-1H-purin-2,6-(3H,7H)-dione

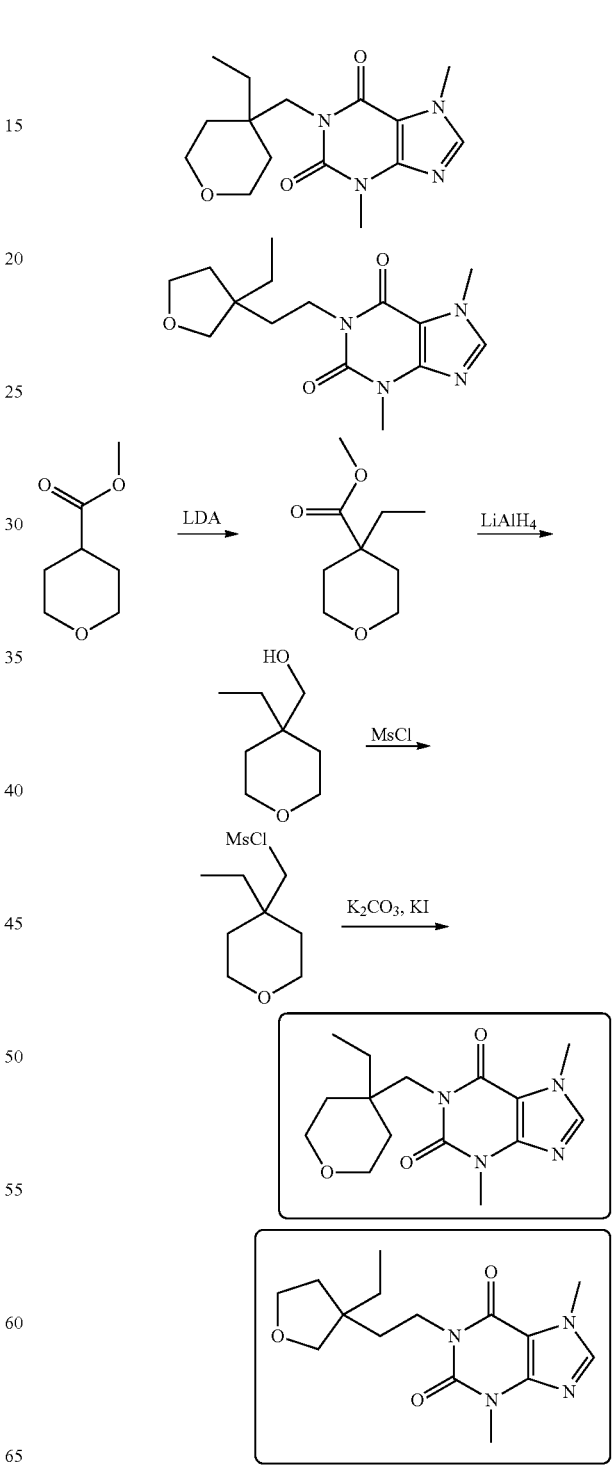

Step 1

Methyl 4-ethyltetrahydro-2H-pyran-4-carboxylate

Methyl tetrahydro-2H-pyran-4-carboxylate (2.50 g, 17.3 mmol) was dissolved in anhydrous tetrahydrofuran (50 mL), and then lithium diisopropylamide solution (2M n-hexane solution, 10.4 mL, 20.8 mmol) was slowly added dropwise at −78° C. under the protection of nitrogen. The reaction solution was stirred at −78° C. for 1 hour. Iodoethane (5.41 g, 34.7 mmol) was added slowly and stirred for 1 hour. The reaction was quenched by adding water (20 mL). The reaction solution was extracted with ethyl acetate (50 mL×3). The organic phases were combined, dried over anhydrous sodium sulfate, and then filtered. The filtrate was concentrated under reduced pressure, and then purified by silica gel column chromatography (10:1 petroleum ether/ethyl acetate, Rf=0.4) to give methyl 4-ethyltetrahydro-2H-pyran-4-carboxylate (1.00 g, yellow oily) with a yield of 33%.

$^1$H NMR: (400 MHz, Methonal-$d_4$) δ3.84-3.81 (m, 2H), 3.73 (s, 3H), 3.47-3.40 (m, 2H), 2.10-2.06 (m, 2H), 1.53-1.28 (m, 2H), 0.85-0.81 (m, 2H), 1.20 (t, J=7.2 Hz, 3H).

Step 2

(4-Ethyltetrahydro-2H-pyran-4-yl)methanol

Methyl 4-ethyltetrahydro-2H-pyran-4-carboxylate (1.00 g, 5.81 mmol) was dissolved in anhydrous tetrahydrofuran (10 mL), and then lithium aluminum hydride (220 mg, 5.81 mmol) was added at 0° C. The reaction solution was heated to 25° C. and then stirred for 1 hour. The reaction was quenched by adding water (20 mL), followed by extraction with ethyl acetate (50 mL×3). The resultant was dried over anhydrous sodium sulfate, and then filtered. The filtrate was concentrated under reduced pressure, and then purified by silica gel column chromatography (1:1 petroleum ether/ethyl acetate, Rf=0.2) to give (4-ethyltetrahydro-2H-pyran-4-yl)methanol (600 mg, yellow oil) with a yield of 72%.

$^1$H NMR: (400 MHz, Methonal-$d_4$) δ3.75-3.66 (m, 4H), 3.45 (s, 2H), 1.54-1.50 (m, 4H), 1.42-1.38 (m, 2H), 0.88-0.84 (m, 3H).

Step 3

(4-Ethyltetrahydro-2H-pyran-4-yl)methyl methanesulfonate (4-Ethyltetrahydro-2H-pyran-4-yl)methanol (600 mg, 4.16 mmol) was dissolved in methylene chloride (10 mL), and then triethylamine (843 mg, 8.32 mmol) and methanesulfonyl chloride (572 mg, 4.99 mmol) were added at 0° C. The reaction solution was allowed for reaction at 0° C. for 2 hours. The reaction was quenched by adding saturated aqueous sodium bicarbonate solution (10 mL), followed by extraction with methylene chloride (50 mL×3). The organic phases were combined, washed with saturated sodium chloride solution (50 mL×3), dried over anhydrous sodium sulfate, and then filtered. The filtrate was concentrated under reduced pressure to give (4-ethyltetrahydro-2H-pyran-4-yl)methyl methanesulfonate (600 mg, yellow oil) with a yield of 65%.

$^1$H NMR: (400 MHz, Methonal-$d_4$) δ4.12 (s, 2H), 3.71-3.69 (m, 4H), 3.11 (s, 3H), 1.61-1.52 (m, 4H), 1.28-1.24 (m, 2H), 0.93-0.89 (m, 3H).

Step 4

1-((4-Ethyltetrahydro-2H-pyran-4-yl)methyl)-3,7-dimethyl-1H-purin-2,6-(3H,7H)-dione

1-(2-(3-Ethyltetrahydro-furan-3-yl)ethyl)-3,7-dimethyl-1H-purin-2,6-(3H, 7H)-dione (4-Ethyltetrahydro-2H-pyran-4-yl)methyl methanesulfonate (300 mg, 1.35 mmol), 3,7-dimethyl-1H-purin-2,6-(3H,7H)-dione (243 mg, 1.35 mmol), potassium iodide (22.4 mg, 0.135 mmol) and potassium carbonate (224 mg, 1.62 mmol) were dissolved in anhydrous N,N-dimethylformamide (10 mL). The reaction solution was heated to 130° C. and allowed for microwave reaction for 2 hours. The reaction solution was cooled to 20° C. and then filtered. The filtrate was purified by preparative high performance liquid chromatography to give 1-((4-ethyltetrahydro-2H-pyran-4-yl)methyl)-3,7-dimethyl-1H-purin-2,6-(3H,7H)-dione (Isomer 1) (120 mg) with a yield of 29%, and 1-(2-(3-ethyltetrahydro-furan-3-yl)ethyl)-3,7-dimethyl-1H-purin-2,6-(3H, 7H)-dione (Isomer 2) (80.0 mg) with a yield of 19%.

1-((4-Ethyltetrahydro-2H-pyran-4-yl)methyl)-3,7-dimethyl-1H-purin-2,6-(3H,7H)-dione. $^1$H NMR: (400 MHz, Methonal-$d_4$) δ7.88 (s, 1H), 4.03 (s, 2H), 3.98 (s, 3H), 3.73-3.72 (m, 2H), 3.65-3.63 (m, 2H), 3.53 (s, 3H), 1.62-1.52 (m, 4H), 1.52-1.43 (m, 2H), 0.98-0.94 (m, 3H). MS-ESI calculated value: [M+H]$^+$ 307; measured value: 307.

1-(2-(3-Ethyltetrahydro-furan-3-yl)ethyl)-3,7-dimethyl-1H-purin-2,6-(3H,7H)-dione. $^1$H NMR: (400 MHz, Methonal-$d_4$) δ7.87 (s, 1H), 4.00-3.98 (m, 5H), 3.87-3.86 (m, 2H), 3.63-3.61 (m, 2H), 3.56 (s, 3H), 1.90-1.80 (m, 1H), 1.75-1.72 (m, 3H), 1.58-1.54 (m, 2H), 1.05-1.01 (m, 3H). MS-ESI calculated value: [M+H]$^+$ 307; measured value: 307.

Example 13

3,7-Dimethyl-1-(2-(tetrahydro-2H-pyran-4-yl)ethyl)-1H-purin-2,6(3H,7H)-dione

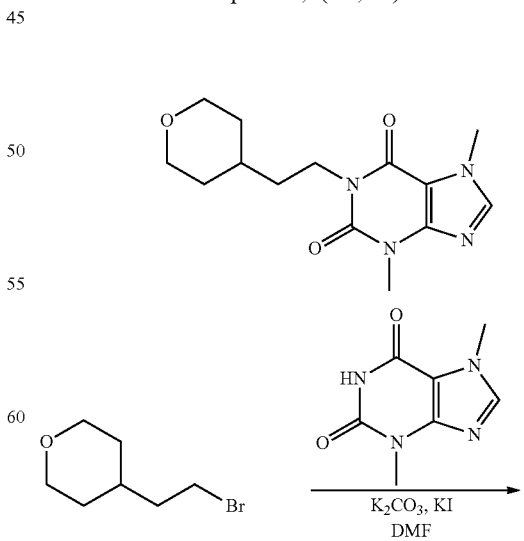

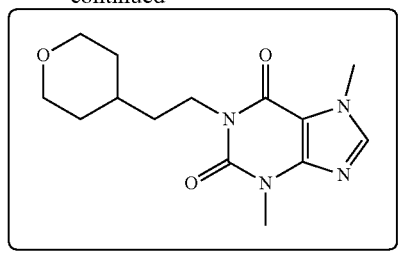

4-(2-Bromoethyl)tetrahydro-2H-pyran (200 mg, 1.00 mmol), 3,7-dimethyl-1H-purin-2,6(3H,7H)-dione (186 mg, 1.00 mmol), potassium iodide (17.0 mg, 0.100 mmol) and potassium carbonate (414 mg, 3.00 mmol) were dissolved in N,N-dimethylformamide (4 mL). The reaction solution was heated to 130° C. and allowed for reaction for 3 hours, and then the reaction solution was than cooled to 25° C. The reaction was quenched by adding saturated brine, followed by extraction with ethyl acetate (50 mL×3). The organic phases were dried over anhydrous sodium sulfate, and then filtered. The filtrate was concentrated under reduced pressure, and then purified by high performance preparative plate (ethyl acetate, Rf=0.5) to give a product 3,7-dimethyl-1-(2-(tetrahydro-2H-pyran-4-yl)ethyl)-1H-purin-2,6(3H,7H)-dione (224 mg) with a yield of 77%.

$^1$H NMR: (400 MHz, Methonal-d$_4$) δ7.86 (s, 1H), 4.06-4.01 (m, 2H), 3.97 (s, 3H), 3.92 (dd, J=12, 3.2 Hz, 2H), 3.53 (s, 3H), 3.44-3.38 (m, 2H), 1.73 (d, J=12.8 Hz, 2H), 1.61-1.55 (m, 3H), 1.38-1.24 (m, 2H). MS-ESI calculated value: [M+H]$^+$ 293; measured value: 293.

Example 14

1-[2-((2S,6S)-2,6-dimethyltetrahydro-2H-pyran-4-yl)-ethyl]-3,7-dimethyl-1H-2,6(3H,7H)-dione

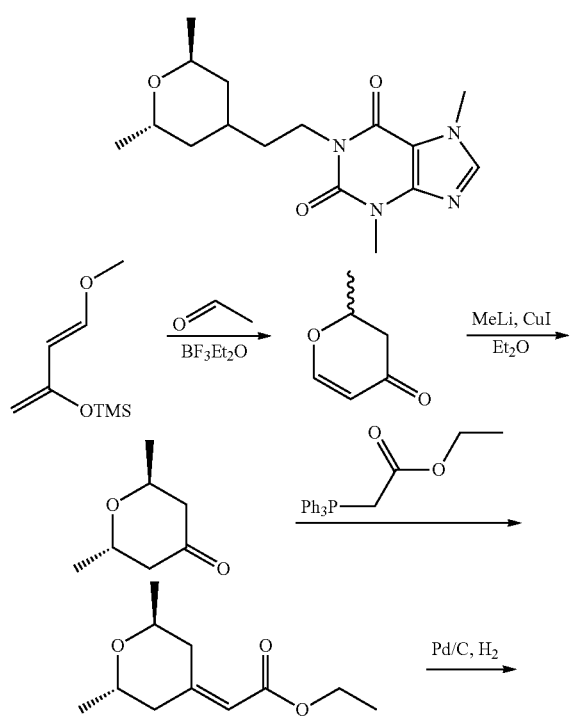

Step 1

2-Methyl-2H-pyran-4(3H)-one (E)-((4-Methoxy-1,3-dien-2-yl)oxy)trimethylsilane (5.00 g, 29.0 mmol) and acetaldehyde (55.0 g, 58.0 mmol) were dissolved in anhydrous diethyl ether (50 mL), and then boron trifluoride diethyl ether (4.33 g, 30.5 mmol) were added at −78° C. The reaction was conducted at −78° C. for 2.5 hours while stirring, and then quenched by adding saturated ammonium chloride solution (40 mL). The reaction solution was extracted with ethyl acetate (20 mL×3), dried over anhydrous sodium sulfate, and then filtered. The filtrate was concentrated under reduced pressure, and then separated and purified by silica gel column chromatography (10:1 petroleum ether/ethyl acetate, Rf=0.6) to give 2-methyl-2H-pyran-4(3H)-one (1.25 g, yellow oil) with a yield of 38%.

$^1$H NMR: (400 MHz, Methonal-d$_4$) δ7.75 (d, J=6.4 Hz, 1H), 5.65 (d, J=6.4 Hz, 1H), 4.63-4.58 (m, 1H), 2.59-2.45 (m, 2H), 1.46 (d, J=3.2 Hz, 3H).

Step 2

(2S,6S)-2,6-dimethyl-tetrahydro-pyran-4-one

Methyllithium (1.6M diethyl ether solution, 20.9 mL, 33.4 mmol) was dissolved in anhydrous diethyl ether solution (30 mL) at 0° C., and then copper iodide (4.25 g, 22.3 mmol) was added under the protection of nitrogen. The reaction solution was allowed for reaction at 0° C. for 0.5 hour. The diethyl ether solution (5 mL) of 2-methyl-2H- pyran-4(3H)-one (1.25 g, 11.2 mmol) was added slowly. The reaction solution was heated to 20° C. and then stirred for 3 hours. The reaction was quenched by adding saturated ammonium chloride solution (20 mL), followed by extraction with ethyl acetate (20 mL×3), dried over anhydrous sodium sulfate, and then filtered. The filtrate was concentrated under reduced pressure, and then separated and purified by silica gel column chromatography (10:1 petroleum ether/ethyl acetate, Rf=0.3) to give (2S,6S)-2,6-dimethyl-tetrahydro-pyran-4-one (400 mg, yellow solid) with a yield of 29%.

$^1$H NMR: (400 MHz, Methonal-$d_4$) δ4.36-4.31 (m, 2H), 2.58-2.53 (m, 2H), 2.28-2.25 (m, 2H), 1.25 (d, J=6.0 Hz, 6H).

Step 3

(2,6-Dimethyl-tetrahydro-pyran-4-ylidene)-ethyl acetate

Triphenylphosphine ethyl acetate (3.26 g, 9.37 mmol) was dissolved in anhydrous toluene (10 mL), and then ((2S,6S)-2,6-dimethyl-tetrahydro-pyran-4-one (400 mg, 3.13 mmol) was added. The reaction solution was heated to 110° C., allowed for reaction for 72 hours, and then cooled to 20° C. The reaction was quenched by adding water (50 mL), followed by extraction with ethyl acetate (20 mL×3), dried over anhydrous sodium sulfate, and then filtered. The filtrate was concentrated under reduced pressure, and then purified by silica gel column chromatography (10:1 petroleum ether/ethyl acetate, Rf=0.7) to give (2,6-dimethyl-tetrahydro-pyran-4-ylidene)-ethyl acetate (200 mg, yellow oil) with a yield of 32%.

$^1$H NMR: (400 MHz, Methonal-$d_4$) δ5.77 (s, 1H), 4.14-4.07 (m, 4H), 2.98-2.97 (m, 1H), 2.84-2.82 (m, 1H), 2.44-2.40 (m, 1H), 2.11-2.09 (m, 1H), 1.28-1.25 (m, 3H), 1.18-1.16 (m, 6H).

Step 4

(2,6-Dimethyl-tetrahydro-pyran-4-yl)-ethyl acetate (2,6-Dimethyl-tetrahydro-pyran-4-ylidene)-ethyl acetate (200 mg, 1.01 mmol) was dissolved in ethyl acetate solution (20 mL), and then wet palladium-carbon (10%, 20.0 mg) was added. The reaction solution was stirred at 25° C. for 2 hours under hydrogen pressure. The reaction solution was filtered and then the filtrate was concentrated under reduced pressure to give (2,6-dimethyl-tetrahydro-pyran-4-yl)-ethyl acetate (150 mg, yellow oil) with a yield of 75%.

$^1$H NMR: (400 MHz, Methonal-$d_4$) δ4.20-4.10 (m, 3H), 3.83-3.82 (m, 1H), 2.28-2.21 (m, 3H), 1.72-1.69 (m, 1H), 1.58-1.55 (m, 1H), 1.31-1.30 (m, 1H), 1.28-1.26 (m, 6H), 1.12-1.11 (m, 1H), 1.02-1.01 (m, 3H).

Step 5

2-(2,6-Dimethyl-tetrahydro-pyran-4-yl)-ethanol (2,6-Dimethyl-tetrahydro-pyran-4-yl)-ethyl acetate (150 mg, 0.750 mmol) was dissolved in anhydrous tetrahydrofuran (2 mL), and then lithium aluminum hydride (57.0 mg, 1.50 mmol) was added at 0° C. The reaction solution was heated to 25° C. and then stirred for 1 hour. The reaction was quenched by adding water (10 mL), followed by extraction with ethyl acetate (10 mL×3), dried over anhydrous sodium sulfate, and then filtered. The filtrate was concentrated under reduced pressure, and purified by preparative TLC plate (3:1 petroleum ether/ethyl acetate, Rf=0.5) to give 2-(2,6-dimethyl-tetrahydro-pyran-4-yl)-ethanol (70.0 mg, yellow oil) with a yield of 86%.

$^1$H NMR: (400 MHz, Methonal-$d_4$) δ4.20-4.18 (m, 1H), 3.83-3.81 (m, 1H), 3.64-3.61 (m, 2H), 1.99-1.98 (m, 1H), 1.70-1.68 (m, 1H), 1.55-1.53 (m, 1H), 1.47-1.42 (m, 3H), 1.31-1.29 (m, 3H), 1.13-1.11 (m, 3H), 0.85-0.82 (m, 1H).

Step 6

2-((2S,6S)-2,6-dimethyltetrahydro-2H-pyran-4-yl) ethyl methanesulfonate 2-(2,6-Dimethyl-tetrahydro-pyran-4-yl)-ethanol (150 mg, 0.949 mmol) was dissolved in methylene chloride (5 mL), and then triethylamine (287 mg, 2.85 mmol) and methanesulfonyl chloride (213 mg, 1.90 mmol) were added at 0° C. The reaction solution was allowed for reaction at 25° C. for 2 hours. The reaction was quenched by adding saturated aqueous sodium bicarbonate solution (10 mL), followed by extraction with methylene chloride (10 mL×3). The organic phases were combined, washed with saturated sodium chloride solution, dried over anhydrous sodium sulfate, and then filtered. The filtrate was concentrated under reduced pressure to give 2-((2S,6S)-2,6-dimethyltetrahydro-2H-pyran-4-yl)ethyl methanesulfonate (200 mg, yellow oil) with a yield of 90%.

$^1$H NMR: (400 MHz, Methonal-$d_4$) δ4.33-4.30 (m, 2H), 4.23-4.20 (m, 1H), 3.85-3.82 (m, 1H), 3.08 (s, 3H), 2.03-2.14 (m, 1H), 1.68-1.67 (m, 1H), 1.65-1.63 (m, 2H), 1.58-1.56 (m, 1H), 1.41-1.39 (m, 1H), 1.31-1.29 (m, 3H), 1.14-1.12 (m, 3H), 0.89-0.86 (m, 1H).

Step 7

1-[2-((2S,6S)-2,6-dimethyltetrahydro-2H-pyran-4-yl)-ethyl]-3,7-dimethyl-1H-2,6 (3H,7H)-dione 2-((2S,6S)-2,6-dimethyltetrahydro-2H-pyran-4-yl)ethyl methanesulfonate (100 mg, 0.424 mmol), 3,7-dimethyl-3,7-dihydro-purin-2,6-dione (83.9 mg, 0.466 mmol), potassium iodide (7.4 mg, 0.047 mmol) and potassium carbonate (109 mg, 0.790 mmol) were dissolved in N,N-dimethylformamide (3 mL). The reaction solution was heated to 120° C. and allowed for reaction for 3 hours. The reaction solution was then cooled to 20° C. and filtered. The filtrate was separated and purified by preparative high performance liquid chromatography to give 1-[2-((2S,6S)-2,6-dimethyl-tetrahydro-2H-pyran-4-yl)-ethyl]-3,7-dimethyl-1H-2,6(3H, 7H)-dione (40.0 mg) with a yield of 30%.

$^1$H NMR: (400 MHz, Methonal-$d_4$) δ8.14 (s, 1H), 4.21-4.18 (m, 1H), 4.07-4.05 (m, 2H), 4.01 (s, 3H), 3.82-3.81 (m, 1H), 3.54 (s, 3H), 1.85-1.66 (m, 1H), 1.55-1.51 (m, 2H), 1.40-1.39 (m, 2H), 1.29-1.28 (m, 1H), 1.27-1.26 (m, 3H), 1.12-1.11 (m, 3H), 0.89-0.86 (m, 1H). MS-ESI calculated value: [M+H]$^+$ 321; measured value: 321.

Example 15

1-(2-(3-Ethyltetrahydro-2H-pyran-4-yl)ethyl)-3,7-dimethyl-1H-purin-2,6-(3H,7H)-dione

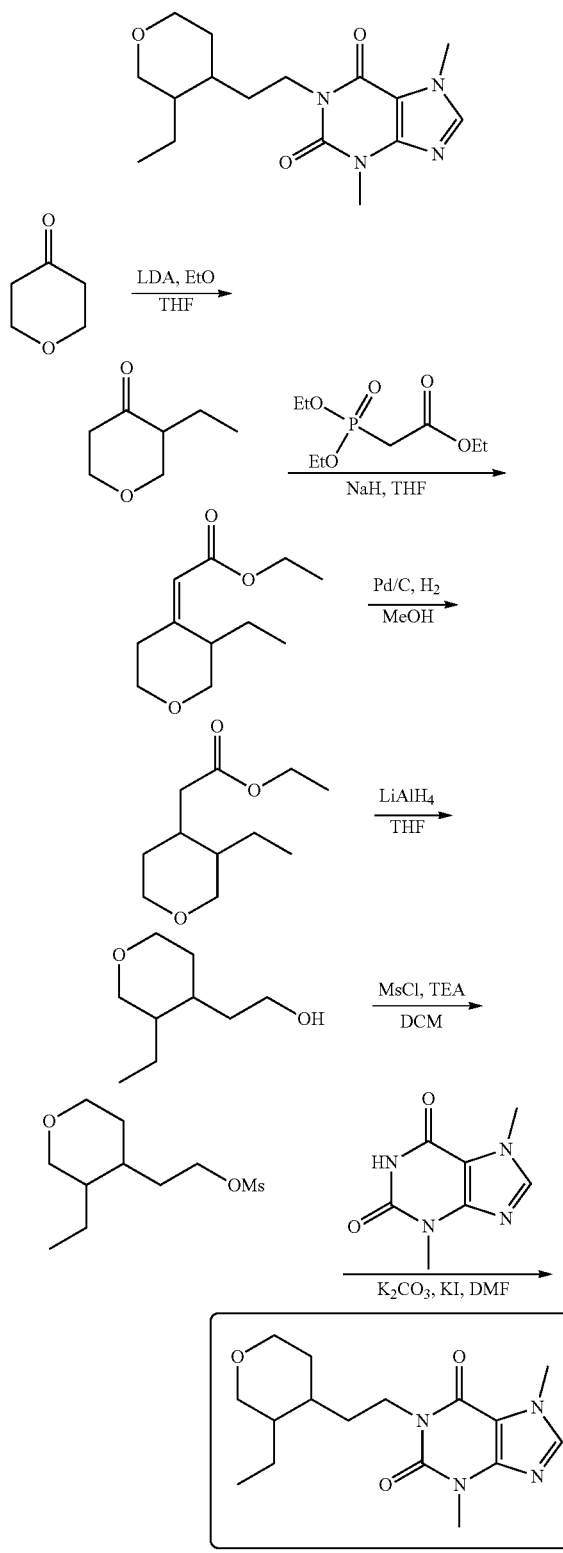

Step 1

3-Ethyldihydro-2H-pyran-4-(3H)-one

Dihydro-2H-pyran-4-(3H)-one (5.00 g, 50.0 mmol) and hexamethylphosphoramide (8.95 g, 50.0 mmol) were dissolved in tetrahydrofuran (50 mL) and then lithium diisopropylamide (50 mL, 2.0 M tetrahydrofuran solution, 100 mmol) was slowly added dropwise under the condition of −78° C., followed by stirred for 30 minutes under the condition of −78° C. Iodoethane (16.2 g, 75.0 mmol) was added into the reaction solution under the condition of 0° C. and then stirred for 2 hours. Water (15 mL) was added into the reaction solution, which was then extracted with ethyl acetate (40 mL×3). The organic phases were combined and washed with saturated sodium chloride (20 mL×2), dried over anhydrous sodium sulfate, and then filtered. The filtrate was concentrated under reduced pressure, and then separated and purified by silica gel column chromatography (10:1 petroleum ether/ethyl acetate, Rf=0.5) to give 3-ethyldihydro-2H-pyran-4-(3H)-one (1.20 g, colorless oil) with a yield of 19%.

$^1$H NMR: (400 MHz, CDCl$_3$) δ4.15-4.11 (m, 2H), 3.77-3.76 (m, 1H), 3.47-3.42 (m, 1H), 2.45-2.40 (m, 3H), 1.80-1.78 (m, 2H), 0.91 (t, J=7.2 Hz, 3H). MS-ESI calculated value: [M+H]$^+$ 129; measured value: 129.

Step 2

Ethyl 2-(3-ethyldihydro-2H-pyran-4(3H)-ylidene)ethyl acetate

3-Ethyldihydro-2H-pyran-4(3H)-one (600 mg, 4.68 mmol) and ethyl 2-(diethoxyphosphoryl)ethyl acetate (1.15 g, 5.15 mmol) were dissolved in tetrahydrofuran (30 mL). Sodium hydride (224 mg, 9.36 mmol) was added into the reaction solution under the condition of 0° C. After stirring at room temperature for 30 minutes, water (10 mL) was added into the reaction solution under the condition of 0° C. The reaction solution was diluted by adding ethyl acetate (30 mL). The organic phases were washed with water (20 mL×2), dried over anhydrous sodium sulfate, and then filtered. The filtrate was concentrated under reduced pressure, and then separated and purified by silica gel column chromatography (10:1 petroleum ether/ethyl acetate, Rf 0.7) to give ethyl 2-(3-ethyldihydro-2H-pyran-4(3H)-ylidene) ethyl acetate (800 mg, yellow oil) with a yield of 86%.

MS-ESI calculated value: [M+H]$^+$ 199; measured value: 199.

Step 3

2-(3-Ethyltetrahydro-2H-pyran-4-yl)ethyl acetate

Ethyl 2-(3-ethyldihydro-2H-pyran-4(3H)-ylidene)ethyl acetate (800 mg, 4.04 mmol) was dissolved in methanol (40 mL), and wet palladium-carbon (10%, 0.02 g) was then added under the condition of room temperature. The reaction system was subjected to hydrogen replacement for 3 times and then allowed for reaction at room temperature for 2 hours. The reaction solution was filtered, followed by concentration to give 2-(3-ethyltetrahydro-2H-pyran-4-yl)ethyl acetate (600 mg, yellow oil) with a yield of 74%. MS-ESI calculated value: [M+H]$^+$ 201; measured value: 201.

Step 4

2-(3-Ethyltetrahydro-2H-pyran-4-yl)ethanol 2-(3-Ethyltetrahydro-2H-pyran-4-yl)ethyl acetate (600 mg, 3.00 mmol) was dissolved in tetrahydrofuran (30 mL), and then lithium aluminium hydride (170 mg, 4.50 mmol) was added under the condition of 0° C. After stirring at room temperature for 2 hours, water (0.2 mL), 15% sodium hydroxide (0.2 mL) and water (0.6 mL) were added into the reaction solution, respectively, followed by stirring for 20 minutes. The reaction solution was diluted by adding ethyl acetate (30 mL). The organic phase was washed with water (20 mL×2), dried over anhydrous sodium sulfate, and then filtered. The filtrate was concentrated under reduced pressure to give 2-(3-ethyltetrahydro-2H-pyran-4-yl)ethanol (400 mg, yellow oil) with a yield of 84%.

MS-ESI calculated value: [M+H]$^+$ 159; measured value: 159.

Step 5

2-(3-Ethyltetrahydro-2H-pyran-4-yl)ethyl methanesulfonate 2-(3-Ethyltetrahydro-2H-pyran-4-yl)ethanol (474 mg, 3.00 mmol) and triethylamine (455 mg, 4.50 mmol) were dissolved in methylene chloride (30 mL). methanesulfonyl chloride (412 mg, 3.60 mmol) was added into the reaction solution under the condition of 0° C., followed by stirring at 0° C. for 2 hours. The reaction solution was diluted by adding methylene chloride (30 mL). The organic phase was washed with water (20 mL×2), dried over anhydrous sodium sulfate, and then filtered. The filtrate was concentrated under reduced pressure to give 2-(3-ethyltetrahydro-2H-pyran-4-yl)ethyl methanesulfonate (600 mg, yellow oil) with a yield of 85%. MS-ESI calculated value: [M+H]$^+$ 237; measured value: 237.

Step 6

1-(2-(3-Ethyltetrahydro-2H-pyran-4-yl)ethyl)-3,7-dimethyl-1H-purin-2,6-(3H,7H)-dione 2-(3-Ethyltetrahydro-2H-pyran-4-yl)ethyl methanesulfonate (400 mg, 1.69 mmol) and 3,7-dimethyl-1H-purin-2,6-(3H,7H)-dione (305 mg, 1.69 mmol) were dissolved in N,N-dimethylformamide (20 mL), and then potassium carbonate (467 mg, 3.38 mmol) and potassium iodide (28.0 mg, 0.169 mmol) were added under the condition of room temperature. The reaction solution was stirred for 2 hours under the condition of 100° C. The reaction solution was then cooled to room temperature for concentration and diluted by adding ethyl acetate (30 mL). The organic phase was washed with water (20 mL×2), dried over anhydrous sodium sulfate, and then filtered. The filtrate was concentrated under reduced pressure, followed by purification by preparative high performance liquid chromatography to give 1-(2-(3-ethyltetrahydro-2H-pyran-4-yl)ethyl)-3,7-dimethyl-1H-purin-2,6-(3H,7H)-dione (200 mg) with a yield of 37%.

$^1$H NMR: (400 MHz, CDCl$_3$) δ7.49 (s, 1H), 3.97-3.95 (m, 5H), 3.83-3.77 (m, 2H), 3.43 (s, 3H), 3.42-3.35 (m, 2H), 1.79-1.41 (m, 8H), 0.91-0.82 (m, 3H). MS-ESI calculated value: [M+H]$^+$ 321; measured value: 321.

Example 16

1-(2-(2-Methyltetrahydro-2H-pyran-4-yl)ethyl)-3,7-dimethyl-1H-purin-2,6(3H,7H)-dione

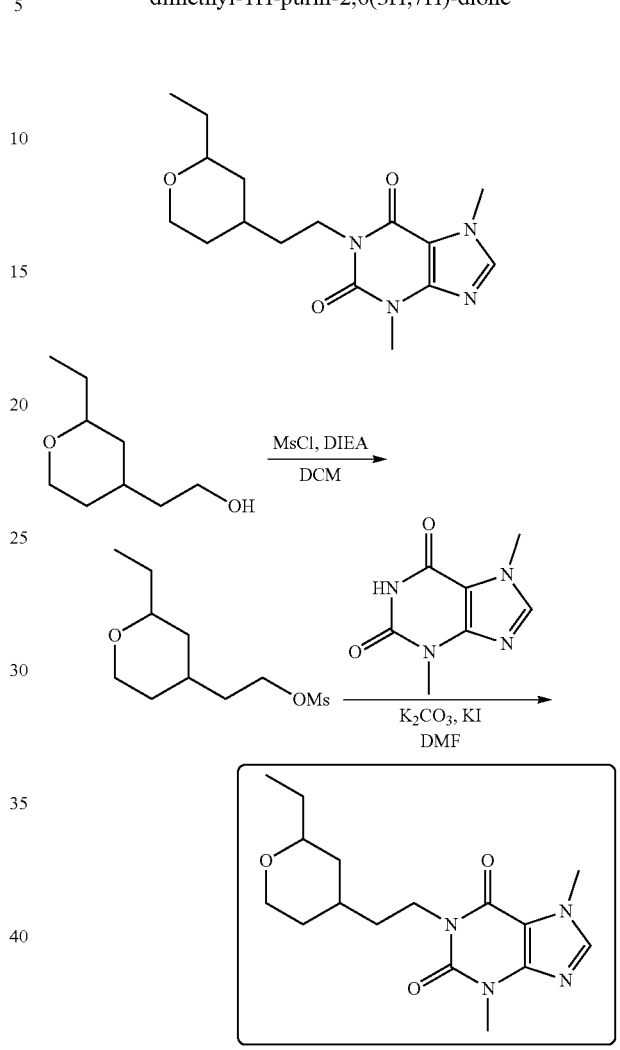

Step 1

2-(2-Methyltetrahydro-2H-pyran-4-yl)ethyl methanesulfonate 2-(2-Methyltetrahydro-2H-pyran-4-yl)ethanol (100 mg, 0.630 mmol) and N,N-diisopropylethylamine (122 mg, 0.940 mmol) were dissolved in methylene chloride (20 mL), and then methanesulfonyl chloride (86.9 mg, 0.750 mmol) was added at 0° C. After stirring at 25° C. for 0.5 hour, the reaction solution was diluted by adding methylene chloride (20 mL), and washed with saturated sodium bicarbonate (30 mL×2). The organic phases were dried over anhydrous sodium sulfate for concentration to give 2-(2-methyltetrahydro-2H-pyran-4-yl)ethyl methanesulfonate (180 mg, yellow oil) with a yield of 100%.

Step 2

1-(2-(2-Methyltetrahydro-2H-pyran-4-yl)ethyl)-3,7-dimethyl-1H-purin-2,6(3H,7H)-dione 2-(2-Methyltetrahydro-2H-pyran-4-yl)ethyl methanesulfonate (180 mg, 0.760 mmol) was dissolved in N,N-dimethylformamide (10 mL), and then 3,7-dimethyl-1H-purin-2,6(3H,7H)-dione (146 mg, 0.800 mmol), potassium iodide (13.0 mg, 0.0800 mmol) and potassium carbonate (211 mg, 1.60 mmol) were added into the reaction solution under the condition of 25° C. The reaction solution was heated to 120° C., allowed for reaction for 2 hours, and then diluted by adding ethyl acetate (30 mL), followed by washing with saturated sodium bicarbonate (20 mL×2). The organic phases were dried over anhydrous sodium sulfate for concentration to obtain a yellow oil, which was separated and purified by high performance liquid chromatography to give 1-(2-(2-methyltetrahydro-2H-pyran-4-yl)ethyl)-3,7-dimethyl-1H-purin-2,6(3H,7H)-dione (50.0 mg) with a yield of 20%.

$^1$H NMR: (400 MHz, Methanol-d$_4$) δ7.87 (s, 1H), 4.05-3.96 (m, 6H), 3.54-3.19 (m, 5H), 1.80-1.45 (m, 8H), 0.98-0.92 (m, 4H). MS-ESI calculated value: [M+H]$^+$ 321; measured value: 321.

Example 17

3,7-Dimethyl-1-(2-morpholinoethyl)-purin-2,6-dione

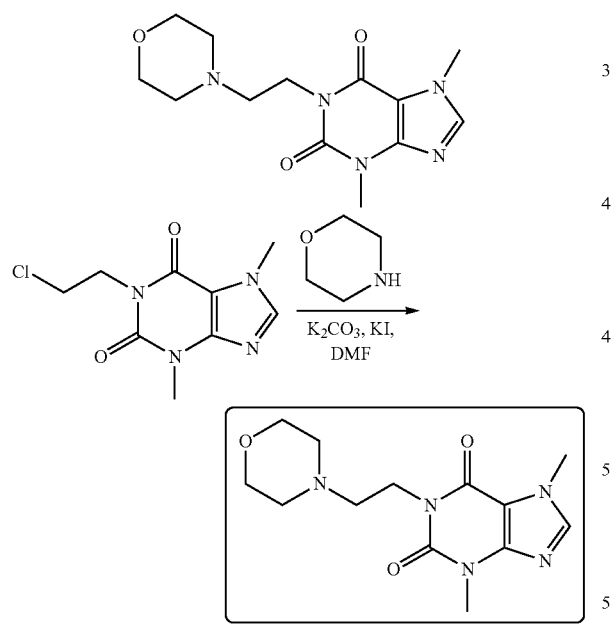

At room temperature, potassium carbonate (138 mg, 1.03 mmol) and potassium iodide (86.3 mg, 0.517 mmol) were added into the acetonitrile solution (2 mL) of the mixture of 1-(3-chloropropyl)-3,7-dimethyl-purin-2,6(3H,7H)-dione (71.9 mg, 0.826 mmol) and morpholine (50.0 mg, 0.207 mmol). The reaction solution was stirred at 90° C. for 4 hours. The reaction was quenched by adding water (5 mL), followed by extraction with ethyl acetate (5 mL×3). The organic phases were washed with saturated brine, dried over anhydrous sodium sulfate and then concentrated under reduced pressure. The concentrate was separated and purified by preparative high performance liquid chromatography to give 3,7-dimethyl-1-(2-morpholinoethyl)-purin-2,6-dione (15.0 mg) with a yield of 25%. $^1$H NMR: (400 MHz, Methonal-d$_4$) δ7.86 (s, 1H), 4.16 (t, J=6.4 Hz, 2H), 3.97 (s, 3H), 3.68-3.65 (m, 4H), 3.52 (s, 3H), 2.65-2.57 (m, 6H). MS-ESI calculated value: [M+H]$^+$ 294; measured value: 294.

Example 18

((-4-Methoxyphenyl)methyl)-3,7-dimethyl-1H-purin-2,6-(3H,7H)-dione

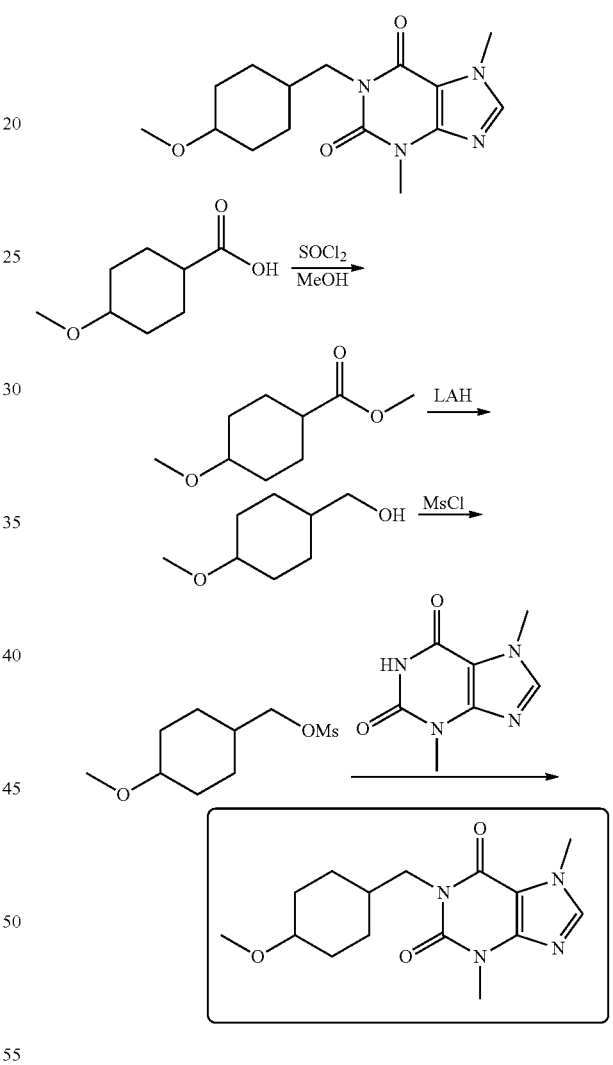

Step 1

4-Methoxycyclohexanecarboxylate

4-Methoxycyclohexanecarboxylic acid (300 mg, 1.90 mmol) was dissolved in methanol (7 mL), and then thionyl chloride (1.13 g, 9.50 mmol) was added slowly at 0° C. The reaction solution was stirred at room temperature for 12 hours. The reaction solution was concentrated under reduced pressure to give a crude product 4-methoxycyclohexanecarboxylate (283 mg, yellow oily) with a yield of 86%.

¹H NMR: (400 MHz, Methonal-d₄) δ3.65 (s, 3H), 3.41-3.35 (m, 1H), 3.30 (s, 3H), 2.44-2.38 (m, 1H), 1.84-1.75 (m, 4H), 1.67-1.54 (m, 4H)

Step 2

(4-Methoxycyclohexyl)methanol

Lithium aluminum hydride (92.8 mg, 2.45 mmol) was slowly added into the tetrahydrofuran (7 mL) containing methyl-4-methoxycyclohexanecarboxylic acid (280 mg, 1.63 mmol) at 0° C. under the protection of nitrogen. The reaction solution was stirred at room temperature for 4 hours, and then cooled to 0° C. in an ice-water bath. Water (0.1 mL), 15% sodium hydroxide (0.1 mL) and water (0.3 mL) was slowly added successively. The reaction solution was heated to room temperature, and then stirred for half an hour, followed by filtration. The filter cake was washed with tetrahydrofuran (8 mL×2) and the filtrate was concentrated under reduced pressure to give (4-methoxycyclohexyl)methanol (213 mg, yellow oily) with a yield of 91%. ¹H NMR: (400 MHz, Methonal-d₄) δ3.49-3.45 (m, 1H), 3.39-3.37 (m, 2H), 3.32 (s, 3H), 1.95-1.80 (m, 3H), 1.56-1.48 (m, 4H), 1.36-1.27 (m, 2H).

Step 3

(4-Methoxycyclohexyl)methyl methanesulfonate (4-Methoxycyclohexyl)methanol (210 mg, 1.46 mmol) and triethylamine (443 mg, 4.38 mmol) were dissolved in methylene chloride (7 mL), and then methanesulfonyl chloride (250 mg, 2.19 mmol) was added slowly at 0° C. The reaction solution was stirred overnight at room temperature, followed by adding water, and extraction with methylene chloride (50 mL×3). The organic phases were washed with saturated brine (25 mL×2), dried over anhydrous sodium sulfate, and then filtered. The filtrate was concentrated under reduced pressure to give a product which was then purified by silica gel column chromatography (5:1 petroleum ether/ethyl acetate, Rf=0.4) to give a product (4-methoxycyclohexyl)methyl methanesulfonate (240 mg, yellow oily) with a yield of 74%. ¹H NMR: (400 MHz, Methonal-d₄) δ4.07 (d, J=6.4 Hz, 2H), 3.51-3.47 (m, 1H), 3.32 (s, 3H), 3.07 (s, 3H), 1.98-1.92 (m, 2H), 1.85-1.78 (m, 1H), 1.63-1.36 (m, 6H).

Step 4

1((-4-Methoxycyclohexyl)methyl)-3,7-dimethyl-1H-purin-2,6-(3H,7H)-dione (4-Methoxycyclohexyl)methyl methanesulfonate (240 mg, 1.08 mmol), 3,7-dimethyl-1H-purin-2,6-(3H,7H)-dione (233 mg, 1.30 mmol) and potassium iodide (17.9 mg, 0.108 mmol) were dissolved in N,N-dimethylformamide (5 mL), and then potassium carbonate (298 mg, 2.16 mmol) was added. The reaction solution was heated and refluxed at 130° C. for 4 hours. Then, the reaction solution was cooled to room temperature and then filtered. The filtrate was concentrated under reduced pressure to give a product which was then purified by preparative high performance liquid chromatography to give a product 1((-4-methoxycyclohexyl)methyl)-3,7-dimethyl-1H-purin-2,6-(3H,7H)-dione (67.0 mg) with a yield of 20%. ¹H NMR: (400 MHz, Methonal-d₄) δ7.88 (s, 1H), 3.99 (s, 3H), 3.89 (d, J=7.2 Hz, 2H), 3.54 (s, 3H), 3.47-3.42 (m, 1H), 3.32 (s, 3H), 1.94-1.87 (m, 3H), 1.47-1.39 (m, 6H). MS-ESI calculated value: [M+H]⁺ 307; measured value: 307.

Example 19

3-Methyl-1-((3-methyloxetan-3-yl)methyl)-7-(2,2,2-trifluoroethyl)-1H-purin-2,6(3H,7H)-dione

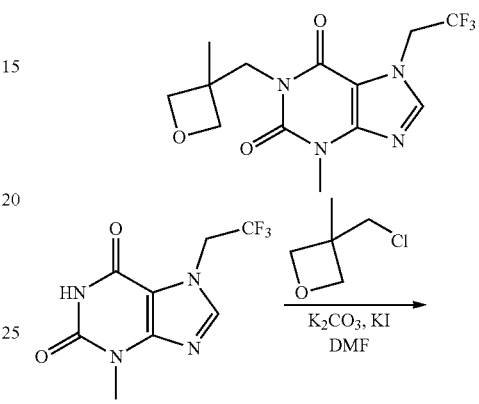

Step 1

3-Methyl-1-((3-methyloxetan-3-yl)methyl)-7-(2,2,2-trifluoroethyl)-1H-purin-2,6 (3H,7H)-dione 3-Methyl-7-(2,2,2-trifluoroethyl)-1H-purin-2,6(3H,7H)-dione (200 mg, 0.806 mmol), 3-(chloromethyl)-3-methyloxetane (97.2 mg, 0.806 mmol) and potassium iodide (13.4 mg, 0.0806 mmol) were dissolved in N,N-dimethylformamide (5 mL), and then potassium carbonate (223 mg, 1.61 mmol) was added. The reaction solution was heated and refluxed at 130° C. for 2.5 hours. Then, the reaction solution was cooled to 25° C. and then filtered. The filtrate was concentrated under reduced pressure to give a product which was then purified by preparative high performance liquid chromatography to give a product 3-methyl-1-((3-methyloxetan-3-yl)methyl)-7-(2,2,2-trifluoroethyl)-1H-purin-2,6 (3H,7H)-dione (48.0 mg) with a yield of 18%. ¹H NMR: (400M Hz, Methonal-d₄) δ8.09 (s, 1H), 5.25-5.18 (m, 2H), 4.75 (d, J=6.4 Hz, 2H), 4.23 (d, J=6.4 Hz, 2H), 4.15 (s, 2H), 3.56 (s, 3H), 1.35 (s, 3H).

MS-ESI calculated value: [M+H]⁺ 333; measured value: 333.

Example 20

1-(2-((2R,6R)-2,6-dimethyltetrahydro-2H-pyran-4-yl)ethyl)-3-methyl-7-(2,2,2-trifluoroethyl)-1H-purin-2,6 (3H,7H)-dione

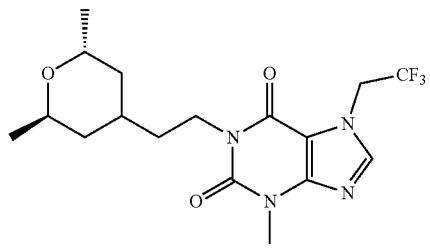

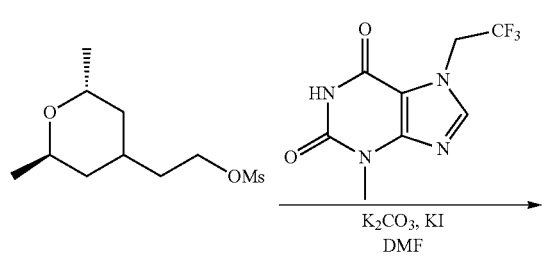

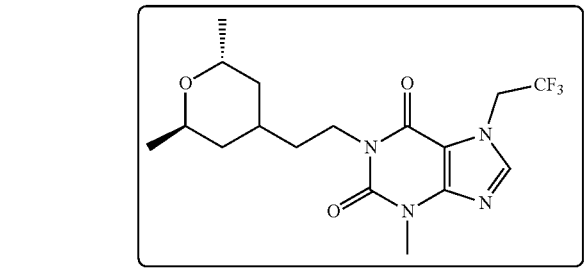

3-Methyl-7-(2,2,2-trifluoroethyl)-1H-purin-2,6(3H,7H)-dione (100 mg, 0.4 mmol), potassium iodide (7.0 mg, 0.040 mmol) and potassium carbonate (165 mg, 1.20 mmol) were dissolved in N,N-dimethylformamide (3 mL). The reaction solution was heated to 130° C. and allowed for reaction for 1 hour. 2-((2S,6S)-2,6-dimethyltetrahydro-2H-pyran-4-yl)ethyl methanesulfonate (50.0 mg, 0.200 mmol) was then added, and the reaction was continued at 130° C. 2.5 hours. The reaction solution was filtered directly and the filtrate was concentrated under reduced pressure. The crude product obtained was purified by preparative high performance liquid chromatography to give a product 1-(2-((2R,6R)-2,6-dimethyltetrahydro-2H-pyran-4-yl)ethyl)-3-methyl-7-(2,2,2-trifluoroethyl)-1H-purin-2,6 (3H,7H)-dione (68.0 mg) with a yield of 87%. $^1$H NMR: (400 MHz, Methonal-$d_4$) δ8.08 (s, 1H), 5.27-5.21 (m, 2H), 4.22-4.15 (m, 1H), 4.10-4.03 (m, 2H), 3.80-3.75 (m, 1H), 3.57 (s, 3H), 1.95-1.30 (m, 7H) 1.28 (d, J=6.8 Hz, 3H), 1.12 (d, J=6.8 Hz, 3H). MS-ESI calculated value: [M+H]$^+$ 389; measured value: 389.

Example 21

1-(2-((2R,6R)-2,6-dimethyltetrahydro-2H-pyran-4-yl)ethyl)yl-7-isopropyl-3-methyl-1H-purin-2,6(3H,7H)-dione

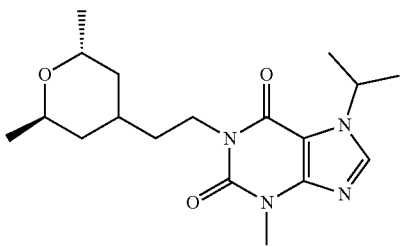

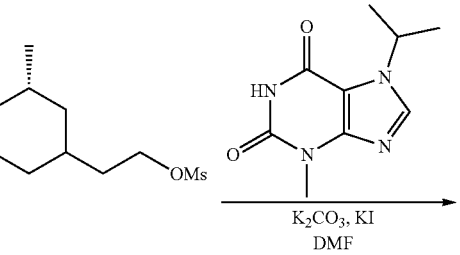

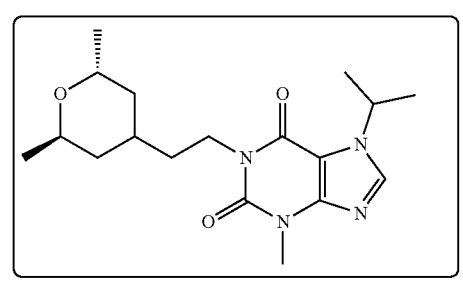

2-((2S,6S)-2,6-dimethyltetrahydro-2H-pyran-4-yl)ethyl methanesulfonate (100 mg, 0.424 mmol), 7-isopropyl-3-methyl-1H-purin-2,6(3H,7H)-dione (100 mg, 0.466 mmol), potassium iodide (7.4 mg, 0.047 mmol) and potassium carbonate (109 mg, 0.790 mmol) were dissolved in anhydrous N,N-dimethylformamide (3 mL). The reaction solution was heated to 120° C. and stirred for 3 hours. The reaction solution was cooled to 20° C. and then filtered. The filtrate was separated and purified by preparative high performance liquid chromatography to give 1-(2-((2R,6R)-2,6-dimethyltetrahydro-2H-pyran-4-yl)ethyl)yl-7-isopropyl-3-methyl-1H-purin-2,6(3H,7H)-dione (70.0 mg) with a yield of 46%.

$^1$H NMR: (400 MHz, Methonal-$d_4$) δ8.92 (s, 1H), 5.21-5.15 (m, 1H), 4.21-4.09 (m, 1H), 4.08-4.06 (m, 2H), 4.05-4.04 (m, 1H), 3.58 (s, 3H), 1.86-1.80 (m, 1H), 1.68-1.66 (m, 2H), 1.65-1.64 (m, 6H), 1.57-1.55 (m, 2H), 1.54-1.52 (m, 1H), 1.30-1.28 (m, 3H), 1.13-1.12 (m, 3H), 0.90-0.87 (m, 1H).

MS-ESI calculated value: [M+H]$^+$ 349; measured value: 349.

Example 22

7-(Cyclopropylmethyl)-3-methyl-1-((3-methyloxetan-3-yl)methyl)-1H-purin-2,6(3H,7H)-dione

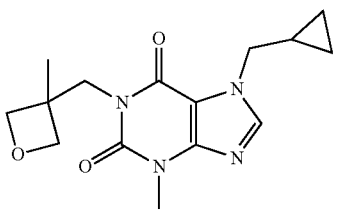

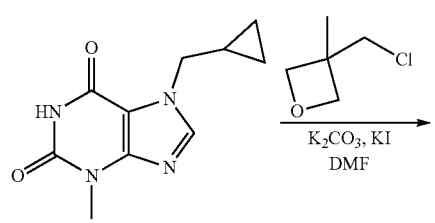

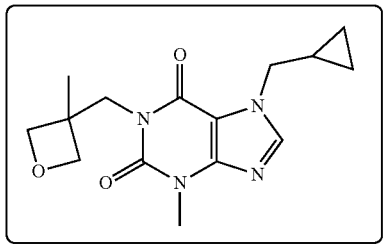

Step 1

7-(Cyclopropylmethyl)-3-methyl-1-((3-methyloxetan-3-yl)methyl)-1H-purin-2,6 (3H,7H)-dione 7-(Cyclopropylmethyl)-3-methyl-1H-purin-2,6(3H,7H)-dione (250 mg, 1.14 mmol), 3-(chloromethyl)-3-methyloxetane (137 mg, 1.14 mmol) and potassium iodide (18.9 mg, 0.114 mmol) were dissolved in N,N-dimethylformamide (5 mL), and then potassium carbonate (315 mg, 2.28 mmol) was added. The reaction solution was heated and refluxed at 130° C. for 2.5 hours. Then, the reaction solution was cooled to 25° C. and then filtered. The filtrate was concentrated under reduced pressure to give a product which was then purified by preparative high performance liquid chromatography to give a product 7-(cyclopropylmethyl)-3-methyl-1-((3-methyloxetan-3-yl)methyl)-1H-purin-2,6(3H, 7H)-dione (55.0 mg) with a yield of 16%. $^1$H NMR: (400M Hz, Methonal-$d_4$) δ8.01 (s, 1H), 4.76 (d, J=6.4 Hz, 2H), 4.24-4.18 (m, 4H), 4.14 (s, 2H), 3.55 (s, 3H), 1.39-1.33 (m, 4H), 0.62-0.56 (m, 2H), 0.48-0.43 (m, 2H). MS-ESI calculated value: [M+H]$^+$ 305; measured value: 305.

Example 23

7-(Cyclopropylmethyl-1-(2-((2R,6R)-2,6-dimethyltetrahydro-2H-pyran-4-yl)ethyl-3-methyl-1H-purin-2,6(3H,7H)-dione

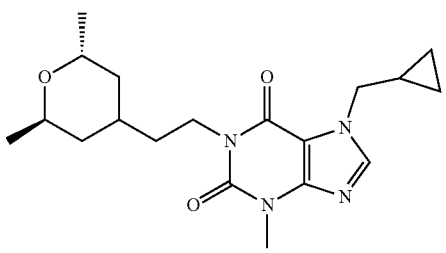

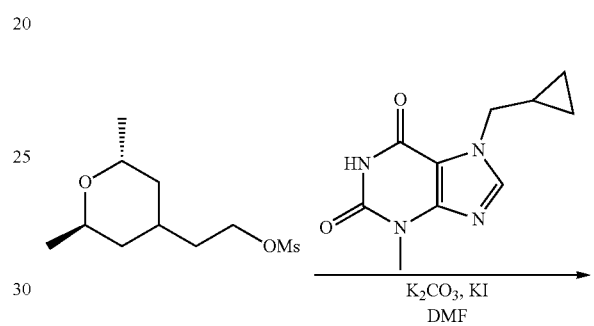

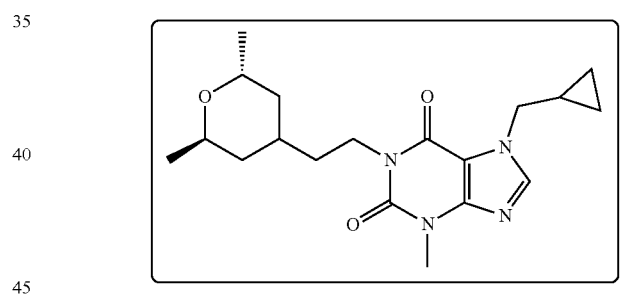

((2S,6S)-2,6-dimethyltetrahydro-2H-pyran-4-yl)ethyl methanesulfonate (100 mg, 0.424 mmol) and 7-(cyclopropylmethyl)-3-methyl-1H-purin-2,6(3H,7H)-dione (102 mg, 0.466 mmol) were dissolved in N,N-dimethylformamide (3 mL), and then potassium carbonate (109 mg, 0.790 mmol) and potassium iodide (7.4 mg, 0.047 mmol) were added under the protection of nitrogen. The reaction solution was heated to 120° C. and stirred for 3 hours. After being cooled to 20° C., the mixture was filtered. The filtrate was separated and purified by preparative high performance liquid chromatography to give 7-(cyclopropylmethyl)-1-(2-((2R,6R)-2,6-dimethyltetrahydro-2H-pyran-4-yl)ethyl)-3-methyl-1H-purin-2,6(3H,7H)-dione (70.0 mg) with a yield of 46%.

$^1$H NMR: (400 MHz, Methonal-$d_4$) δ8.02 (s, 1H), 4.25-4.21 (m, 3H), 4.20-4.19 (m, 2H), 4.08-4.02 (m, 1H), 3.55 (s, 3H), 1.87-1.80 (m, 1H), 1.66-1.56 (m, 2H), 1.54-1.50 (m, 2H), 1.42-1.40 (m, 2H), 1.29-1.27 (m, 3H), 1.13-1.12 (m, 3H), 0.89-0.86 (m, 1H), 0.63-0.60 (m, 2H), 0.49-0.47 (m, 2H).

MS-ESI calculated value: [M+H]$^+$ 361; measured value: 361.

Example 24

7-(Cyclopropylmethyl)-1-((4-methoxycyclohexyl)methyl)-3-methyl-purin-2,6-dione

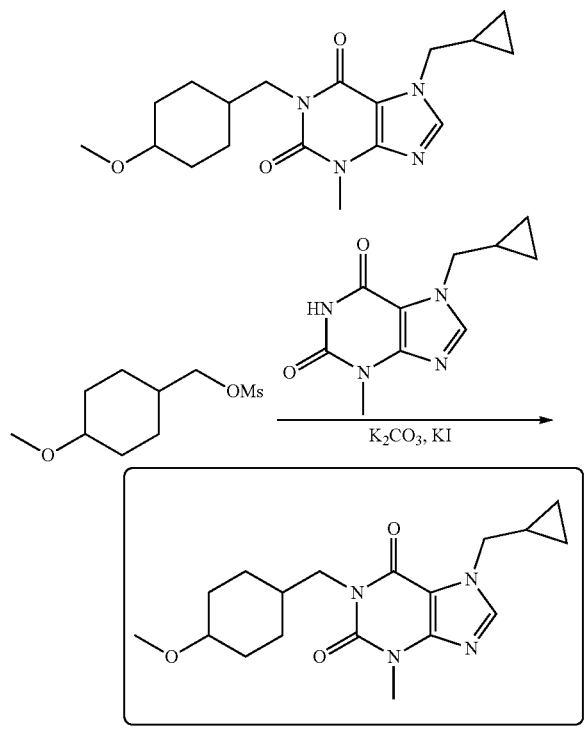

Step 1

7-(Cyclopropylmethyl)-1-((4-methoxycyclohexyl)methyl)-3-methyl-purin-2,6-dione (4-Methoxycyclohexyl)methyl methanesulfonate (30.0 mg, 0.135 mmol), 7-(cyclopropylmethyl)-3-methyl-purin-2,6-dione (26.8 mg, 0.121 mmol), potassium iodide (2.2 mg, 0.014 mmol) and potassium carbonate (37.3 mg, 0.269 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 7-(cyclopropylmethyl)-1-((4-methoxycyclohexyl)methyl)-3-methyl-purin-2,6-dione (20.0 mg) with a yield of 43%. $^1$H NMR: (400 MHz, Methonal-$d_4$) δ8.01 (s, 1H), 4.20 (d, J=7.2 Hz, 2H), 3.88 (d, J=16.0 Hz, 2H), 3.56 (s, 3H), 3.34 (s, 3H), 3.17-3.14 (m, 1H), 2.09-2.06 (m, 2H), 1.75-1.73 (m, 3H), 1.41-1.39 (m, 1H), 1.34-1.10 (m, 4H), 0.63-0.61 (m, 2H), 0.48-0.47 (m, 2H).

MS-ESI calculated value: [M+H]$^+$ 347; measured value: 347.

Example 25

7-Isobutyl-3-methyl-1-((3-methyloxetan-3-yl)methyl)-1H-purin-2,6(3H,7H)-dione

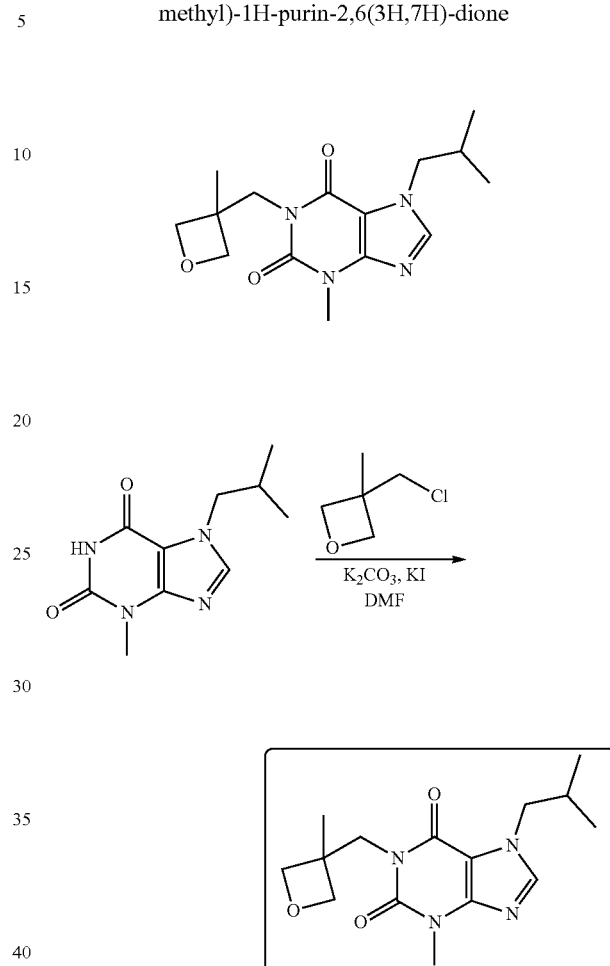

Step 1

7-Isobutyl-3-methyl-1-((3-methyloxetan-3-yl)methyl)-1H-purin-2,6(3H,7H)-dione 7-Isobutyl-3-methyl-1H-purin-2,6(3H,7H)-dione (200 mg, 0.900 mmol), 3-(chloromethyl)-3-methyloxetane (109 mg, 0.900 mmol) and potassium iodide (14.9 mg, 0.0900 mmol) were dissolved in N,N-dimethylformamide (5 mL), and then potassium carbonate (249 mg, 1.80 mmol) was added. The reaction solution was heated and refluxed at 130° C. for 2.5 hours. Then, the reaction solution was cooled to 25° C. and then filtered. The filtrate was concentrated under reduced pressure to give a product which was then purified by preparative high performance liquid chromatography to give a product 7-isobutyl-3-methyl-1-((3-methyloxetan-3-yl)methyl)-1H-purin-2,6(3H,7H)-dione (34.0 mg) with a yield of 12%. $^1$H NMR: (400M Hz, Methonal-$d_4$) δ7.95 (s, 1H), 4.75 (d, J=1.2 Hz, 2H), 4.22 (d, J=6.4 Hz, 2H), 4.15-4.12 (m, 4H), 3.55 (s, 3H), 2.23-2.12 (m, 1H), 1.35 (s, 3H), 0.92 (d, J=6.8 Hz, 6H). MS-ESI calculated value: [M+H]$^+$ 307; measured value: 307.

Example 26

1-(2-((2R,6R)-2,6-dimethyltetrahydro-2H-pyran-4-yl)ethyl)-7-isobutyl-3-methyl-1H-purin-2,6(3H,7H)-dione

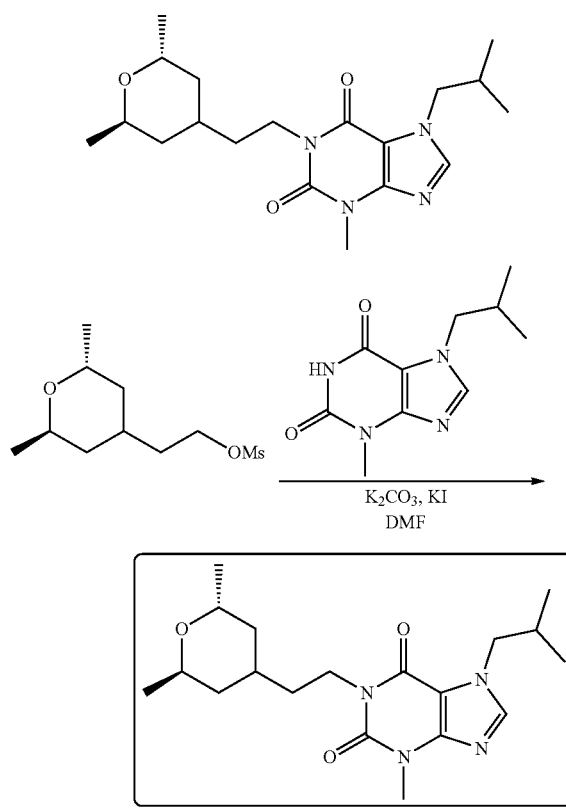

7-Isobutyl-3-methyl-1H-purin-2,6(3H,7H)-dione (90.0 mg, 0.400 mmol), potassium iodide (7.0 mg, 0.040 mmol) and potassium carbonate (165 mg, 1.20 mmol) were dissolved in N,N-dimethylformamide (3 mL). The reaction solution was heated to 130° C. and allowed for reaction for 1 hour. 2-((2S,6S)-2,6-dimethyltetrahydro-2H-pyran-4-yl) ethyl methanesulfonate (50.0 mg, 0.200 mmol) was then added, and the reaction was continued at 130° C. for 2.5 hours. The reaction solution was filtered directly and the filtrate was concentrated under reduced pressure. The crude product obtained was purified by preparative high performance liquid chromatography to give a product 1-(2-((2R,6R)-2,6-dimethyltetrahydro-2H-pyran-4-yl)ethyl)-7-isobutyl-3-methyl-1H-purin-2,6(3H, 7H)-dione (71.0 mg) with a yield of 97%.

$^1$H NMR: (400 MHz, Methonal-$d_4$) δ7.93 (s, 1H), 4.24-3.98 (m, 5H), 3.86-3.78 (m, 1H), 3.55 (s, 3H), 2.26-2.16 (m, 1H), 1.79-1.77 (m, 1H), 1.72-1.65 (m, 1H), 1.60-1.47 (m, 2H), 1.45-1.38 (m, 1H), 1.28 (d, J=6.8 Hz, 3H), 1.12 (d, J=6.8 Hz, 3H), 0.94-0.88 (m, 8H). MS-ESI calculated value: [M+H]$^+$ 363; measured value: 363.

Example 27

4-Methyl-6-((3-methyloxetan-3-yl)methyl)-1-(2,2,2-trifluoroethyl)-pyrazolo[4,3-d]pyrimidin-5,7-dione

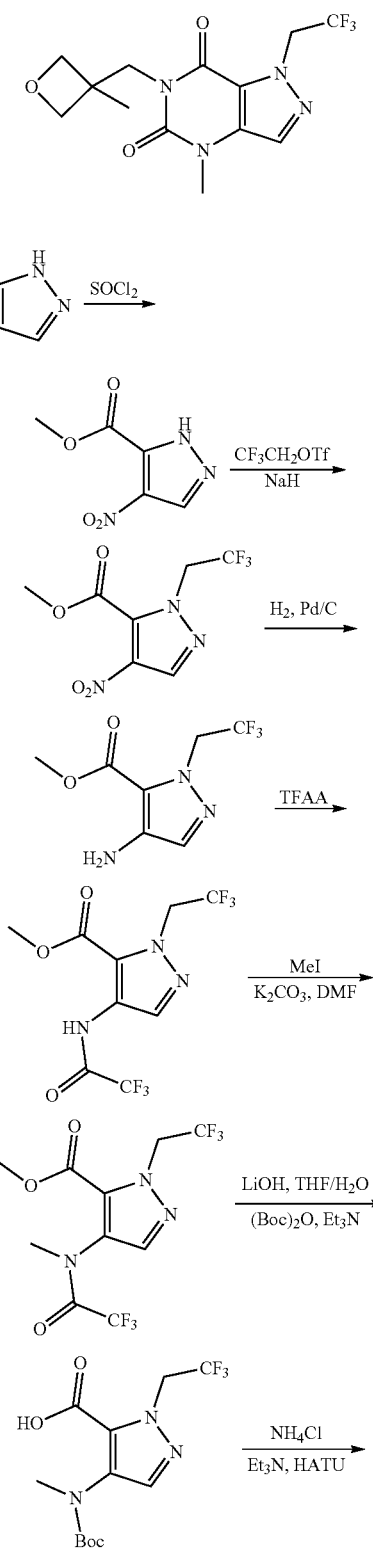

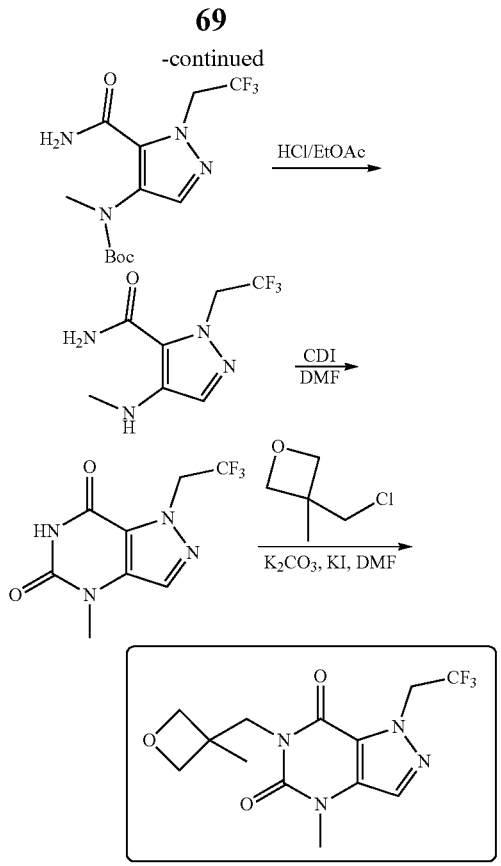

Step 1

Methyl 4-nitro-pyrazol-5-carboxylate

4-Nitro-pyrazol-5-carboxylic acid (45.0 g, 286 mmol) was dissolved in methanol (700 mL), and then thionyl chloride (102 g, 859 mmol) was added dropwise at 0° C. The reaction solution was allowed for reaction at 25° C. while stirring for 18 hours. The reaction solution was concentrated under reduced pressure to give methyl 4-nitro-pyrazol-5-carboxylate (49.0 g, white solid) with a yield of 100%. $^1$H NMR: (400 MHz, CDCl$_3$) δ8.53 (s, 1H), 4.06 (s, 3H). MS-ESI calculated value: [M+H]$^+$ 172; measured value: 172.

Step 2

Methyl 4-nitro-1-(2,2,2-trifluoroethyl)-pyrazol-5-carboxylate

Methyl 4-nitro-pyrazol-5-carboxylate (25.0 g, 146 mmol) was dissolved in N,N-dimethylformamide (350 mL), and then sodium hydride (6.43 g, 161 mmol) was added in batches at 0° C. After reaction at 0° C. while stirring for 1 hour, 2,2,2-trifluoroethyl trifluoromethanesulfonate (33.9 g, 146 mmol) was added dropwise. The reaction solution was allowed for reaction at 25° C. while stirring for 18 hours. Then, water (1.2 L) was added into the reaction solution, and the reaction solution was extracted with ethyl acetate (300 mL×2). The organic phases were combined, washed with saturated brine (500 mL), dried over anhydrous sodium sulfate, and the filtered. The filtrate was concentrated under reduced pressure, and the residue was separated and purified by silica gel column chromatography (5:1 petroleum ether/ethyl acetate, Rf=0.3) to give methyl 4-nitro-1-(2,2,2-trifluoroethyl)-pyrazol-5-carboxylate (8.00 g, colorless oil) with a yield of 22%. $^1$H NMR: (400 MHz, CDCl$_3$) δ8.13 (s, 1H), 5.06 (q, J=8.0 Hz, 2H), 4.04 (s, 3H). MS-ESI calculated value: [M+H]$^+$ 254; measured value: 254.

Step 3

Methyl 4-amino-1-(2,2,2-trifluoroethyl)-pyrazol-5-carboxylate

Methyl 4-nitro-1-(2,2,2-trifluoroethyl)-pyrazol-5-carboxylate (7.50 g, 29.6 mmol) was dissolved in methanol (100 mL), and then dry palladium-carbon (palladium 10%, water 1%, 750 mg) was added. The reaction solution was allowed for reaction at room temperature for 3 hours under 40 psi hydrogen pressure. The reaction solution was filtered and then the filtrate was concentrated under reduced pressure to give methyl 4-amino-1-(2,2,2-trifluoroethyl)-pyrazol-5-carboxylate (6.30 g, similar white solid) with a yield of 95%.

$^1$H NMR: (400 MHz, CDCl$_3$) δ7.25 (s, 1H), 5.10 (q, J=8.4 Hz, 2H), 4.21 (s, 2H), 3.94 (s, 3H).

MS-ESI calculated value: [M+H]$^+$ 224; measured value: 224.

Step 4

Methyl 4-(2,2,2-trifluoroacetamide)-1-(2,2,2-trifluoroethyl)-pyrazol-5-carboxylate Methyl 4-amino-1-(2,2,2-trifluoroethyl)-pyrazol-5-carboxylate (6.30 g, 28.2 mmol) was dissolved in methylene chloride (100 mL), and then trifluoroacetic anhydride (8.89 g, 42.4 mmol) was added dropwise under the protection of nitrogen. The reaction solution was stirred at room temperature for 2 hours. The reaction was quenched by adding saturated sodium bicarbonate solution (100 mL), followed by extraction with methylene chloride (100 mL) and washing with saturated brine (50 mL). The organic phase was dried over anhydrous sodium sulfate and concentrated under reduced pressure to give methyl 4-(2,2,2-trifluoroacetamide)-1-(2,2,2-trifluoroethyl)-pyrazol-5-carboxylate (9.20 g crude product, yellow oil). $^1$H NMR: (400 MHz, CDCl$_3$) δ9.66 (s, 1H), 8.45 (s, 1H), 5.18 (q, J=8.0 Hz, 2H), 4.06 (s, 3H). MS-ESI calculated value: [M+H]$^+$ 320; measured value: 320.

Step 5

Methyl 4-(2,2,2-trifluoro-N-methylacetamide)-1-(2,2,2-trifluoroethyl)-pyrazol-5-carboxylate Methyl 4-(2,2,2-trifluoroacetamide)-1-(2,2,2-trifluoroethyl)-pyrazol-5-carboxylate (9.20 g, 28.8 mmol) was dissolved in N,N-dimethylformamide (50 mL), and then potassium carbonate (5.98 g, 43.3 mmol) was added. The reaction solution was heated to 80° C., allowed for reaction for 1 hour, and then cooled to room temperature, followed by adding iodomethane (6.14 g, 43.2 mmol). The reaction solution was stirred at room temperature for 18 hours. Water (300 mL) was added into the reaction solution, followed by extraction with ethyl acetate (100 mL×3). The organic phases were combined, washed with saturated brine (100 mL), dried over anhydrous sodium sulfate and then filtered. The filtrate was concentrated under reduced pressure to give methyl 4-(2,2,2-trifluoro-N-methylacetamide)-1-(2,2,2-trifluoroethyl)-pyrazol-5-carboxylate (9.80 g crude product, yellow oil). $^1$H NMR: (400 MHz, CDCl$_3$) δ7.65 (s, 1H), 5.45-5.15 (m, 2H), 3.93 (s, 3H), 3.29 (s, 3H). MS-ESI calculated value: [M+H]$^+$ 334; measured value: 334.

Step 6

4-[(Tert-butoxycarbonyl)(methyl)amino]-1-(2,2,2-trifluoroethyl)-pyrazol-5-carboxylic acid Methyl 4-(2,2,2-trifluoro-N-methylacetamide)-1-(2,2,2-trifluoroethyl)-pyrazol-5-carboxylate (9.90 g, 29.7 mmol) was dissolved in tetrahydrofuran (40 mL) and water (40 mL), and then lithium hydroxide monohydrate (6.23 g, 0.149 mol) was added, allowing for reaction at room temperature while stirring for 18 hours. After adding di-tert-butyl dicarbonate (13.0 g, 59.4 mmol), the reaction solution was allowed for reaction at room temperature for 6 hours. The reaction solution was concentrated under reduced pressure, followed by adjusting the pH value to pH=4 with 2N hydrochloric acid solution, and then filtered. The filter cake was dried to give 4-[(tert-butoxycarbonyl)(methyl)amino]-1-(2,2,2-trifluoroethyl)-pyrazol-5-carboxylic acid (8.00 g, white solid) with a yield of 83%. $^1$H NMR: (400 MHz, CDCl$_3$) δ7.58 (s, 1H), 5.25 (q, J=8.0 Hz, 2H), 3.27 (s, 3H), 1.42 (s, 9H). MS-ESI calculated value: [M+H]$^+$ 324; measured value: 324.

Step 7

4-[(Tert-butoxycarbonyl)(methyl)amino]-1-(2,2,2-trifluoroethyl)-pyrazol-5-carboxamide 4-[Tert-butoxycarbonyl(methyl)amino]-2-(2,2,2-trifluoroethyl)pyrazole-5-carboxylic acid, 2-(7-azobenzotriazole)-tetramethyluronium hexafluorophosphate (13.8 g, 36.2 mmol) and ammonium chloride (2.98 g, 55.7 mmol) were dissolved in methylene chloride (120 mL), and then triethylamine (4.23 g, 41.8 mmol) was added dropwise at room temperature. The reaction solution was stirred at room temperature for 18 hours. Then, water (100 mL) was added into the reaction solution, followed by extraction with methylene chloride (100 mL×2). The organic phases were combined, washed successively with saturated sodium bicarbonate (50 mL) and saturated brine (50 mL), dried over anhydrous sodium sulfate and then filtered. The filtrate was concentrated under reduced pressure, the residue was treated with ethanol (20 mL) to give 4-[(tert-butoxycarbonyl)(methyl)amino]-1-(2,2,2-trifluoroethyl)-pyrazol-5-carboxamide (6.00 g, white solid) with a yield of 67%. $^1$H NMR: (400 MHz, CDCl$_3$) δ7.54 (s, 1H), 5.25 (q, J=8.0 Hz, 2H), 3.22 (s, 3H), 1.48 (s, 9H). MS-ESI calculated value: [M+H]$^+$ 323; measured value: 323.

Step 8

4-(Methylamino)-2-(2,2,2-trifluoroethyl)pyrazole-5-carboxamide

4-[(Tert-butoxycarbonyl)(methyl)amino]-1-(2,2,2-trifluoroethyl)-pyrazol-5-carboxamide (5.00 g, 15.51 mmol) was dissolved in hydrochloric acid-ethyl acetate (50 mL). After reacting at room temperature while stirring for 18 hours, the reaction solution was concentrated under reduced pressure. The residue was dissolved by methanol (50 mL), and then potassium carbonate (5.36 g, 38.8 mmol) was added. The reaction solution was stirred at room temperature for 2 hours, and then concentrated under reduced pressure. The residue was extracted with methylene chloride (100 mL) and filtered. The filtrate was spin-dried to give 4-(methylamino)-2-(2,2,2-trifluoroethyl)pyrazole-5-carboxamide (2.90 g, white solid) with a yield of 84%. $^1$H NMR: (400 MHz, Methanol-d$_4$) δ7.93 (s, 1H), 5.26 (q, J=8.4 Hz, 2H), 3.13 (s, 3H).

MS-ESI calculated value: [M+H]$^+$ 223; measured value: 223.

Step 9

4-Methyl-1-(2,2,2-trifluoroethyl)-pyrazolo[4,3-d]pyrimidin-5,7-dione 4-(Methylamino)-2-(2,2,2-trifluoroethyl)pyrazole-5-carboxamide (2.70 g, 12.2 mmol) and 1,1-carbonyldiimidazole (3.94 g, 24.3 mmol) were dissolved in N,N-dimethylformamide (20 mL). The reaction solution was heated to 140° C. and allowed for reaction for 1 hour. After cooling to room temperature, water (100 mL) was added into the reaction solution. The solid was precipitated and collected by filtration. The filter cake was dried to give 4-methyl-1-(2,2,2-trifluoroethyl)-pyrazolo[4,3-d]pyrimidin-5,7-dione (1.80 g, white solid) with a yield of 60%. $^1$H NMR: (400 MHz, DMSO-d$_6$) δ11.56 (s, 1H), 7.95 (s, 1H), 5.35 (q, J=8.8 Hz, 2H), 3.33 (s, 3H). MS-ESI calculated value: [M+H]$^+$ 249; measured value: 249.

Step 10

4-Methyl-6-((3-methyloxetan-3-yl)methyl)-1-(2,2,2-trifluoroethyl)-pyrazolo[4,3-d]pyrimidin-5,7-dione 4-Methyl-1-(2,2,2-trifluoroethyl)pyrazolo[4,3-d]pyrimidin-5,7-dione (70.0 mg, 0.282 mmol) was dissolved in N,N-dimethylformamide (2 mL), and then 3-(chloromethyl)-3-methyl-oxetane (40.8 mg, 0.338 mmol), potassium carbonate (78.0 mg, 0.564 mmol) and potassium iodide (56.2 mg, 0.338 mmol) were added. The reaction solution was heated to 120° C. and then stirred for 1 hour. The reaction solution was cooled to room temperature, and the filtered. The filtrate was concentrated under reduced pressure, the residue was purified by high performance liquid chromatography to give 4-methyl-6-[(3-methyloxetan-3-yl)methyl]-1-(2,2,2-trifluoroethyl)pyrazolo[4,3-d]pyrimidin-5,7-di one (30.0 mg) with a yield of 32%. $^1$H NMR: (400 MHz, CDCl$_3$) δ7.57 (s, 1H), 5.21 (q, J=8.0 Hz, 2H), 4.72 (d, J=6.0 Hz, 2H), 4.26 (d, J=6.0 Hz, 2H), 4.16 (s, 2H), 3.52 (s, 3H), 1.40 (s, 3H).

MS-ESI calculated value: [M+H]$^+$ 333; measured value: 333.

Example 28

6-((3-Ethyloxetan-3-yl)methyl)-4-methyl-1-(2,2,2-trifluoroethyl)-pyrazolo[4,3-d]pyrimidin-5,7-dione

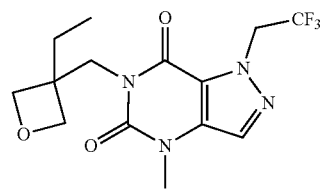

-continued

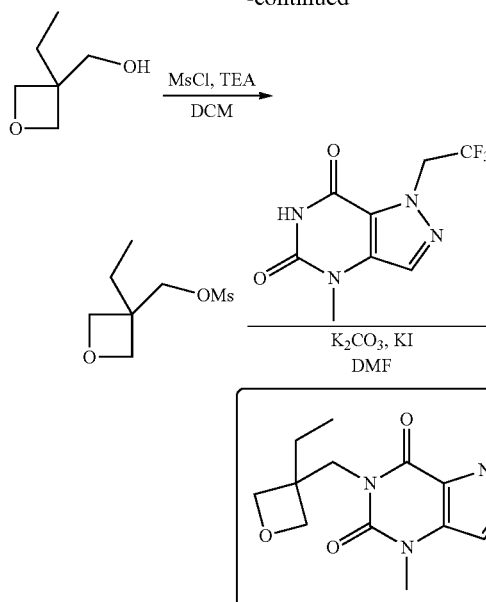

Step 1

(3-Ethyloxetan-3-yl)methyl methanesulfonate (3-Ethyloxetan-3-yl)methanol (1.00 g, 8.61 mmol) and triethylamine (1.74 g, 17.2 mmol) were dissolved in anhydrous methylene chloride (15 mL), and then methanesulfonyl chloride (1.28 g, 11.2 mmol) was slowly added at 0° C. under the protection of nitrogen. The reaction solution was stirred at 0° C. for 1 hour. The reaction was quenched by adding saturated sodium bicarbonate solution (50 mL), followed by extraction with methylene chloride (20 mL×2). The organic phases were combined, washed with saturated sodium chloride solution (50 mL×2), dried over anhydrous magnesium sulfate, and then filtered. The filtrate was concentrated under reduced pressure to give (3-ethyloxetan-3-yl)methyl methanesulfonate (1.30 g, yellow oily) with a yield of 78%. MS-ESI calculated value: $[M+H]^+$ 195; measured value: 195.

Step 2

6-((3-Ethyloxetan-3-yl)methyl)-4-methyl-1-(2,2,2-trifluoroethyl)-pyrazolo[4,3-d]pyrimidin-5,7-dione 4-Methyl-1-(2,2,2-trifluoroethyl)pyrazolo[4,3-d]pyrimidin-5,7-dione (30.0 mg, 0.121 mmol), (3-ethyloxetan-3-yl) methyl methanesulfonate (35.2 mg, 0.181 mmol), potassium carbonate (33.2 mg, 0.242 mmol) and potassium iodide (4.0 mg, 0.024 mmol) were dissolved in N,N-dimethylformamide (10 mL). The reaction solution was heated to 120° C. and stirred for 3 hours. The reaction solution was cooled to room temperature, and poured into water (30 mL), followed by extraction with ethyl acetate (20 mL×3). The organic phases were combined, dried over anhydrous sodium sulfate, and then filtered. The filtrate was concentrate and the crude product was separated and purified by preparative high performance liquid chromatography to give 6-((3-ethyloxetan-3-yl)methyl)-4-methyl-1-(2,2,2-trifluoroethyl)-pyrazolo[4,3-d]pyrimidin-5,7-dione (10 mg) with a yield of 24%. $^1$H NMR: (400 MHz, Methonal-$d_4$) δ7.86 (s, 1H), 5.37-5.31 (m, 2H), 4.64 (d, J=6.4 Hz, 2H), 4.30 (d, J=6.4 Hz, 2H), 4.14 (s, 2H), 3.54 (s, 3H), 1.84-1.79 (m, 2H), 1.07 (t, J=7.2 Hz, 3H). MS-ESI calculated value: $[M+H]^+$ 347; measured value: 347.

Example 29

4-Methyl-6-((tetrahydrofuran-3-yl)methyl)-1-(2,2,2-trifluoroethyl)-pyrazolo[4,3-d]pyrimidin-5,7-dione

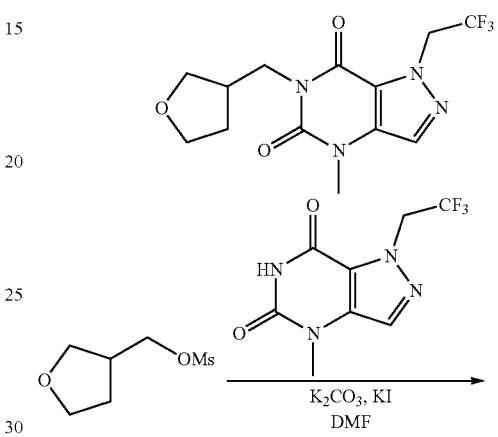

Step 1

4-Methyl-6-((tetrahydrofuran-3-yl)methyl)-1-(2,2,2-trifluoroethyl)-pyrazolo[4,3-d]pyrimidin-5,7-dione Tetrahydrofuran-3-yl-methyl methanesulfonate (30.0 mg, 0.166 mmol), 4-methyl-1-(2,2,2-trifluoroethyl)pyrazolo[4,3-d]pyrimidin-5,7-dione (41.3 mg, 0.166 mmol), potassium carbonate (46.0 mg, 0.333 mmol) and potassium iodide (5.5 mg, 0.033 mmol) were dissolved in N,N-dimethylformamide (5 mL). The reaction solution was heated to 120° C. and stirred for 3 hours. Then, the reaction solution was cooled to room temperature, and poured into water (20 mL), followed by extraction with ethyl acetate (20 mL×3). The organic phases were combined, dried over anhydrous sodium sulfate, and then filtered. The filtrate was concentrated and then separated and purified by preparative high performance liquid chromatography to give 4-methyl-6-((tetrahydrofuran-3-yl)methyl)-1-(2,2,2-trifluoroethyl)-pyrazolo[4,3-d]pyrimidin-5,7-dione (10.0 mg) with a yield of 18%. $^1$H NMR: (400 MHz, Methonal-$d_4$) δ7.83 (s, 1H), 5.38-5.30 (m, 2H), 4.10-4.04 (m, 2H), 3.92-3.87 (m, 1H), 3.78-3.75 (m, 2H), 3.64-3.62 (m, 1H), 3.52 (s, 3H), 2.76-2.72 (m, 1H), 2.04-2.01 (m, 1H), 1.79-1.72 (m, 1H). MS-ESI calculated value: $[M+H]^+$ 333; measured value: 333.

Example 30

6-((3-Ethyloxetan-3-yl)methyl)-4-methyl-1-(2,2,2-trifluoroethyl)-pyrazolo[4,3-d]pyrimidin-5,7-dione

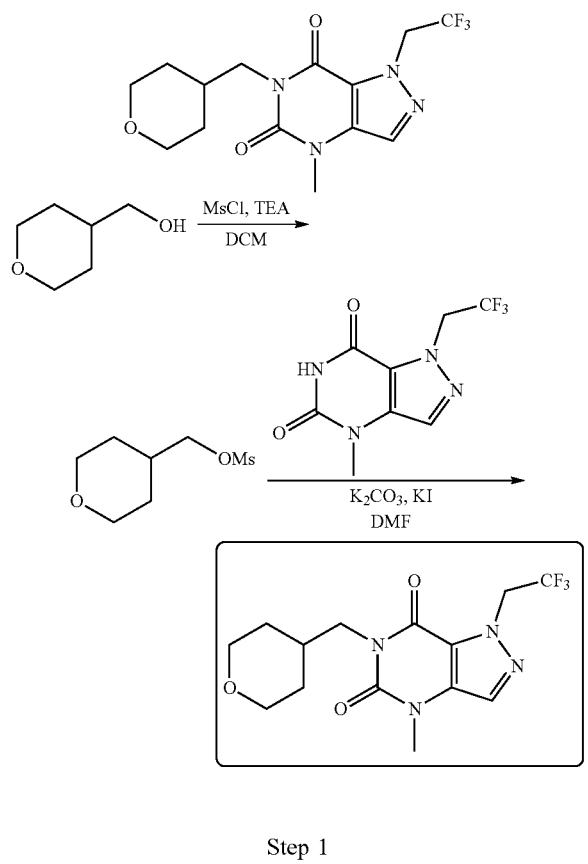

Step 1

(Tetrahydropyran-4-yl)methyl methanesulfonate

Tetrahydropyran-4-ylmethanol (1.00 g, 8.61 mmol) and triethylamine (1.74 g, 17.2 mmol) were dissolved in anhydrous methylene chloride (20 mL), and then methanesulfonyl chloride (1.28 g, 11.2 mmol) was slowly added at 0° C. under the protection of nitrogen. The reaction solution was stirred at 0° C. for 1 hour. The reaction was quenched by adding saturated sodium bicarbonate solution (50 mL), followed by extraction with methylene chloride (20 mL×2). The organic phases were combined, washed with saturated sodium chloride solution (50 mL×2), dried over anhydrous magnesium sulfate, and then filtered. The filtrate was concentrated under reduced pressure to give (tetrahydropyran-4-yl)methyl methanesulfonate (1.30 g, yellow oily) with a yield of 78%. MS-ESI calculated value: [M+H]$^+$ 195; measured value: 195.

Step 2

4-Methyl-6-((tetrahydropyran-4-yl)methyl)-1-(2,2,2-trifluoroethyl)-pyrazolo[4,3-d]pyrimidin-5,7-dione 4-Methyl-1-(2,2,2-trifluoroethyl)pyrazolo[4,3-d]pyrimidin-5,7-dione (30.0 mg, 0.121 mmol), (tetrahydropyran-4-yl)methyl methanesulfonate (35.2 mg, 0.181 mmol), potassium carbonate (33.2 mg, 0.242 mmol) and potassium iodide (4.0 mg, 0.024 mmol) were dissolved in N,N-dimethylformamide (10 mL). The reaction solution was heated to 120° C. and stirred for 3 hours. The reaction solution was cooled to room temperature, and poured into water (30 mL), followed by extraction with ethyl acetate (20 mL×3). The organic phases were combined, dried over anhydrous sodium sulfate, and then filtered. The filtrate was concentrated and then separated and purified by preparative high performance liquid chromatography to give 4-methyl-6-((tetrahydropyran-4-yl)methyl)-1-(2,2,2-trifluoroethyl)-pyrazolo[4,3-d]pyrimidin-5,7-dione (10.0 mg) with a yield of 24%. $^1$H NMR: (400 MHz, Methonal-d$_4$) δ7.80 (s, 1H), 5.33-5.27 (m, 2H), 3.93-3.89 (m, 4H), 3.49 (s, 3H), 3.36-3.34 (m, 2H), 2.08-2.05 (m, 1H), 1.57-1.53 (m, 2H), 1.44-1.37 (m, 2H). MS-ESI calculated value: [M+H]$^+$ 347; measured value: 347.

Example 31

4-Methyl-6-(2-(tetrahydropyran-4-yl)ethyl)-1-(2,2,2-trifluoroethyl)-pyrazolo[4,3-d]pyrimidin-5,7-dione

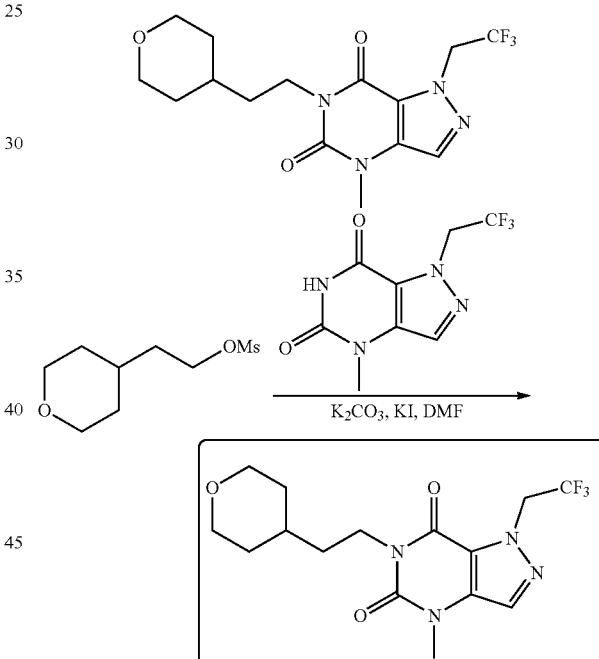

Step 1

4-Methyl-6-(2-(tetrahydropyran-4-yl)ethyl)-1-(2,2,2-trifluoroethyl)-pyrazolo[4,3-d]pyrimidin-5,7-dione 2-Tetrahydropyran-4-yl-ethyl methanesulfonate (50.0 mg, 0.240 mmol), 4-methyl-1-(2,2,2-trifluoroethyl)pyrazolo[4,3-d]pyrimidin-5,7-dione (59.6 mg, 0.240 mmol), potassium carbonate (66.4 mg, 0.480 mmol) and potassium iodide (7.9 mg, 0.048 mmol) were dissolved in N,N-dimethylformamide (5 mL). The reaction solution was heated to 120° C. and stirred for 3 hours. Then, the reaction solution was cooled to room temperature, and poured into water (20 mL), followed by extraction with ethyl acetate (20 mL×3). The organic phases were combined, dried over anhydrous sodium sulfate, and then filtered. The filtrate was concentrated and the crude product was separated and purified by preparative high performance liquid chromatography to give 4-methyl-6-(2-(tetrahydropyran-4-yl)ethyl)-1-(2,2,2-trifluoroethyl)-pyrazolo[4,3-d]pyrimidin-5,7-dione (20.0 mg) with a yield of 23%. $^1$H NMR: (400 MHz, Methonal-d$_4$) δ7.82 (s, 1H), 5.36-5.27 (m, 2H), 4.08-4.05 (m, 2H), 3.95-3.91 (m, 2H), 3.51 (s, 3H), 3.44-3.41 (m, 2H), 1.76-1.73 (m, 2H), 1.60-1.58 (m, 3H), 1.37-1.30 (m, 2H). MS-ESI calculated value: [M+H]$^+$ 361; measured value: 361.

Example 32

6-((4-Methoxycyclohexyl)methyl)-4-methyl-1-(2,2,2-trifluoroethyl)-pyrazolo[4,3-d]pyrimidin-5,7-dione

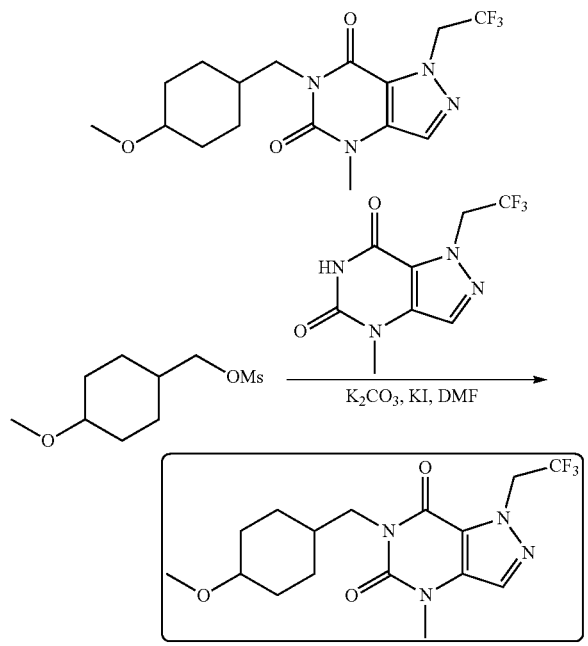

Step 1

6-((4-Methoxycyclohexyl)methyl)-4-methyl-1-(2,2,2-trifluoroethyl)-pyrazolo[4,3-d]pyrimidin-5,7-dione 4-Methyl-1-(2,2,2-trifluoroethyl)pyrazolo[4,3-d]pyrimidin-5,7-dione (50.0 mg, 0.201 mmol), ((4-methoxycyclohexyl)methyl methanesulfonate (44.8 mg, 0.201 mmol), potassium carbonate (55.7 mg, 0.403 mmol) and potassium iodide (6.7 mg, 0.040 mmol) were dissolved in N,N-dimethylformamide (5 mL). The reaction solution was heated to 120° C. and stirred for 3 hours. Then, the reaction solution was cooled to room temperature, and poured into water (20 mL), followed by extraction with ethyl acetate (20 mL×3). The organic phases were combined, dried over anhydrous sodium sulfate, and then filtered. The filtrate was concentrated and then was separated and purified by preparative high performance liquid chromatography to give 6-((4-methoxycyclohexyl)methyl)-4-methyl-1-(2,2,2-trifluoroethyl)-pyrazolo[4,3-d]pyrimidin-5,7-dione (20.0 mg) with a yield of 26%. $^1$H NMR: (400 MHz, Methonal-d$_4$) δ7.82 (s, 1H), 5.36-5.30 (m, 2H), 3.89 (d, J=6.8 Hz, 2H), 3.51 (s, 3H), 3.39 (s, 3H), 3.21-3.15 (m, 1H), 2.09-2.08 (m, 2H), 1.81-1.73 (m, 3H), 1.16-1.10 (m, 4H). MS-ESI calculated value: [M+H]$^+$ 375; measured value: 375.

Example 33

1-(Cyclopropylmethyl)-4-methyl-6-((3-methyloxetan-3-yl)methyl)-pyrazolo[4,3-d]pyrimidin-5,7-dione

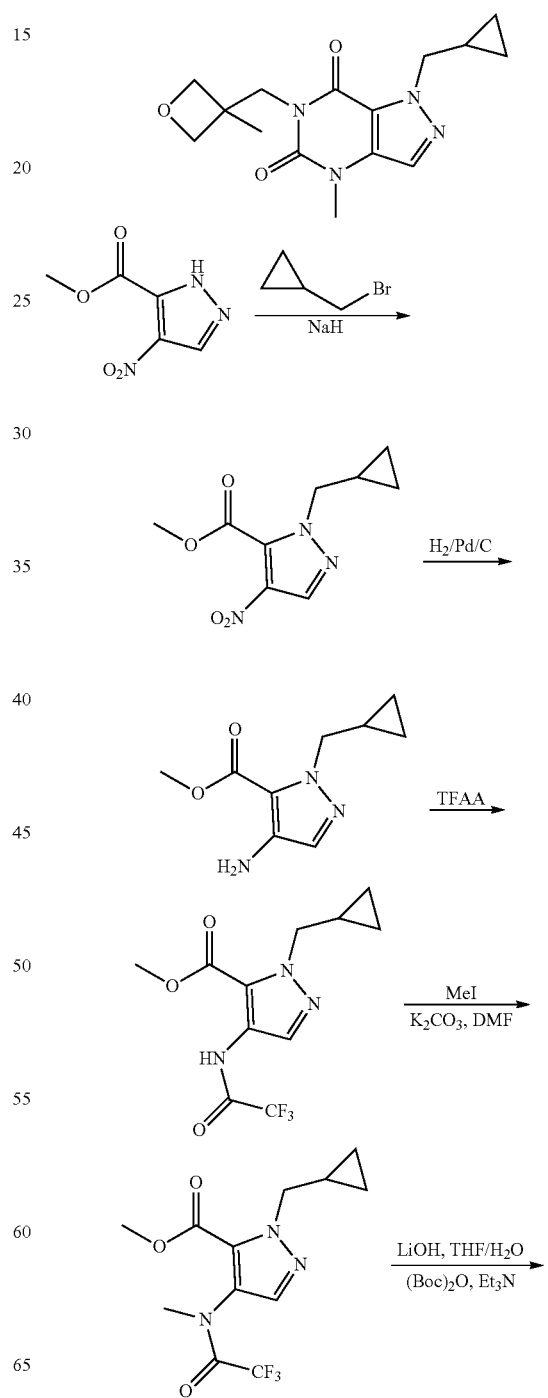

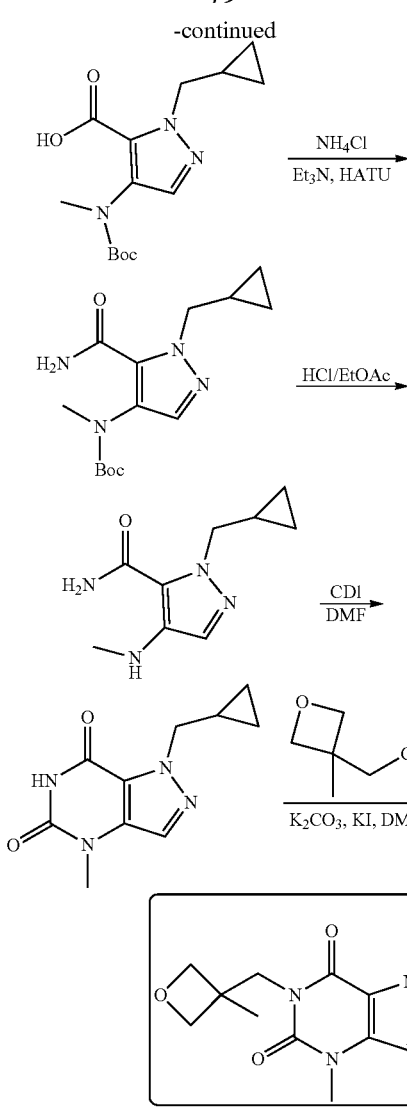

Step 1

Methyl 1-(cyclopropylmethyl)-4-nitro-pyrazol-5-carboxylate

Methyl 4-nitro-pyrazol-5-carboxylate (22.0 g, 129 mmol) was dissolved in N,N-dimethylformamide (350 mL), and then sodium hydride (5.66 g, 141 mmol) was added in batches at 0° C. The reaction solution was stirred at 0° C. for 1 hour, and then sodium iodide was added (21.2 g, 141 mmol), and bromomethylcyclopropane (19.1 g, 141 mmol) was added dropwise. The reaction solution was stirred at 25° C. for 18 hours. Water (1.2 L) was added into the reaction solution, followed by extraction with ethyl acetate (300 mL×2). The organic phases were combined, washed with saturated brine (500 mL), dried over anhydrous sodium sulfate and then filtered. The filtrate was concentrated under reduced pressure, and the residue was separated and purified by silica gel column chromatography (5:1 petroleum ether/ethyl acetate, Rf=0.3) to give methyl 1-(cyclopropylmethyl)-4-nitro-pyrazol-5-carboxylate (5.00 g, colorless oil) with a yield of 17%. $^1$H NMR: (400 MHz, CDCl$_3$) δ8.04 (s, 1H), 4.14 (d, J=7.6 Hz, 2H), 4.03 (s, 3H), 1.40-1.23 (m, 1H), 0.75-0.55 (m, 2H), 0.47-0.34 (m, 2H). MS-ESI calculated value: [M+H]$^+$ 226; measured value: 226.

Step 2

Methyl 4-amino-1-(cyclopropylmethyl)-pyrazol-5-carboxylate

Methyl 1-(cyclopropylmethyl)-4-nitro-pyrazol-5-carboxylate (5.00 g, 22.2 mmol) was dissolved in methanol (70 mL), and then dry palladium-carbon (palladium 10%, water 1%, 500 mg) was added. The reaction was conducted at room temperature for 3 hours under 40 psi hydrogen pressure. The reaction solution was filtered and then the filtrate was concentrated under reduced pressure to give methyl 4-amino-1-(cyclopropylmethyl)-pyrazol-5-carboxylate (4.30 g, similar white solid) with a yield of 99%. $^1$H NMR: (400 MHz, CDCl$_3$) δ7.11 (s, 1H), 4.27 (d, J=7.6 Hz, 2H), 4.11 (s, 2H), 3.91 (s, 3H), 1.46-1.21 (m, 1H), 0.53-0.43 (m, 2H), 0.41-0.32 (m, 2H). MS-ESI calculated value: [M+H]$^+$ 196; measured value: 196.

Step 3

Methyl 1-(cyclopropylmethyl)-4-(2,2,2-trifluoroacetamido)-pyrazol-5-carboxylate

Methyl 4-amino-1-(cyclopropylmethyl)-pyrazol-5-carboxylate (4.30 g, 22.0 mmol) was dissolved in methylene chloride (40 mL), and then trifluoroacetic anhydride (6.94 g, 33.1 mmol) was added dropwise under the protection of nitrogen. The reaction solution was stirred at room temperature for 2 hours. The reaction was quenched by adding saturated sodium bicarbonate solution (50 mL), followed by extraction with methylene chloride (40 mL) and washing with saturated brine (50 mL). The organic phase was dried over anhydrous sodium sulfate and concentrated under reduced pressure to give methyl 1-(cyclopropylmethyl)-4-(2,2,2-trifluoroacetamido)-pyrazol-5-carboxylate (6.30 g, colorless oil) with a yield of 98%.

$^1$H NMR: (400 MHz, CDCl$_3$) δ9.72 (s, 1H), 8.28 (s, 1H), 4.37 (d, J=7.2 Hz, 2H), 4.09 (s, 3H), 1.39-1.23 (m, 1H), 0.60-0.48 (m, 2H), 0.45-0.37 (m, 2H). MS-ESI calculated value: [M+H]$^+$ 292; measured value: 292.

Step 4

Methyl 1-(cyclopropylmethyl)-4-(2,2,2-trifluoro-N-methylacetamido)-pyrazol-5-carboxylate Methyl 1-(cyclopropylmethyl)-4-(2,2,2-trifluoroacetamido)-pyrazol-5-carboxylate (6.20 g, 21.3 mmol) was dissolved in N,N-dimethylformamide (50 mL), and then potassium carbonate (4.41 g, 31.9 mmol) was added. The reaction solution was heated to 80° C. and allowed for reaction for 1 hour. The reaction solution was cooled to room temperature, and then iodomethane (4.53 g, 31.9 mmol) was added. The reaction solution was stirred at room temperature for 18 hours. Water (300 mL) was added into the reaction solution, followed by extraction with ethyl acetate (100 mL×3). The organic phases were combined, washed with saturated brine (100 mL), dried over anhydrous sodium sulfate, and then filtered. The filtrate was concentrated under reduced pressure to give methyl 1-(cyclopropylmethyl)-4-(2,2,2-trifluoro-N-methylacetamido)-pyrazol-5-carboxylate (6.44 g, yellow oil) with a yield of 99%. $^1$H NMR: (400 MHz, CDCl$_3$) δ7.50 (s, 1H), 4.43 (d, J=7.2 Hz, 2H), 3.90 (s, 3H), 3.28 (s, 3H), 1.43-1.27 (m, 1H), 0.60-0.47 (m, 2H), 0.45-0.33 (m, 2H). MS-ESI calculated value: [M+H]$^+$ 306; measured value: 306.

Step 5

4-[Tert-butoxycarbonyl)(methyl)amino]1-(cyclopropylmethyl)-pyrazol-5-carboxylic acid Methyl 1-(cyclopropylmethyl)-4-(2,2,2-trifluoro-N-methylacetamido)-pyrazol-5-carboxylate (6.40 g, 21.0 mmol) was dissolved in tetrahydrofuran (30 mL) and water (30 mL), and then lithium hydroxide monohydrate (4.40 g, 105 mmol) was added. The reaction solution was allowed for reaction at room temperature while stirring for 18 hours. Di-tert-butyl dicarbonate (9.15 g, 41.9 mmol) was added, and the reaction solution was allowed for reaction at room temperature for 16 hours. The reaction solution was concentrated under reduced pressure, followed by adjusting the pH value to pH=4 with 2N hydrochloric acid solution, and then filtered. The filter cake was dried to give 4-((tert-butoxycarbonyl)(methyl)amino)-1-(cyclopropylmethyl)-pyrazol-5-carboxylic acid (4.50 g, white solid) with a yield of 73%. $^1$H NMR: (400 MHz, CDCl$_3$) δ7.46 (s, 1H), 4.38 (d, J=6.8 Hz, 2H), 3.21 (s, 3H), 1.58-1.25 (m, 10H), 0.60-0.47 (m, 2H), 0.45-0.37 (m, 2H). MS-ESI calculated value: [M+H]$^+$ 296; measured value: 296.

Step 6

Tert-butyl (5-Carbamoyl-1-(cyclopropylmethyl)-pyrazol-4-yl)(methyl) carbamate 4-[Tert-butoxycarbonyl)(methyl)amino]1-(cyclopropylmethyl)-pyrazol-5-carboxylic acid (3.40 g, 11.5 mmol), 2-(7-azabenzotriazole)-tetramethyluronium hexafluorophosphate (5.69 g, 15.0 mmol) and ammonium chloride (1.23 g, 23.0 mmol) were dissolved in methylene chloride (120 mL), and then triethylamine (1.75 g, 17.3 mmol) was added dropwise at room temperature. The reaction solution was stirred at room temperature for 18 hours. Water (50 mL) was added into the reaction solution, followed by extraction with methylene chloride (500 mL×2). The organic phases were combined, washed successively with saturated sodium bicarbonate (50 mL) and saturated brine (50 mL), dried over anhydrous sodium sulfate, and then filtered. The filtrate was concentrated under reduced pressure, the residue was treated with ethanol (20 mL) to give tert-butyl (5-carbamoyl-1-(cyclopropylmethyl)-pyrazol-4-yl)(methyl) carbamate (3.00 g, crude product, yellow oil). MS-ESI calculated value: [M+H]$^+$ 295; measured value: 295.

Step 7

1-(Cyclopropylmethyl)-4-(methylamino)-pyrazol-5-carboxamide

Tert-butyl (5-Carbamoyl-1-(cyclopropylmethyl)-pyrazol-4-yl)(methyl) carbamate (3.30 g, 11.2 mmol) was dissolved in hydrochloric acid-ethyl acetate (25 mL). After reacting at room temperature while stirring for 18 hours, the reaction solution was concentrated under reduced pressure. The residue was dissolved by methanol (40 mL), and then potassium carbonate (3.10 g, 22.4 mmol) was added, followed by stirring at room temperature for 2 hours. The reaction solution was filtered and the filtrate was concentrated under reduced pressure. The residue was extracted with methylene chloride (60 mL), followed by filtration. The filtrate was spin-dried and the residue was beaten with methylene chloride (15 mL), followed by filtration to give 1-(cyclopropylmethyl)-4-(methylamino)-pyrazol-5-carboxamide (1.45 g, white solid) with a yield of 67%. $^1$H NMR: (400 MHz, CDCl$_3$) δ7.34 (s, 2H), 7.17 (s, 1H), 4.62-4.47 (m, 1H), 4.21 (d, J=6.8 Hz, 2H), 2.65 (d, J=5.6 Hz, 3H), 1.22-1.10 (m, 1H), 0.43-0.34 (m, 2H), 0.31-0.23 (m, 2H).

MS-ESI calculated value: [M+H]$^+$ 195; measured value: 195.

Step 8

1-(Cyclopropylmethyl)-4-methyl-pyrazolo[4,3-d]pyrimidin-5,7-dione 1-(Cyclopropylmethyl)-4-(methylamino)-pyrazol-5-carboxamide (1.45 g, 7.47 mmol) was dissolved in N,N-dimethylformamide (10 mL), and then sodium hydride (627 mg, 15.7 mmol) was added in batches at 0° C. The reaction solution was stirred at 0° C. for 1 hour under the protection of nitrogen. After adding 1,1-carbonyldiimidazole (1.82 g, 11.2 mmol), the reaction solution was heated to 75° C. and allowed for reaction for 2 hours and then cooled to room temperature. The reaction was quenched by adding water (80 mL), followed by filtration. The filter cake wad dried to give 1-(cyclopropylmethyl)-4-methyl-pyrazolo[4,3-d]pyrimidin-5,7-dione (1.60 g, white solid) with a yield of 97%. $^1$H NMR: (400 MHz, DMSO-d$_6$) δ11.35 (s, 1H), 7.72 (s, 1H), 4.29 (d, J=6.8 Hz, 2H), 3.32 (s, 3H), 1.17-1.07 (m, 1H), 0.54-0.32 (m, 4H). MS-ESI calculated value: [M+H]$^+$ 221; measured value: 221.

Step 9

1-(Cyclopropylmethyl)-4-methyl-6-((3-methyloxetan-3-yl)methyl)-pyrazolo[4,3-d]pyrimidin-5,7-dione 1-(Cyclopropylmethyl)-4-methyl-pyrazolo[4,3-d]pyrimidin-5,7-dione (62.1 mg, 0.282 mmol) was dissolved in N,N-dimethylformamide (2 mL), and then 3-(chloromethyl)-3-methyl-oxetane (40.8 mg, 0.338 mmol), potassium carbonate (78.0 mg, 0.564 mmol) and potassium iodide (56.2 mg, 0.338 mmol) were added. The reaction solution was heated to 120° C. and then stirred for 1 hour. The reaction solution was cooled to room temperature and then filtered. The filtrate was concentrated under reduced pressure, and the residue was purified by high performance liquid chromatography to give 1-(cyclopropylmethyl)-4-methyl-6-((3-methyloxetan-3-yl)methyl)-pyrazolo[4,3-d]pyrimidin-5,7-dione (46.0 mg) with a yield of 54%. $^1$H NMR: (400 MHz, CDCl$_3$) δ7.42 (s, 1H), 4.73 (d, J=6.4 Hz, 2H), 4.43 (d, J=6.8 Hz, 2H), 4.26 (d, J=6.4 Hz, 2H), 4.14 (s, 2H), 3.50 (s, 3H), 1.41 (s, 3H), 1.40-1.28 (m, 1H), 0.60-0.52 (m, 2H), 0.51-0.38 (m, 2H). MS-ESI calculated value: [M+H]$^+$ 305; measured value: 305.

Example 34

1-(Cyclopropylmethyl)-6-((3-ethyloxetan-3-yl)methyl)-4-methyl-pyrazolo[4,3-d]pyrimidin-5,7-dione

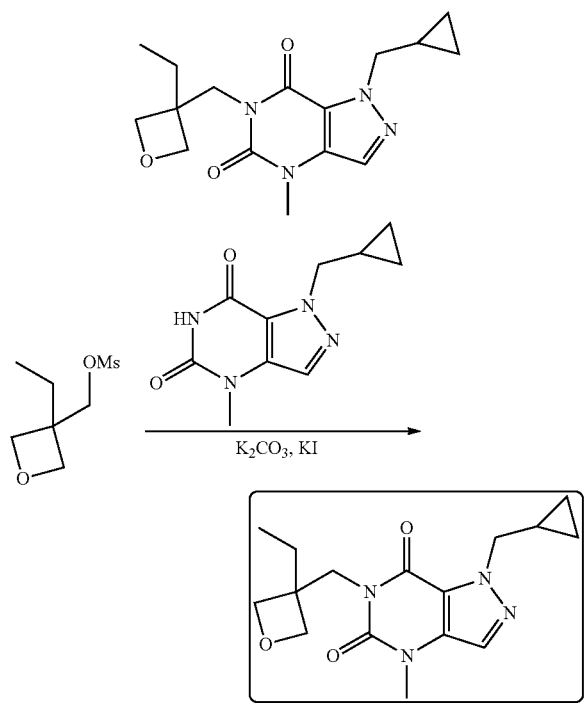

Step 1

1-(Cyclopropylmethyl)-6-((3-ethyloxetan-3-yl)methyl)-4-methyl-pyrazolo[4,3-d]pyrimidin-5,7-dione (3-Ethyloxetan-3-yl)methyl methanesulfonate (34.4 mg, 0.177 mmol), 1-(cyclopropylmethyl)-4-methyl-pyrazolo[4,3-d]pyrimidin-5,7-dione (30.0 mg, 0.136 mmol), potassium iodide (2.3 mg, 0.014 mmol) and potassium carbonate (56.5 mg, 0.408 mmol) were dissolved in N,N-dimethylformamide (3 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-(cyclopropylmethyl)-6-((3-ethyloxetan-3-yl)methyl)-4-methyl-pyrazolo[4,3-d]pyrimidin-5,7-dione (21.0 mg) with a yield of 48%. $^1$H NMR: (400 MHz, CDCl$_3$) δ7.44 (s, 1H), 4.62 (d, J=6.4 Hz, 2H), 4.44 (d, J=7.6 Hz, 2H), 4.30 (d, J=6.8 Hz, 2H), 4.10 (s, 2H), 3.52 (s, 3H), 1.88-1.83 (m, 2H), 1.37-1.36 (m, 1H), 1.11-1.07 (m, 3H), 0.56-0.46 (m, 4H). MS-ESI calculated value: [M+H]$^+$ 319; measured value: 319.

Example 35

1-(Cyclopropylmethyl)-4-methyl-6-((tetrahydrofuran-3-yl)methyl)-pyrazolo[4,3-d]pyrimidin-5,7-dione

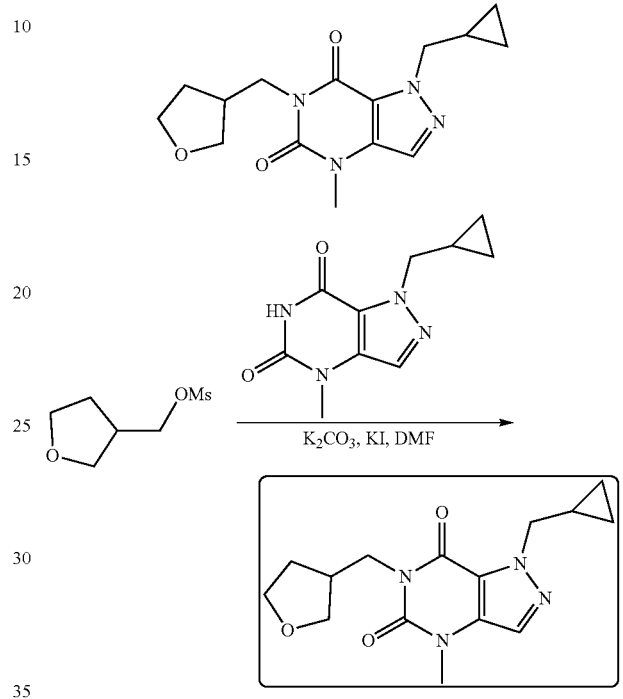

Step 1

1-(Cyclopropylmethyl)-4-methyl-6-((tetrahydrofuran-3-yl)methyl)-pyrazolo[4,3-d]pyrimidin-5,7-dione (Tetrahydrofuran-3-yl)methyl methanesulfonate (53.1 mg, 0.295 mmol), 1-(cyclopropylmethyl)-4-methyl-pyrazolo[4,3-d]pyrimidin-5,7-dione (50.0 mg, 0.227 mmol) and potassium carbonate (94.1 mg, 0.681 mmol) were dissolved in N,N-dimethylformamide (5 mL), and then potassium iodide (3.8 mg, 0.023 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 1-(cyclopropylmethyl)-4-methyl-6-((tetrahydrofuran-3-yl)methyl)-pyrazolo[4,3-d]pyrimidin-5,7-di one (36.0 mg) with a yield of 52%. $^1$H NMR: (400 MHz, Methonal-d$_4$) δ7.63 (s, 1H), 4.41 (d, J=7.2 Hz, 2H), 3.95-3.90 (m, 1H), 3.87-3.82 (m, 1H), 3.77-3.72 (m, 1H), 3.61-3.54 (m, 2H), 3.45-3.42 (m, 1H), 3.14 (s, 3H), 2.59-2.52 (m, 1H), 1.87-1.79 (m, 1H), 1.62-1.53 (m, 1H), 1.22-1.12 (m, 1H), 0.36-0.25 (m, 4H). MS-ESI calculated value: [M+H]$^+$ 305; measured value: 305.

85

Example 36

1-(Cyclopropylmethyl)-4-methyl-6-((tetrahydropyran-4-yl)methyl)-pyrazolo[4,3-d]pyrimidin-5,7-dione

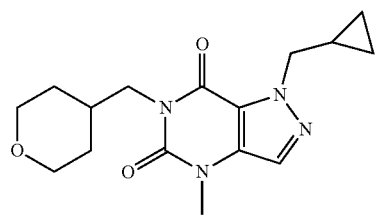

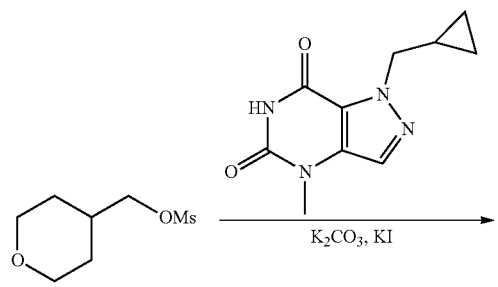

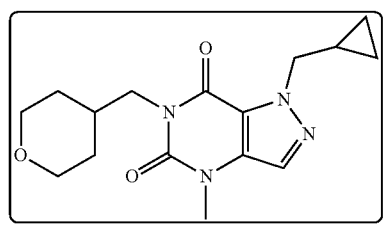

Step 1

1-(Cyclopropylmethyl)-4-methyl-6-((tetrahydropyran-4-yl)methyl)-pyrazolo[4,3-d]pyrimidin-5,7-dione (Tetrahydropyran-4-yl)methyl methanesulfonate (34.4 mg, 0.177 mmol), 1-(cyclopropylmethyl)-4-methyl-pyrazolo[4,3-d]pyrimidin-5,7-dione (30.0 mg, 0.136 mmol), potassium iodide (2.3 mg, 0.014 mmol) and potassium carbonate (56.5 mg, 0.408 mmol) were dissolved in N,N-dimethylformamide (3 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-(cyclopropylmethyl)-4-methyl-6-((tetrahydropyran-4-yl)methyl)-pyrazolo[4,3-d]pyrimidin-5,7-dione (30.0 mg) with a yield of 69%. $^1$H NMR: (400 MHz, CDCl$_3$) δ7.42 (s, 1H), 4.45 (d, J=7.6 Hz, 2H), 4.00-3.95 (m, 4H), 3.49 (s, 3H), 3.39-3.33 (m, 2H), 2.10-2.06 (m, 1H), 1.48-1.40 (m, 5H), 0.57-0.48 (m, 4H). MS-ESI calculated value: [M+H]$^+$ 319; measured value: 319.

86

Example 37

1-(Cyclopropylmethyl)-4-methyl-6-(2-(tetrahydropyran-4-yl)ethyl)-pyrazolo[4,3-d]pyrimidin-5,7-dione

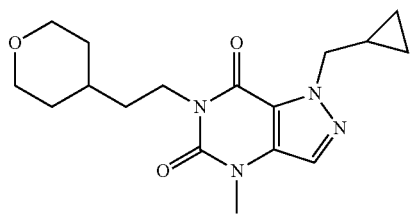

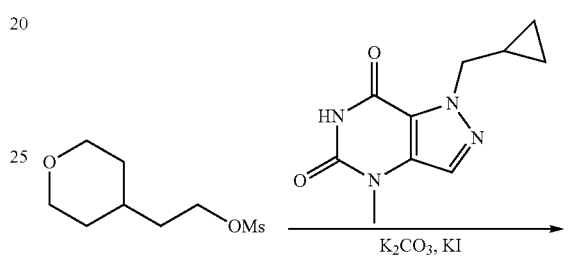

Step 1

1-(Cyclopropylmethyl)-4-methyl-6-(2-(tetrahydropyran-4-yl)ethyl)-pyrazolo[4,3-d]pyrimidin-5,7-dione 2-(Tetrahydropyran-4-yl)ethyl methanesulfonate (50.0 mg, 0.227 mmol), 1-(cyclopropylmethyl)-4-methyl-pyrazolo[4,3-d]pyrimidin-5,7-dione (47.3 mg, 0.227 mmol), potassium iodide (3.8 mg, 0.023 mmol) and potassium carbonate (62.3 mg, 0.454 mmol) were dissolved in N,N-dimethylformamide (3 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-(cyclopropylmethyl)-4-methyl-6-(2-(tetrahydropyran-4-yl)ethyl)-pyrazolo[4,3-d]pyrimidin-5,7-dione (20.0 mg) with a yield of 27%. $^1$H NMR: (400 MHz, CDCL$_3$) δ7.40 (s, 1H), 4.43 (d, J=7.2 Hz, 2H), 4.08-4.05 (m, 2H), 3.98-3.94 (m, 2H), 3.49 (s, 3H), 3.38 (t, J=1.6 Hz, 2H), 1.73-1.69 (m, 2H), 1.62-1.59 (m, 4H), 1.39-1.36 (m, 2H), 0.55-0.46 (m, 4H). MS-ESI calculated value: [M+H]$^+$ 333; measured value: 333.

Example 38

1-(Cyclopropylmethyl)-6-((4-methoxycyclohexyl)methyl)-4-methyl-pyrazolo[4,3-d]pyrimidin-5,7-dione

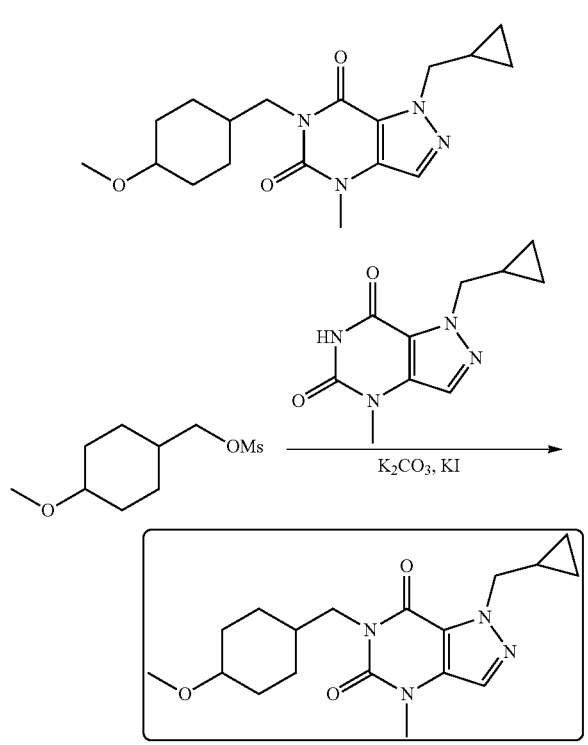

Step 1

1-(Cyclopropylmethyl)-6-((4-methoxycyclohexyl)methyl)-4-methyl-pyrazolo[4,3-d]pyrimidin-5,7-dione (4-Methoxycyclohexyl)methyl methanesulfonate (30.0 mg, 0.135 mmol), 1-(cyclopropylmethyl)-4-methyl-pyrazolo[4,3-d]pyrimidin-5,7-dione (26.8 mg, 0.121 mmol), potassium iodide (2.2 mg, 0.014 mmol) and potassium carbonate (37.3 mg, 0.269 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-(cyclopropylmethyl)-6-((4-methoxycyclohexyl)methyl)-4-methyl-pyrazolo[4,3-d]pyrimidin-5,7-dione (16.0 mg) with a yield of 34%. $^1$H NMR: (400 MHz, Methonal-$d_4$) δ7.64 (s, 1H), 4.42 (d, J=6.8 Hz, 2H), 3.89 (d, J=6.8 Hz, 2H), 3.50 (s, 3H), 3.35 (s, 3H), 3.20-3.15 (m, 1H), 2.10-2.06 (m, 2H), 1.76-1.73 (m, 3H), 1.38-1.36 (m, 1H), 1.16-1.12 (m, 4H), 0.55-0.46 (m, 4H). MS-ESI calculated value: [M+H]$^+$ 347; measured value: 347.

Example 39

1-Methyl-3-((3-methyloxetan-3-yl)methyl)pyrido[2,3-d]pyrimidin-2,4-dione

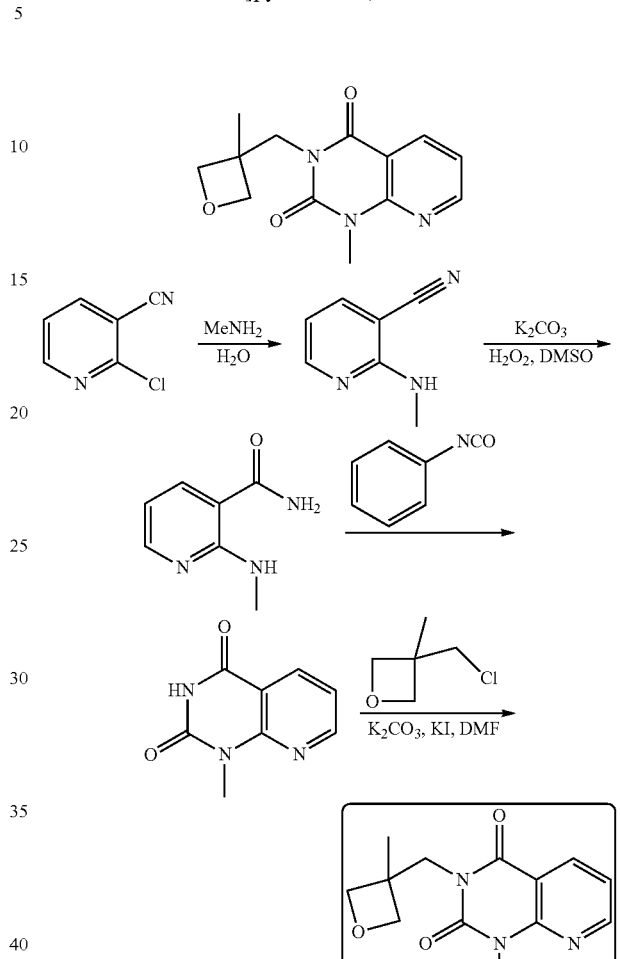

Step 1

2-(Methylamino)nicotinonitrile

2-Chloro-3-cyanopyridine (30.0 g, 216 mmol) was added into 40% methylamine aqueous solution (300 mL), which was heated to 80° C. and then stirred for 2 hours. The reaction solution was concentrated by reduced pressure distillation. The solid obtained by filtration was washed with water (30 mL×3) and then dried to give 2-(methylamino)nicotinonitrile (22.3 g, pale yellow solid) with a yield of 76%. $^1$H NMR: (400 MHz, Methonal-$d_4$) δ8.25-8.22 (m, 1H), 7.79-7.74 (m, 1H), 6.65-6.59 (m, 1H), 2.96 (s, 3H).

Step 2

2-(Methylamino)pyridin-3-carboxamide 2-(Methylamino)nicotinonitrile (600 mg, 4.51 mmol), potassium carbonate (1.87 mg, 0.130 mmol), hydrogen peroxide (0.1 mL) were dissolved in dimethyl sulfoxide (10 mL), followed by reaction at room temperature for 1 hour. The reaction was quenched by adding water (10 mL). The reaction solution was extracted with ethyl acetate (10 mL×3), dried over anhydrous sodium sulfate, and then filtered. The filtrate was concentrated under reduced pressure and then purified by silica gel preparative plate (1:1 petroleum ether/ethyl acetate, Rf=0.2) to give 2-(methylamino)pyridin-3-carboxamide (500 mg, white solid) with a yield of 73%. $^1$H NMR: (400 MHz, DMSO-d$_6$) δ8.45-8.40 (br, 1H), 8.28 (d, J=2.0 Hz, 1H), 7.95-7.93 (m, 2H), 7.35-7.30 (br, 1H), 6.53 (dd, J=7.6, 2.0 Hz, 1H), 3.03 (d, J=4.8 Hz, 3H). MS-ESI calculated value: [M+H]$^+$ 152; measured value: 152.

Step 3

1-Methylpyrido[2,3-d]pyrimidin-2,4(1H,3H)-dione 2-(Methylamino)pyridin-3-carboxamide (100 mg, 0.661 mmol) and phenyl isocyanate (157 mg, 1.32 mmol) were dissolved in toluene (10 mL), followed by stirring at 110° C. for 12 hours. The reaction was quenched by adding water (10 mL). The reaction solution was filtered to give 1-methylpyrido[2,3-d]pyrimidin-2,4(1H,3H)-dione (20.0 mg, yellow solid) with a yield of 17%.

$^1$H NMR: (400 MHz, DMSO-d$_6$) δ11.72 (s, 1H), 8.72 (d, J=2.0 Hz, 1H), 8.31 (d, J=7.6 Hz, 1H), 7.29 (dd, J=7.6, 2.0 Hz, 1H), 3.48 (s, 3H). MS-ESI calculated value: [M+H]$^+$ 178; measured value: 178.

Step 4

1-Methylpyrido[2,3-d]pyrimidin-2,4-dione (70.0 mg, 0.395 mmol) was dissolved in N,N-dimethylformamide (2 mL), and then 3-(chloromethyl)-3-methyl-oxetane (52.4 mg, 0.435 mmol), potassium carbonate (109 mg, 0.790 mmol) and potassium iodide (78.7 mg, 0.474 mmol) were added. The reaction solution was heated to 120° C. and then stirred for 1 hour. The reaction solution was cooled to room temperature and then filtered. The filtrate was concentrated under reduced pressure, and the residue was purified by high performance liquid chromatography to give 1-methyl-3-((3-methyloxetan-3-yl)methyl)pyrido[2,3-d]pyrimidin-2,4-dione (44.0 mg) with a yield of 43%. $^1$H NMR: (400 MHz, CDCl$_3$) δ8.69 (d, J=2.0 Hz, 1H), 8.46 (d, J=5.6 Hz, 1H), 7.27-7.18 (m, 1H), 4.76 (d, J=6.8 Hz, 2H), 4.28 (d, J=6.8 Hz, 2H), 4.23 (s, 2H), 3.73 (s, 3H), 1.41 (s, 3H). MS-ESI calculated value: [M+H]$^+$ 262; measured value: 262.

Example 40

3-((3-Ethyloxetan-3-yl)methyl)-1-methylpyrido[2,3-d]pyrimidin-2,4-dione

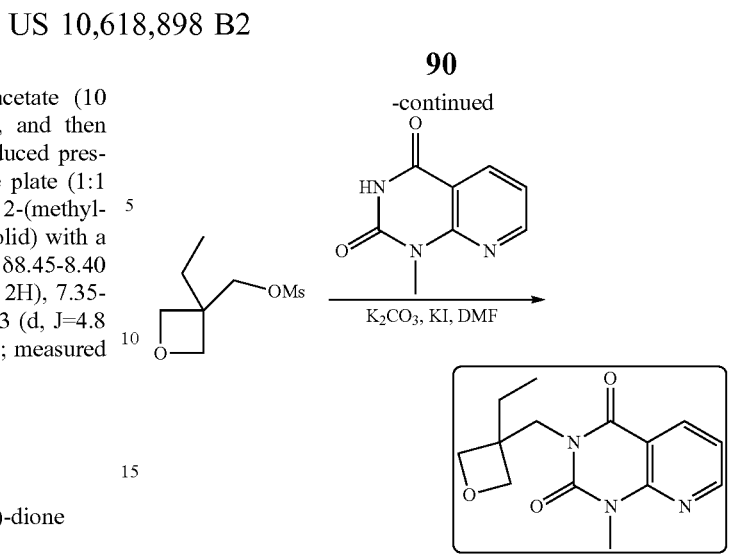

Step 1

3-((3-Ethyloxetan-3-yl)methyl)-1-methylpyrido[2,3-d]pyrimidin-2,4-dione

1-Methylpyrido[2,3-d]pyrimidin-2,4-dione (30.0 mg, 0.169 mmol), (3-ethyloxetan-3-yl)methyl methanesulfonate (49.3 mg, 0.254 mmol), potassium carbonate (46.8 mg, 0.338 mmol) and potassium iodide (5.6 mg, 0.034 mmol) were dissolved in N,N-dimethylformamide (10 mL). The reaction solution was heated to 120° C. and stirred for 3 hours. The reaction solution was cooled to room temperature, and poured into water (30 mL), followed by extraction with ethyl acetate (20 mL×3). The organic phases were combined, dried over anhydrous sodium sulfate, and then filtered. The filtrate was concentrated and then separated and purified by preparative high performance liquid chromatography to give 3-((3-ethyloxetan-3-yl)methyl)-1-methylpyrido[2,3-d]pyrimidin-2,4-dione (10.0 mg) with a yield of 21%. $^1$H NMR: (400 MHz, Methonal-d$_4$) δ8.74-8.73 (m, 1H), 8.48-8.46 (m, 1H), 7.35-7.32 (m, 1H), 4.67 (d, J=6.8 Hz, 2H), 4.32 (d, J=6.8 Hz, 2H), 4.20 (s, 2H), 3.72 (s, 3H), 1.84-1.79 (m, 2H), 1.08 (t, J=7.2 Hz, 3H). MS-ESI calculated value: [M+H]$^+$ 276; measured value: 276.

Example 41

1-Methyl-3-(tetrahydrofuran-3-ylmethyl)pyrido[2,3-d]pyrimidin-2,4-dione

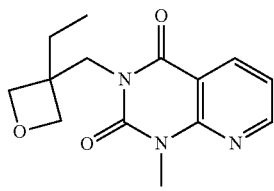

-continued

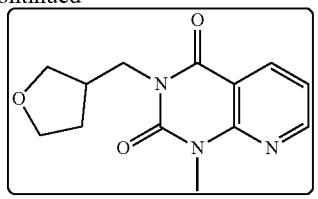

Step 1 1-Methyl-3-(tetrahydrofuran-3-ylmethyl)pyrido[2,3-d]pyrimidin-2,4-dione Tetrahydrofuran-3-yl-methyl methanesulfonate (30.0 mg, 0.166 mmol), 1-methylpyrido[2,3-d]pyrimidin-2,4-dione (29.5 mg, 0.166 mmol), potassium carbonate (46.0 mg, 0.333 mmol) and potassium iodide (5.5 mg, 0.033 mmol) were dissolved in N,N-dimethylformamide (5 mL). The reaction solution was heated to 120° C. and stirred for 3 hours. Then, the reaction solution was cooled to room temperature, and poured into water (20 mL), followed by extraction with ethyl acetate (20 mL×3). The organic phases were combined, dried over anhydrous sodium sulfate, and then filtered. The filtrate was concentrated and then was separated and purified by preparative high performance liquid chromatography to give 1-methyl-3-(tetrahydrofuran-3-ylmethyl)pyrido[2,3-d]pyrimidin-2,4-dione (10.0 mg) with a yield of 23%. $^1$H NMR: (400 MHz, Methonal-$d_4$) δ8.65-8.63 (m, 1H), 8.46-8.41 (m, 1H), 7.33-7.30 (m, 1H), 4.14-4.12 (m, 2H), 4.09-4.07 (m, 1H), 3.79-3.75 (m, 2H), 3.69 (s, 3H), 3.65-3.62 (m, 1H), 2.79-2.75 (m, 1H), 2.06-2.01 (m, 1H), 1.78-1.75 (m, 1H). MS-ESI calculated value: [M+H]$^+$ 262; measured value: 262.

Example 42

1-Methyl-3-((tetrahydropyran-4-yl)methyl)pyrido[2,3-d]pyrimidin-2,4-dione

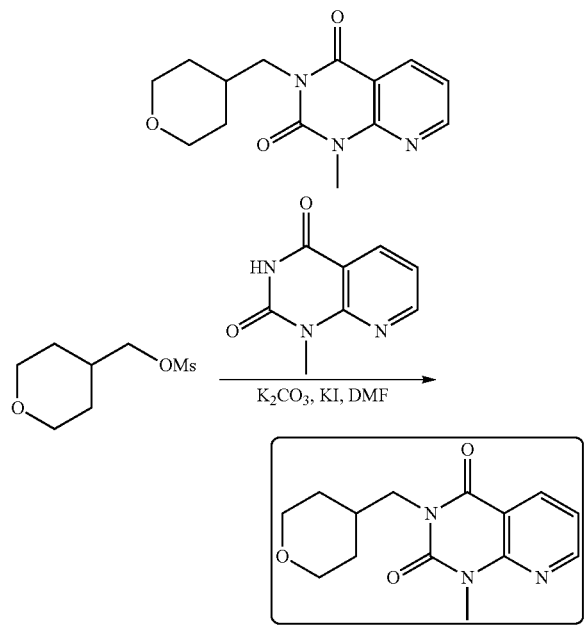

Step 1

1-Methyl-3-((tetrahydropyran-4-yl)methyl)pyrido[2,3-d]pyrimidin-2,4-dione

1-Methylpyrido[2,3-d]pyrimidin-2,4-dione (30.0 mg, 0.169 mmol), tetrahydropyran-4-yl-methyl methanesulfonate (49.4 mg, 0.254 mmol), potassium carbonate (46.8 mg, 0.338 mmol) and potassium iodide (5.6 mg, 0.034 mmol) were dissolved in N,N-dimethylformamide (10 mL). The reaction solution was heated to 120° C. and stirred for 3 hours. The reaction solution was cooled to room temperature, and poured into water (30 mL), followed by extraction with ethyl acetate (20 mL×3). The organic phases were combined, dried over anhydrous sodium sulfate, and then filtered. The filtrate was concentrated and then separated and purified by preparative high performance liquid chromatography to give 1-methyl-3-((tetrahydropyran-4-yl)methyl)pyrido[2,3-d]pyrimidin-2,4-dione (10.0 mg, yellow oily) with a yield of 21%. $^1$H NMR: (400 MHz, Methonal-$d_4$) δ8.71-8.69 (m, 1H), 8.48-8.40 (m, 1H), 7.33-7.30 (m, 1H), 3.99-3.91 (m, 4H), 3.69 (s, 3H), 3.39-3.33 (m, 2H), 2.13-2.10 (m, 1H), 1.62-1.58 (m, 2H), 1.44-1.40 (m, 2H). MS-ESI calculated value: [M+H]$^+$ 276; measured value: 276.

Example 43

1-Methyl-3-(2-(tetrahydropyran-4-yl)ethyl)pyrido[2,3-d]pyrimidin-2,4-dione

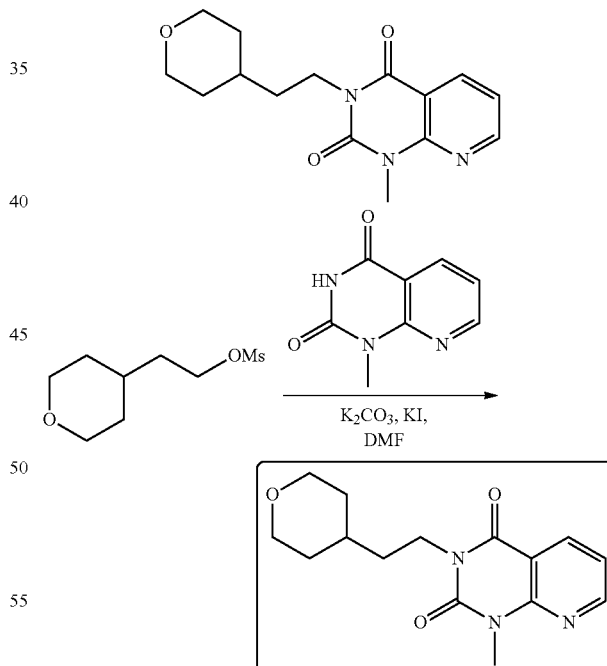

Step 1

1-Methyl-3-(2-(tetrahydropyran-4-yl)ethyl)pyrido[2,3-d]pyrimidin-2,4-dione

2-Tetrahydropyran-4-yl-ethyl methanesulfonate (50.0 mg, 0.240 mmol), 1-methylpyrido[2,3-d]pyrimidin-2,4-dione (42.5 mg, 0.240 mmol), potassium carbonate (66.4 mg, 0.480 mmol) and potassium iodide (7.9 mg, 0.048 mmol) were dissolved in N,N-dimethylformamide (5 mL). The reaction solution was heated to 120° C. and stirred for 3 hours. Then, the reaction solution was cooled to room temperature, and poured into water (20 mL), followed by extraction with ethyl acetate (20 mL×3). The organic phases were combined, dried over anhydrous sodium sulfate, and then filtered. The filtrate was concentrated and then was separated and purified by preparative high performance liquid chromatography to give 1-methyl-3-(2-(tetrahydropyran-4-yl)ethyl)pyrido[2,3-d]pyrimidin-2,4-dione (20.0 mg) with a yield of 29%. $^1$H NMR: (400 MHz, Methonal-$d_4$) δ8.72-8.71 (m, 1H), 8.47-8.45 (m, 1H), 7.34-7.31 (m, 1H), 4.14-4.10 (m, 2H), 3.96-3.93 (m, 2H), 3.70 (s, 3H), 3.43-3.40 (m, 2H), 1.78-1.75 (m, 2H), 1.66-1.62 (m, 3H), 1.38-1.32 (m, 2H). MS-ESI calculated value: $[M+H]^+$ 290; measured value: 290.

Example 44

3-((4-Methoxycyclohexyl)methyl)-1-methylpyrido[2,3-d]pyrimidin-2,4-dione

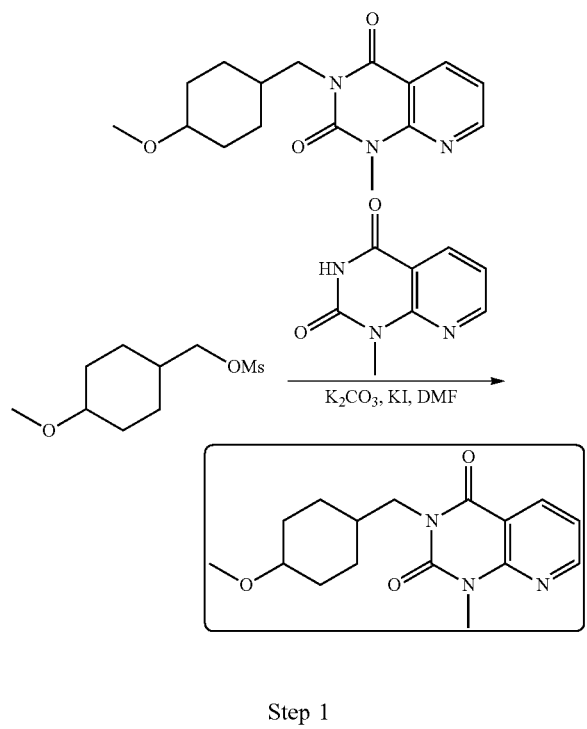

Step 1

3-((4-Methoxycyclohexyl)methyl)-1-methylpyrido[2,3-d]pyrimidin-2,4-dione

1-Methylpyrido[2,3-d]pyrimidin-2,4-dione (50.0 mg, 0.282 mmol), (4-methoxycyclohexyl)methyl methanesulfonate (62.7 mg, 0.282 mmol), potassium carbonate (78.0 mg, 0.564 mmol) and potassium iodide (9.4 mg, 0.056 mmol) were dissolved in N,N-dimethylformamide (5 mL). The reaction solution was heated to 120° C. and stirred for 3 hours. The reaction solution was cooled to room temperature, and then poured into water (20 mL), followed by extraction with ethyl acetate (20 mL×3). The organic phases were combined, dried over anhydrous sodium sulfate, and then filtered. The filtrate was concentrated and then was separated and purified by preparative high performance liquid chromatography to give 3-((4-methoxycyclohexyl)methyl)-1-methylpyrido[2,3-d]pyrimidin-2,4-dione (20.0 mg) with a yield of 23%. $^1$H NMR: (400 MHz, Methonal-$d_4$) δ8.73-8.71 (m, 1H), 8.47-8.45 (m, 1H), 7.34-7.31 (m, 1H), 3.95 (d, J=6.8 Hz, 2H), 3.71 (s, 3H), 3.36 (s, 3H), 3.20-3.16 (m, 1H), 2.10-2.08 (m, 2H), 1.84-1.76 (m, 3H), 1.21-1.08 (m, 4H). MS-ESI calculated value: $[M+H]^+$ 304; measured value: 304.

Example 45

1-Methyl-3-((3-epoxypropan-3-yl)methyl)pyrido[3,4-d]pyrimidin-2,4-dione

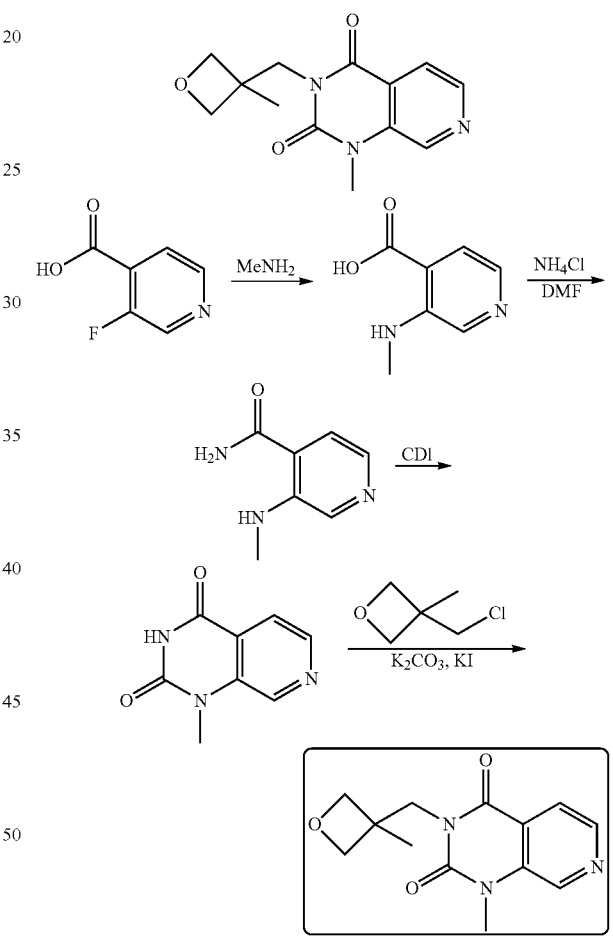

Step 1

3-(Methylamino)isonicotinic acid

3-Fluoroisonicotinic acid (3.00 g, 21.3 mmol) was dissolved in dioxane (6 mL), and then 30% methylamine aqueous solution (22.0 g, 213 mmol) was added. The reaction solution was heated to 140° C. and then stirred for 14 hours. Concentrated hydrochloric acid (12N, 3 mL) was added to adjust the pH value to pH=3, followed by filtration. The filter cake was dried to give 3-(methylamino)isonicotinic acid (3.00 g, yellow solid) with a yield of 93%. $^1$H NMR: (400 MHz, DMSO-$d_6$) δ8.46 (s, 1H), 7.89 (s, 1H), 7.69 (d, J=4.8 Hz, 1H), 7.50 (d, J=4.8 Hz, 1H), 2.80 (s, 3H).

Step 2

3-(Methylamino)isonicotinamide 3-(Methylamino)isonicotinic acid (4.00 g, 26.3 mmol), 1-hydroxybenzotriazole (10.7 g, 78.9 mmol), 1-(3-dimethylaminopropyl)-3-ethylcarbodiimide (15.1 g, 78.9 mmol) and ammonium chloride (5.63 g, 105 mmol) were dissolved in N,N-dimethylformamide (5 mL). The reaction solution was stirred at 25° C. for 24 hours. The reaction was quenched by adding water (100 mL). The mixture was extracted with isopropanol/chloroform (1:3) (50 mL×2). The organic phases were combined, concentrated under reduced pressure. Methylene chloride/methanol (10:1, 30 mL) was added into the residue and then stirred for 10 minutes, followed by filtration. The filter cake was dried to give 3-(methylamino)isonicotinamide (3.50 g, yellow solid) with a yield of 88%. $^1$H NMR: (400 MHz, DMSO-$d_6$) δ8.09 (s, 2H), 7.80 (d, J=5.2 Hz, 1H), 7.62-7.61 (m, 1H), 7.52-7.48 (m, 1H), 7.43 (d, J=5.2 Hz, 1H), 2.84 (d, J=5.2 Hz, 3H).

Step 3

1-Methylpyrido[3,4-d]pyrimidin-2,4-dione

Under the condition of 0° C., sodium hydride (1.80 g, 45.0 mmol) was added into the N,N-dimethylformamide solution (50 mL) of 3-(methylamino)isonicotinamide (3.40 g, 22.5 mmol). The reaction solution was stirred at 0° C. for 1 hour. Then carbonyldiimidazole (5.47 g, 33.7 mmol) was added. The reaction mixture was allowed for reaction at room temperature for 1 hour. The reaction solution was cooled to 0° C., quenched by adding water (20 mL). The white solid was precipitated and then filtered. The filter cake was dried to give 1-methylpyrido[3,4-d]pyrimidin-2,4-dione (3.50 g, yellow solid) with a yield of 95%. $^1$H NMR: (400 MHz, DMSO-$d_6$) δ11.83 (s, 1H), 8.86 (s, 1H), 8.48 (d, J=4.8 Hz, 1H), 7.82 (d, J=4.8 Hz, 1H), 3.49 (s, 3H).

Step 4

1-Methyl-3-((3-epoxypropan-3-yl)methyl)pyrido[3,4-d]pyrimidin-2,4-dione 3-(Chloromethyl)-3-methyl-oxetane (22.5 mg, 0.186 mmol), 1-methylpyrido[3,4-d]pyrimidin-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-((3-epoxypropan-3-yl)methyl)pyrido[3,4-d]pyrimidin-2,4-dione (10.0 mg) with a yield of 19%. $^1$H NMR: (400 MHz, Methonal-$d_4$) δ8.88 (s, 1H), 8.53 (d, J=5.2 Hz, 1H), 8.03 (d, J=5.2 Hz, 1H), 4.78 (d, J=6.4 Hz, 2H), 4.28-4.26 (m, 4H), 3.69 (s, 3H), 1.38 (s, 3H). MS-ESI calculated value: [M+H]$^+$ 262; measured value: 262.

Example 46

3-((3-Ethyloxetan-3-yl)methyl)-1-methylpyrido[3,4-d]pyrimidin-2,4-dione

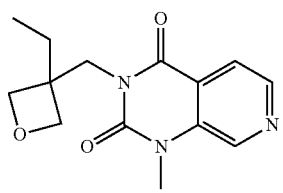

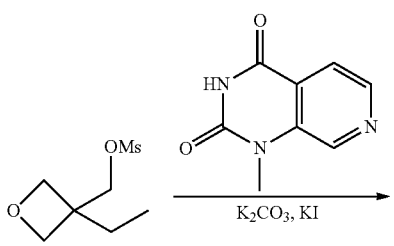

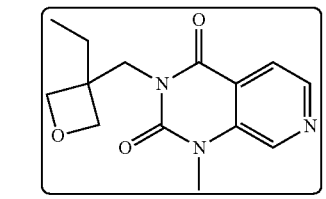

Step 1

3-((3-Ethyloxetan-3-yl)methyl)-1-methylpyrido[3,4-d]pyrimidin-2,4-dione (3-Ethyloxetan-3-yl)methyl methanesulfonate (36.2 mg, 0.186 mmol), 1-methylpyrido[3,4-d]pyrimidin-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 3-((3-ethyloxetan-3-yl)methyl)-1-methylpyrido[3,4-d]pyrimidin-2,4-dione (11.0 mg) with a yield of 22%. $^1$H NMR: (400 MHz, CDCl$_3$) δ8.79 (s, 1H), 8.60 (d, J=4.8 Hz, 1H), 8.01 (d, J=4.8 Hz, 1H), 4.62 (d, J=6.8 Hz, 2H), 4.32 (d, J=6.4 Hz, 2H), 4.20 (s, 2H), 3.71 (s, 3H), 1.85-1.79 (m, 2H), 1.10-1.07 (m, 3H). MS-ESI calculated value: [M+H]$^+$ 276; measured value: 276.

Example 47

1-Methyl-3-((tetrahydrofuran-3-yl)methyl)pyrido[3,4-d]pyrimidin-2,4-dione

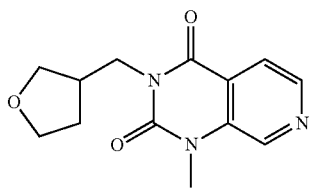

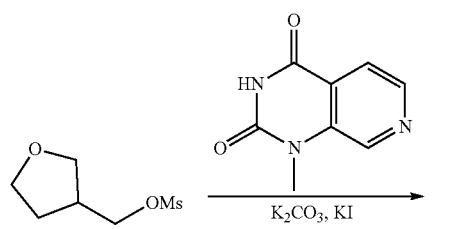

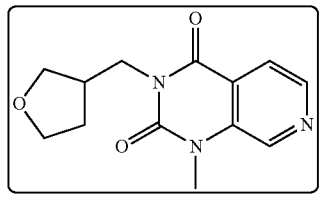

Step 1

1-Methyl-3-((tetrahydrofuran-3-yl)methyl)pyrido[3,4-d]pyrimidin-2,4-dione 3-(Tetrahydrofuran-3-yl)methyl methanesulfonate (33.6 mg, 0.186 mmol), 1-methylpyrido[3,4-d]pyrimidin-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-((tetrahydrofuran-3-yl)methyl)pyrido[3,4-d]pyrimidin-2,4-dione (21.0 mg) with a yield of 45%. $^1$H NMR: (400 MHz, CDCl$_3$) δ8.78 (s, 1H), 8.60 (d, J=4.8 Hz, 1H), 8.03 (d, J=4.8 Hz, 1H), 4.23-4.21 (m, 2H), 3.85-3.81 (m, 3H), 3.71 (s, 3H), 3.66-3.65 (m, 1H), 2.81-2.77 (m, 1H), 2.05-2.00 (m, 1H), 1.81-1.77 (m, 1H). MS-ESI calculated value: [M+H]$^+$ 262; measured value: 262.

Example 48

1-Methyl-3-((tetrahydropyran-4-yl)methyl)pyrido[3,4-d]pyrimidin-2,4-dione

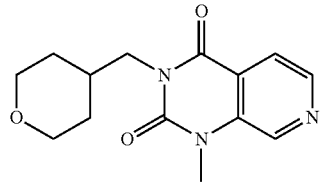

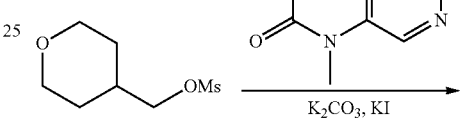

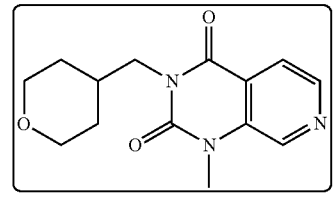

Step 1

1-Methyl-3-((tetrahydropyran-4-yl)methyl)pyrido[3,4-d]pyrimidin-2,4-dione (Tetrahydropyran-4-yl)methyl methanesulfonate (36.2 mg, 0.186 mmol), 1-methylpyrido[3,4-d]pyrimidin-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-((tetrahydropyran-4-yl)methyl)pyrido[3,4-d]pyrimidin-2,4-dione (10.0 mg) with a yield of 21%. $^1$H NMR: (400 MHz, CDCl$_3$) δ8.76 (s, 1H), 8.58 (d, J=4.8 Hz, 1H), 8.01 (d, J=4.8 Hz, 1H), 4.03 (d, J=7.2 Hz, 2H), 3.99-3.95 (m, 2H), 3.70 (s, 3H), 3.37-3.18 (m, 2H), 2.13-2.09 (m, 1H), 1.57-1.48 (m, 4H). MS-ESI calculated value: [M+H]$^+$ 276; measured value: 276.

Example 49

1-Methyl-3-(2-(tetrahydropyran-4-yl)ethyl)pyrido[3,4-d]pyrimidin-2,4-dione

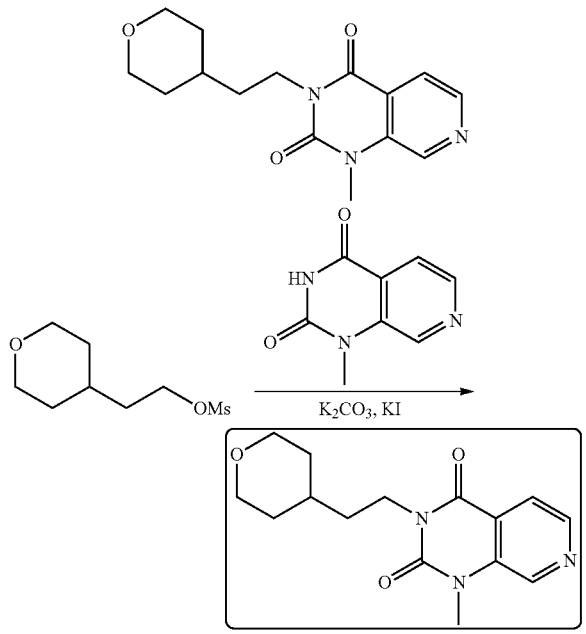

Step 1

1-Methyl-3-(2-(tetrahydropyran-4-yl)ethyl)pyrido[3,4-d]pyrimidin-2,4-dione 2-(Tetrahydropyran-4-yl)ethyl methanesulfonate (38.8 mg, 0.186 mmol), 1-methylpyrido[3,4-d]pyrimidin-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-(2-(tetrahydropyran-4-yl)ethyl)pyrido[3,4-d]pyrimidin-2,4-dione (10.0 mg) with a yield of 20%. $^1$H NMR: (400 MHz, CDCl$_3$) δ9.17 (s, 1H), 8.62-8.60 (m, 1H), 8.43-8.41 (m, 1H), 4.16-4.13 (m, 2H), 3.99-3.95 (m, 2H), 3.77 (s, 3H), 3.42-3.36 (m, 2H), 1.72-1.64 (m, 5H), 1.43-1.34 (m, 2H). MS-ESI calculated value: [M+H]$^+$ 290; measured value: 290.

Example 50

3-((4-Methoxycyclohexyl)methyl)-1-methylpyrido[3,4-d]pyrimidin-2,4-dione

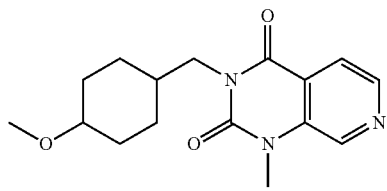

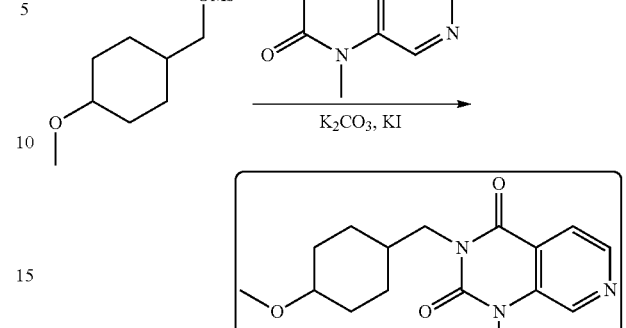

Step 1

3-((4-Methoxycyclohexyl)methyl)-1-methylpyrido[3,4-d]pyrimidin-2,4-dione (4-Methoxycyclohexyl)methyl methanesulfonate (41.4 mg, 0.186 mmol), 1-methylpyrido[3,4-d]pyrimidin-2,4-dione (30.0 mg, 0.169 mmol), potassium iodide (2.8 mg, 0.017 mmol) and potassium carbonate (46.8 mg, 0.338 mmol) were dissolved in N,N-dimethylformamide (5 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 3-((4-methoxycyclohexyl)methyl)-1-methylpyrido[3,4-d]pyrimidin-2,4-dione (10.0 mg) with a yield of 19%. $^1$H NMR: (400 MHz, CDCl$_3$) δ8.76 (s, 1H), 8.58 (d, J=4.8 Hz, 1H), 8.01 (d, J=4.8 Hz, 1H), 3.99 (d, J=7.2 Hz, 2H), 3.69 (s, 3H), 3.35 (s, 3H), 3.15-3.11 (m, 1H), 2.08-1.97 (m, 2H), 1.86-1.82 (m, 3H), 1.23-1.10 (m, 4H). MS-ESI calculated value: [M+H]$^+$ 304; measured value: 304.

Example 51

1-Methyl-3-((3-methylpyridin-3-yl)methyl)pyrido[4,3-d]pyrimidin-2,4-dione

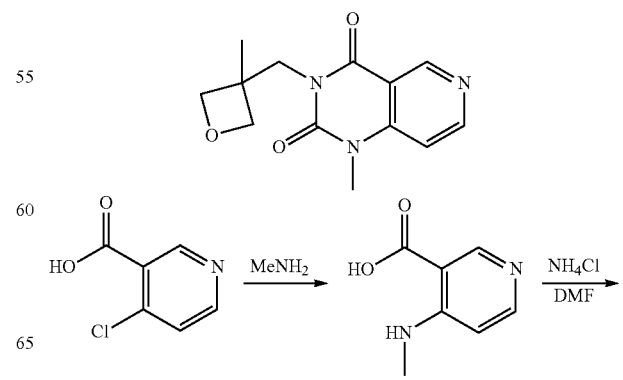

-continued

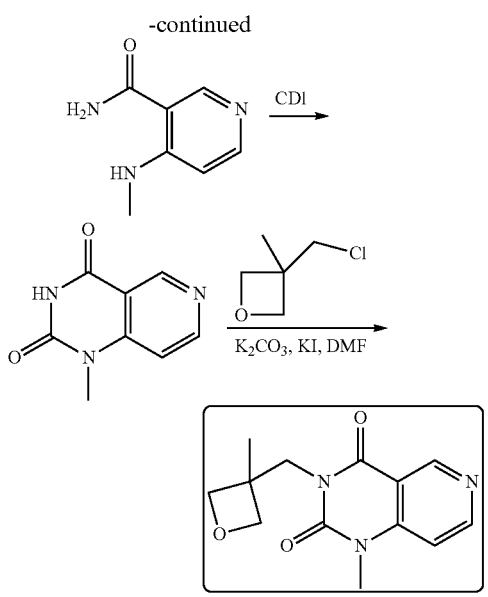

Step 1

4-(Methylamino)nicotinic acid

4-Chloronicotinic acid (7.00 g, 44.3 mmol) was dissolved in dioxane (14 mL), and then 30% methylamine aqueous solution (55.2 g, 444 mmol) was added. The reaction solution was heated in microwave to 100° C. and stirred for 50 minutes. Hydrochloric acid solution (4N, 5 mL) was added to adjust the pH value to pH=3, followed by filtration. The filter cake was dried to give 4-(methylamino)nicotinic acid (5.00 g, white solid) with a yield of 74%. $^1$H NMR: (400 MHz, DMSO-$d_6$) δ8.52 (s, 1H), 8.13 (d, J=6.8 Hz, 1H), 6.78 (d, J=6.8 Hz, 1H), 2.95 (d, J=4.4 Hz, 3H).

Step 2

4-(Methylamino)nicotinamide 4-(Methylamino)nicotinic acid (5.20 g, 34.2 mmol), 1-hydroxybenzotriazole (27.7 g, 205 mmol), 1-ethyl-(3-dimethylaminopropyl)carbodiimide hydrochloride (39.3 g, 205 mmol) and ammonium chloride (14.6 g, 273 mmol) were dissolved in N,N-dimethylformamide (50 mL). The reaction solution was stirred at 25° C. for 8 hours. The reaction was quenched by adding water (100 mL). The mixture was extracted with isopropanol/chloroform (1:3) (30 mL×5). The organic phases were combined, and concentrated under reduced pressure. The residue was added into methylene chloride/methanol (10:1, 50 mL) and then stirred for 10 minutes, followed by filtration. The filter cake was dried to give 4-(methylamino)nicotinamide (4.70 g, white solid) with a yield of 91%. $^1$H NMR: (400 MHz, DMSO-$d_6$) δ9.67 (d, J=7.6 Hz, 1H), 8.77 (s, 1H), 8.52 (s, 1H), 8.30-8.28 (m, 1H), 7.87 (s, 1H), 7.01 (d, J=7.6 Hz, 1H), 3.01 (s, 3H).

Step 3

1-Methylpyrido[4,3-d]pyrimidin-2,4-dione

Under the condition of 0° C., sodium hydride (1.52 g, 63.5 mmol) was added into the N,N-dimethylformamide solution (50 mL) of 4-(methylamino)nicotinamide (4.80 g, 31.8 mmol). The reaction solution was stirred at 0° C. for 1 hour. Carbonyldiimidazole (7.72 g, 47.6 mmol) was then added. The reaction mixture was allowed for reaction at 75° C. for 2 hours. The reaction solution was cooled to room temperature, quenched by adding water (50 mL). Hydrochloric acid solution (12N, 5 mL) was added to adjust the pH value to pH=3. The white solid was precipitated and then filtered. The filter cake was dried to give 1-methylpyrido[4,3-d]pyrimidin-2,4-dione (3.50 g, yellow solid) with a yield of 95%. $^1$H NMR: (400 MHz, DMSO-$d_6$) δ11.76 (s, 1H), 8.97 (s, 1H), 8.69 (d, J=6.0 Hz, 1H), 7.38 (d, J=6.0 Hz, 1H), 3.39 (s, 3H).

Step 4

1-Methyl-3-((3-methylpyridin-3-yl)methyl)pyrido[4,3-d]pyrimidin-2,4-dione 3-(Chloromethyl)-3-methyloxetane (26.5 mg, 0.220 mmol), 1-methylpyrido[4,3-d]pyrimidin-2,4-dione (30.0 mg, 0.169 mmol) and potassium carbonate (70.2 mg, 0.508 mmol) were dissolved in N,N-dimethylformamide (3 mL), and then potassium iodide (2.8 mg, 0.017 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 1-methyl-3-((3-methylpyridin-3-yl)methyl)pyrido[4,3-d]pyrimidin-2,4-dione (22.0 mg) with a yield of 48%. $^1$H NMR: (400 MHz, Methonal-$d_4$) δ9.14 (s, 1H), 8.71 (d, J=6.4 Hz, 1H), 7.44 (d, J=6.4 Hz, 1H), 4.79 (d, J=6.0 Hz, 2H), 4.27 (d, J=6.0 Hz, 2H), 4.25 (s, 2H), 3.61 (s, 3H), 1.38 (s, 3H). MS-ESI calculated value: [M+H]$^+$ 262; measured value: 262.

Example 52

3-((3-Ethyloxetan-3-yl)methyl)-1-methylpyrido[4,3-d]pyrimidin-2,4-dione

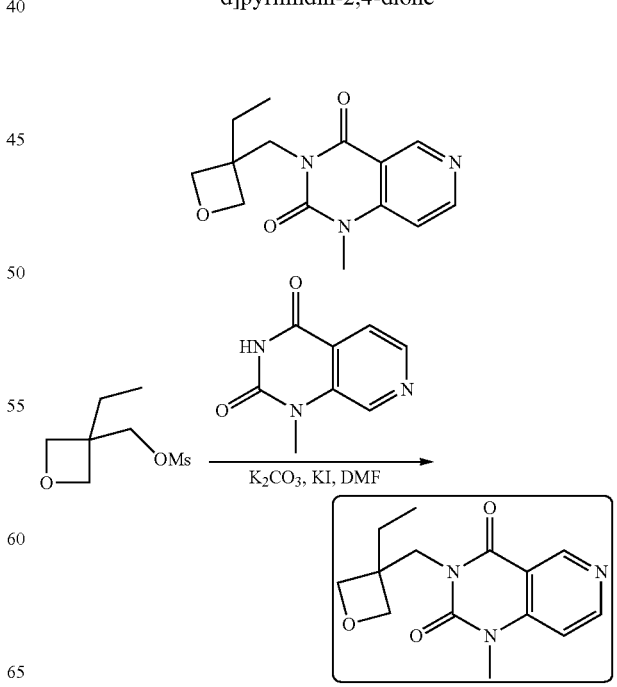

Step 1

3-((3-Ethyloxetan-3-yl)methyl)-1-methylpyrido[4,3-d]pyrimidin-2,4-dione (3-Ethyloxetan-3-yl)methyl methanesulfonate (42.7 mg, 0.220 mmol), 1-methylpyrido[4,3-d]pyrimidin-2,4-dione (30.0 mg, 0.169 mmol) and potassium carbonate (70.2 mg, 0.508 mmol) were dissolved in N,N-dimethylformamide (3 mL), and then potassium iodide (2.8 mg, 0.017 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 3-((3-ethyloxetan-3-yl)methyl)-1-methylpyrido[4,3-d]pyrimidin-2,4-dione (20.0 mg) with a yield of 42%. $^1$H NMR: (400 MHz, CDCl$_3$) δ9.29 (s, 1H), 8.75 (d, J=6.0 Hz, 1H), 7.09 (d, J=6.0 Hz, 1H), 4.61 (d, J=6.4 Hz, 2H), 4.31 (d, J=6.4 Hz, 2H), 4.17 (s, 2H), 3.59 (s, 3H), 1.83-1.78 (q, J=7.6 Hz, 2H), 1.07 (t, J=7.6 Hz, 3H). MS-ESI calculated value: [M+H]$^+$ 276; measured value: 276.

Example 53

1-Methyl-3-((tetrahydrofuran-3-yl)methyl)pyrido[4,3-d]pyrimidin-2,4-dione

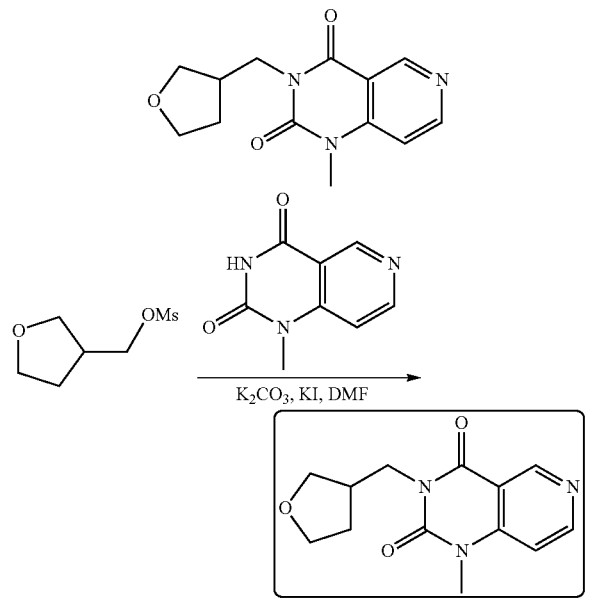

Step 1

1-Methyl-3-((tetrahydrofuran-3-yl)methyl)pyrido[4,3-d]pyrimidin-2,4-dione (Tetrahydrofuran-3-yl)methyl methanesulfonate (39.6 mg, 0.220 mmol), 1-methylpyrido[4,3-d]pyrimidin-2,4-dione (30.0 mg, 0.169 mmol) and potassium carbonate (70.2 mg, 0.508 mmol) were dissolved in N,N-dimethylformamide (3 mL), and then potassium iodide (2.8 mg, 0.017 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 1-methyl-3-((tetrahydrofuran-3-yl)methyl)pyrido[4,3-d]pyrimidin-2,4-dione (20.0 mg) with a yield of 43%. $^1$H NMR: (400 MHz, Methonal-d$_4$) δ9.11 (s, 1H), 8.68 (d, J=6.0 Hz, 1H), 7.42 (d, J=6.0 Hz, 1H), 4.17-4.04 (m, 2H), 3.96-3.91 (m, 1H), 3.81-3.73 (m, 2H), 3.65-3.61 (m, 1H), 3.60 (s, 3H), 2.81-2.71 (m, 1H), 2.08-2.00 (m, 1H), 1.81-1.73 (m, 1H). MS-ESI calculated value: [M+H]$^+$ 262; measured value: 262.

Example 54

1-Methyl-3-((tetrahydropyran-4-yl)methyl)pyrido[4,3-d]pyrimidin-2,4-dione

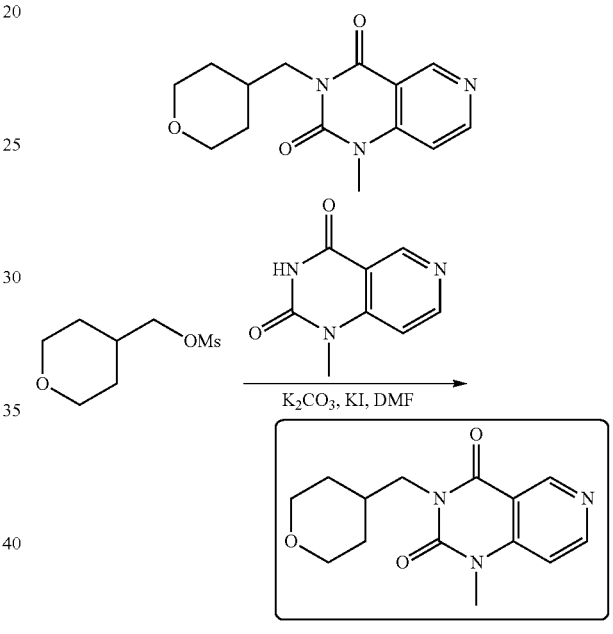

Step 1

1-Methyl-3-((tetrahydropyran-4-yl)methyl)pyrido[4,3-d]pyrimidin-2,4-dione (Tetrahydropyran-4-yl)methyl methanesulfonate (42.7 mg, 0.220 mmol), 1-methylpyrido[4,3-d]pyrimidin-2,4-dione (30.0 mg, 0.169 mmol) and potassium carbonate (70.2 mg, 0.508 mmol) were dissolved in N,N-dimethylformamide (3 mL), and then potassium iodide (2.8 mg, 0.017 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 1-methyl-3-((tetrahydropyran-4-yl)methyl)pyrido[4,3-d]pyrimidin-2,4-dione (19.0 mg) with a yield of 40%. $^1$H NMR: (400 MHz, Methonal-d$_4$) δ9.12 (s, 1H), 8.69 (d, J=6.0 Hz, 1H), 7.42 (d, J=6.0 Hz, 1H), 3.99 (d, J=7.2 Hz, 2H), 3.96-3.92 (m, 2H), 3.60 (s, 3H), 3.37-3.33 (m, 2H), 2.13-2.11 (m, 1H), 1.63-1.59 (m, 2H), 1.47-1.37 (m, 2H). MS-ESI calculated value: [M+H]$^+$ 276; measured value: 276.

Example 55

1-Methyl-3-(2-(tetrahydropyran-4-yl)ethyl)pyrido[4,3-d]pyrimidin-2,4-dione

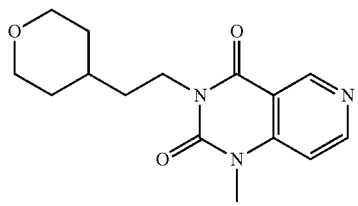

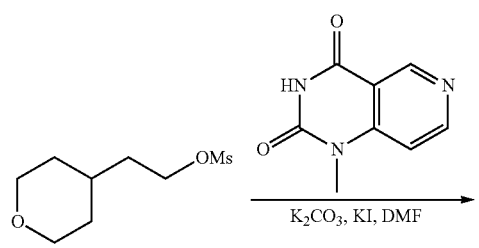

Step 1

1-Methyl-3-(2-(tetrahydropyran-4-yl)ethyl)pyrido[4,3-d]pyrimidin-2,4-dione 2-(Tetrahydropyran-4-yl)ethyl methanesulfonate (35.2 mg, 0.169 mmol), 1-methylpyrido[4,3-d]pyrimidin-2,4-dione (30.0 mg, 0.169 mmol) and potassium carbonate (70.2 mg, 0.508 mmol) were dissolved in N,N-dimethylformamide (3 mL), and then potassium iodide (2.8 mg, 0.017 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 1-methyl-3-(2-(tetrahydropyran-4-yl)ethyl)pyrido[4,3-d]pyrimidin-2,4-dione (25.0 mg) with a yield of 51%. $^1$H NMR: (400 MHz, Methonal-$d_4$) δ9.12 (s, 1H), 8.69 (d, J=6.4 Hz, 1H), 7.43 (d, J=6.4 Hz, 1H), 4.10 (t, J=7.4 Hz, 2H), 3.96-3.92 (m, 2H), 3.60 (s, 3H), 3.46-3.39 (m, 2H), 1.75 (d, J=12.8 Hz, 2H), 1.66-1.61 (m, 3H), 1.37-1.31 (m, 2H). MS-ESI calculated value: [M+H]$^+$ 290; measured value: 290.

Example 56

3-((4-Methoxycyclohexyl)methyl)-1-methylpyrido[4,3-d]pyrimidin-2,4-dione

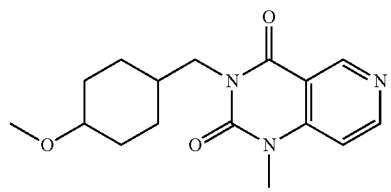

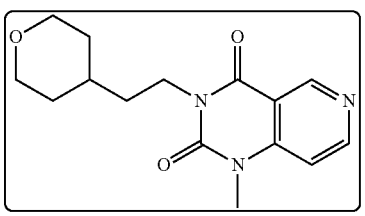

Step 1

3-((4-Methoxycyclohexyl)methyl)-1-methylpyrido[4,3-d]pyrimidin-2,4-dione (4-Methoxycyclohexyl)methyl methanesulfonate (37.6 mg, 0.169 mmol), 1-methylpyrido[4,3-d]pyrimidin-2,4-dione (30.0 mg, 0.169 mmol) and potassium carbonate (70.2 mg, 0.508 mmol) were dissolved in N,N-dimethylformamide (3 mL), and then potassium iodide (2.8 mg, 0.017 mmol) was added. The reaction solution was stirred at 120° C. for 3 hours. The reaction solution was filtered directly and the filtrate was concentrated under reduced pressure. The crude product obtained was purified by preparative high performance liquid chromatography to give a product 3-((4-methoxycyclohexyl)methyl)-1-methylpyrido[4,3-d]pyrimidin-2,4-dione (20.0 mg) with a yield of 37%. $^1$H NMR: (400 MHz, Methonal-$d_4$) δ9.14 (s, 1H), 8.69 (d, J=6.0 Hz, 1H), 7.43 (d, J=6.0 Hz, 1H), 3.95 (d, J=6.8 Hz, 2H), 3.64 (s, 3H), 3.35 (s, 3H), 3.22-3.16 (m, 1H), 2.09 (d, J=8.8 Hz, 2H), 1.85-1.77 (m, 3H), 1.18-1.12 (m, 4H). MS-ESI calculated value: [M+H]$^+$ 304, measured value: 304.

Example 57

1-Methyl-3-[(3-methylpyridin-3-yl)methyl]pyrido[3,2-d]pyrimidin-2,4-dione

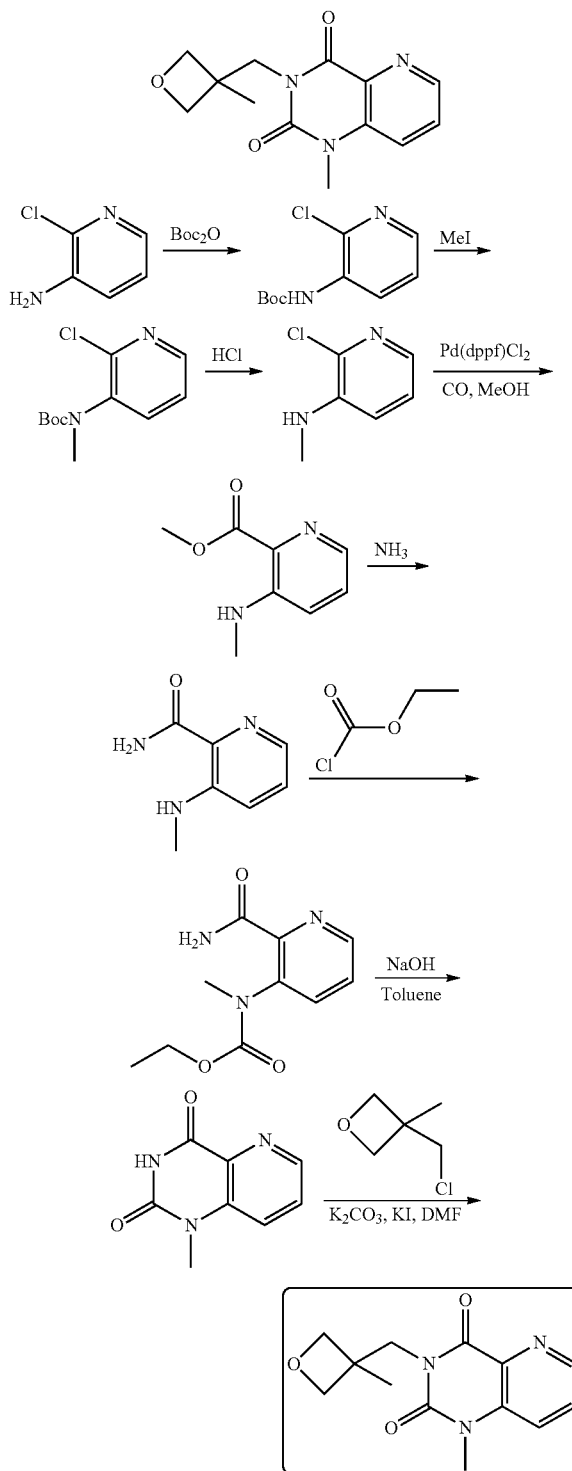

Step 1

Tert-butyl N-(2-chloro-3-pyridinyl) carbamate

2-Chloropyridin-3-amine (30.0 g, 233 mmol) was dissolved in methylene chloride (250 mL), and then triethylamine (47.2 g, 467 mmol) was added. Di-tert-butyl dicarbonate (102 g, 467 mmol) was added dropwise at 0° C. The reaction solution was stirred at 25° C. for 18 hours. The reaction was quenched by adding water (100 mL). The reaction solution was extracted with ethyl acetate (100 mL×3). The organic phases were combined, dried over anhydrous sodium sulfate, and then filtered. The filtrate was concentrated under reduced pressure, the residue was separated and purified by silica gel column chromatography (15:1 petroleum ether/ethyl acetate, Rf=0.6) to give tert-butyl N-(2-chloro-3-pyridinyl) carbamate (11.0 g, white solid) with a yield of 21%. $^1$H NMR: (400 MHz, DMSO-d$_6$) δ8.89 (s, 1H), 8.17-8.16 (m, 1H), 8.03-8.01 (m, 1H), 7.43-7.39 (m, 11-), 1.47 (s, 9H).

Step 2

Tert-butyl (2-chloropyridin-3-yl)(methyl) carbamate

Tert-butyl N-(2-chloro-3-pyridinyl) carbamate (11.0 g, 48.1 mmol) was dissolved in anhydrous tetrahydrofuran (150 mL), and then sodium-hydrogen (1.39 g, 57.7 mmol) was slowly added at 0° C. under the protection of nitrogen. The reaction solution was stirred at 0° C. for half an hour. Iodomethane (10.2 g, 72.2 mmol) was slowly added and stirred at room temperature for 12 hours. The reaction was quenched by adding water (50 mL). The reaction solution was extracted with ethyl acetate (80 mL×3). The organic phases were combined, washed with saturated brine (150 mL), dried over anhydrous sodium sulfate, and then filtered. The filtrate was concentrated under reduced pressure to give tert-butyl (2-chloropyridin-3-yl)(methyl) carbamate (11.0 g, colorless oil) with a yield of 94%. $^1$H NMR: (400 Hz, DMSO-d$_6$) 58.33 (d, J=4.8 Hz, 1H), 7.92-7.90 (m, 1H), 7.48 (d, J=8.0 Hz, 1H), 3.06 (s, 3H), 1.45-1.14 (m, 9H). MS-ESI calculated value: [M+H]$^+$ 243; measured value: 243.

Step 3

2-Chloro-N-methylpyridin-3-amine

Tert-butyl (2-chloropyridin-3-yl)(methyl) carbamate (11.0 g, 45.3 mmol) was dissolved in ethyl acetate (50 mL), and then 4M hydrochloric acid-ethyl acetate (150 mL) was added dropwise at 0° C., followed by stirring at 25° C. for 15 hours. The reaction solution was concentrated under reduced pressure, and then purified by silica gel column chromatography (10:1 petroleum ether/ethyl acetate, Rf=0.3) to give 2-chloro-N-methylpyridin-3-amine (5.50 g, colorless oil) with a yield of 85%. $^1$H NMR: (400 Hz, DMSO-d$_6$) 57.56 (d, J=4.8 Hz, 1H), 7.20-7.17 (m, 1H), 6.95 (d, J=8.0 Hz, 1H), 5.76-5.73 (m, 1H), 2.73 (d, J=4.8 Hz, 3H). MS-ESI calculated value: [M+H]$^+$ 143; measured value: 143.

Step 4

Methyl 3-(methylamino) pyridinecarboxylate

2-Chloro-N-methylpyridin-3-amine (5.50 g, 38.6 mmol) was dissolved in methanol (100 mL). 1,1'-Bis(diphenylphosphino)ferrocene palladium chloride (2.82 g, 3.86 mmol) was added into the reaction solution under the condition of 25° C. The reaction solution was allowed for reaction in a carbon monoxide atmosphere (50 psi) at 50° C. for 56 hours. The reaction solution was cooled to 25° C., concentrated under reduced pressure, separated and purified by silica gel column chromatography (5:1 petroleum ether/ethyl acetate, Rf=0.5) to give methyl 3-(methylamino) pyridinecarboxylate (6.00 g, colorless oil) with a yield of 94%. $^1$H NMR: (400 MHz, Methonal-d$_4$) δ7.84 (d, J=4.8 Hz, 1H), 7.45-7.42 (m, 1H), 7.29 (d, J=8.0 Hz, 1H), 3.93 (s, 3H), 2.94 (s, 3H).

MS-ESI calculated value: [M+H]$^+$ 167; measured value: 167.

Step 5

3-(Methylamino)pyridin-2-carboxamide

Methyl 3-(methylamino)pyridin-2-carboxylate (6.00 g, 36.1 mmol) dissolved in methanol (100 mL), and then aqueous ammonia (1.27 g, 36.1 mmol) was added. The reaction solution was stirred at 40° C. for 18 hours. Water (200 mL) was added into the reaction solution, followed by extraction with ethyl acetate (100 mL×2). The organic phases were combined, dried over anhydrous sodium sulfate, and then filtered. The filtrate was concentrated under reduced pressure to give 3-(methylamino)pyridin-2-carboxamide (3.50 g, yellow solid) with a yield of 64%. $^1$H NMR: (400 MHz, DMSO-d$_6$) 58.27-8.23 (br, 1H), 7.80-7.95 (br, 1H), 7.76 (d, J=4.0 Hz, 1H), 7.37-7.32 (m, 2H), 7.11 (d, J=8.0 Hz, 1H), 2.79 (d, J=4.8 Hz, 3H).

Step 6

Ethyl N-[(2-formylamino-3-pyridinyl)-N-methyl]-carbamate 3-(Methylamino)pyridin-2-carboxamide (1.70 g, 10.9 mmol) was dissolved in ethyl chloroformate (35.3 g, 326 mmol). The reaction solution was stirred at 90° C. for 1 hour. The reaction solution was quenched with saturated aqueous sodium bicarbonate solution (20 mL), and extracted with ethyl acetate (20 mL×2). The organic phases were concentrated under reduced pressure, and the residue was separated and purified by silica gel column chromatography (1:1 petroleum ether/ethyl acetate, Rf=0.2) to give ethyl N-[(2-formylamino-3-pyridinyl)-N-methyl]-carbamate (2.00 g, white solid) with a yield of 83%. $^1$H NMR: (400 MHz, DMSO-d$_6$) δ8.48 (d, J=4.0 Hz, 1H), 7.90 (br, 1H), 7.82 (d, J=8.0 Hz, 1H), 7.60-7.56 (m, 1H), 7.50 (br, 1H), 3.88 (q, J=7.2 Hz, 2H), 3.12 (s, 3H), 1.00 (t, J=7.2 Hz, 3H).

Step 7

1-Methylpyrido[3,2-d]pyrimidin-2,4-dione

Ethyl N-[(2-formylamino-3-pyridinyl)-N-methyl]-carbamate (2.00 g, 8.96 mmol) and sodium hydroxide (717 mg, 17.9 mmol) were dissolved in toluene (25 mL). The reaction solution was stirred at 110° C. for 0.5 hour. The reaction solution was diluted by adding water (15 mL), followed by adjusting the pH value to pH=7 with 1N hydrochloric acid solution. The reaction solution was filtered and the filter cake was diluted with methanol (15 mL), followed by concentration under reduced pressure to give 1-methyl-pyrido[3,2-d]pyrimidin-2,4-dione (1.09 g, white solid) with a yield of 69%. $^1$H NMR: (400 MHz, DMSO-d$_6$) δ11.72 (s, 1H), 8.50 (d, J=4.8 Hz, 1H), 7.89 (dd, J=8.0, 4.8 Hz, 1H), 7.74-7.71 (m, 1H), 3.41 (s, 3H).

Step 8

1-Methyl-3-[(3-methylpyridin-3-yl)methyl]pyrido[3,2-d]pyrimidin-2,4-dione

1-Methylpyrido[3,2-d]pyrimidin-2,4-dione (30.0 mg, 0.169 mmol), 3-(chloromethyl)-3-methyloxetane (26.5 mg, 0.220 mmol) and potassium carbonate (58.5 mg, 0.424 mmol) were dissolved in N,N-dimethylformamide (4 mL), and then potassium iodide (2.8 mg, 0.017 mmol) was added. The reaction solution was heated and refluxed at 120° C. for 3 hours. The reaction solution was filtered directly and the filtrate was concentrated under reduced pressure. The crude product obtained was purified by preparative high performance liquid chromatography to give a product 1-methyl-3-[(3-methylpyridin-3-yl)methyl]pyrido[3,2-d]pyrimidin-2,4-dione (12.0 mg) with a yield of 27%. $^1$H NMR: (400 MHz, Methonal-d$_4$) δ8.57 (d, J=4.8 Hz, 1H), 8.00 (d, J=8.0 Hz, 1H), 7.82-7.77 (m, 1H), 4.80 (d, J=6.0 Hz, 2H), 4.31-4.25 (m, 4H), 3.64 (s, 3H), 1.40 (s, 3H). MS-ESI calculated value: [M+H]$^+$ 262; measured value: 262.

Example 58

3-[(3-Ethyloxetan-3-yl)methyl]-1-methylpyrido[3,2-d]pyrimidin-2,4-dione

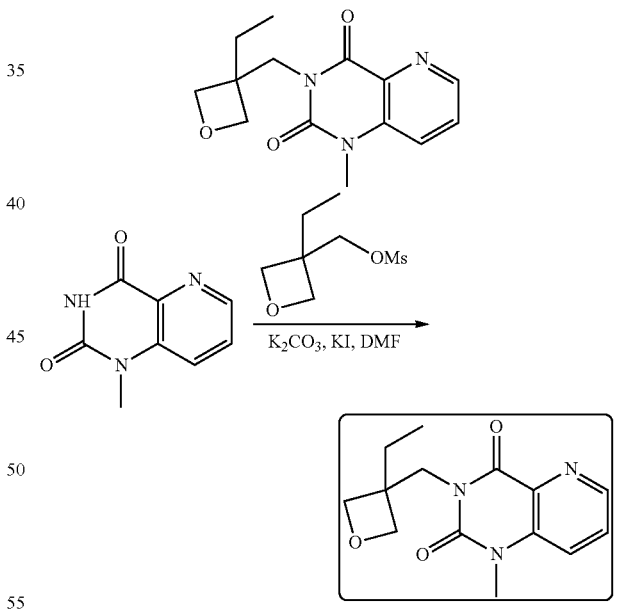

Step 1

3-[(3-Ethyloxetan-3-yl)methyl]-1-methylpyrido[3,2-d]pyrimidin-2,4-dione

1-Methylpyrido[3,2-d]pyrimidin-2,4-dione (30.0 mg, 169 mmol), (3-ethyloxetan-3-yl)methyl methanesulfonate (42.8 mg, 220 mmol) and potassium carbonate (70.2 mg, 508 mmol) were dissolved in N,N-dimethylformamide (4 mL), and then potassium iodide (2.80 mg, 0.017 mmol) was added. The reaction solution was heated and refluxed at 120° C. for 3 hours. The reaction solution was filtered directly and the filtrate was concentrated under reduced pressure. The crude product obtained was purified by preparative high performance liquid chromatography to give a product 3-[(3-ethyloxetan-3-yl)methyl]-1-methylpyrido[3,2-d]pyrimidin-2,4-dione (16.0 mg) with a yield of 34%. $^1$H NMR: (400 MHz, Methonal-d$_4$) δ8.57 (d, J=4.4 Hz, 1H), 8.00 (d, J=4.4 Hz, 1H), 7.83-7.79 (m, 1H), 4.69 (d, J=6.8 Hz, 2H), 4.33 (d, J=6.8 Hz, 2H), 4.25 (s, 2H), 3.65 (s, 3H), 1.86-1.80 (m, 2H), 1.09 (t, J=7.4 Hz, 3H). MS-ESI calculated value: [M+H]$^+$ 276; measured value: 276.

Example 59

1-Methyl-3-((tetrahydrofuran-3-yl)methyl)pyrido[3,2-d]pyrimidin-2,4-dione

Example 60

1-Methyl-3-((tetrahydropyran-4-yl)methyl)pyrido[3,2-d]pyrimidin-2,4-dione

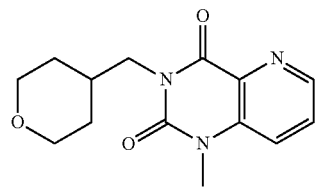

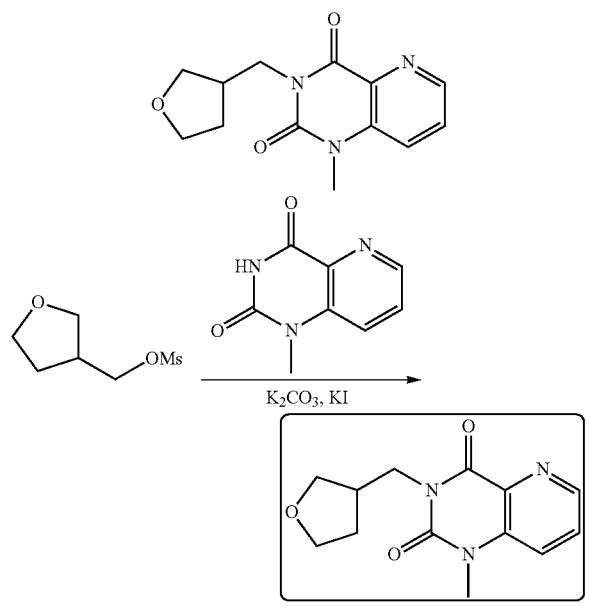

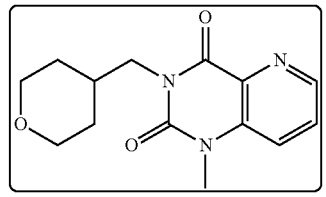

Step 1

1-Methyl-3-((tetrahydropyran-4-yl)methyl)pyrido[3,2-d]pyrimidin-2,4-dione

Step 1

1-Methyl-3-((tetrahydrofuran-3-yl)methyl)pyrido[3,2-d]pyrimidin-2,4-dione (Tetrahydrofuran-3-yl)methyl methanesulfonate (30.5 mg, 0.169 mmol), 1-methylpyrido[3,2-d]pyrimidin-2,4-dione (25.0 mg, 0.141 mmol), potassium iodide (2.3 mg, 0.014 mmol) and potassium carbonate (39.0 mg, 0.282 mmol) were dissolved in N,N-dimethylformamide (3 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-((tetrahydrofuran-3-yl)methyl)pyrido[3,2-d]pyrimidin-2,4-dione (20.0 mg) with a yield of 54%. $^1$H NMR: (400 MHz, Methonal-d$_4$) δ8.56 (d, J=4.4 Hz, 1H), 7.98 (d, J=8.0 Hz, 1H), 7.81-7.77 (m, 1H), 4.21-4.14 (m, 2H), 3.96-3.90 (m, 1H), 3.81-3.78 (m, 2H), 3.67-3.63 (m, 4H), 2.82-2.79 (m, 1H), 2.06-2.03 (m, 1H), 1.83-1.79 (m, 1H). MS-ESI calculated value: [M+H]$^+$ 262; measured value: 262.

(Tetrahydropyran-4-yl)methyl methanesulfonate (39.5 mg, 0.203 mmol), 1-methylpyrido[3,2-d]pyrimidin-2,4-dione (30.0 mg, 0.169 mmol), potassium iodide (2.8 mg, 0.017 mmol) and potassium carbonate (46.8 mg, 0.339 mmol) were dissolved in N,N-dimethylformamide (3 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-((tetrahydropyran-4-yl)methyl)pyrido[3,2-d]pyrimidin-2,4-dione (20.0 mg) with a yield of 43%. $^1$H NMR: (400 MHz, Methonal-d$_4$) δ8.56 (d, J=3.6 Hz, 1H), 7.98 (d, J=8.0 Hz, 1H), 7.81-7.77 (m, 1H), 4.06-4.04 (m, 2H), 3.96-3.93 (m, 2H), 3.63 (s, 3H), 3.38-3.33 (m, 2H), 2.17-2.14 (m, 1H), 1.64-1.61 (m, 2H), 1.49-1.44 (m, 2H). MS-ESI calculated value: [M+H]$^+$ 276; measured value: 276.

Example 61

1-Methyl-3-(2-(tetrahydropyran-4-yl)ethyl)pyrido[3,2-d]pyrimidin-2,4-dione

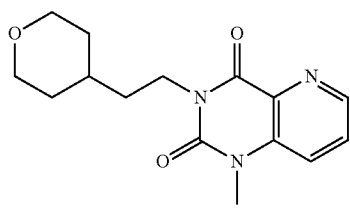

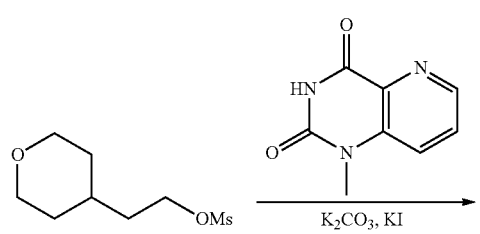

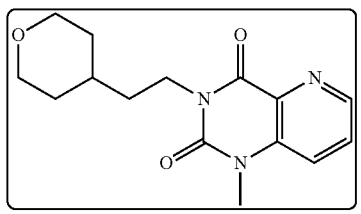

Step 1

1-Methyl-3-(2-(tetrahydropyran-4-yl)ethyl)pyrido[3,2-d]pyrimidin-2,4-dione 2-(Tetrahydropyran-4-yl)ethyl methanesulfonate (35.3 mg, 0.169 mmol), 1-methylpyrido[3,2-d]pyrimidin-2,4-dione (25.0 mg, 0.141 mmol), potassium iodide (2.3 mg, 0.014 mmol) and potassium carbonate (39.0 mg, 0.282 mmol) were dissolved in N,N-dimethylformamide (3 mL). The reaction solution was heated to 120° C. and stirred for 3 hours, and then cooled to room temperature, followed by filtration. The filtrate was concentrated under reduced pressure, and the residue was then purified by preparative high performance liquid chromatography to give 1-methyl-3-(2-(tetrahydropyran-4-yl)ethyl)pyrido[3,2-d]pyrimidin-2,4-dione (20.0 mg) with a yield of 49%. $^1$H NMR: (400 MHz, Methonal-$d_4$) δ8.55 (d, J=4.0 Hz, 1H), 7.99 (d, J=8.0 Hz, 1H), 7.78 (d, J=8.0, 4.0 Hz, 1H), 4.19-4.15 (m, 2H), 3.95-3.93 (m, 2H), 3.63 (s, 3H), 3.47-3.40 (m, 2H), 1.79-1.76 (m, 2H), 1.68-1.64 (m, 3H), 1.37-1.33 (m, 2H). MS-ESI calculated value: [M+H]$^+$ 290; measured value: 290.

Example 62

3-((4-Methoxycyclohexyl)methyl)-1-methylpyrido[3,2-d]pyrimidin-2,4-dione

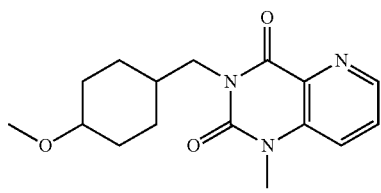

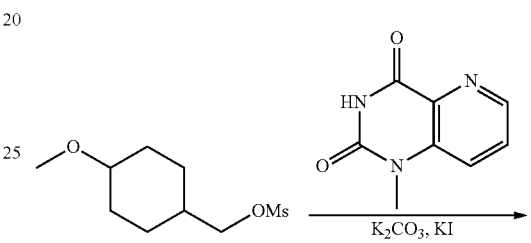

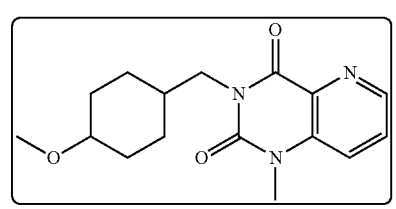

Step 1

3-((4-Methoxycyclohexyl)methyl)-1-methylpyrido[3,2-d]pyrimidin-2,4-dione (4-Methoxycyclohexyl)methyl methanesulfonate (37.7 mg, 0.169 mmol), 1-methylpyrido[3,2-d]pyrimidin-2,4-dione (25.0 mg, 0.141 mmol), potassium iodide (2.3 mg, 0.014 mmol) and potassium carbonate (39.0 mg, 0.282 mmol) were dissolved in N,N-dimethylformamide (3 mL). The reaction solution was heated to 120° C. and stirred for 3 hours. Then the reaction solution was cooled to room temperature, and filtered. The filtrate was concentrated under reduced pressure, and the residue was then purified by preparative high performance liquid chromatography to give 3-((4-methoxycyclohexyl)methyl)-1-methylpyrido[3,2-d]pyrimidin-2,4-dione (20.0 mg) with a yield of 47%. $^1$H NMR: (400 MHz, Methonal-$d_4$) δ8.55 (d, J=4.0 Hz, 1H), 7.97 (d, J=8.4 Hz, 1H), 7.80-7.77 (m, 1H), 3.99-3.97 (m, 2H), 3.62 (s, 3H), 3.33 (s, 3H), 3.18-3.15 (m, 1H), 2.09-2.06 (m, 2H), 1.86-1.76 (m, 3H), 1.19-1.10 (m, 4H). MS-ESI calculated value: [M+H]$^+$ 304; measured value: 304.

Example 63

1-Methyl-3-((3-methyloxetan-3-yl)methyl)pteridin-2,4-dione

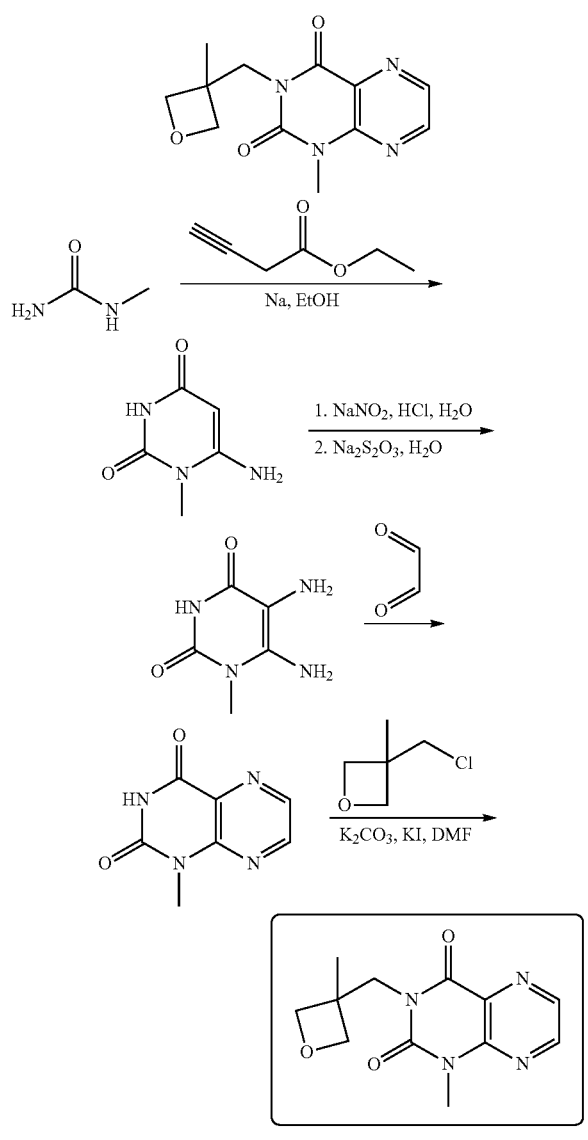

Step 1

6-Amino-1-methylpyrimidin-2,4-dione

At 25° C., metallic sodium (7.80 g, 340 mmol) was added into anhydrous ethanol (180 mL) in batches while stirring, followed by heating to 80° C. and refluxing for 0.5 hour. Methylurea (12.6 g, 170 mmol) was then added in batches, and refluxing was continued for 0.5 hour. Ethyl cyanoacetate (19.0 g, 170 mmol) was added into the reaction solution dropwise, and a large amount of precipitate was produced. Refluxing was continued for 3 hours, and then ethanol was recovered under reduced pressure. The residue was dissolved in water (50 mL), and the pH value was adjusted to pH=7 with diluted hydrochloric acid (1N), followed by filtration to give 6-amino-1-methylpyrimidin-2,4-dione (7.60 g, white solid) with a yield of 32%. $^1$H NMR: (400 MHz, DMSO-$d_6$) δ10.39 (s, 1H), 6.79 (s, 2H), 4.54 (s, 1H), 3.14 (s, 3H). MS-ESI calculated value: [M+H]$^+$ 142; measured value: 142.

Step 2 5,6-Diamino-1-methylpyrimidin-2,4-dione

6-Amino-1-methylpyrimidin-2,4-dione (10.0 g, 70.1 mmol) was dissolved in water (100 mL), and then hydrochloric acid (7 mL, 84.0 mmol, 12N) was added dropwise at 0° C. while stirring. Sodium nitrite (5.80 g, 84.2 mmol) was dissolved in water (50 mL), which was added dropwise into the reactants, then a purple precipitate appeared. The reaction solution was stirred 25° C. for 2 hours, the then was filtered. The filtrate was washed with cold water to give a purple solid. The solid was dissolved in water (100 mL), and then sodium hypodisulfite (18.7 g, 118 mmol) was added in batches while stirring. The reaction solution was heated to 60° C. and stirred for 0.5 hour, and then was cooled to 25° C. and stirred for 16 hours. The reaction solution was filtered and the filtrate was washed with water (50 mL), ethanol (50 mL) and propanone (50 mL), respectively, followed by drying to give a product 5,6-diamino-1-methylpyrimidin-2,4-dione (8.60 g, pale yellow solid), with a yield of 93%. $^1$H NMR (400 MHz, DMSO-$d_6$) δ10.49 (s, 1H), 6.15 (s, 2H), 3.25 (s, 3H), 2.95 (s, 2H). MS-ESI calculated value: [M+H]$^+$ 157; measured value: 157.

Step 3

1-Methylpteridin-2,4-dione 5,6-Diamino-1-methylpyrimidin-2,4-dione (4.00 g, 25.6 mmol) was dissolved in water (150 mL), and then glyoxal (5.58 g, 38.4 mmol, 40% aqueous solution) was added at one time at 25° C. The reaction solution was heated to 60° C. and stirred for 16 hours, and then filtered. The solid obtained was washed with water (50 mL) to give a product 1-methylpteridin-2,4-dione (3.60 g, yellow solid) with a yield of 79%.

Step 4

1-Methyl-3-((3-methyloxetan-3-yl)methyl)pteridin-2,4-dione

1-Methylpteridin-2,4-dione (299 mg, 1.68 mmol) was dissolved in N,N-dimethylformamide (8 mL), and then 3-(chloromethyl)-3-methyl-oxetane (222 mg, 1.85 mmol), potassium iodide (334 mg, 2.02 mmol) and potassium carbonate (464 mg, 3.36 mmol) were added at 25° C. The reaction solution was heated to 120° C. and stirred for 17 hours. The reaction solution was cooled to room temperature and then filtered. The filtrate was concentrated under reduced pressure, and the residue was purified by high performance liquid chromatography to give 1-methyl-3-((3-methyloxetan-3-yl)methyl)pteridin-2,4-dione (40.0 mg) with a yield of 9%. $^1$H NMR: (400 MHz, CDCl$_3$) δ8.68 (d, J=4.0 Hz, 1H), 8.62 (d, J=4.0 Hz, 1H), 4.78 (d, J=8.0 Hz, 2H), 4.32-4.29 (m, 4H), 3.73 (s, 3H), 1.42 (s, 3H). Calculated value: [M+H]$^+$ 263; measured value: 263.

Example 64

3-((3-Ethyloxetan-3-yl)methyl)-1-methylpteridin-2,4-dione

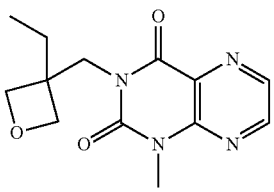

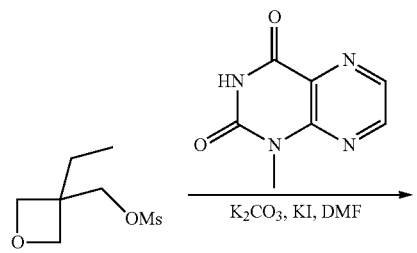

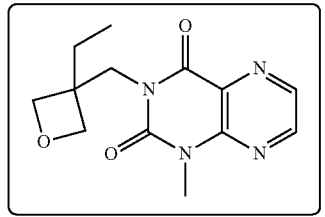

Step 1

3-((3-Ethyloxetan-3-yl)methyl)-1-methylpteridin-2,4-dione

1-Methylpteridin-2,4-dione (100 mg, 0.560 mmol) was dissolved in N,N-dimethylformamide (4 mL), and then (3-ethyloxetan-3-yl)methyl methanesulfonate (119 mg, 0.620 mmol), potassium iodide (19.0 mg, 0.110 mmol) and potassium carbonate (155 mg, 1.12 mmol) were added at 25° C. The reaction solution was heated to 120° C. and stirred for 16 hours. The reaction solution was cooled to room temperature and then filtered. The filtrate was concentrated under reduced pressure, and the residue was purified by preparative high performance liquid chromatography to give a product 3-((3-ethyloxetan-3-yl)methyl)-1-methylpteridin-2,4-dione (18.0 mg) with a yield of 12%.

$^1$H NMR: (400 MHz, CDCl$_3$) δ8.68 (d, J=2.0 Hz, 1H), 8.62 (d, J=2.0 Hz, 1H), 4.66 (d, J=6.4 Hz, 2H), 4.35 (d, J=6.8 Hz, 2H), 4.26 (s, 2H), 3.73 (s, 3H), 1.86-1.80 (m, 2H), 1.09 (t, J=7.2 Hz, 3H).

MS-ESI calculated value: [M+H]$^+$ 277; measured value: 277.

Example 65

1-Methyl-3-((tetrahydrofuran-3-yl)methyl)pteridin-2,4-dione

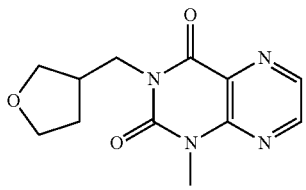

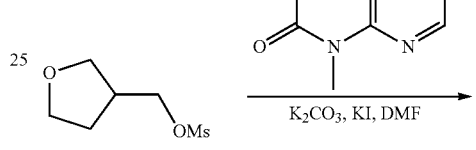

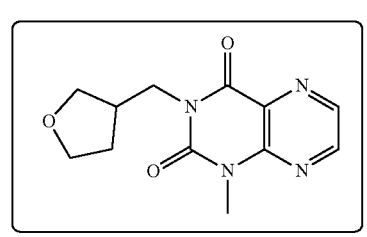

Step 1

1-Methyl-3-((tetrahydrofuran-3-yl)methyl)pteridin-2,4-dione

1-Methylpteridin-2,4-dione (60.0 mg, 0.337 mmol) was dissolved in N,N-dimethylformamide (4 mL), and then (tetrahydrofuran-3-yl)methyl methanesulfonate (61.0 mg, 0.337 mmol), potassium iodide (11.0 mg, 0.0670 mmol) and potassium carbonate (93.0 mg, 0.674 mmol) were added at 25° C. The reaction solution was heated to 120° C. and stirred for 16 hours. The reaction solution was cooled to room temperature and then filtered. The filtrate was concentrated under reduced pressure, and the residue was purified by preparative high performance liquid chromatography to give a product 1-methyl-3-((tetrahydrofuran-3-yl)methyl)pteridin-2,4-dione (6.0 mg) with a yield of 7%. $^1$H NMR: (400 MHz, CDCl$_3$) δ8.66 (d, J=2.4 Hz, 1H), 8.61 (d, J=2.4 Hz, 1H), 4.31-4.25 (m, 1H), 4.18-4.12 (m, 1H), 3.98-3.94 (m, 1H), 3.87-3.78 (m, 2H), 3.73 (s, 3H), 3.67-3.63 (m, 1H), 2.84-2.78 (m, 1H), 2.04-1.98 (m, 1H), 1.83-1.75 (m, 1H).

MS-ESI calculated value: [M+H]$^+$ 263; measured value: 263.

Example 66

1-Methyl-3-((tetrahydropyran-4-yl)methyl)pteridin-2,4-dione

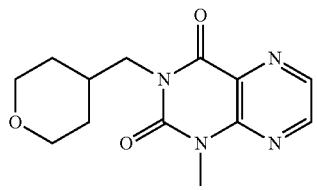

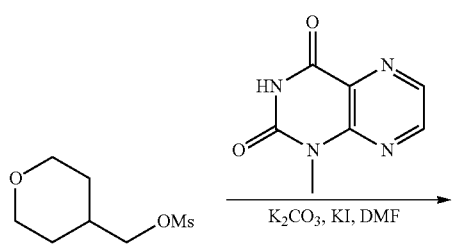

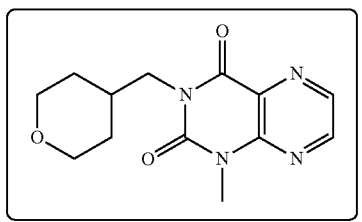

Step 1

1-Methyl-3-((tetrahydropyran-4-yl)methyl)pteridin-2,4-dione

1-Methylpteridin-2,4-dione (100 mg, 0.560 mmol) was dissolved in N,N-dimethylformamide (4 mL), and then (tetrahydropyran-4-yl)methyl methanesulfonate (119 mg, 0.622 mmol), potassium iodide (19.0 mg, 0.112 mmol) and potassium carbonate (155 mg, 1.12 mmol) were added at 25° C. The reaction solution was heated to 120° C. and stirred for 16 hours. The reaction solution was cooled to room temperature and then filtered. The filtrate was concentrated under reduced pressure, and the residue was purified by preparative high performance liquid chromatography to give a product 1-methyl-3-((tetrahydropyran-4-yl)methyl)pteridin-2,4-dione (14.0 mg) with a yield of 9%.

$^1$H NMR: (400 MHz, CDCl$_3$) δ8.65 (d, J=2.0 Hz, 1H), 8.60 (d, J=2.0 Hz, 1H), 4.08 (d, J=7.2 Hz, 2H), 3.98-3.95 (m, 2H), 3.72 (s, 3H), 3.37-3.31 (m, 2H), 2.19-2.09 (m, 1H), 1.61-1.49 (m, 4H).

MS-ESI calculated value: [M+H]$^+$ 277; measured value: 277.

Example 67

1-Methyl-3-(2-(tetrahydropyran-4-yl)ethyl)pteridin-2,4-dione

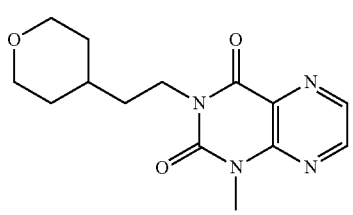

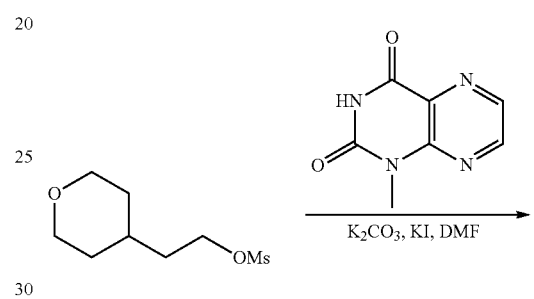

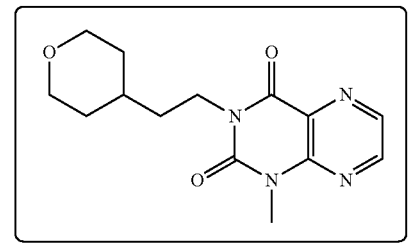

Step 1

1-Methyl-3-(2-(tetrahydropyran-4-yl)ethyl)pteridin-2,4-dione 2-(Tetrahydropyran-4-yl)ethyl methanesulfonate (117 mg, 0.561 mmol), 1-methylpteridin-2,4-dione (100 mg, 0.561 mmol) and potassium carbonate (233 mg, 1.68 mmol) were dissolved in N,N-dimethylformamide (5 mL), and then potassium iodide (9.3 mg, 0.0561 mmol) was added. The reaction solution was stirred at 120° C. for 3 hours. The reaction solution was cooled to room temperature and then filtered. The filtrate was concentrated under reduced pressure. The crude product obtained was purified by preparative high performance liquid chromatography to give a product 1-methyl-3-(2-(tetrahydropyran-4-yl)ethyl)pteridin-2,4-dione (12.0 mg) with a yield of 7.4%. $^1$H NMR: (400 MHz, CDCl$_3$) δ8.65 (d, J=2.4 Hz, 1H), 8.60 (d, J=2.4 Hz, 1H), 4.18 (t, J=7.2 Hz, 2H), 3.98-3.95 (m, 2H), 3.72 (s, 3H), 3.42-3.37 (m, 2H), 1.73 (d, J=12.8 Hz, 2H), 1.67 (t, J=7.2 Hz, 2H), 1.58 (s, 1H), 1.43-1.33 (m, 2H). MS-ESI calculated value: [M+H]$^+$ 291; measured value: 291.

Example 68

3-((4-Methoxycyclohexyl)methyl)-1-methylpteridin-2,4-dione

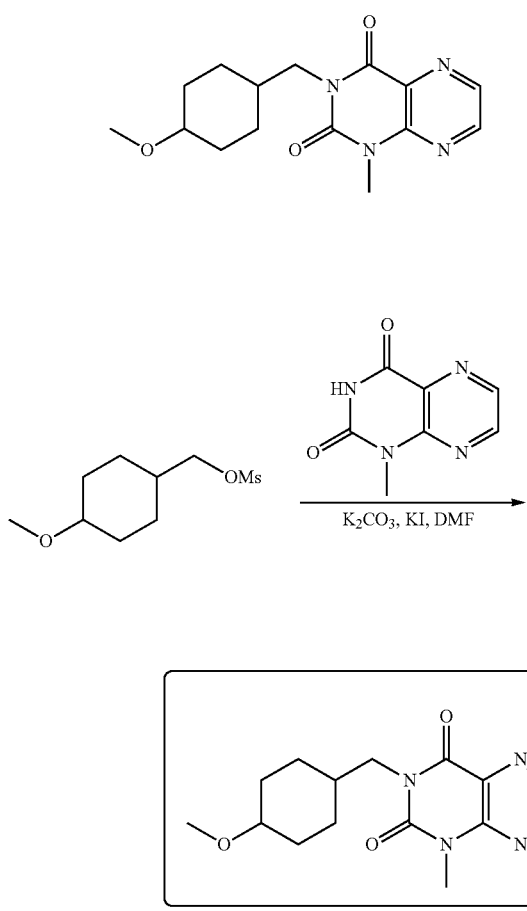

Step 1

3-((4-Methoxycyclohexyl)methyl)-1-methylpteridin-2,4-dione (4-Methoxycyclohexyl)methyl methanesulfonate (162 mg, 0.729 mmol), 1-methylpteridin-2,4-dione (100 mg, 0.561 mmol) and potassium carbonate (233 mg, 1.68 mmol) were dissolved in N,N-dimethylformamide (5 mL), and then potassium iodide (9.3 mg, 0.056 mmol) was added. The reaction solution was stirred at 120° C. for 3 hours. The reaction solution was cooled to room temperature and then filtered. The filtrate was concentrated under reduced pressure. The crude product obtained was purified by preparative high performance liquid chromatography to give a product 3-((4-methoxycyclohexyl)methyl)-1-methylpteridin-2,4-dione (19.0 mg) with a yield of 11%. $^1$H NMR: (400 MHz, CDCl$_3$) δ8.64 (d, J=2.0 Hz, 1H), 8.59 (d, J=2.0 Hz, 1H), 4.03 (d, J=7.2 Hz, 2H), 3.72 (s, 3H), 3.34 (s, 3H), 3.15-3.09 (m, 1H), 2.08-2.06 (m, 2H), 1.90-1.84 (m, 1H), 1.77 (d, J=10.0 Hz, 2H), 1.20-1.13 (m, 4H). MS-ESI calculated value: [M+H]$^+$ 305; measured value: 305.

Example 69

1-Methyl-3-((3-methylpyridin-3-yl)methyl)pyrimido[4,5-d]pyrimidin-2,4-dione

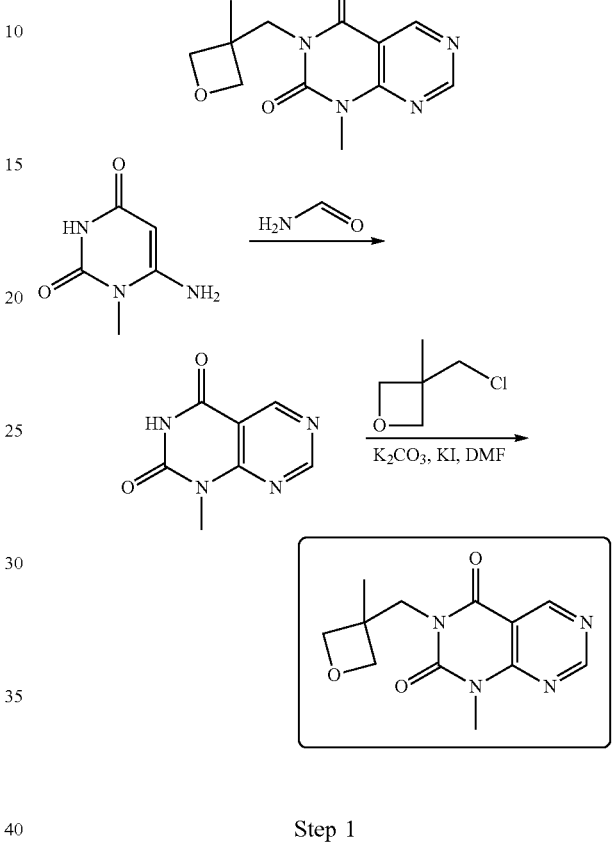

Step 1

1-Methylpyrimido[4,5-d]pyrimidin-2,4-dione

6-Amino-1-methylpyrimidin-2,4-dione (3.50 g, 24.8 mmol) was added into formamide (5.00 g, 111 mmol). The reaction solution was heated to 180° C. and stirred for 3 hours, and then cooled to room temperature, followed by filtration. Water (10 mL) was added into the filtrate and stirred, and the solution was then filtered to give 1-methylpyrimido[4,5-d]pyrimidin-2,4-dione (1.60 g, pale yellow solid), with a yield of 36%. $^1$H NMR: (400 MHz, DMSO-d$_6$) δ9.16 (s, 1H), 9.08 (s, 1H), 3.43 (s, 3H).

Step 2

1-Methyl-3-((3-methylpyridin-3-yl)methyl)pyrimido[4,5-d]pyrimidin-2,4-dione

1-Methylpyrimido[4,5-d]pyrimidin-2,4-dione (300 mg, 1.68 mmol) was dissolved in N,N-dimethylformamide (8 mL), and then 3-(chloromethyl)-3-methyloxetane (403 mg, 1.85 mmol), potassium carbonate (465 mg, 3.37 mmol) and potassium iodide (335 mg, 2.02 mmol) were added at 25° C. The reaction solution was heated to 120° C. and stirred for 16 hours. The reaction solution was cooled to room temperature and then filtered. The filtrate was concentrated under reduced pressure, and the residue was purified by high performance liquid chromatography to give 1-methyl-3-((3-methylpyridin-3-yl)methyl)pyrimido[4,5-d]pyrimidin-2,4-dione (135 mg) with a yield of 31%. $^1$H NMR: (400 MHz, CDCl$_3$) δ9.29 (s, 1H), 9.16 (s, 1H), 4.73 (d, J=6.4 Hz, 2H), 4.29 (d, J=6.4 Hz, 2H), 4.22 (s, 2H), 3.69 (s, 3H), 1.39 (s, 3H). MS-ESI calculated value: [M+H]$^+$ 263; measured value: 263.

Example 70

3-((3-Ethyloxetan-3-yl)methyl)-1-methylpyrimido[4,5-d]pyrimidin-2,4-dione

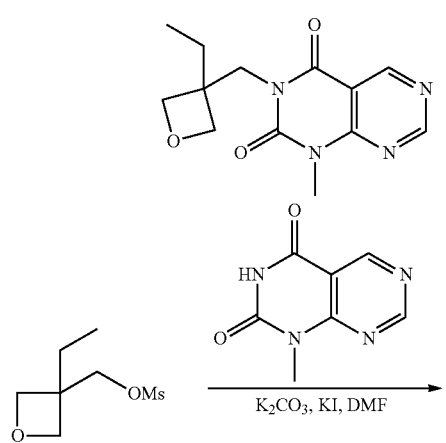

Step 1

3-((3-Ethyloxetan-3-yl)methyl)-1-methylpyrimido[4,5-d]pyrimidin-2,4-dione

1-Methylpyrimido[4,5-d]pyrimidin-2,4-dione (60 mg, 0.337 mmol) was dissolved in N,N-dimethylformamide (4 mL), and then (3-ethyloxetan-3-yl)methyl methanesulfonate (71.0 mg, 0.370 mmol), potassium iodide (11.0 mg, 0.0674 mmol) and potassium carbonate (93.0 mg, 0.673 mmol) were added at 25° C. The reaction solution was heated to 120° C. and stirred for 16 hours. The reaction solution was cooled to room temperature and then filtered. The filtrate was concentrated under reduced pressure, and the residue was purified by preparative high performance liquid chromatography to give a product 3-((3-ethyloxetan-3-yl)methyl)-1-methylpyrimido[4,5-d]pyrimidin-2,4-dione (43.0 mg) with a yield of 46%. $^1$H NMR: (400 MHz, CDCl$_3$) δ9.31 (s, 1H), 9.17 (s, 1H), 4.61 (d, J=6.4 Hz, 2H), 4.34 (d, J=6.4 Hz, 2H), 4.18 (s, 2H), 3.71 (s, 3H), 1.81 (q, J=7.2 Hz, 2H), 1.08 (t, J=7.2 Hz, 3H).

MS-ESI calculated value: [M+H]$^+$ 277; measured value: 277.

Example 71

1-Methyl-3-((tetrahydrofuran-3-yl)methyl)pyrimido[4,5-d]pyrimidin-2,4-dione

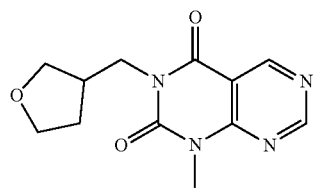

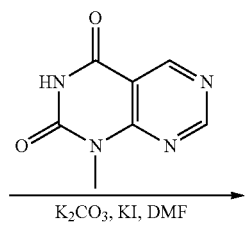

Step 1

1-Methyl-3-((tetrahydrofuran-3-yl)methyl)pyrimido[4,5-d]pyrimidin-2,4-dione

1-Methylpyrimido[4,5-d]pyrimidin-2,4-dione (50.0 mg, 0.281 mmol) was dissolved in N,N-dimethylformamide (4 mL), and then (tetrahydrofuran-3-yl)methyl methanesulfonate (56.0 mg, 0.308 mmol), potassium iodide (9.0 mg, 0.056 mmol) and potassium carbonate (78.0 mg, 0.561 mmol) were added at 25° C. The reaction solution was heated to 120° C. and stirred for 16 hours. The reaction solution was cooled to room temperature and then filtered. The filtrate was concentrated under reduced pressure, and the residue was purified by preparative high performance liquid chromatography to give a product 1-methyl-3-((tetrahydrofuran-3-yl)methyl)pyrimido[4,5-d]pyrimidin-2,4-dione (45.0 mg) with a yield of 61%. $^1$H NMR: (400 MHz, CDCl$_3$) δ9.30 (s, 1H), 9.15 (s, 1H), 4.23-4.14 (m, 1H), 4.11-4.03 (m, 1H), 3.99-3.92 (m, 1H), 3.85-3.75 (m, 2H), 3.69 (s, 3H), 3.64-3.59 (m, 1H), 2.82-2.70 (m, 1H), 2.06-1.96 (m, 1H), 1.80-1.64 (m, 1H). MS-ESI calculated value: [M+H]$^+$ 263; measured value: 263.

Example 72

1-Methyl-3-((tetrahydropyran-4-yl)methyl)pyrimido[4,5-d]pyrimidin-2,4-dione

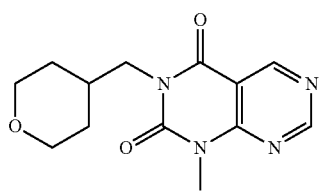

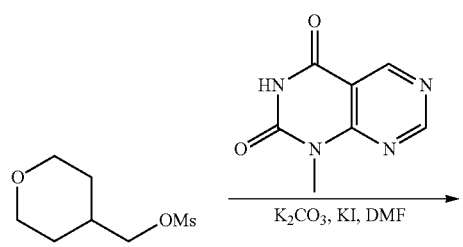

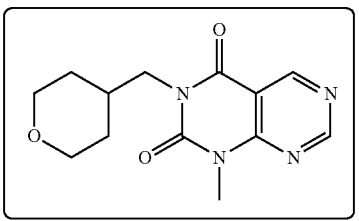

Step 1

1-Methyl-3-((tetrahydropyran-4-yl)methyl)pyrimido[4,5-d]pyrimidin-2,4-dione

1-Methylpteridin-2,4-dione (60.0 mg, 0.337 mmol) was dissolved in N,N-dimethylformamide (4 mL), and then (tetrahydropyran-4-yl)methyl methanesulfonate (72.0 mg, 0.370 mmol), potassium iodide (11.0 mg, 0.674 mmol) and potassium carbonate (93.0 mg, 0.674 mmol) were added at 25° C. The reaction solution was heated to 120° C. and stirred for 16 hours. The reaction solution was cooled to room temperature and then filtered. The filtrate was concentrated under reduced pressure, and the residue was purified by preparative high performance liquid chromatography to give a product 1-methyl-3-((tetrahydropyran-4-yl)methyl)pyrimido[4,5-d]pyrimidin-2,4-dione (43.0 mg) with a yield of 46%. $^1$H NMR: (400 MHz, CDCl$_3$) δ9.30 (s, 1H), 9.15 (s, 1H), 4.02-3.94 (m, 4H), 3.69 (s, 3H), 3.38-3.30 (m, 2H), 2.15-2.03 (m, 1H), 1.67-1.58 (m, 2H), 1.54-1.44 (m, 2H).

MS-ESI calculated value: [M+H]$^+$ 277; measured value: 277.

Example 73

1-Methyl-3-(2-(tetrahydropyran-4-yl)ethyl)pyrimido[4,5-d]pyrimidin-2,4-dione

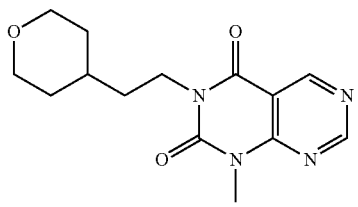

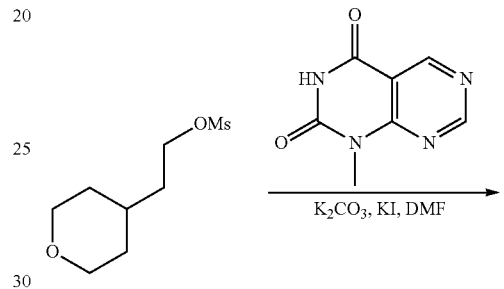

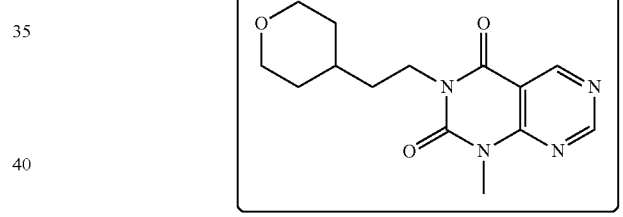

Step 1

1-Methyl-3-(2-(tetrahydropyran-4-yl)ethyl)pyrimido[4,5-d]pyrimidin-2,4-dione 2-(Tetrahydropyran-4-yl)ethyl methanesulfonate (117 mg, 0.561 mmol), 1-methylpyrimido[4,5-d]pyrimidin-2,4-dione (100.0 mg, 0.561 mmol) and potassium carbonate (233 mg, 1.68 mmol) were dissolved in N,N-dimethylformamide (5 mL), and then potassium iodide (4.7 mg, 0.028 mmol) was added. The reaction solution was stirred at 120° C. for 3 hours. The reaction solution was cooled to room temperature and then filtered. The filtrate was concentrated under reduced pressure. The crude product obtained was purified by preparative high performance liquid chromatography to give a product 1-methyl-3-(2-(tetrahydropyran-4-yl)ethyl)pyrimido[4,5-d]pyrimidin-2,4-dione (49.0 mg) with a yield of 30%. $^1$H NMR: (400 MHz, CDCl$_3$) δ9.32 (s, 1H), 9.17 (s, 1H), 4.13 (t, J=7.2 Hz, 2H), 4.01-3.97 (m, 2H), 3.71 (s, 3H), 3.41 (t, J=10.8 Hz, 2H), 1.75-1.69 (m, 2H), 1.67-1.63 (m, 2H), 1.60 (s, 1H), 1.42-1.36 (m, 2H). MS-ESI calculated value: [M+H]$^+$ 291; measured value: 291.

Example 74

3-((4-Methoxycyclohexyl)methyl)-1-methylpyrimido[4,5-d]pyrimidin-2,4-dione

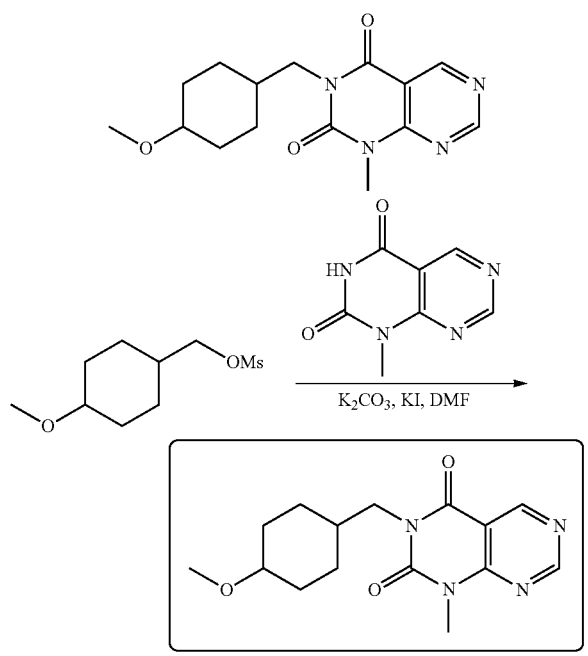

Step 1

3-((4-Methoxycyclohexyl)methyl)-1-methylpyrimido[4,5-d]pyrimidin-2,4-dione (4-Methoxycyclohexyl)methyl methanesulfonate (81.1 mg, 0.364 mmol), 1-methylpyrimido[4,5-d]pyrimidin-2,4-dione (50.0 mg, 0.280 mmol) and potassium carbonate (38.7 mg, 0.280 mmol) were dissolved in N,N-dimethylformamide (5 mL), and then potassium iodide (46.5 mg, 0.280 mmol) was added. The reaction solution was stirred at 120° C. for 3 hours. The reaction solution was cooled to room temperature and then filtered. The filtrate was concentrated under reduced pressure. The crude product obtained was purified by preparative high performance liquid chromatography to give a product 3-((4-methoxycyclohexyl)methyl)-1-methylpyrimido[4,5-d]pyrimidin-2,4-dione (53.0 mg) with a yield of 62%. $^1$H NMR: (400 MHz, Methonal-d$_4$) δ9.20 (s, 1H), 9.13 (s, 1H), 3.93 (d, J=7.2 Hz, 2H), 3.67 (s, 3H), 3.35 (s, 3H), 3.22-3.16 (m, 1H), 2.10-2.07 (m, 2H), 1.84-1.78 (m, 3H), 1.21-1.08 (m, 4H). MS-ESI calculated value: [M+H]$^+$ 305; measured value: 305.

Experimental Example 1 In Vitro Evaluation of PDE2 Phosphodiesterase Inhibitory Activity Experiment Objective: Determining the concentration of AMP/GMP produced in the reaction system by way of detecting the AlexaFluor 633 fluorescent dye substituted on AMP/GMP antibody by fluorescence polarization assay, and thereby to calculate the IC$_{50}$ value of PDE2 phosphodiesterase inhibition by the test compound.

Experimental Materials:
Detecting buffer solution: 10 mM Tris-HCl, pH 7.5, 5 mM MgCl$_2$, 0.01% Brij 35, 1 mM DTT, and 1% DMSO.
Enzyme: Recombinant full-length human PDE2A protein with an N-terminal GST-tag expressed in insect Sf9 cells by baculovirus
Substrate: 1 μM cGMP
Detection System:
Transcreener® AMP$^2$/GMP$^2$ antibody, AMP2/GMP2 AlexaFluor 633 fluorescent dye
Experimental Operation:
The enzyme solution was prepared by using the freshly prepared buffer solution, and then was added into the reaction wells. The DMSO solution of the test compound was added via Echo550, a nanoliter-scale contactless acoustic liquid transferring system, and then pre-incubated at room temperature for 10 minutes. The substrate (1 μLM cGMP) was added to initiate the reaction at room temperature for one hour. The detection system (Transcreener® AMP$^2$/GMP$^2$ antibody, AMP2/GMP2 AlexaFluor 633 fluorescent dye) was then added, and the reaction was conducted at room temperature for 90 minutes. Fluorescence polarization was then detected by using Ex/Em 620/688.

The intensity of fluorescence polarization was converted to nM concentration by the AMP/GMP standard curve, and then calculate the relative enzyme activity inhibition relative to the DMSO blank. The IC$_{50}$ values and curves were calculated by using the Prism software package (GraphPad Software, San Diego Calif., USA)
Experimental Results:

TABLE 1

| Results of PDE2 phosphodiesterase inhibitory activity assay | |
|---|---|
| Test Compounds (compounds obtained in each example) | PDE2 phosphodiesterase inhibitory activity |
| Example 1 | -- |
| Example 2 | -- |
| Example 3 | + |
| Example 4 | + |
| Example 5 | + |
| Example 6 | -- |
| Example 7 | -- |
| Example 8 | -- |
| Example 9 | -- |
| Example 10 | -- |
| Example 11 Isomer 1 | + |
| Example 11 Isomer 2 | -- |
| Example 12 Isomer 1 | + |
| Example 12 Isomer 2 | + |
| Example 13 | -- |
| Example 14 | + |
| Example 15 | + |
| Example 16 | + |
| Example 18 | + |
| Example 19 | -- |
| Example 20 | + |
| Example 21 | + |
| Example 22 | -- |
| Example 23 | + |
| Example 25 | -- |
| Example 26 | + |
| Example 33 | + |
| Example 39 | -- |

Notes:
10 μM <+ ≤50 μM;
1 μM <++ ≤10 μM;
+++ ≤1 μM;
-- N/A

Conclusion: The compounds of the present invention have significant and even unexpected PDE2A protease inhibitory activity.

Experimental Example 2: In Vitro Evaluation of the Compound's Impact on Induction of TNF-α in Rat Blood by LPS Experiment Objective: Determining the impact of the compounds on induction of TNF-α in rat blood by LPS in vitro, and evaluating the effect of the compounds on inhibiting induction of TNF-α in rat blood by LPS.

Experimental Materials:
Sprague Dawley rats (male, 210-260 g, 8-10 weeks old, Shanghai SLAC)
Rat TNF-alpha Quantikine ELISA Kit (R&D, # SRTA00)

Experimental Operation:
The test compound solutions were prepared at a concentration of 1 mM. 40 μl of each of the solutions was added into a 48-well cell culture plate (at the final concentration of 100 μM). After the rat was anesthetized with isoflurane, the blood was collected from the heart (heparin for anticoagulation). The blood was added into the 48-well plate containing the test compound, in the amount of 320 μL per well. The 48-well plate was placed into a cell incubator, and then taken out after 30 minutes of incubation. Then, 40 μL of LPS solution (100 μg/ml) was added and mixed. The 48-well plate was placed into the incubator for further incubation. After 5 hours, the 48-well plate was taken out and the blood sample was transferred to a 1.5 mL centrifuge tube, followed by centrifugation in a centrifuge (4,500 rpm, 4° C., 5 minutes). The supernatant was separated and the plasma was obtained. The plasma was subpackaged in portions, quickly frozen, and stored in a −80° C. refrigerator. In the next day, the TNF-α level of the plasma samples was determined by using the R&D ELISA kit in accordance with the instructions.

Experimental Results:

TABLE 2

Results of TNFα inhibitory activity assay

| Test Compounds (compounds obtained in each example) | Rate of TNFα inhibition |
| --- | --- |
| Example 3 | + |
| Example 17 | -- |

Notes:
80% >+ ≥60%;
++ ≥80%;
-- N/A

Conclusion: The compounds of the present invention have significant and even unexpected TNFα inhibitory activity.

The invention claimed is:
1. A compound as shown in Formula (I), tautomers or pharmaceutically acceptable salts thereof,

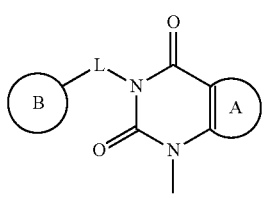

(I)

wherein,
ring B is

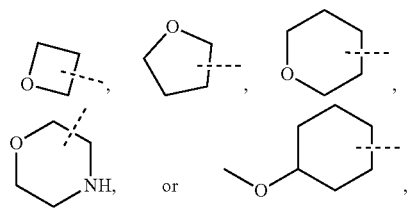

optionally substituted with 1 to 3 R groups;
L is $C_{1-3}$ alkyl optionally substituted with 1 to 2 R groups;
ring A is 5- to 6-membered aryl or heteroaryl optionally substituted with 1 or 2 $R_1$ groups;
$R_1$ is selected from the group consisting of halogen, OH, $NH_2$, and the following groups optionally substituted with 1 to 3 $R_2$ groups: $C_{1-6}$ alkyl or heteroalkyl, 3- to 6-membered cycloalkyl or heterocycloalkyl, or $C_{1-6}$ alkyl or heteroalkyl substituted with 3- to 6-membered cycloalkyl or heterocycloalkyl;
$R_2$ is selected from the group consisting of halogen, OH, $NH_2$, Me, $CF_3$, OMe, and $OCF_3$;
the "hetero" represents heteroatoms selected from the group consisting of O, S, and N, and the numbers of heteroatoms on each heteroalkyl or heterocycloalkyl are each independently selected from the group consisting of 1, 2 and 3;
R is selected from the group consisting of halogen, N(R')(R'), and $C_{1-3}$ alkyl or heteroalkyl optionally substituted with 1 to 3 R' groups; and
R' is selected from the group consisting of H, halogen, $NH_2$, Me, $CF_3$, OMe, and $OCF_3$.

2. The compound, tautomers or pharmaceutically acceptable salts thereof according to claim 1, wherein said $R_1$ is selected from the group consisting of halogen, OH, $NH_2$, and the following groups optionally substituted with 1 to 3 $R_2$ groups: $C_{1-4}$ alkyl or heteroalkyl, or $C_{1-3}$ alkyl or heteroalkyl substituted with 3- to 5-membered cycloalkyl or heterocycloalkyl.

3. The compound, tautomers or pharmaceutically acceptable salts thereof according to claim 1, wherein R is selected from the group consisting of F, Cl, Br, I, Me,

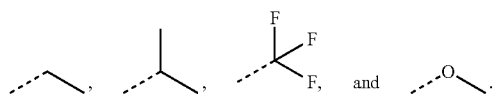

4. The compound, tautomers or pharmaceutically acceptable salts thereof according to claim 1, wherein, said ring B is

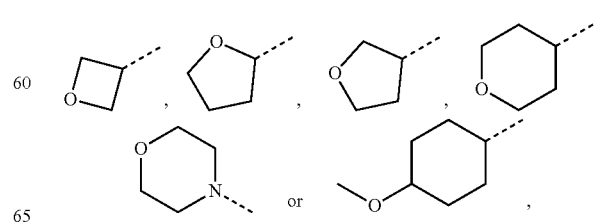

optionally substituted with 1 to 3 R groups.

5. The compound, tautomers or pharmaceutically acceptable salts thereof according to claim 1, wherein, said L is methylene,

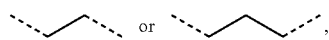

optionally substituted with 1 to 2 R groups.

6. The compound, tautomers or pharmaceutically acceptable salts thereof according to claim 1, wherein said ring A is imidazolyl, pyrazolyl, pyridinyl, pyrazinyl, pyridazinyl, pyrimidinyl, or phenyl, optionally substituted with 1 or 2 $R_1$ groups.

7. The compound, tautomers or pharmaceutically acceptable salts thereof according to claim 6, wherein said ring A is

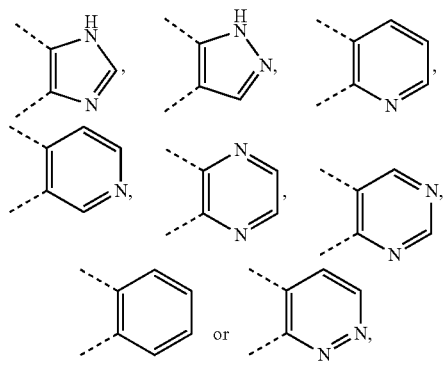

optionally substituted with 1 or 2 $R_1$ groups.

8. The compound, tautomers or pharmaceutically acceptable salts thereof according to claim 6, wherein said structural unit

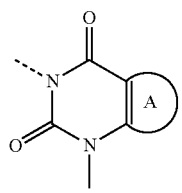

is selected from the group consisting of:

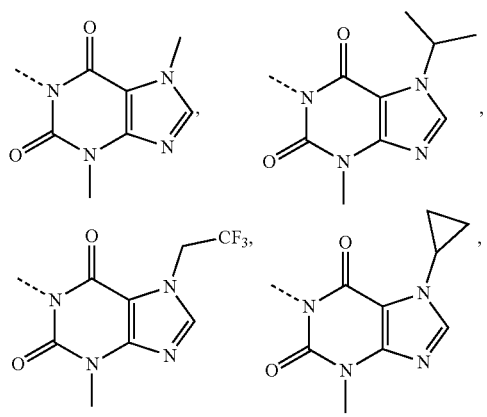

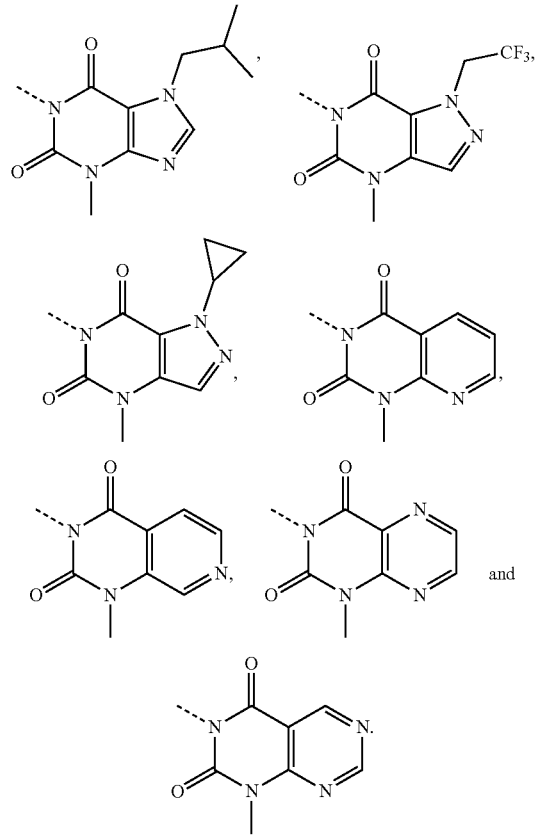

9. The compound, tautomers or pharmaceutically acceptable salts thereof according to claim 1, wherein said compound is selected from the group consisting of:

| Compound | Structure |
| --- | --- |
| 1 | 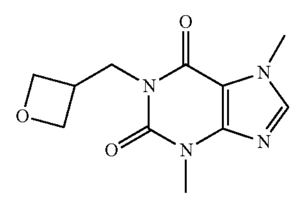 [SMILES: Cn1cnc2c1c(=O)n(CC1COC1)c(=O)n2C] |
| 2 | 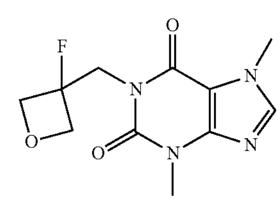 [SMILES: Cn1cnc2c1c(=O)n(CC1(F)COC1)c(=O)n2C] |
| 3 | 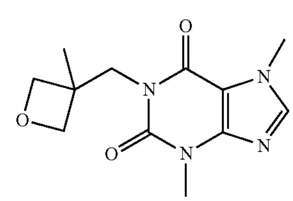 [SMILES: Cn1cnc2c1c(=O)n(CC1(C)COC1)c(=O)n2C] |

-continued

| Compound | Structure |
|---|---|
| 4 | 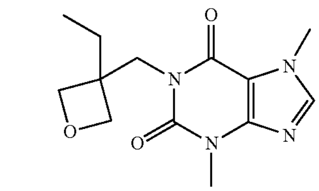 [SMILES: CCC1(Cn2c(=O)c3c(ncn3C)n(C)c2=O)COC1] |
| 5 | 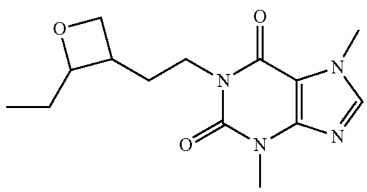 [SMILES: CCC1OCC1CCn1c(=O)c2c(ncn2C)n(C)c1=O] |
| 6 | 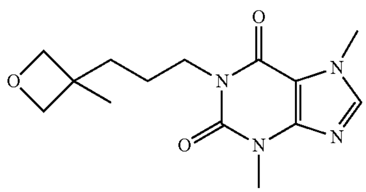 [SMILES: Cn1cnc2c1c(=O)n(CCCC1(C)COC1)c(=O)n2C] |
| 7 | 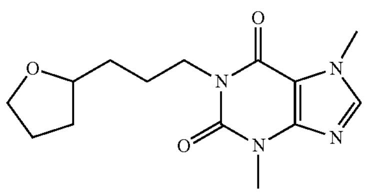 [SMILES: Cn1cnc2c1c(=O)n(CCCC1CCCO1)c(=O)n2C] |
| 8 | 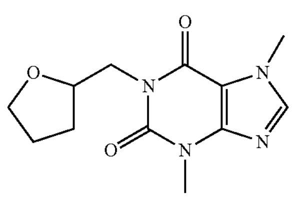 [SMILES: Cn1cnc2c1c(=O)n(CC1CCCO1)c(=O)n2C] |
| 9 | 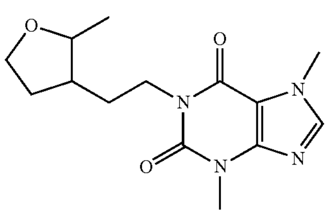 [SMILES: CC1OCCC1CCn1c(=O)c2c(ncn2C)n(C)c1=O] |
| 10 | 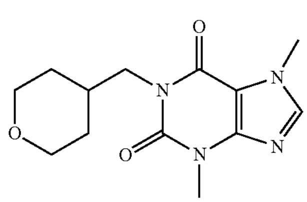 [SMILES: Cn1cnc2c1c(=O)n(CC1CCOCC1)c(=O)n2C] |

-continued

| Compound | Structure |
|---|---|
| 11 | |
| 12 | |
| 13 | |
| 14 | |
| 15 | |

-continued

| Compound | Structure |
|---|---|
| 16 | 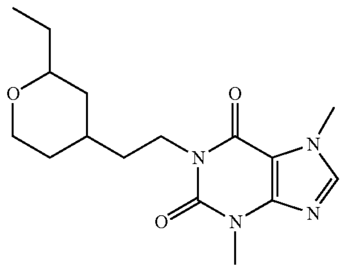 [SMILES: CCC1CC(CCn2c(=O)c3c(ncn3C)n(C)c2=O)CCO1] |
| 17 | 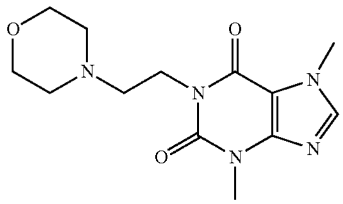 [SMILES: Cn1cnc2c1c(=O)n(CCN1CCOCC1)c(=O)n2C] |
| 18 | 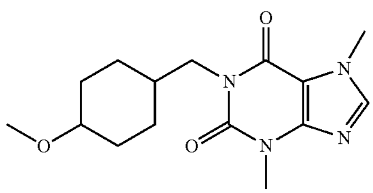 [SMILES: COC1CCC(Cn2c(=O)c3c(ncn3C)n(C)c2=O)CC1] |
| 19 | 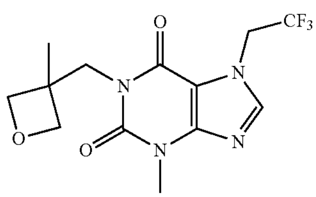 [SMILES: Cn1c(=O)n(CC2(C)COC2)c(=O)c2c1ncn2CC(F)(F)F] |
| 20 | 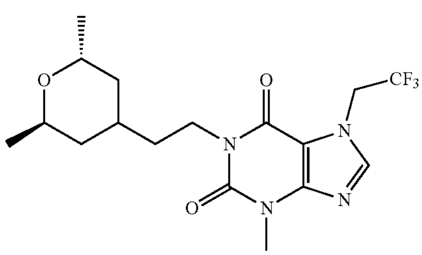 [SMILES: C[C@@H]1CC(CCn2c(=O)c3c(ncn3CC(F)(F)F)n(C)c2=O)C[C@@H](C)O1] |
| 21 | 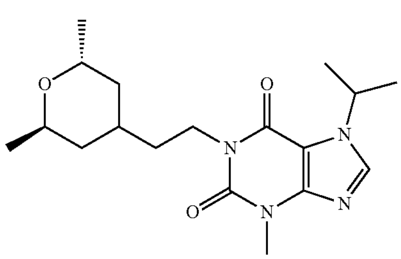 [SMILES: CC(C)n1cnc2c1c(=O)n(CCC1C[C@@H](C)O[C@H](C)C1)c(=O)n2C] |

-continued

| Compound | Structure |
|---|---|
| 22 | 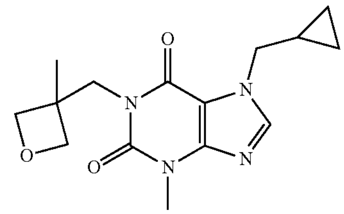 [SMILES: Cn1c(=O)n(CC2(C)COC2)c(=O)c2c1ncn2CC1CC1] |
| 23 | 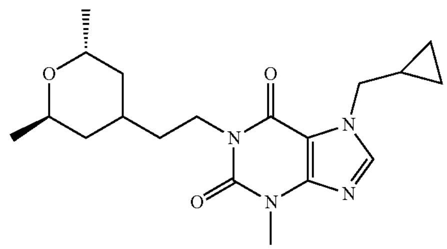 [SMILES: C[C@@H]1CC(CCn2c(=O)c3c(ncn3CC3CC3)n(C)c2=O)C[C@@H](C)O1] |
| 24 | 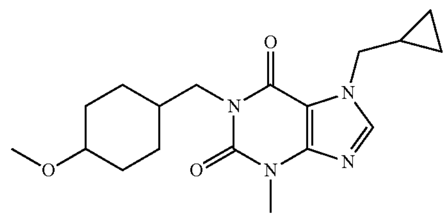 [SMILES: COC1CCC(Cn2c(=O)c3c(ncn3CC3CC3)n(C)c2=O)CC1] |
| 25 | 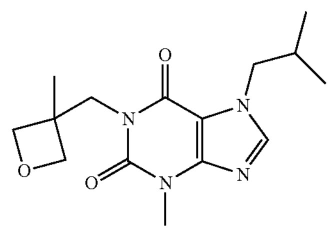 [SMILES: CC(C)Cn1cnc2c1c(=O)n(CC1(C)COC1)c(=O)n2C] |
| 26 | 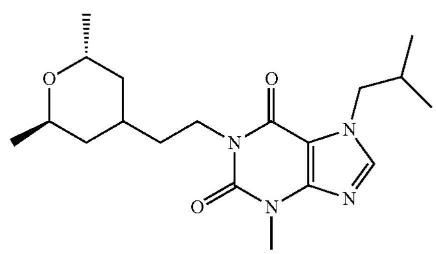 [SMILES: CC(C)Cn1cnc2c1c(=O)n(CCC1C[C@@H](C)O[C@H](C)C1)c(=O)n2C] |
| 27 | 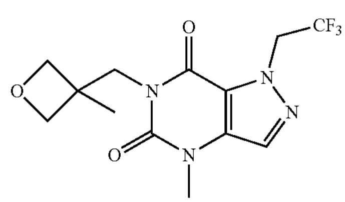 [SMILES: Cn1c(=O)n(CC2(C)COC2)c(=O)c2c1cnn2CC(F)(F)F] |
| 28 | 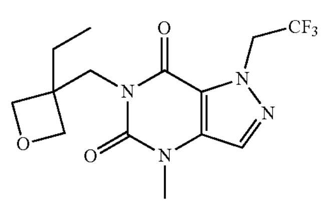 [SMILES: CCC1(Cn2c(=O)c3c(cnn3CC(F)(F)F)n(C)c2=O)COC1] |

-continued

| Compound | Structure |
|----------|-----------|
| 29 | 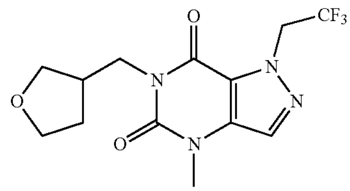 [SMILES: Cn1c(=O)n(CC2CCOC2)c(=O)c2c1cnn2CC(F)(F)F] |
| 30 | 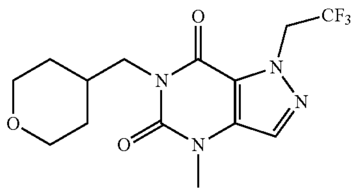 [SMILES: Cn1c(=O)n(CC2CCOCC2)c(=O)c2c1cnn2CC(F)(F)F] |
| 31 | 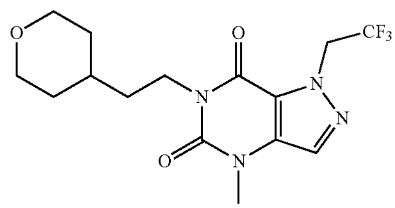 [SMILES: Cn1c(=O)n(CCC2CCOCC2)c(=O)c2c1cnn2CC(F)(F)F] |
| 32 | 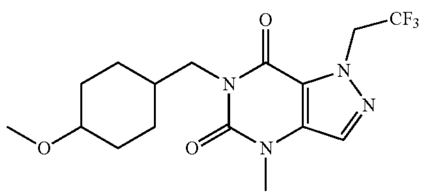 [SMILES: COC1CCC(Cn2c(=O)c3c(cnn3CC(F)(F)F)n(C)c2=O)CC1] |
| 33 | 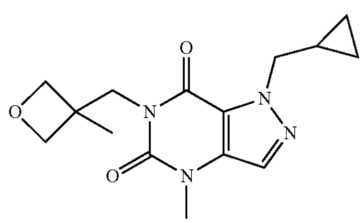 [SMILES: Cn1c(=O)n(CC2(C)COC2)c(=O)c2c1cnn2CC1CC1] |
| 34 | 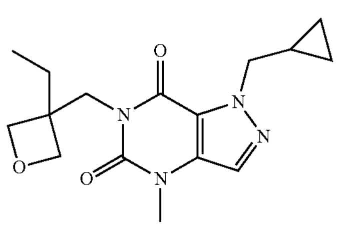 [SMILES: CCC1(Cn2c(=O)c3c(cnn3CC3CC3)n(C)c2=O)COC1] |
| 35 | 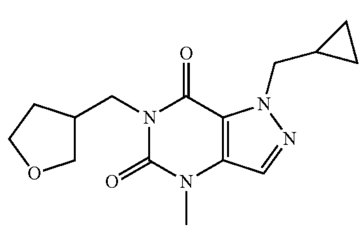 [SMILES: Cn1c(=O)n(CC2CCOC2)c(=O)c2c1cnn2CC1CC1] |
| 36 | |
| 37 | |
| 38 | |
| 39 | |
| 40 | |
| 41 | |
| 42 | |

-continued

| Compound | Structure |
|----------|-----------|
| 43 | 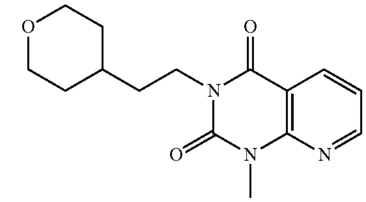 [SMILES: Cn1c(=O)n(CCC2CCOCC2)c(=O)c2cccnc21] |
| 44 | 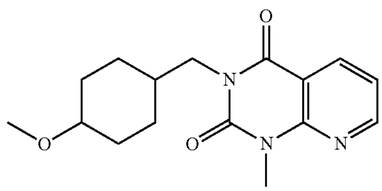 [SMILES: COC1CCC(Cn2c(=O)c3cccnc3n(C)c2=O)CC1] |
| 45 | 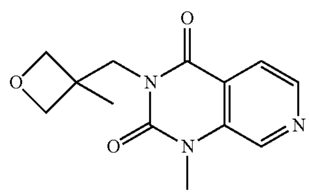 [SMILES: Cn1c(=O)n(CC2(C)COC2)c(=O)c2ccncc21] |
| 46 | 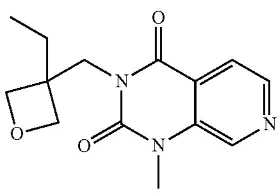 [SMILES: CCC1(Cn2c(=O)c3ccncc3n(C)c2=O)COC1] |
| 47 | 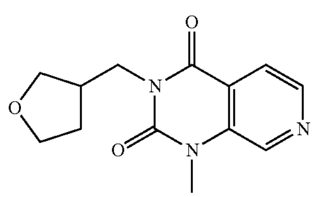 [SMILES: Cn1c(=O)n(CC2CCOC2)c(=O)c2ccncc21] |
| 48 | 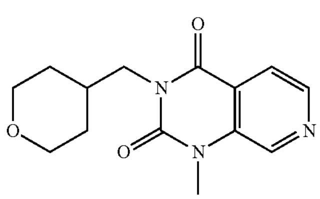 [SMILES: Cn1c(=O)n(CC2CCOCC2)c(=O)c2ccncc21] |
| 49 | 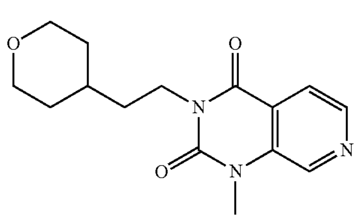 [SMILES: Cn1c(=O)n(CCC2CCOCC2)c(=O)c2ccncc21] |
| 50 | 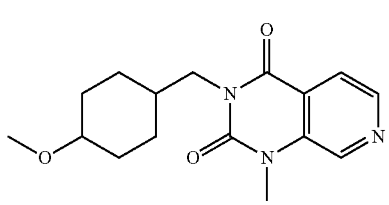 [SMILES: COC1CCC(Cn2c(=O)c3ccncc3n(C)c2=O)CC1] |

-continued

| Compound | Structure |
|----------|-----------|
| 51 | |
| 52 | |
| 53 | |
| 54 | |
| 55 | |
| 56 | |
| 57 | |

-continued

| Compound | Structure |
|---|---|
| 58 | 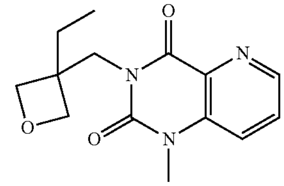 [SMILES: CCC1(Cn2c(=O)c3ncccc3n(C)c2=O)COC1] |
| 59 | 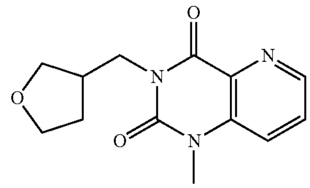 [SMILES: Cn1c(=O)n(CC2CCOC2)c(=O)c2ncccc21] |
| 60 | 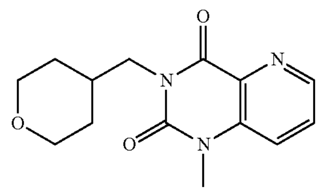 [SMILES: Cn1c(=O)n(CC2CCOCC2)c(=O)c2ncccc21] |
| 61 | 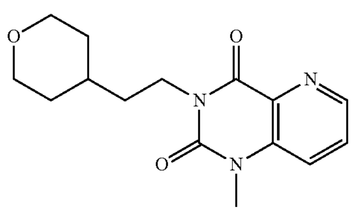 |
| 62 | 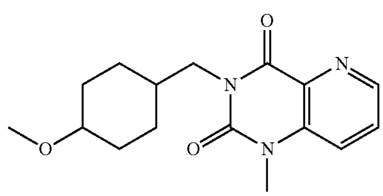 [SMILES: COC1CCC(Cn2c(=O)c3ncccc3n(C)c2=O)CC1] |
| 63 | 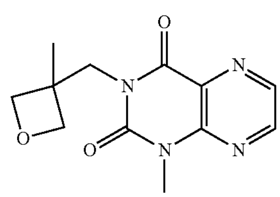 [SMILES: Cn1c(=O)n(CC2(C)COC2)c(=O)c2nccnc21] |
| 64 | 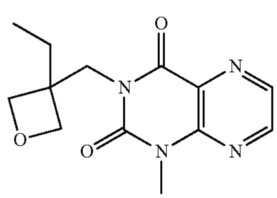 [SMILES: CCC1(Cn2c(=O)c3nccnc3n(C)c2=O)COC1] |
| 65 | 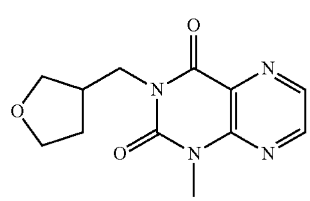 [SMILES: Cn1c(=O)n(CC2CCOC2)c(=O)c2nccnc21] |

-continued

| Compound | Structure |
|---|---|
| 66 | 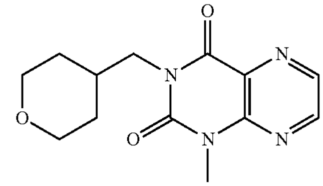 [SMILES: Cn1c(=O)n(CC2CCOCC2)c(=O)c2nccnc21] |
| 67 | 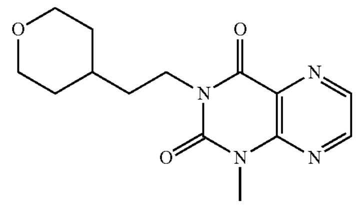 [SMILES: Cn1c(=O)n(CCC2CCOCC2)c(=O)c2nccnc21] |
| 68 | 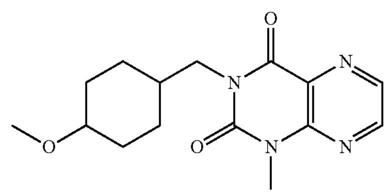 [SMILES: COC1CCC(Cn2c(=O)c3nccnc3n(C)c2=O)CC1] |
| 69 | 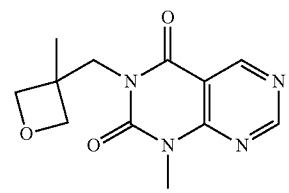 [SMILES: Cn1c(=O)n(CC2(C)COC2)c(=O)c2cncnc21] |
| 70 | 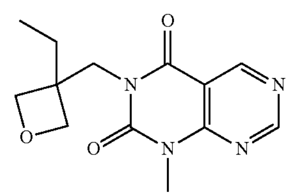 [SMILES: CCC1(Cn2c(=O)c3cncnc3n(C)c2=O)COC1] |
| 71 | 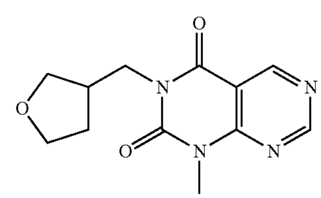 [SMILES: Cn1c(=O)n(CC2CCOC2)c(=O)c2cncnc21] |
| 72 | 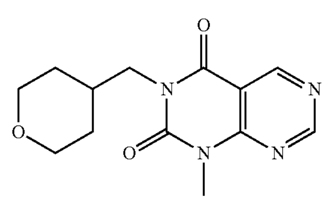 [SMILES: Cn1c(=O)n(CC2CCOCC2)c(=O)c2cncnc21] |
| 73 | 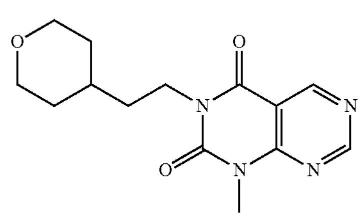 [SMILES: Cn1c(=O)n(CCC2CCOCC2)c(=O)c2cncnc21] |

| Compound | Structure |
|---|---|
| 74 | 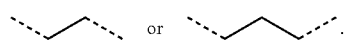 |

10. A method for treating central diseases, cardiovascular diseases, or inflammatory diseases, the method comprising administering to a patient in need a therapeutically effective amount of the compound, tautomers or pharmaceutically acceptable salts thereof according to claim 1.

11. The compound, tautomers or pharmaceutically acceptable salts thereof according to claim 1, wherein $R_1$ is selected from the group consisting of Me, $CF_3$, Et, $CH_2CF_3$,

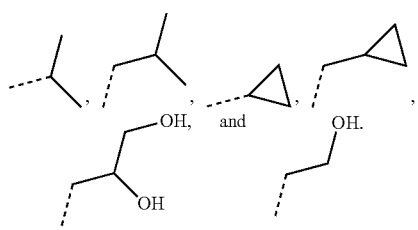

12. The compound, tautomers or pharmaceutically acceptable salts thereof according to claim 1, wherein said ring B is selected from the group consisting of:

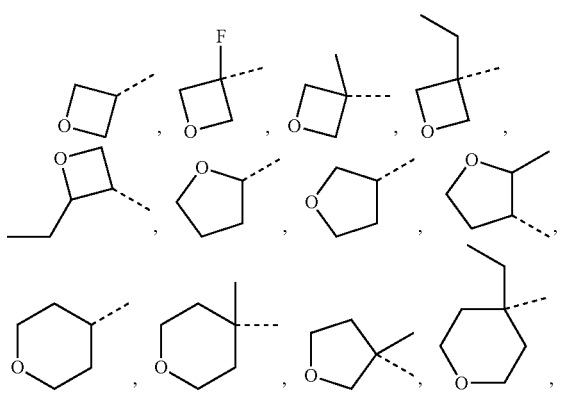

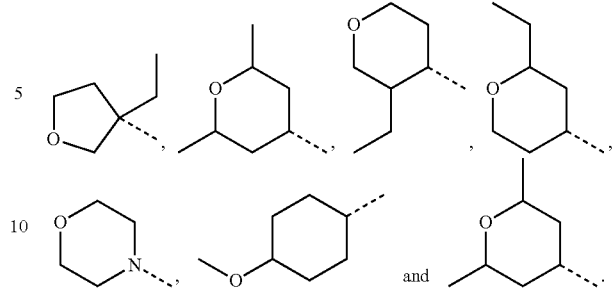

13. The compound, tautomers or pharmaceutically acceptable salts thereof according to claim 1, wherein, said L is methylene, 14. The compound, tautomers or pharmaceutically acceptable salts thereof according to claim 6, wherein said ring A is selected from the group consisting of:

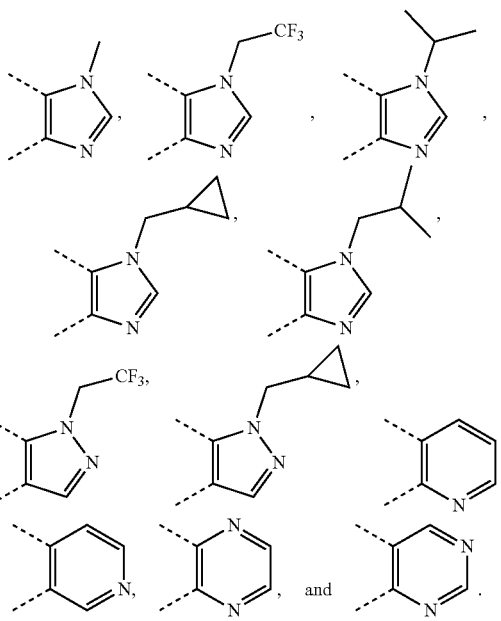

* * * * *